(12) United States Patent (10) Patent No.: US 7,946,982 B2
Hamada (45) Date of Patent: May 24, 2011

(54) MINIMAL INCISION MAXIMAL ACCESS MIS SPINE INSTRUMENTATION AND METHOD

(75) Inventor: James S. Hamada, Torrance, CA (US)

(73) Assignee: K2M, Inc., Leesburg, VA (US)

( * ) Notice: Subject to any disclaimer, the term of this patent is extended or adjusted under 35 U.S.C. 154(b) by 688 days.

(21) Appl. No.: 11/510,804

(22) Filed: Aug. 25, 2006

(65) Prior Publication Data

US 2007/0038216 A1 Feb. 15, 2007

Related U.S. Application Data

(60) Continuation-in-part of application No. 11/489,858, filed on Jul. 19, 2006, now Pat. No. 7,850,608, which is a continuation-in-part of application No. 11/267,618, filed on Nov. 4, 2005, which is a continuation-in-part of application No. 11/230,420, filed on Sep. 19, 2005, which is a continuation-in-part of application No. 11/165,295, filed on Jun. 22, 2005, now Pat. No. 7,883,522, which is a continuation-in-part of application No. 11/001,628, filed on Nov. 30, 2004, now Pat. No. 7,173,240, which is a division of application No. 10/280,624, filed on Oct. 25, 2002, now Pat. No. 6,849,064.

(51) Int. Cl.
 *A61B 1/32* (2006.01)
(52) U.S. Cl. ....................................... 600/233
(58) Field of Classification Search .................. 600/201, 600/205, 208, 210, 215–219, 222, 225, 231, 600/233
See application file for complete search history.

(56) References Cited

U.S. PATENT DOCUMENTS

| 1,613,141 A | 1/1927 | Stein |
| 2,693,795 A | 11/1954 | Grieshaber |
| 3,129,706 A | 4/1964 | Reynolds |
| 3,227,156 A | 1/1966 | Gauthier |
| 3,724,449 A | 4/1973 | Gauthier |
| 3,750,652 A | 8/1973 | Sherwin |
| 4,263,899 A | 4/1981 | Burgin |

(Continued)

FOREIGN PATENT DOCUMENTS

DE 201 109 12/1907

(Continued)

OTHER PUBLICATIONS

International Search Report for European Application No. EP 1 949 860, as published on Oct. 1, 2008.

(Continued)

*Primary Examiner* — Eduardo C Robert
*Assistant Examiner* — Sameh Boles
(74) *Attorney, Agent, or Firm* — Carter, DeLuca, Farrell & Schmidt, LLP

(57) ABSTRACT a minimal incision maximal access system allows for maximum desirable work space exposure within the incision along with maximum access to the operative field utilizing a minimum incision as small as the width of the working tube. Instead of multiple insertions of dilating tubes the design is a streamlined single entry device to avoid repetitive skin surface entry. The system offers the capability to expand to optimum exposure size for the surgery utilizing retractors depending from a bi-hinged frame having internal or external controls to control the angle and separation of the retractors. Interchangeable retractor blades can be attached to the frame. Both retractor blades are independently controlled as to displacement and angle.

6 Claims, 75 Drawing Sheets

U.S. PATENT DOCUMENTS

| | | |
|---|---|---|
| 4,300,541 A | 11/1981 | Burgin |
| 4,545,374 A | 10/1985 | Jacobson |
| 4,747,394 A | 5/1988 | Watanabe |
| 4,852,552 A | 8/1989 | Chaux |
| 4,924,857 A | 5/1990 | Mahmoodian |
| 4,926,849 A | 5/1990 | Downey |
| 4,989,587 A | 2/1991 | Farley |
| 4,991,566 A * | 2/1991 | Shulman et al. ............ 600/213 |
| 5,503,617 A | 4/1996 | Jako |
| 5,505,690 A | 4/1996 | Patton et al. |
| 5,529,571 A | 6/1996 | Daniel |
| 5,582,577 A | 12/1996 | Lund |
| 5,616,117 A | 4/1997 | Dinkler et al. |
| 5,667,520 A | 9/1997 | Bonutti |
| 5,707,359 A | 1/1998 | Bufalini |
| 5,707,362 A | 1/1998 | Yoon |
| 5,813,978 A | 9/1998 | Jako |
| 5,885,210 A | 3/1999 | Cox |
| 5,902,233 A | 5/1999 | Farley et al. |
| 5,931,777 A | 8/1999 | Sava |
| 5,944,658 A | 8/1999 | Koros et al. |
| 5,967,972 A | 10/1999 | Santilli et al. |
| 6,224,545 B1 * | 5/2001 | Cocchia et al. ............ 600/233 |
| 6,241,659 B1 | 6/2001 | Bookwalter et al. |
| 6,524,320 B2 | 2/2003 | DiPoto |
| 6,530,926 B1 | 3/2003 | Davison |
| 6,616,605 B2 | 9/2003 | Wright |
| 6,652,553 B2 | 11/2003 | Davison et al. |
| 6,688,195 B1 | 2/2004 | Hsien |
| 6,743,206 B1 | 6/2004 | Smith et al. |
| 6,767,355 B2 | 7/2004 | Frova et al. |
| 6,796,422 B1 | 9/2004 | Lu |
| 6,849,064 B2 | 2/2005 | Hamada |
| 6,869,398 B2 | 3/2005 | Obenchain et al. |
| 6,945,933 B2 | 9/2005 | Branch et al. |
| 7,056,329 B2 | 6/2006 | Kerr |
| 2003/0004401 A1 | 1/2003 | Ball |
| 2003/0191371 A1 * | 10/2003 | Smith et al. ............ 600/210 |
| 2004/0024291 A1 | 2/2004 | Zinkel |
| 2004/0093000 A1 | 5/2004 | Kerr |
| 2004/0176665 A1 | 9/2004 | Branch et al. |
| 2004/0215199 A1 | 10/2004 | Zinkel |
| 2004/0230100 A1 | 11/2004 | Shluzas |
| 2004/0230191 A1 * | 11/2004 | Frey et al. ............ 606/57 |
| 2005/0070765 A1 | 3/2005 | Abdelgany et al. |
| 2005/0080320 A1 | 4/2005 | Lee et al. |
| 2005/0159650 A1 | 7/2005 | Raymond et al. |
| 2005/0159651 A1 | 7/2005 | Raymond et al. |
| 2005/0215866 A1 | 9/2005 | Kim |
| 2005/0234304 A1 | 10/2005 | Dewey et al. |
| 2005/0277812 A1 | 12/2005 | Myles |
| 2006/0052812 A1 | 3/2006 | Winer |
| 2006/0142643 A1 | 6/2006 | Parker |
| 2006/0178693 A1 | 8/2006 | Hamada |
| 2007/0055247 A1 | 3/2007 | Jahng |

FOREIGN PATENT DOCUMENTS

| | | |
|---|---|---|
| DE | 28 01 696 | 7/1979 |
| EP | 0 455 282 | 11/1991 |
| EP | 1632185 | 3/2006 |
| WO | WO 2005/094695 | 10/2005 |

OTHER PUBLICATIONS

The Supplementary European Search Report for Application No. EP 03 80 9631 dated Mar. 17, 2009.

About Endius/Corporate Overview, (Internet Reference, 2002).

Aldrich, "Posterolateral microdiscectomy for cervical monoradiculopathy caused by posterolateral soft cervical disc dequestration", *J. Neurosurg.* 72:370-377 (1990).

Aronson, "The management of soft cervical disc protrusions using the Smith-Robinson approach", *Clinical Neurosurgery* 20:253-258 (1973).

Caspar, "A new surgical procedure for lumbar disc herniation causing less tissue damage through a microsurgical approach", *Adv Neurosurg* 4:72-80 (1977).

Cloward, "The Anterior Approach for Removal of Ruptured Cervical Disks", Presented at the meeting of the Harvey Cushing Society, Washington, DC, Apr. 22, 1958, pp. 602-617.

Fessler, et al., "Minimally Invasive Cervical Microendoscopic Foraminotomy: An Initial Clinical Experience", *Neurosurgery* 51(2):2-10 (2002).

Fessler, et al., "A minimally invasive technique for decompression of the lumbar spine", *Spine* 27:432-438 (2002).

Foley, et al., "Microendoscopic Discectomy", *Techniques in Neurosurgery* 3(4):301-307 (1997).

Henderson, et al., "Posterior-Lateral Foraminotomy as an Exclusive Operative Technique for Cervical Radiculopathy: A Review of 846 consecutively Operated Cases", *Neurosurgery*, 13(5): 504-521 (1983).

Hermantin, et al., "A Prospective, Randomized Study Comparing the Results of Open discectomy with Those of Video-Assisted Arthroscopic Microdiscectomy", *The Journal of Bone and Joint Surgery* 81A(7):958-965 (1999).

Kawaguchi, et al., "Back Muscle Injury After Posterior Lumbar Spine Surgery", *Spine*, 21(8):941-944 (1996).

Lin, et al., "Posterior Lumbar Interbody Fusion", *Clinical Orthopedics and Related Research*, No. 180, pp. 154-168 (1983).

Lin, "Posterior Lumbar Interbody Fusion Technique: Complications and Pitfalls", *PLIF Complications and Pitfalls*, No. 193, pp. 90-102 (1985).

Malis, "Instrumentation and Techniques in Microsurgery", *Clinical Neurosurgery*, 26:626-636 (1979).

Rantanen, et al., "The Lumbar Multifidus Muscle Five Years After Surgery for a Lumbar Intervertebral Disc Herniation", *Spine*, 18(5):268-274 (1993).

Roh, et al., "Endoscopic Foraminotomy Using MED System in Cadaveric Specimens", *Spine*, 25(2):260-264 (2000).

Sihvonen, et al., "Local denervation atrophy of paraspinal muscles in postoperative failed back syndrome", *Spine* 18:575-581 (1993).

Styf, et al., "The Effects of External Compression by Three Different Retractors on Pressure in the Erector Spine Muscles During and After Posterior Lumbar Spine Surgery in Humans", *Spine*, 23(3):354-358 (1998).

Tsai, et al., "Microscopic Laminotomies for Degenerative Lumbar Spinal Stenosis", *Journal of Spinal disorders*, 11(5):389-394 (1998).

Weber et al, "Posterior surgical approach to the lumbar spine and its effect on the multifidus muscle", *Spine* 22:1765-1772 (1992).

Weiner, et al., "Microdecompression for Lumbar Spinal Canal Stenosis", *Spine*, 24(21):2268-2272 (1999).

* cited by examiner

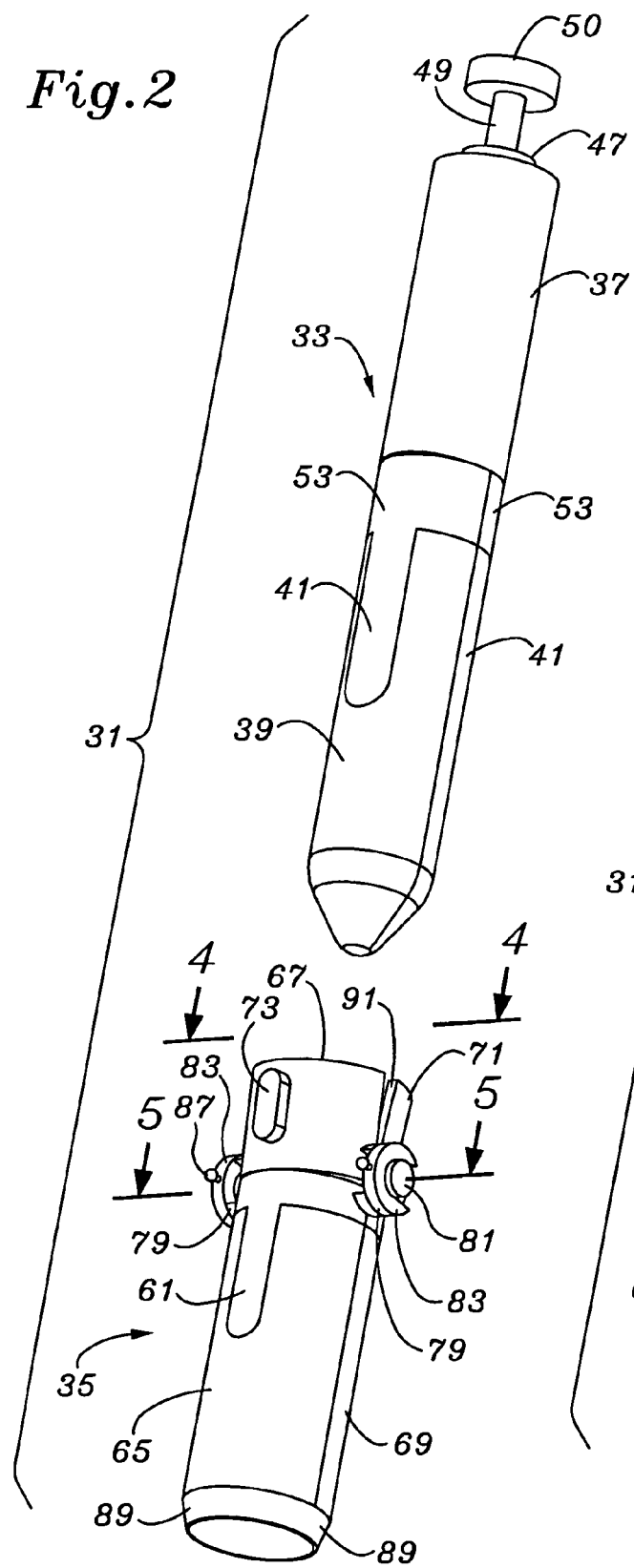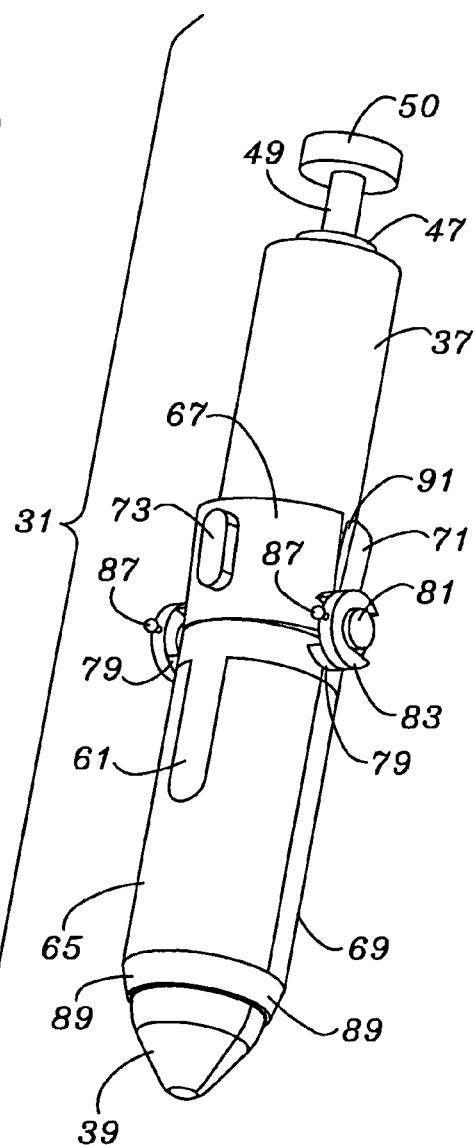

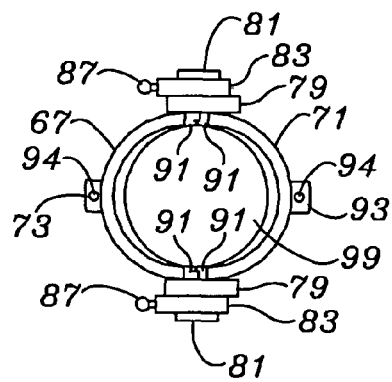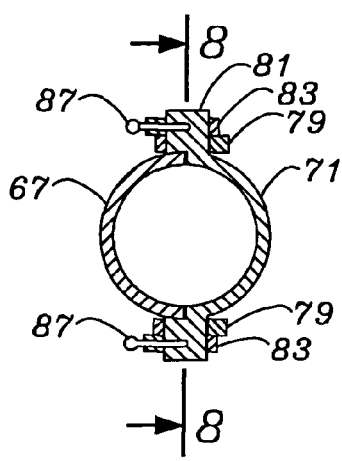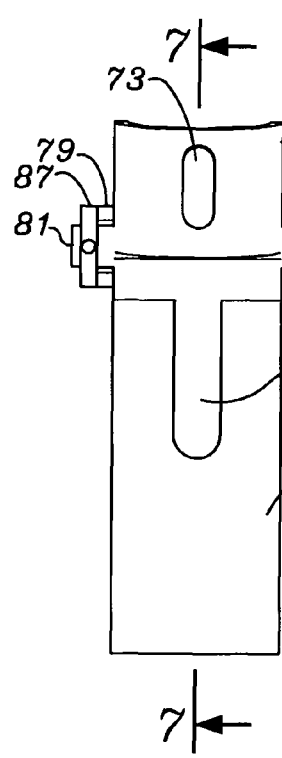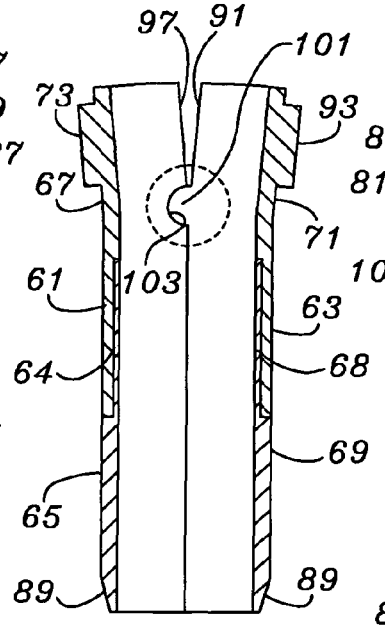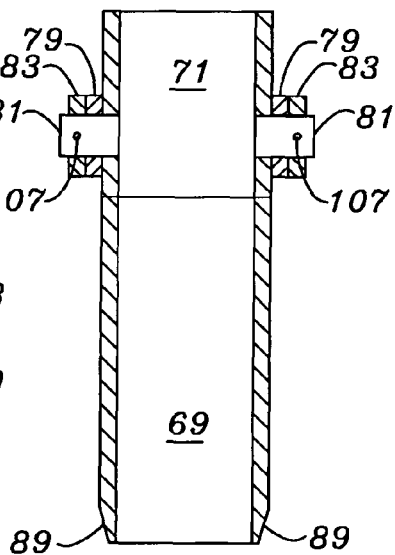

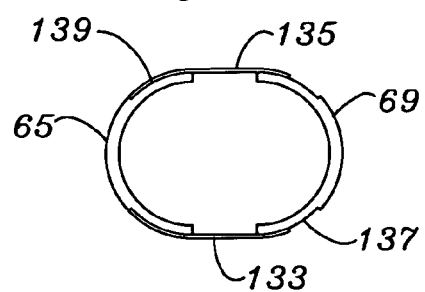
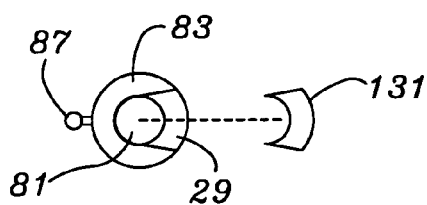
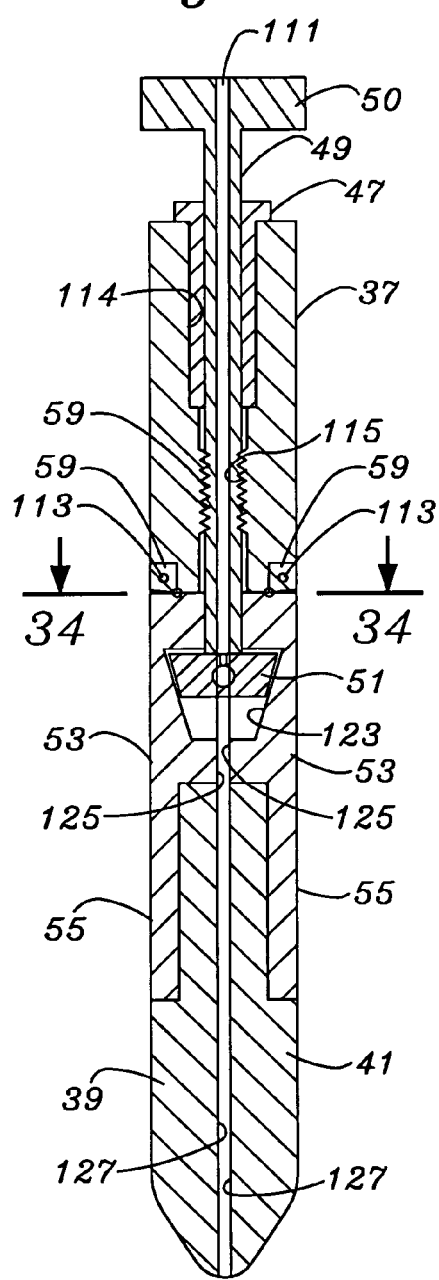
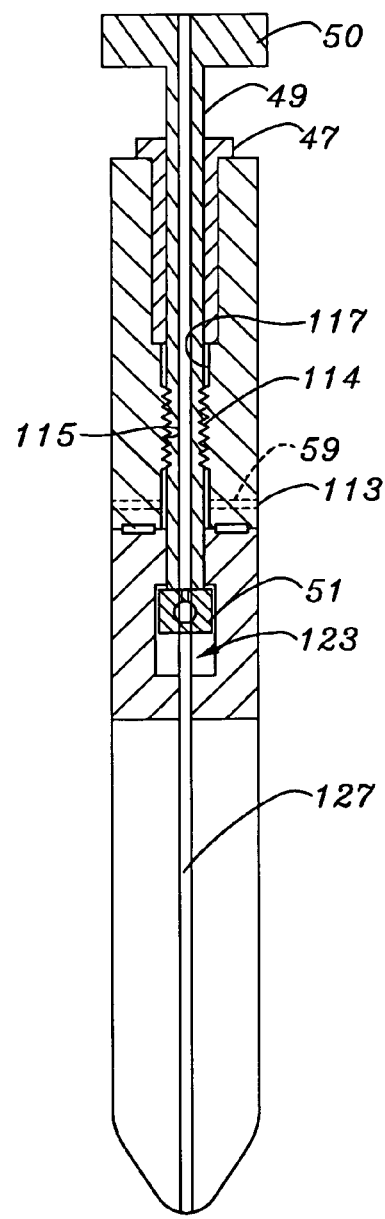

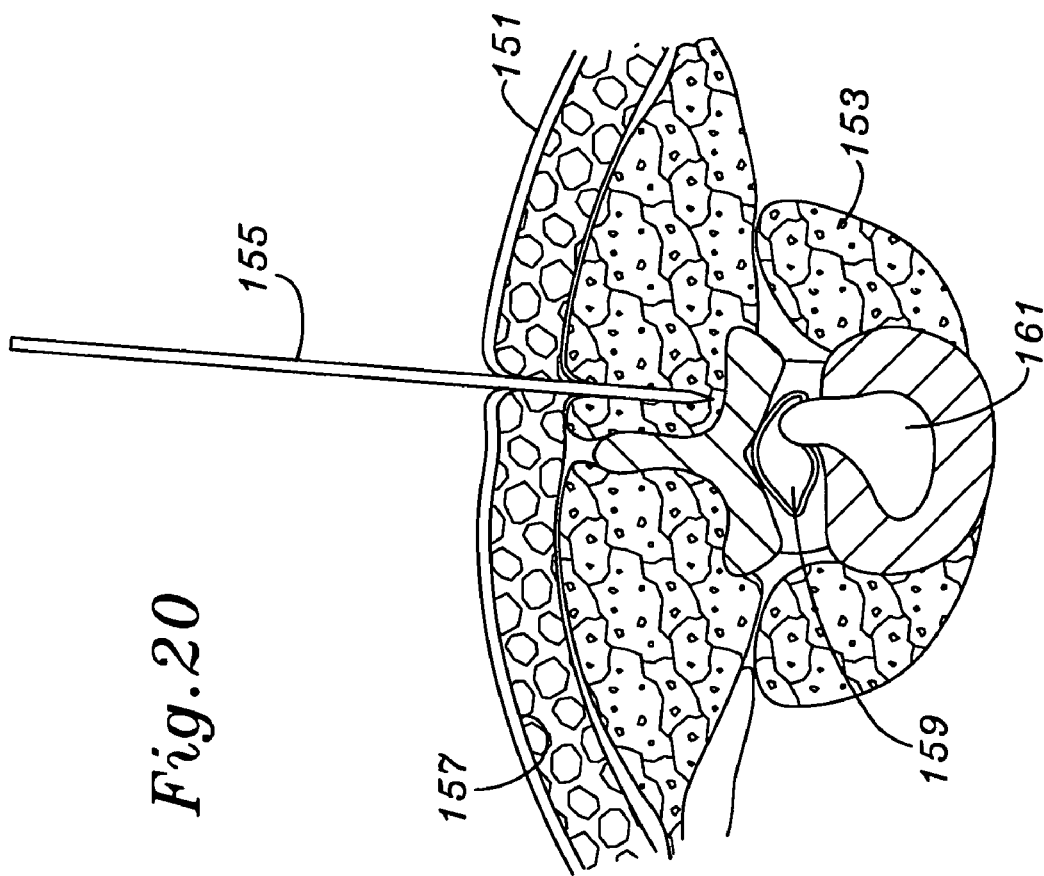
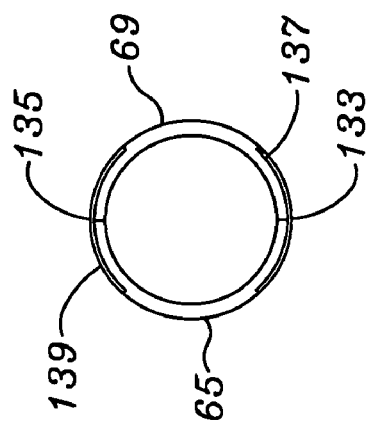

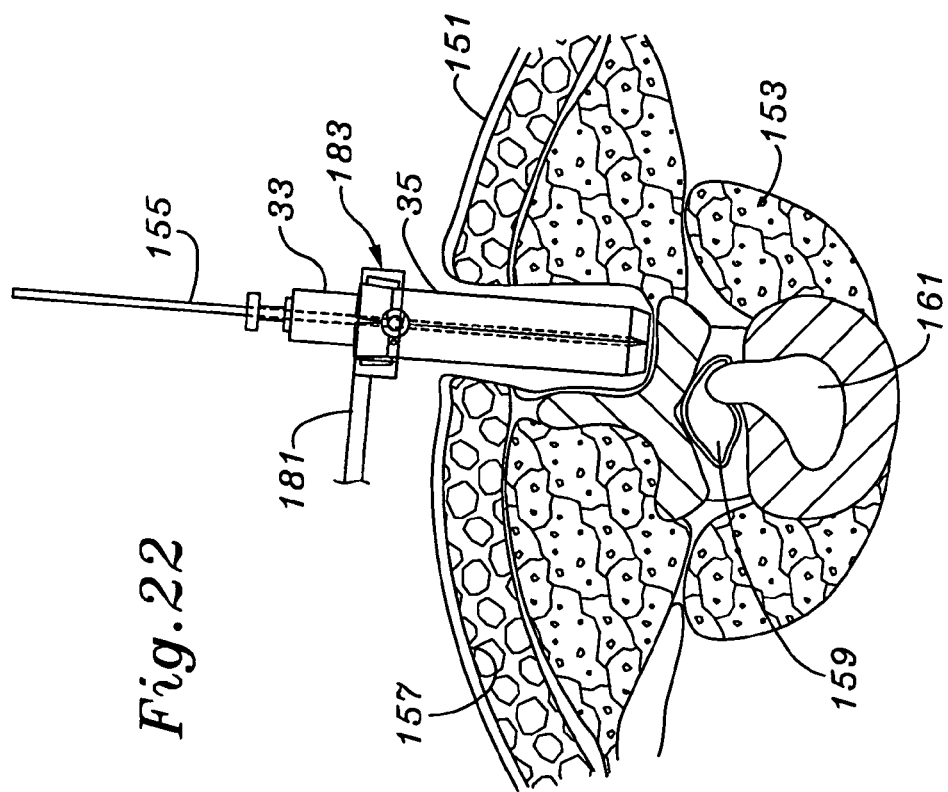
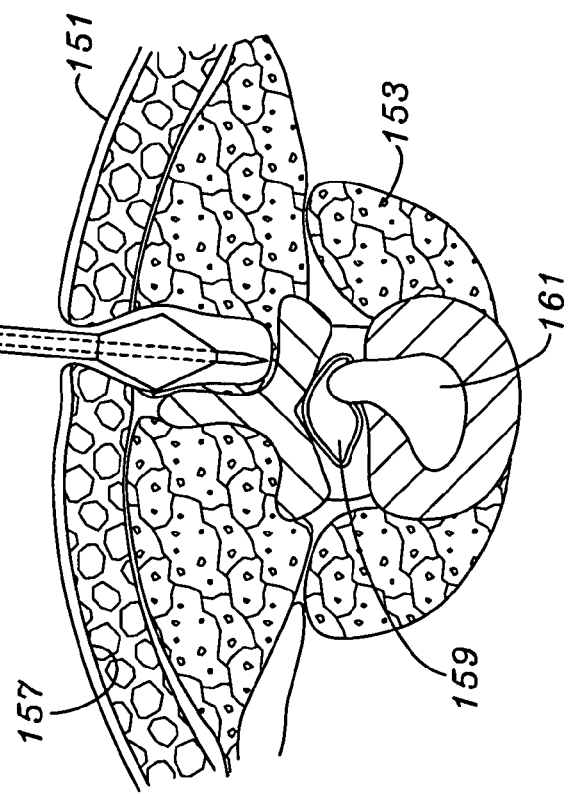

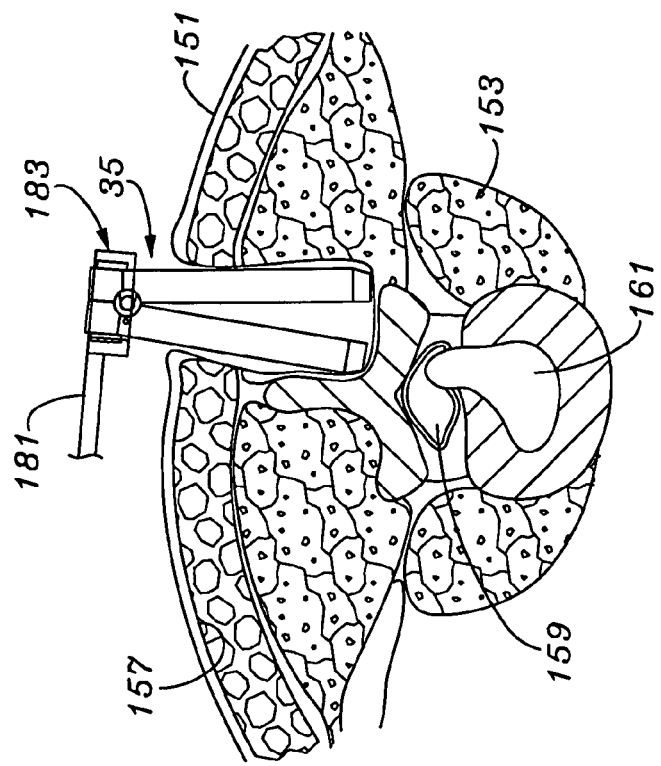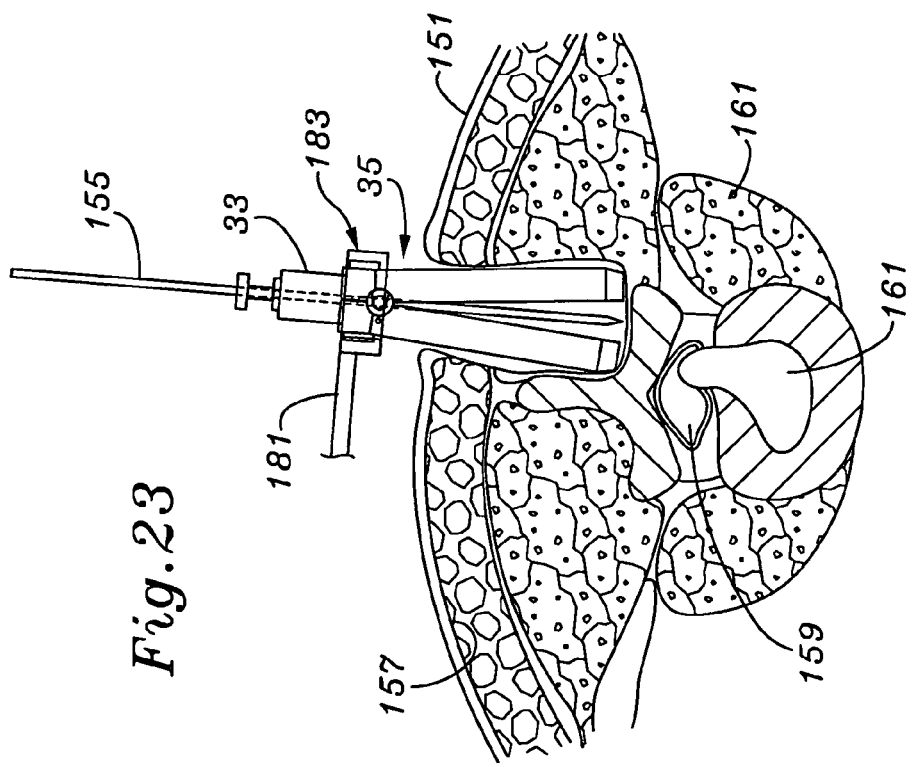

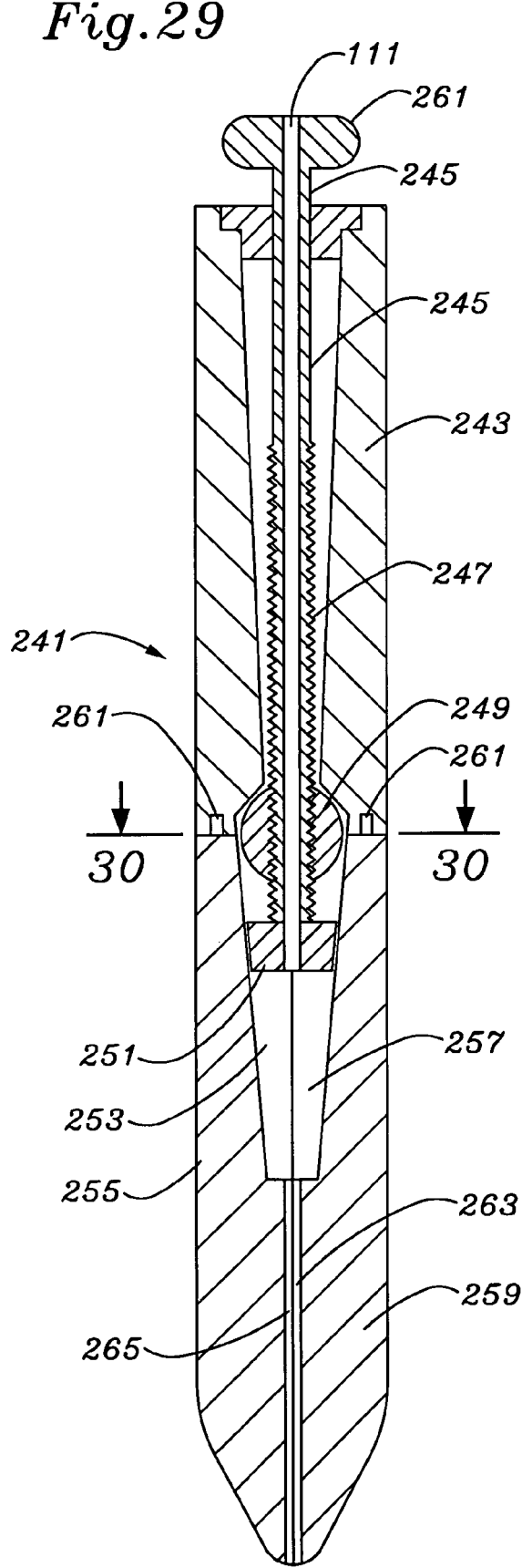
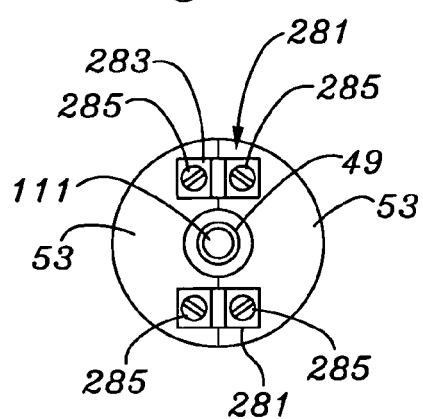
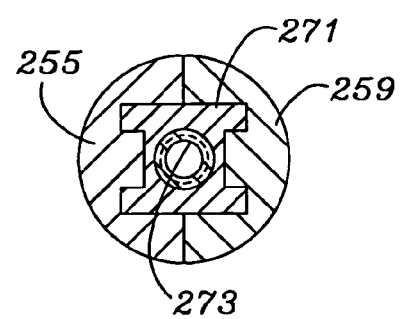

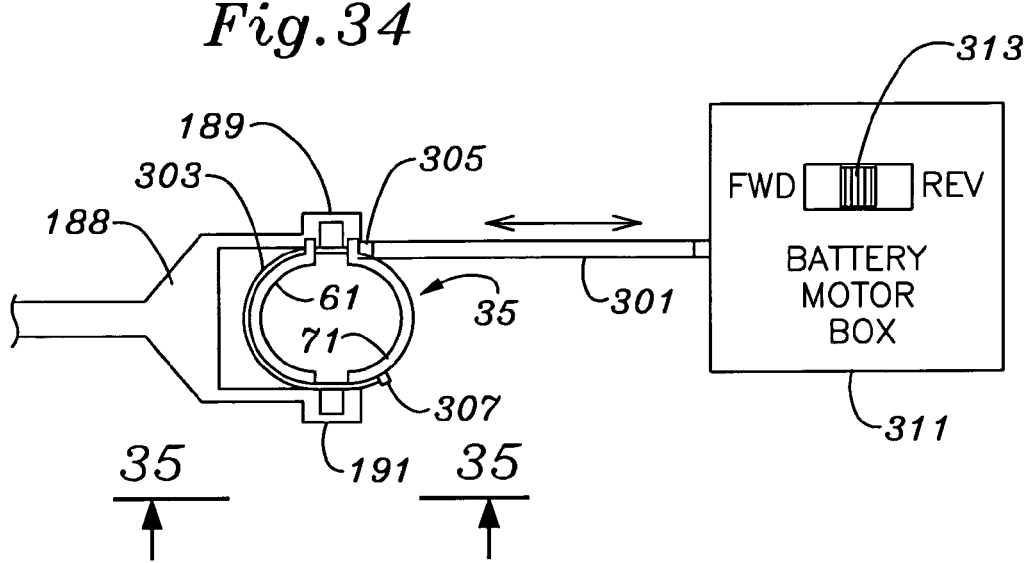
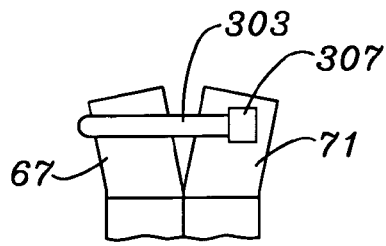
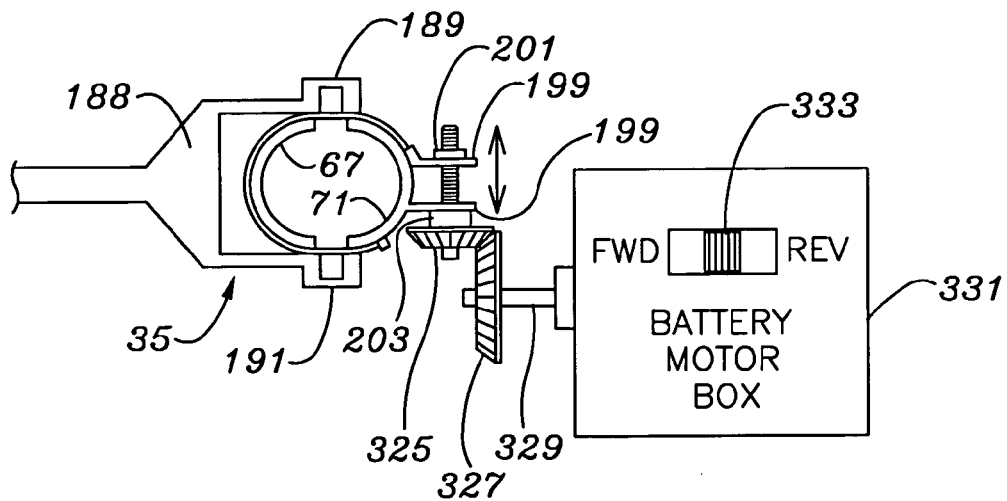

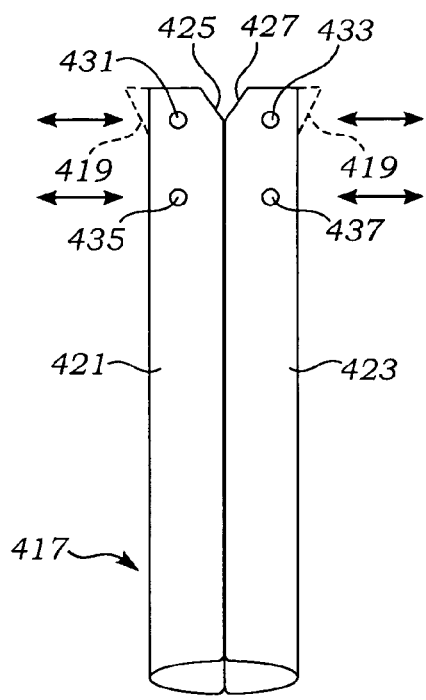
Fig.37
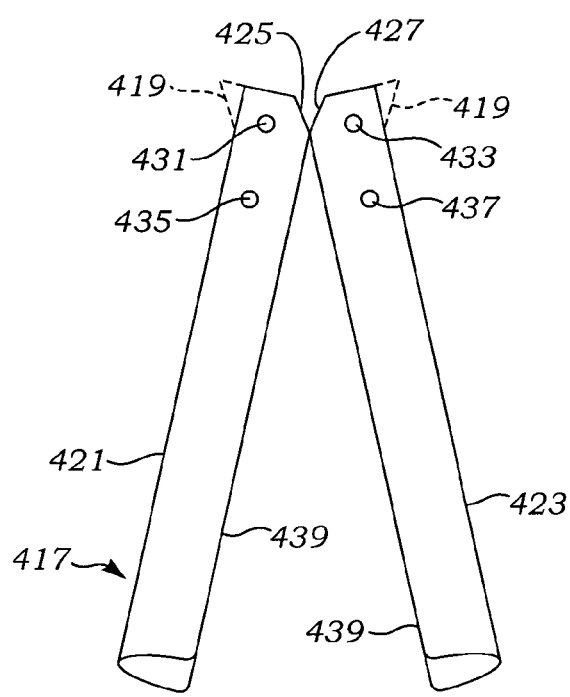
Fig.38
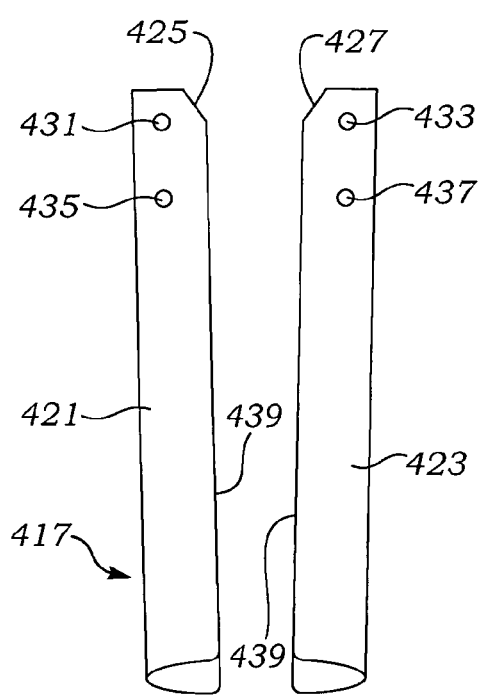
Fig.39
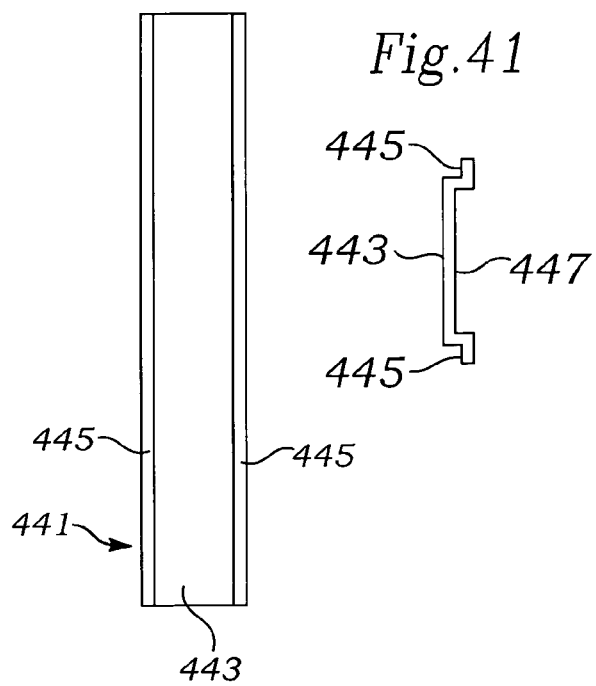
Fig.40
Fig.41

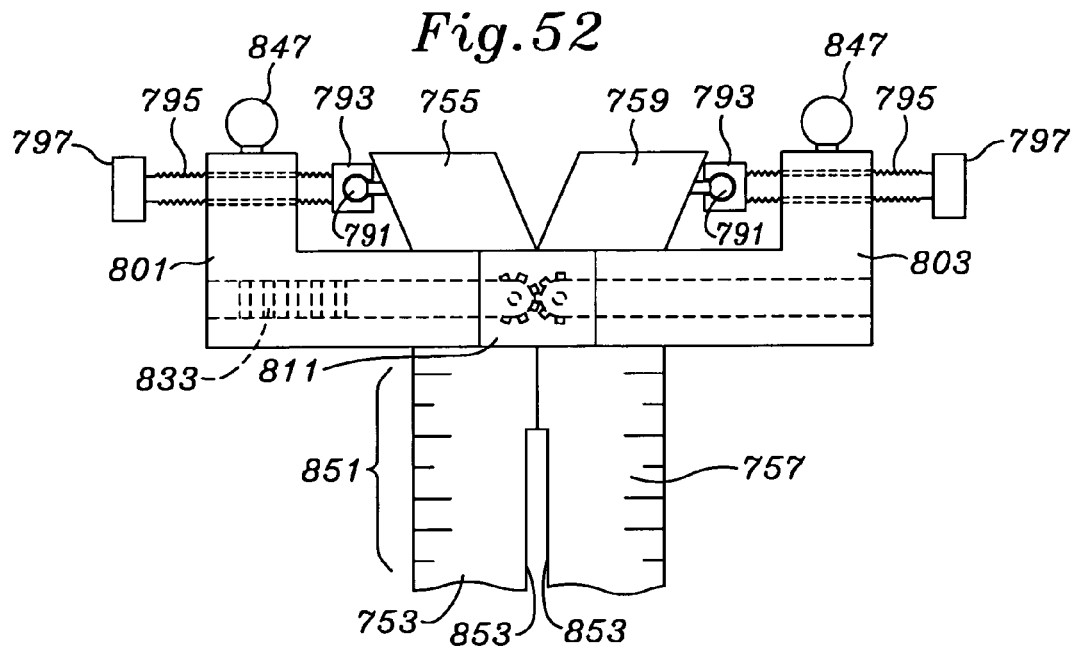
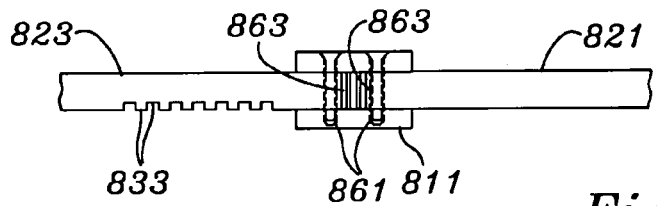
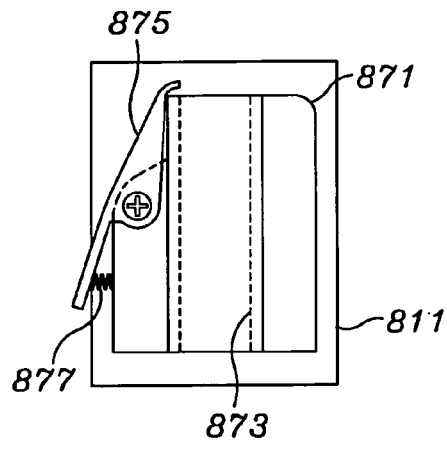
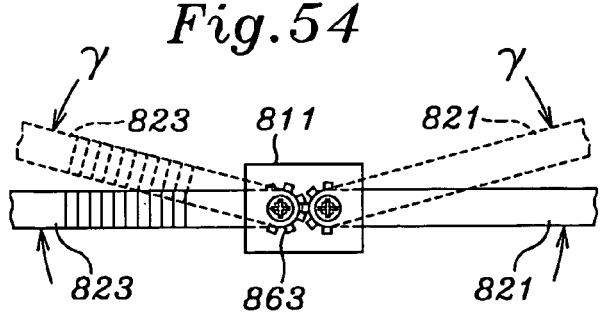

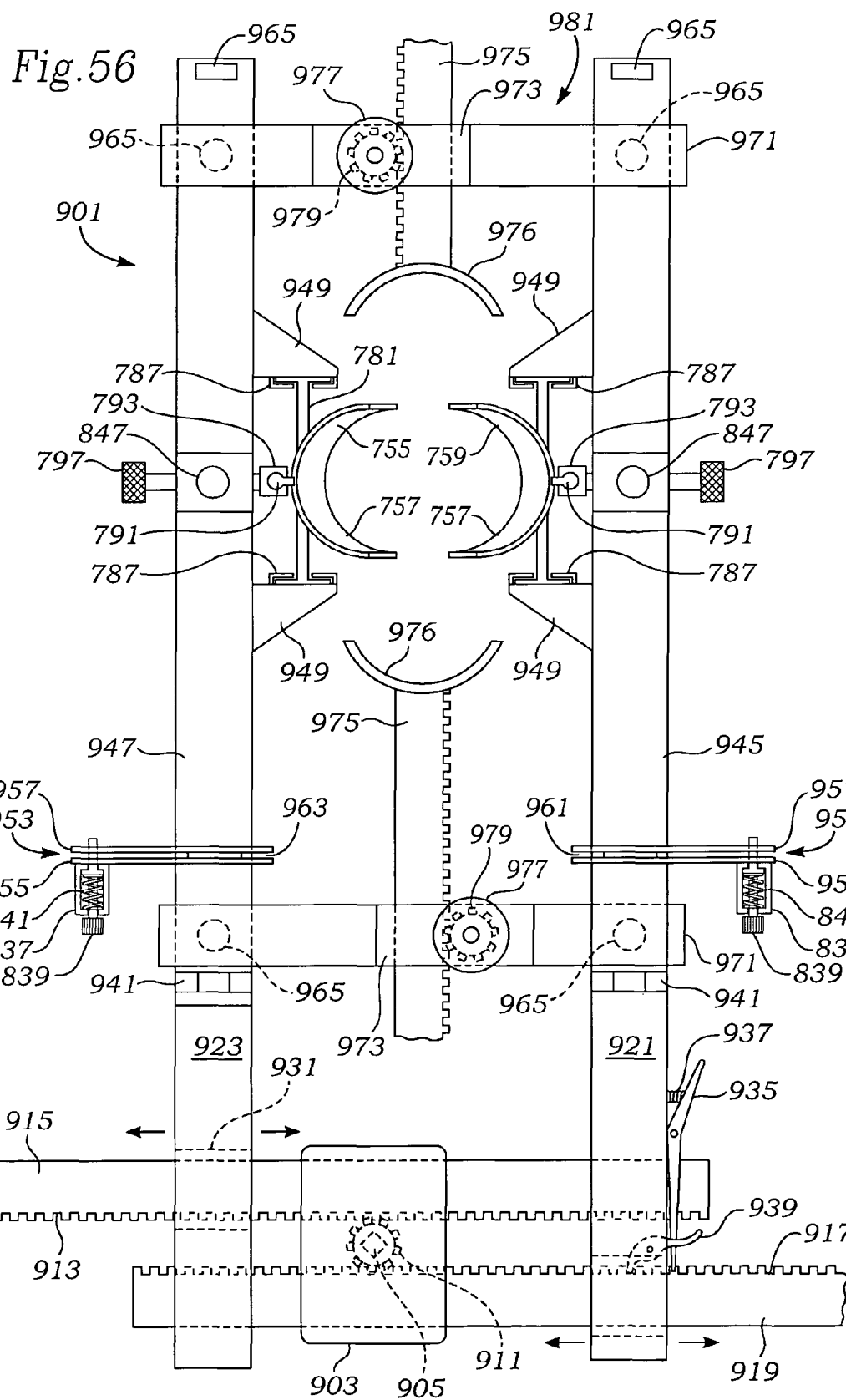

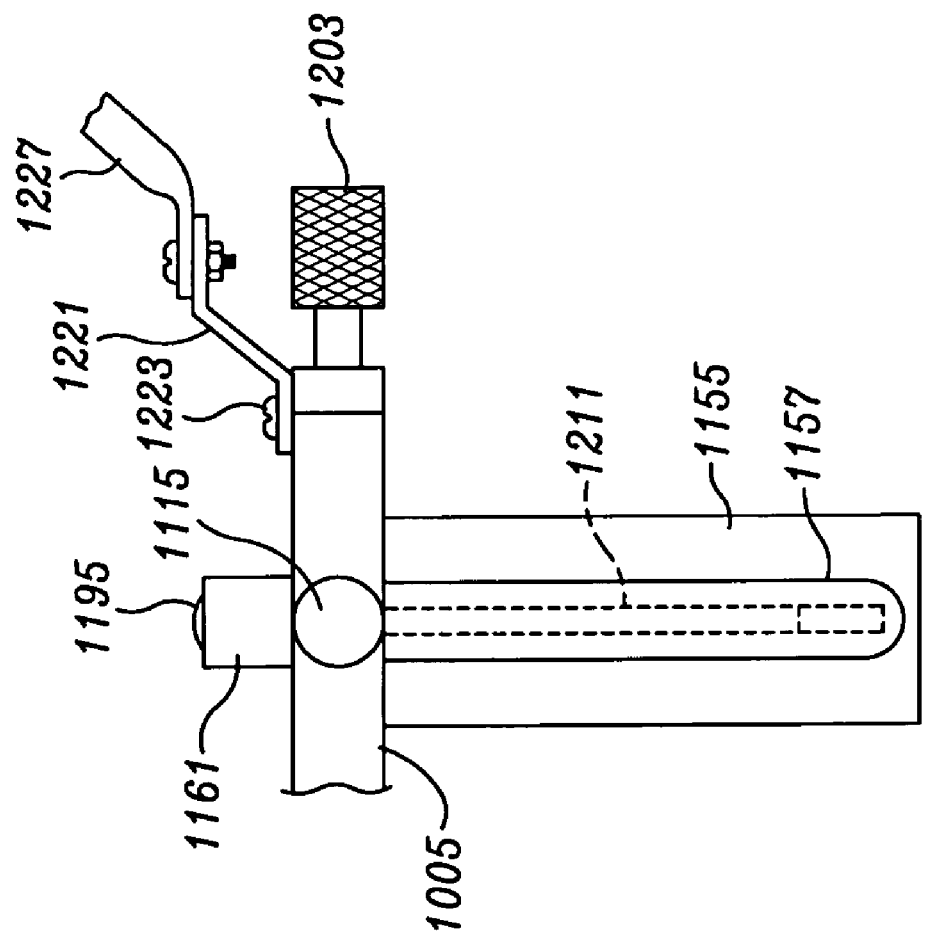

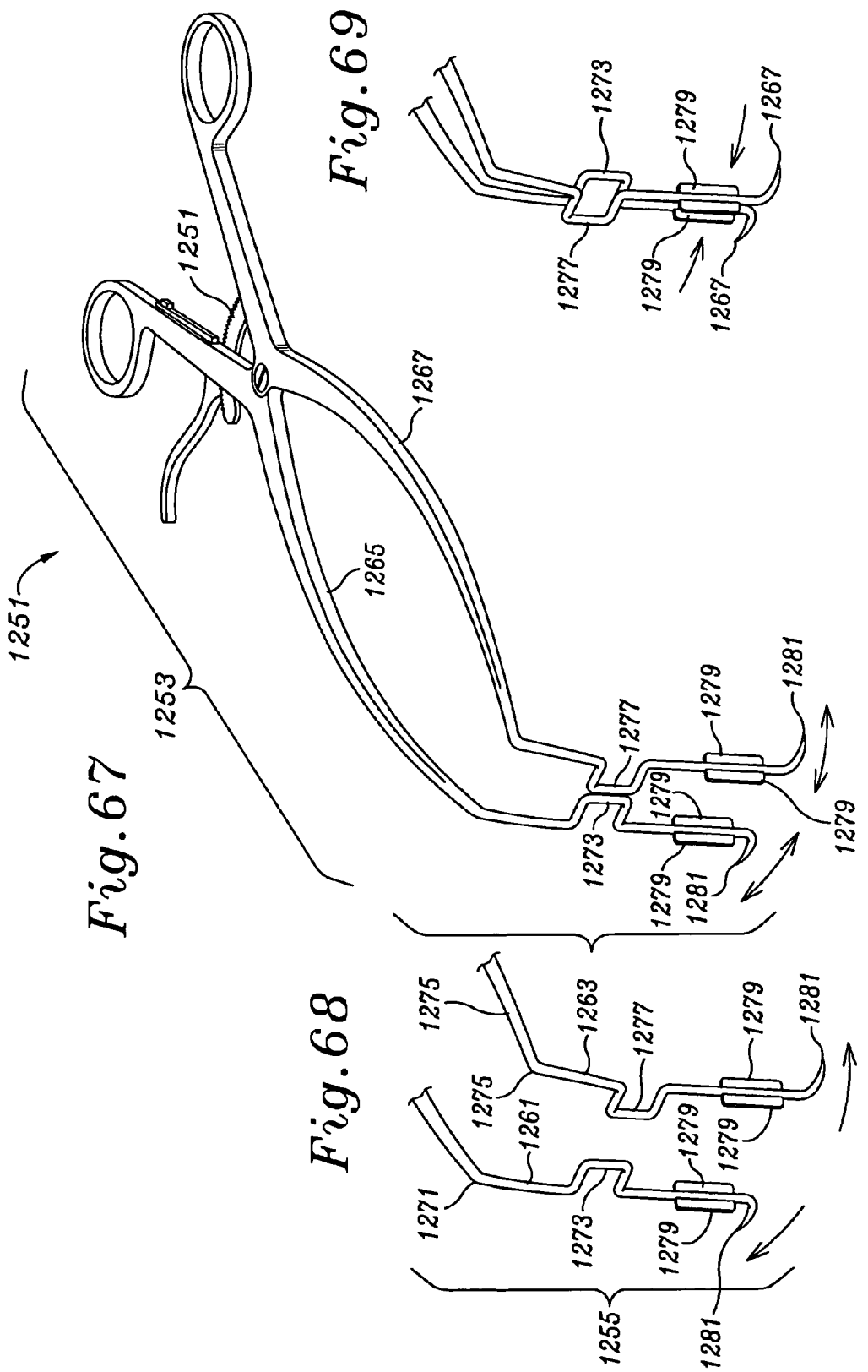

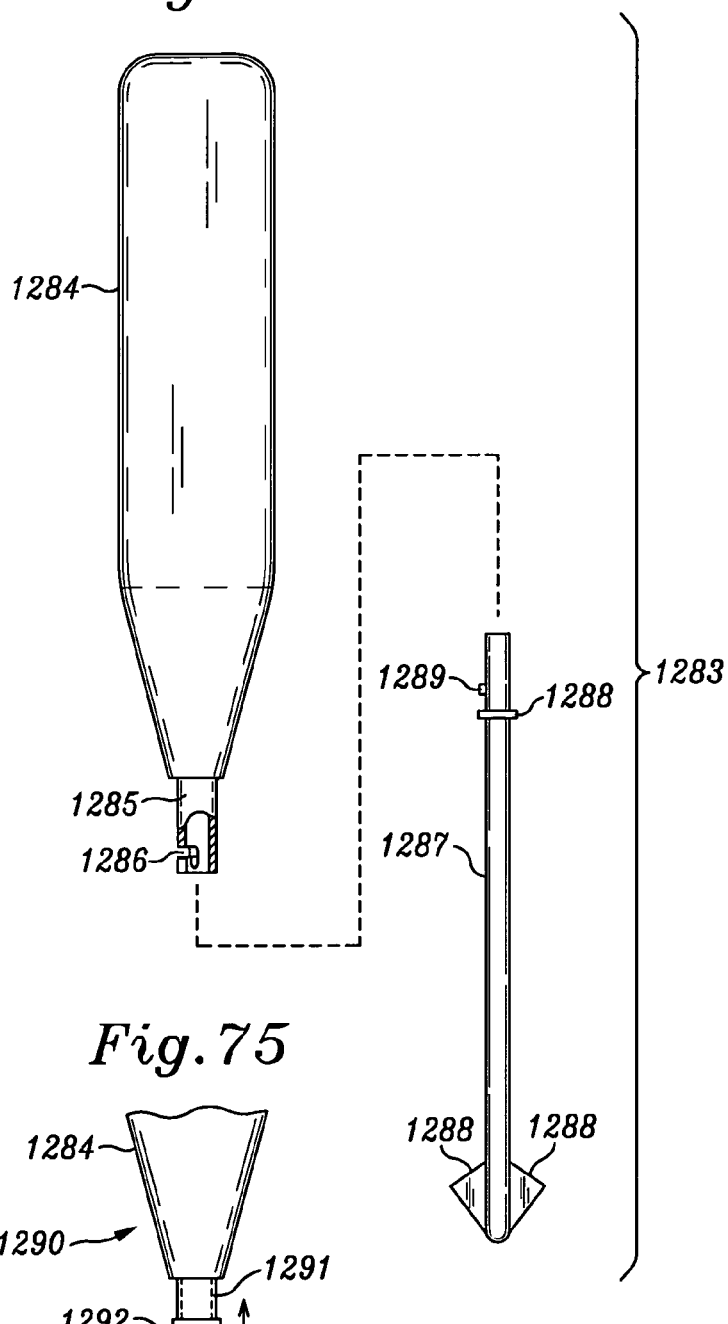
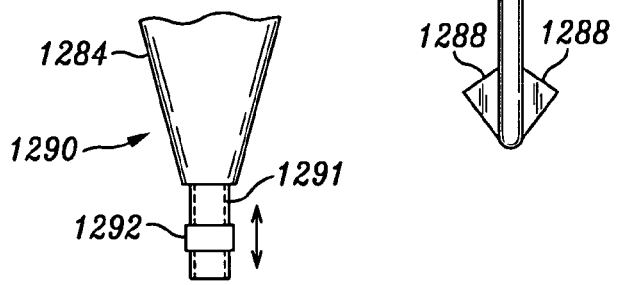
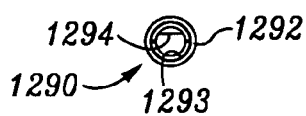

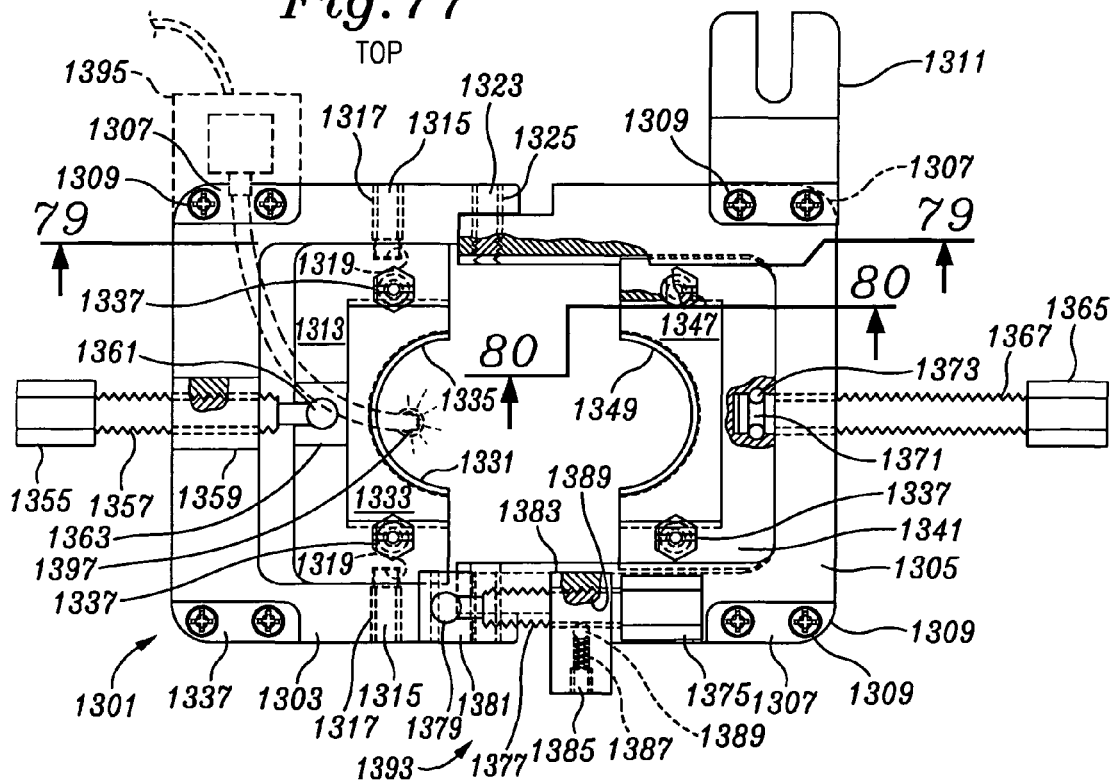
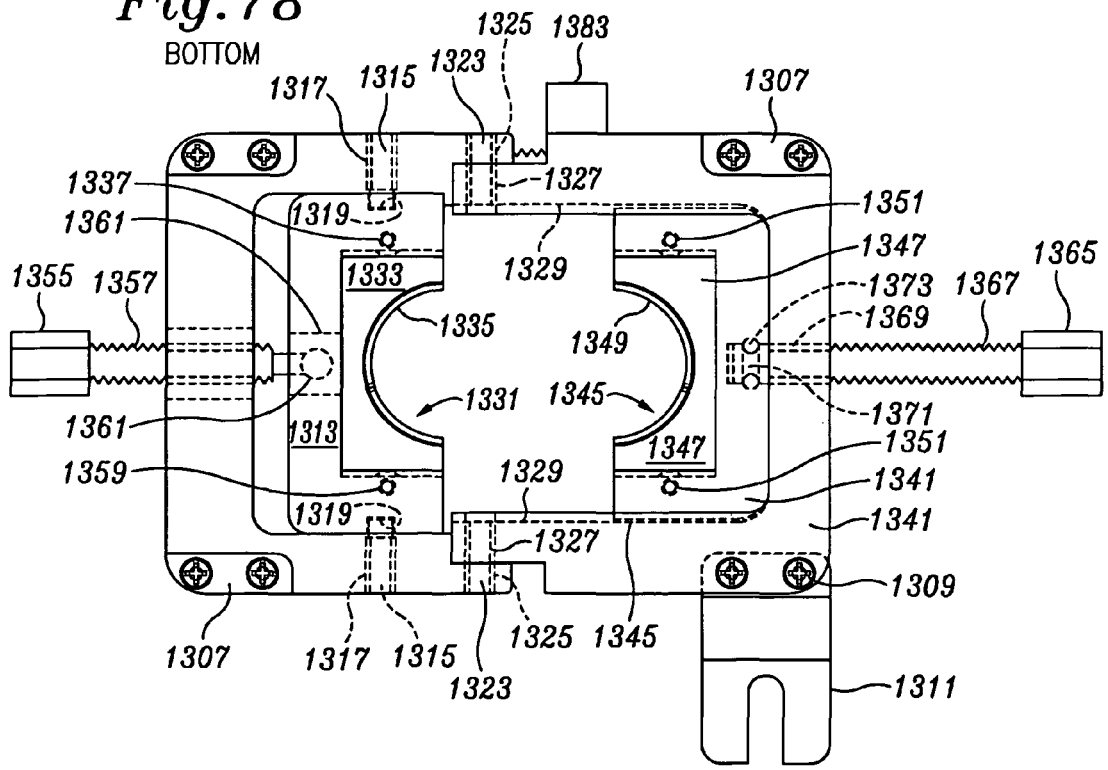

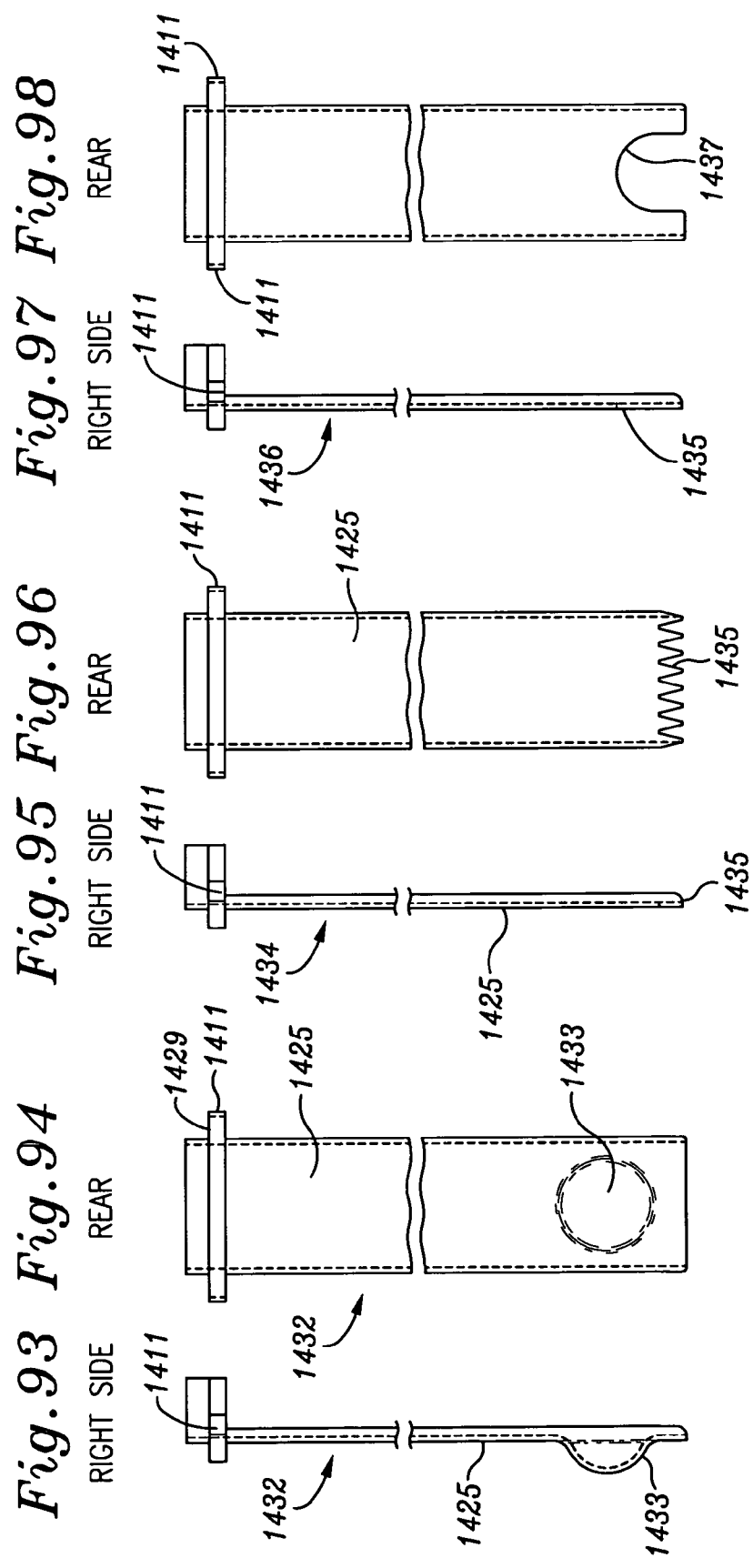

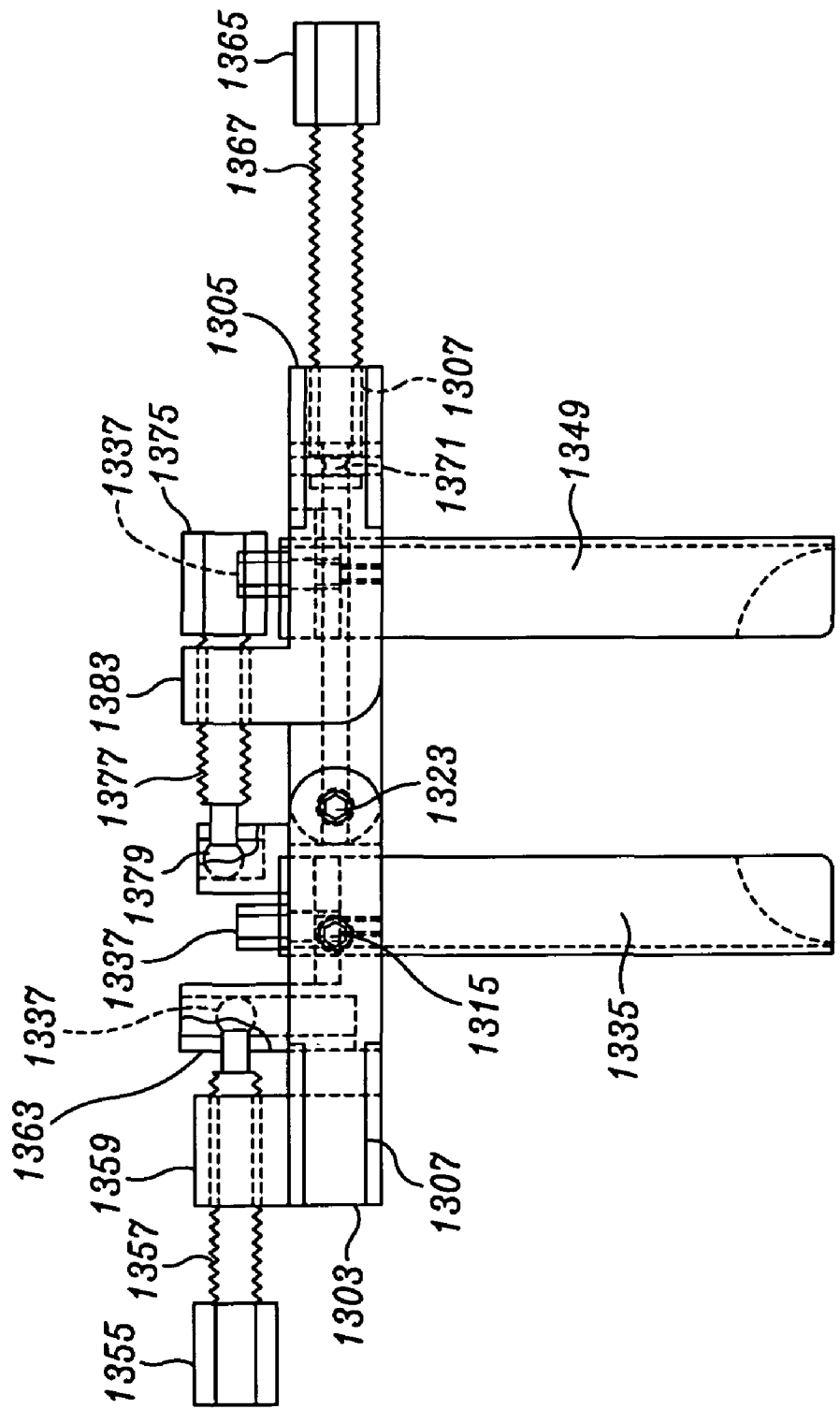

RIGHT SIDE

RIGHT SIDE

RIGHT SIDE

RIGHT SIDE

RIGHT SIDE

RIGHT SIDE

TOP

LEFT SIDE

LEFT SIDE

Fig. 109 TOP

LEFT SIDE (PARTIALLY BROKEN VIEW OF CLAMP FIXTURE)

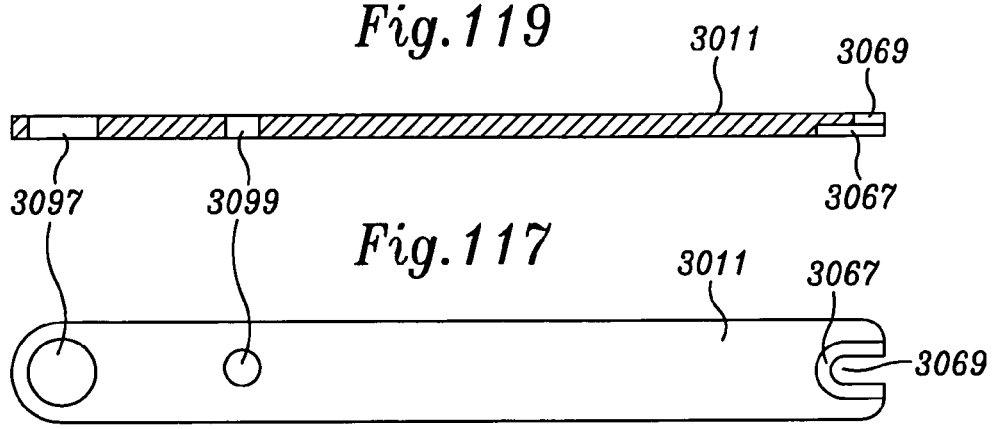
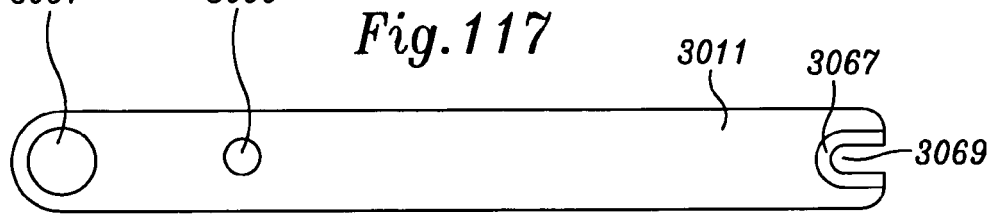
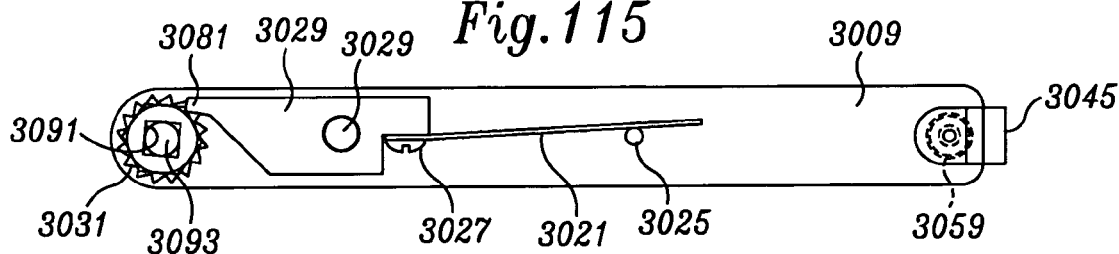
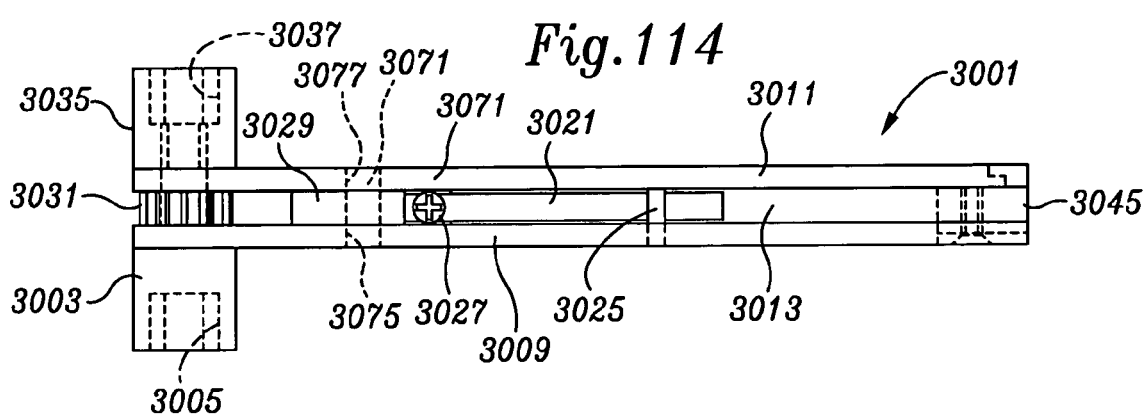
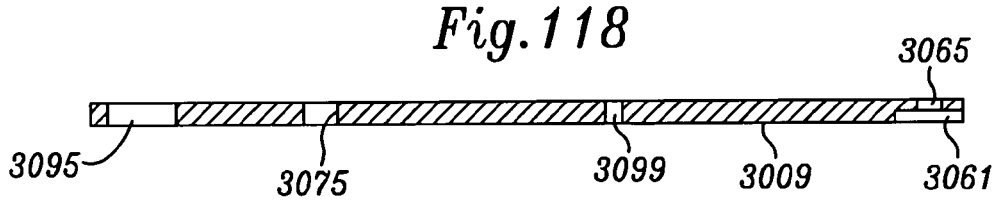
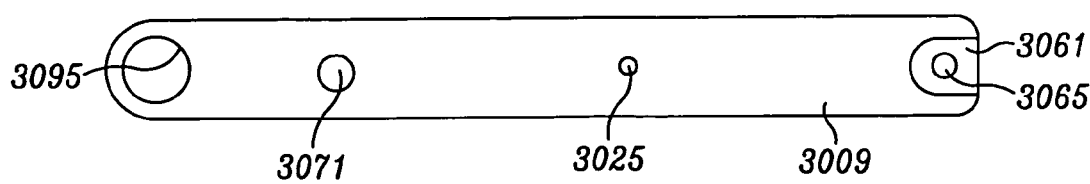

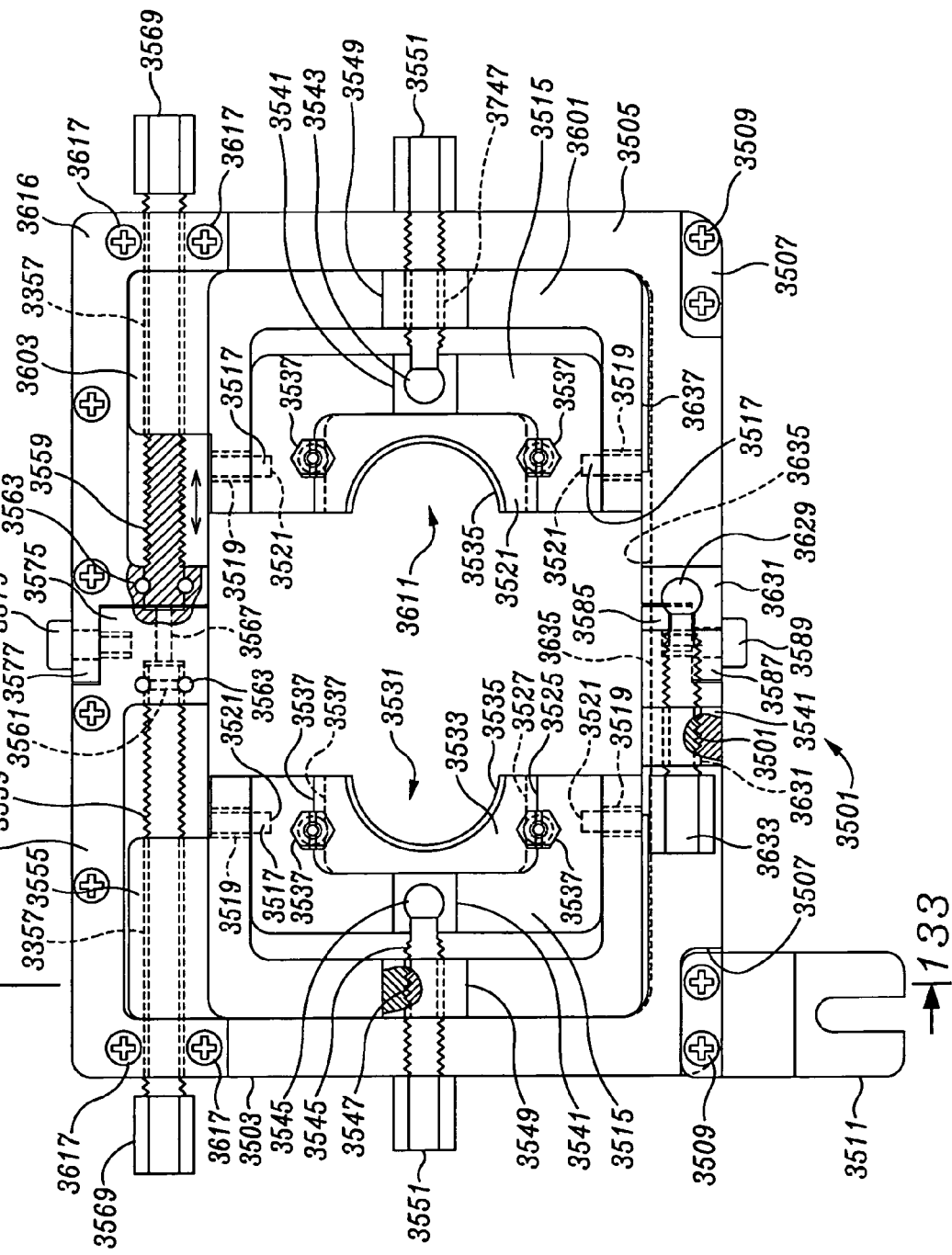

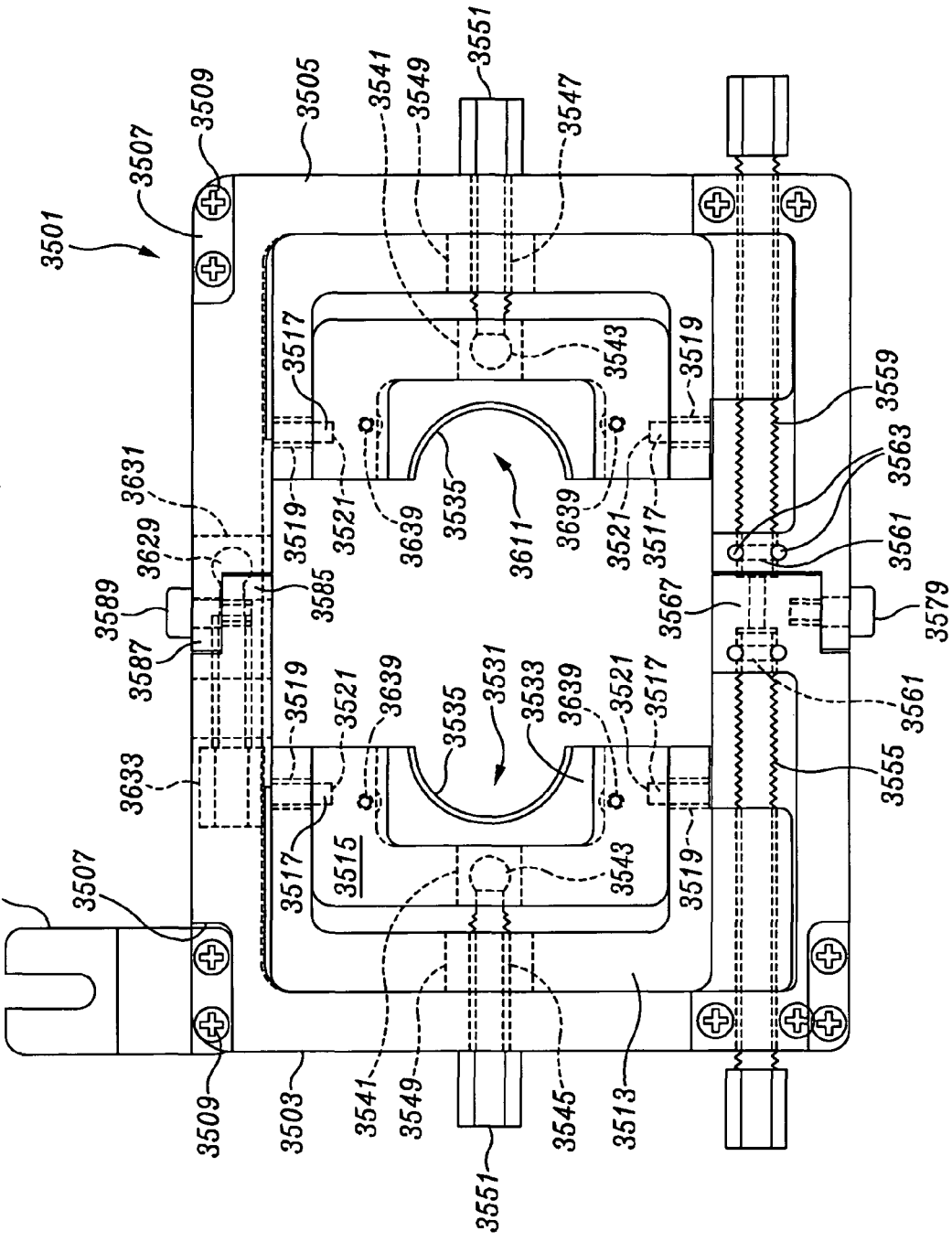
Fig. 132 (VERSION 4 BOTTOM VIEW)

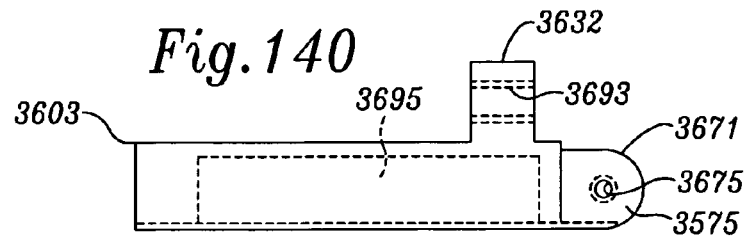
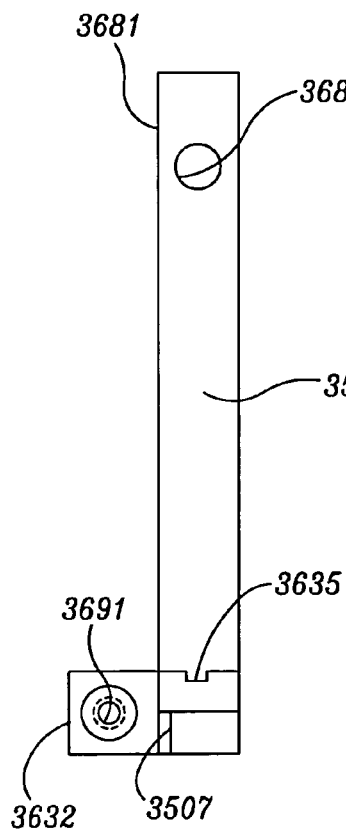
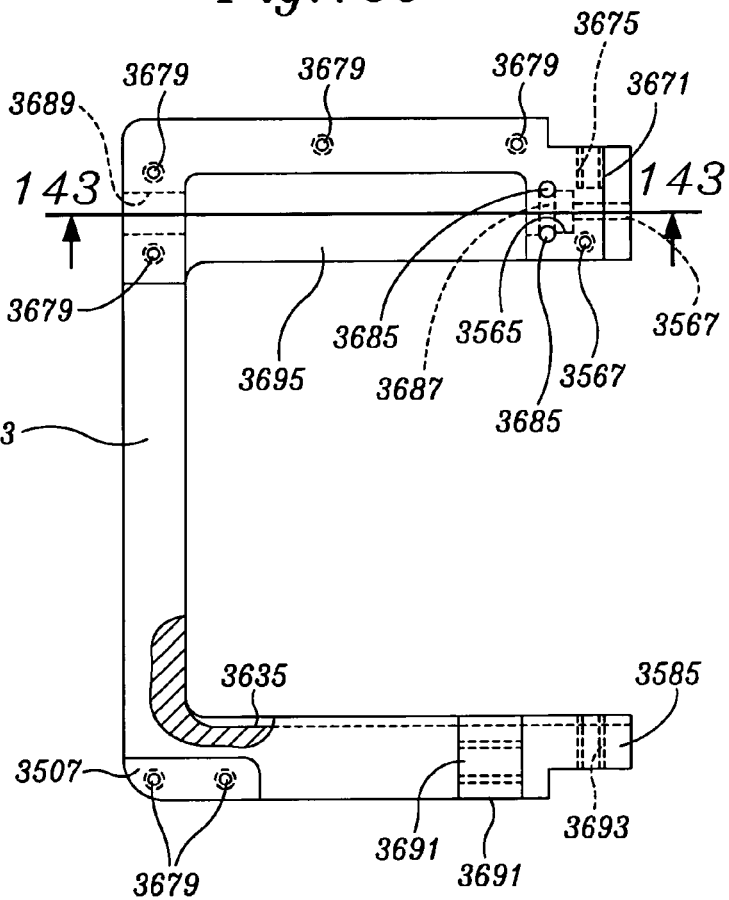
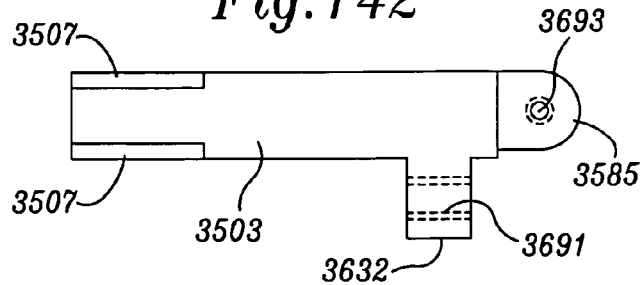

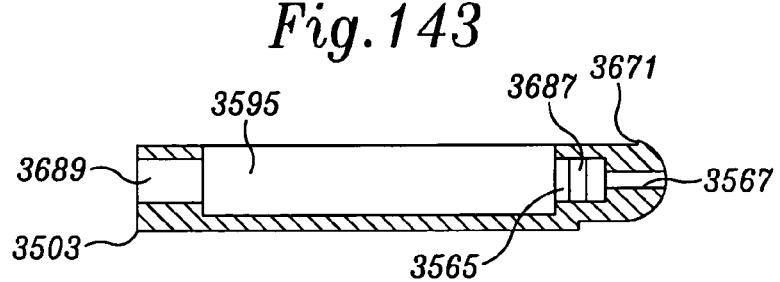
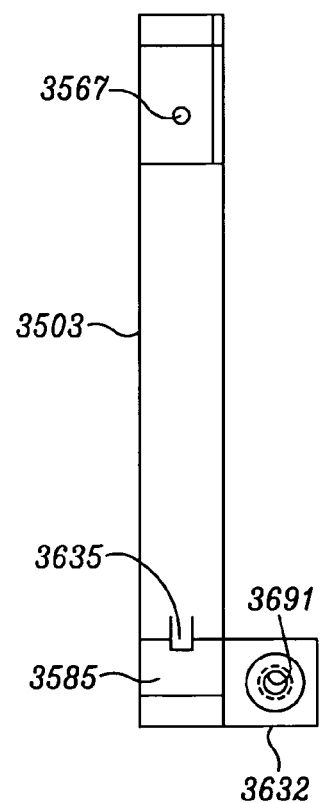
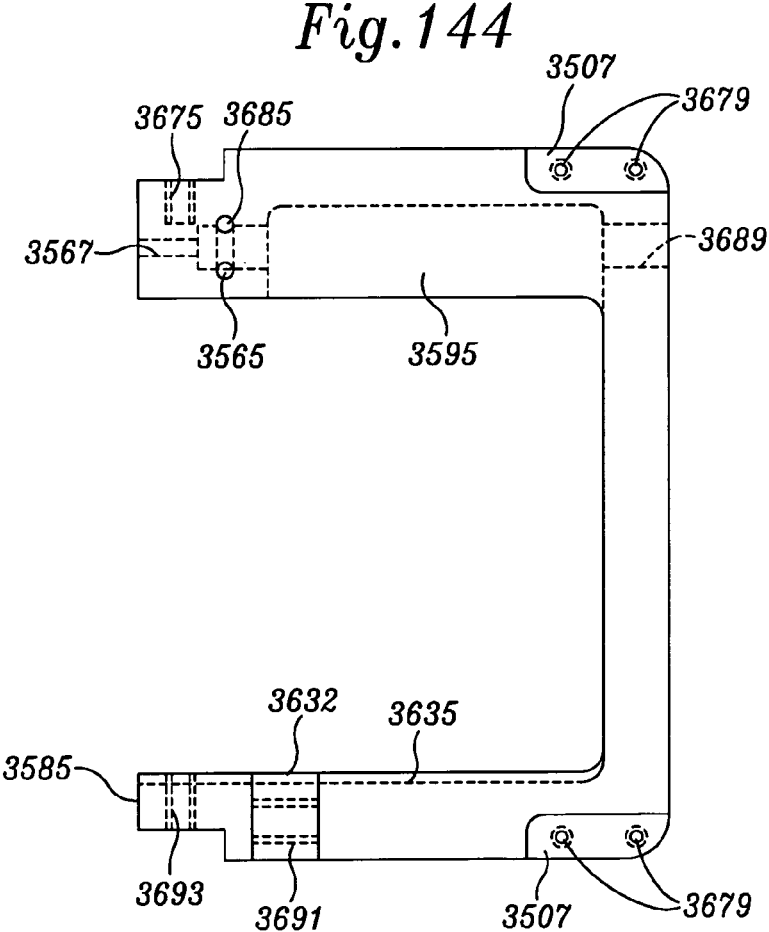

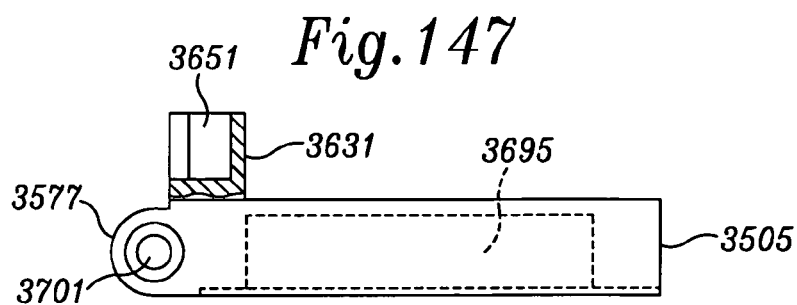
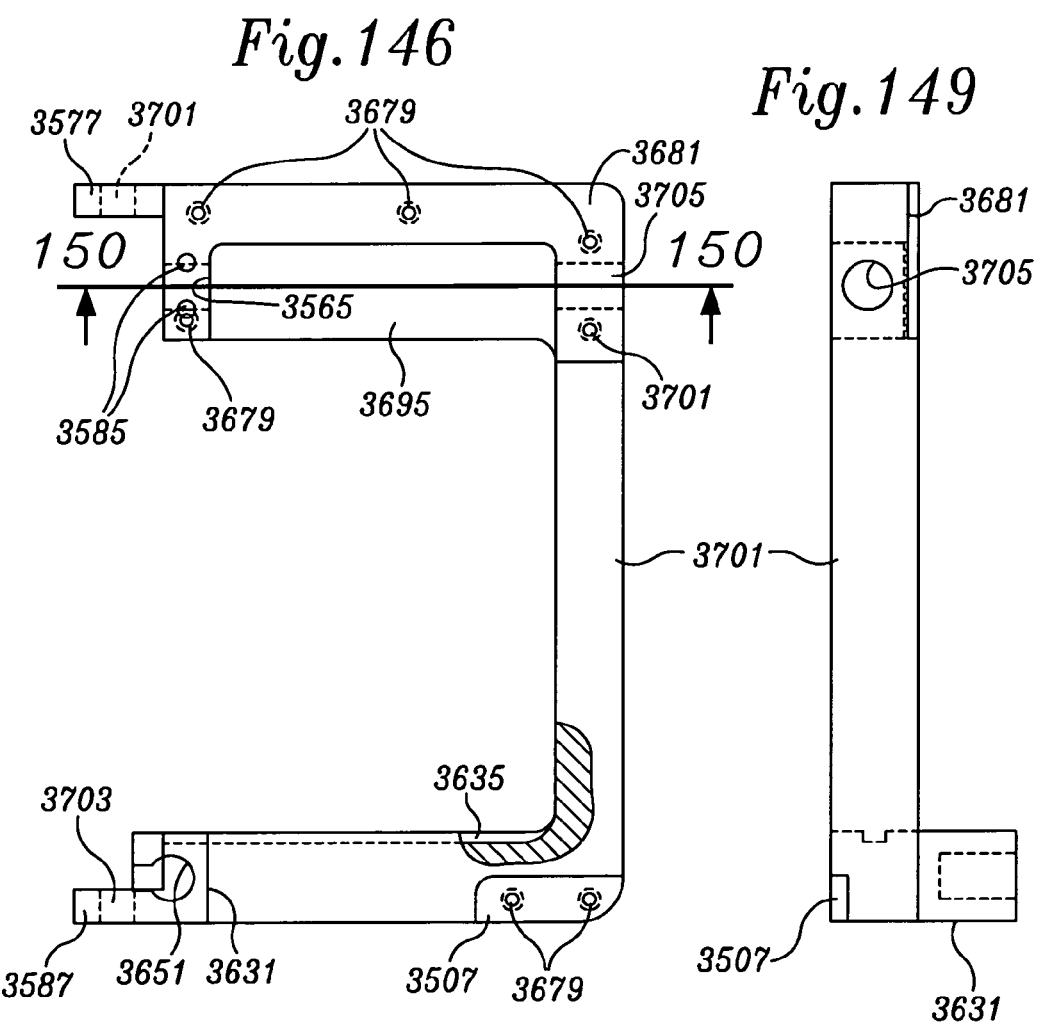
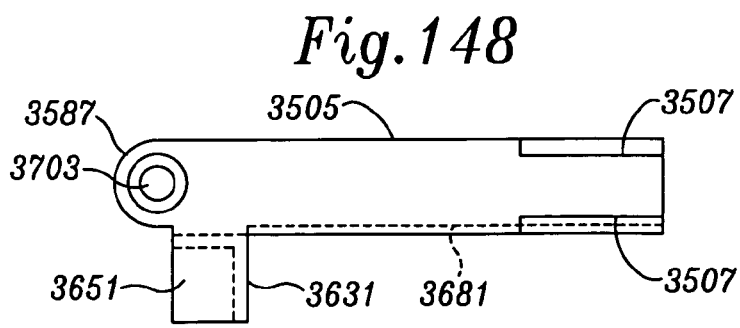

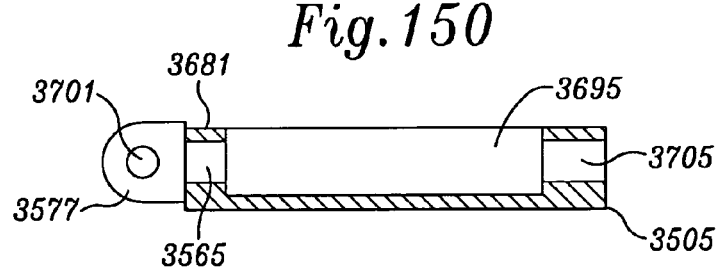
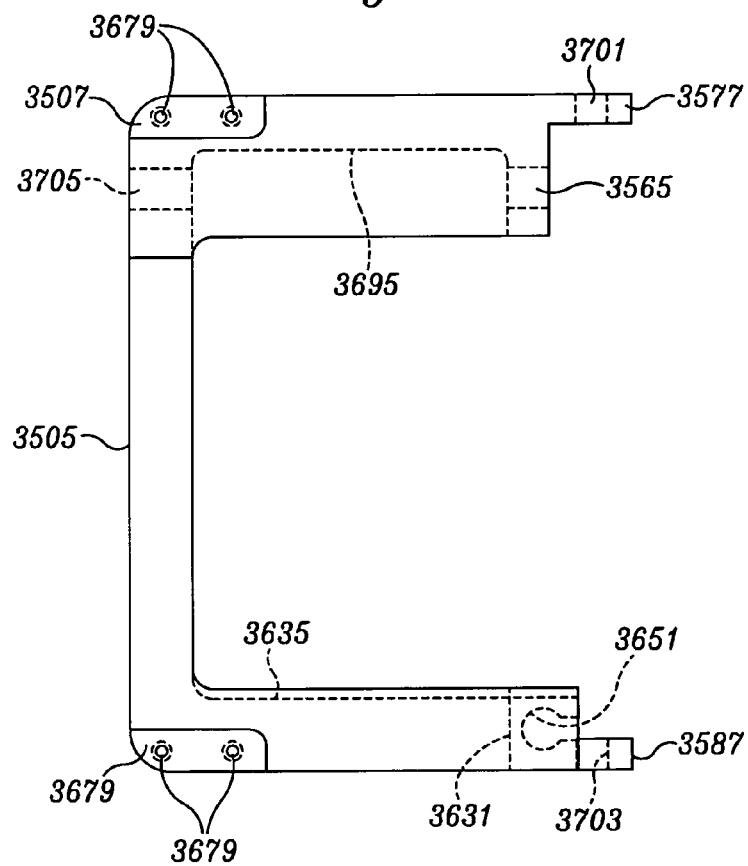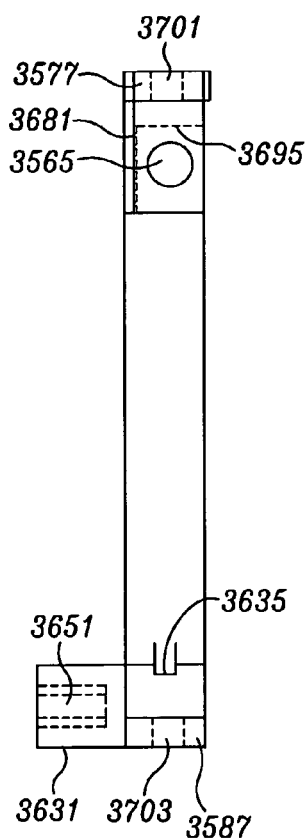

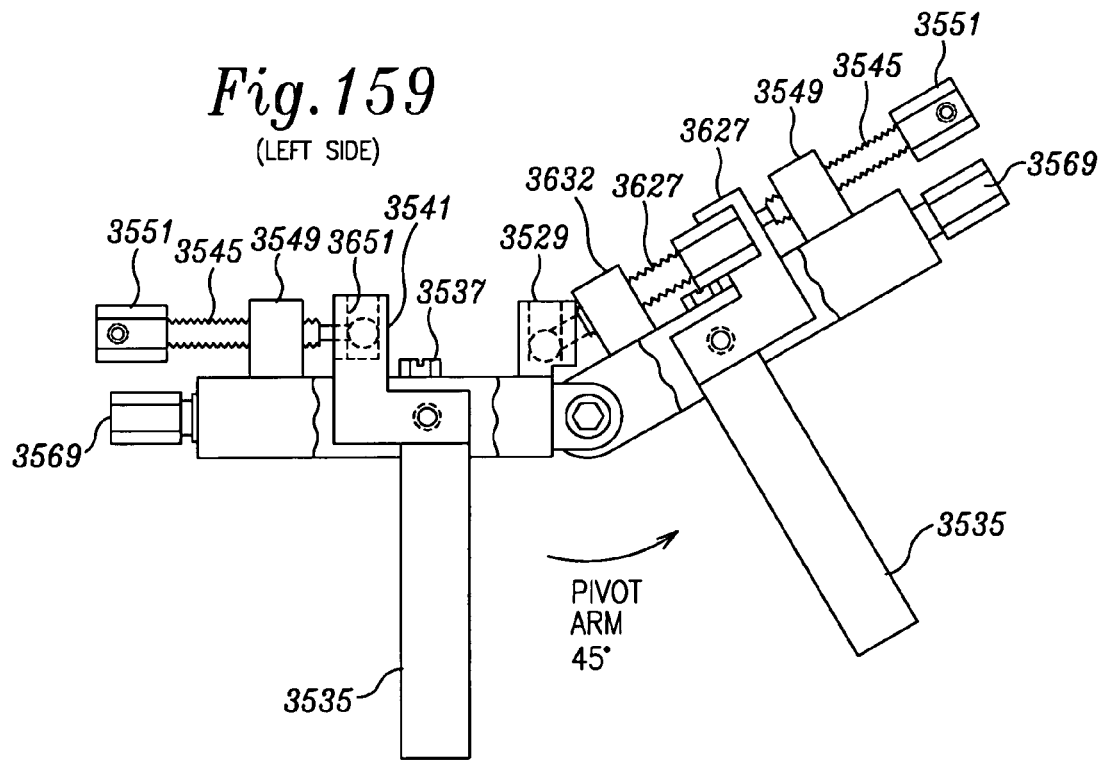
Fig.159 (LEFT SIDE)
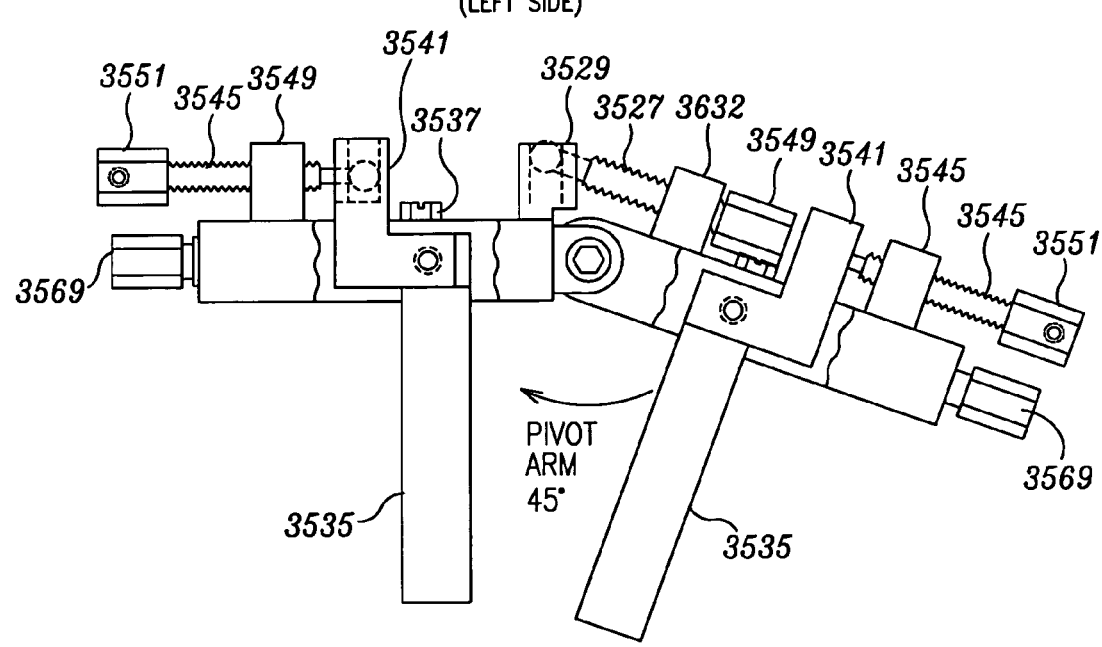
Fig.160 (LEFT SIDE)

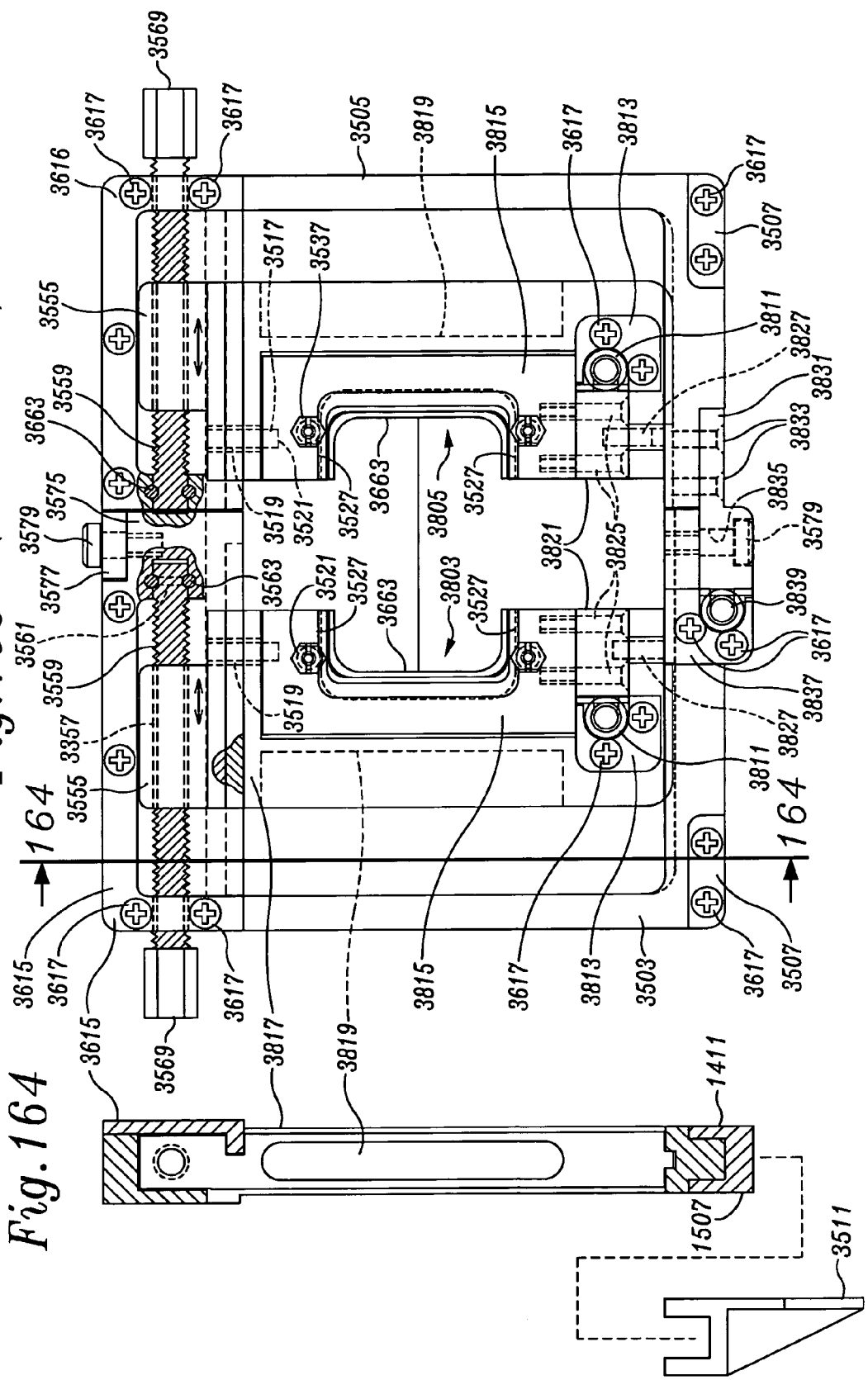

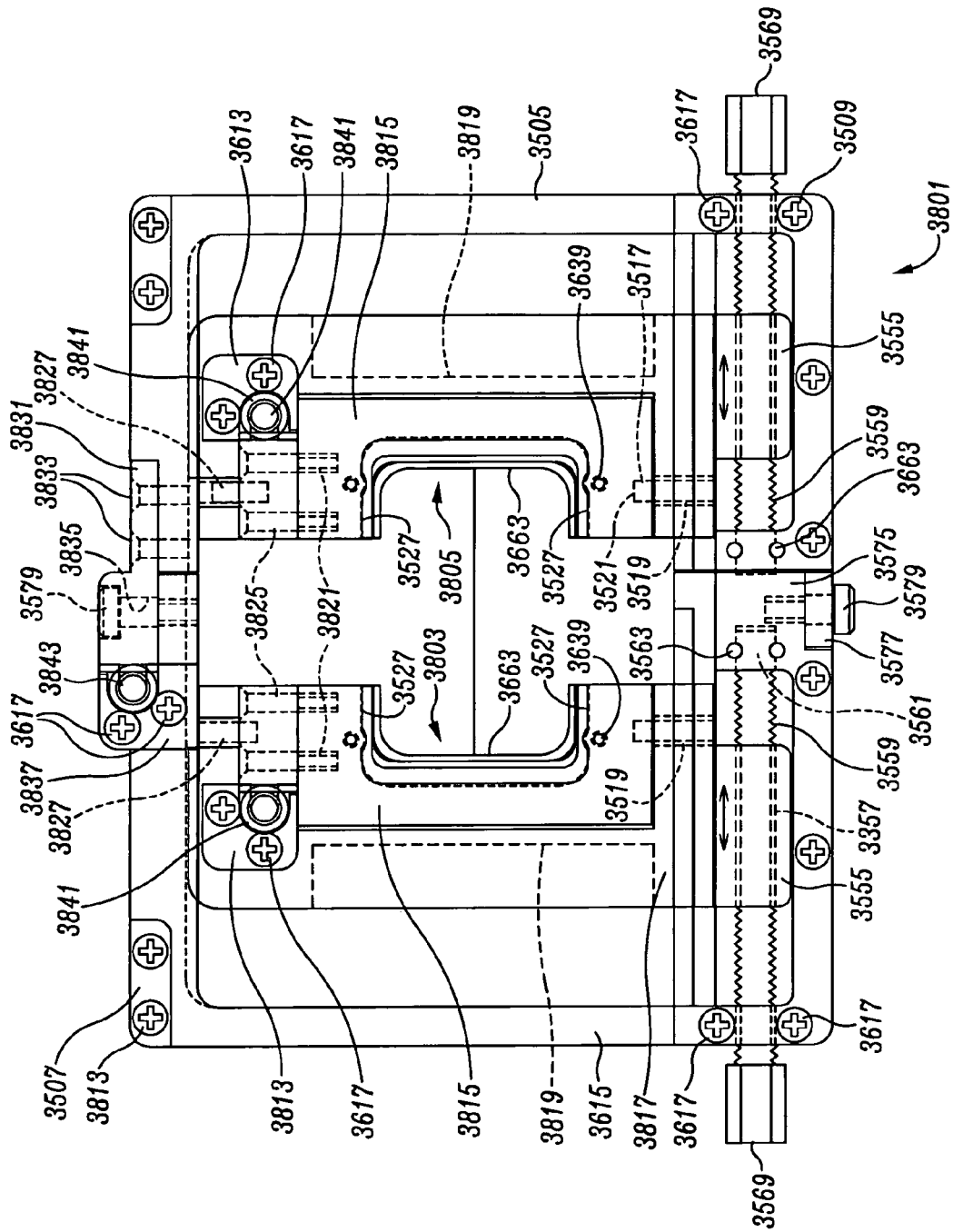
Fig. 165 (VERSION 5 BOTTOM VIEW)

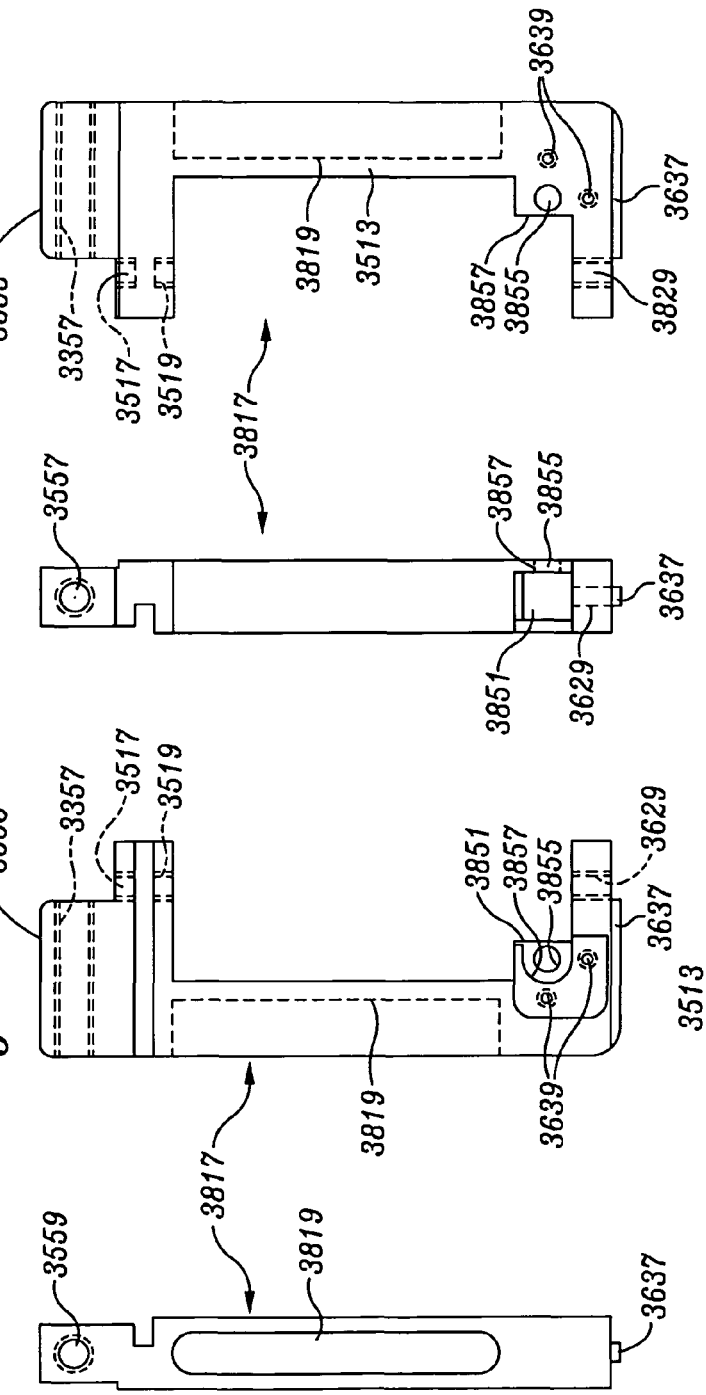

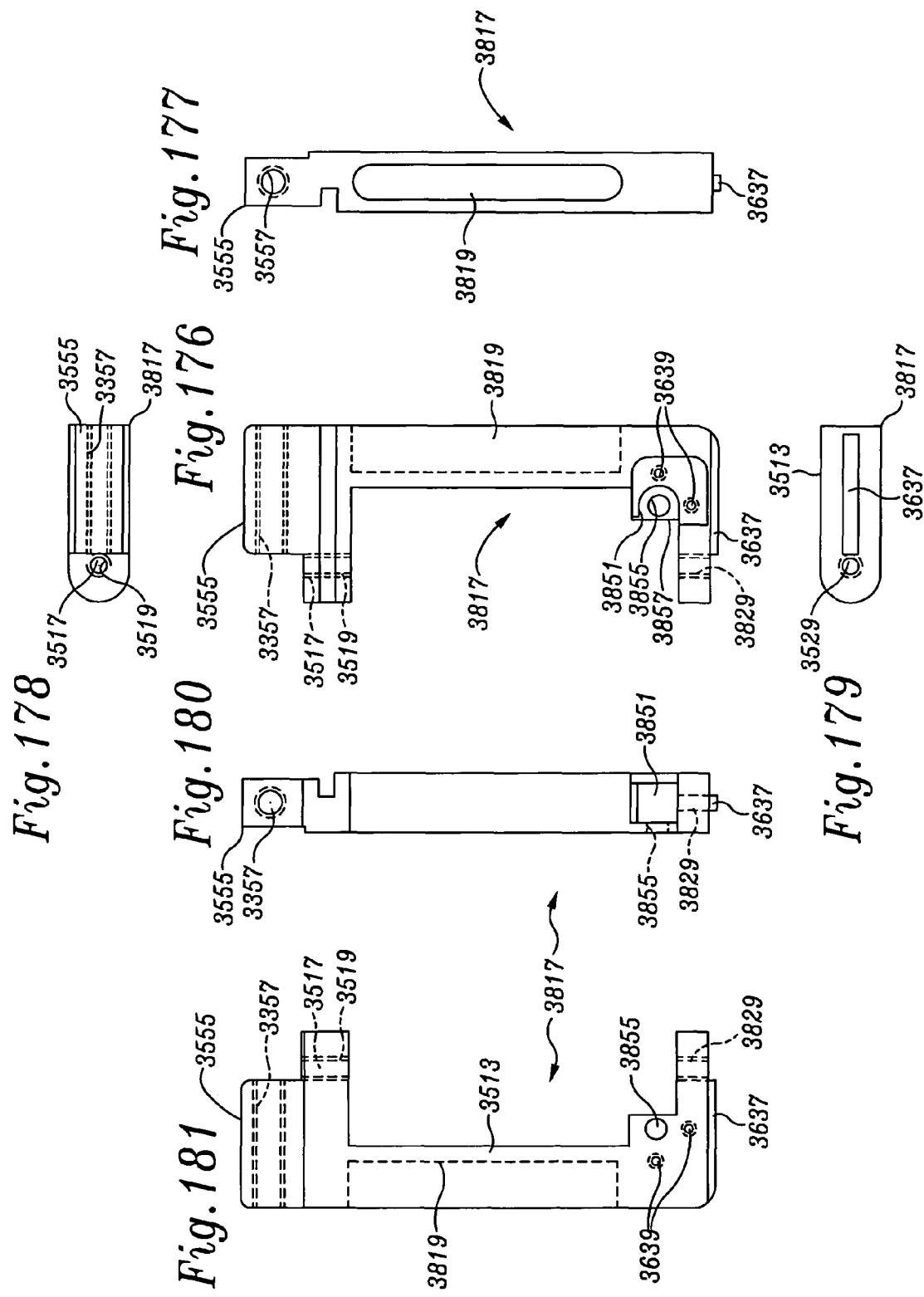

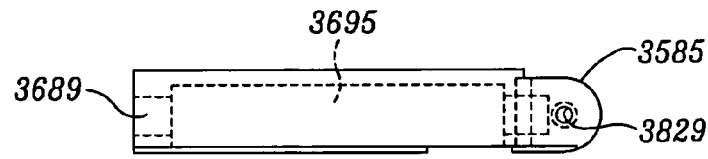
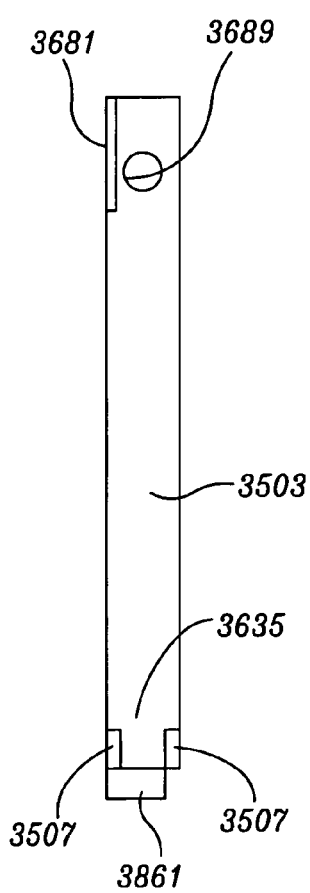
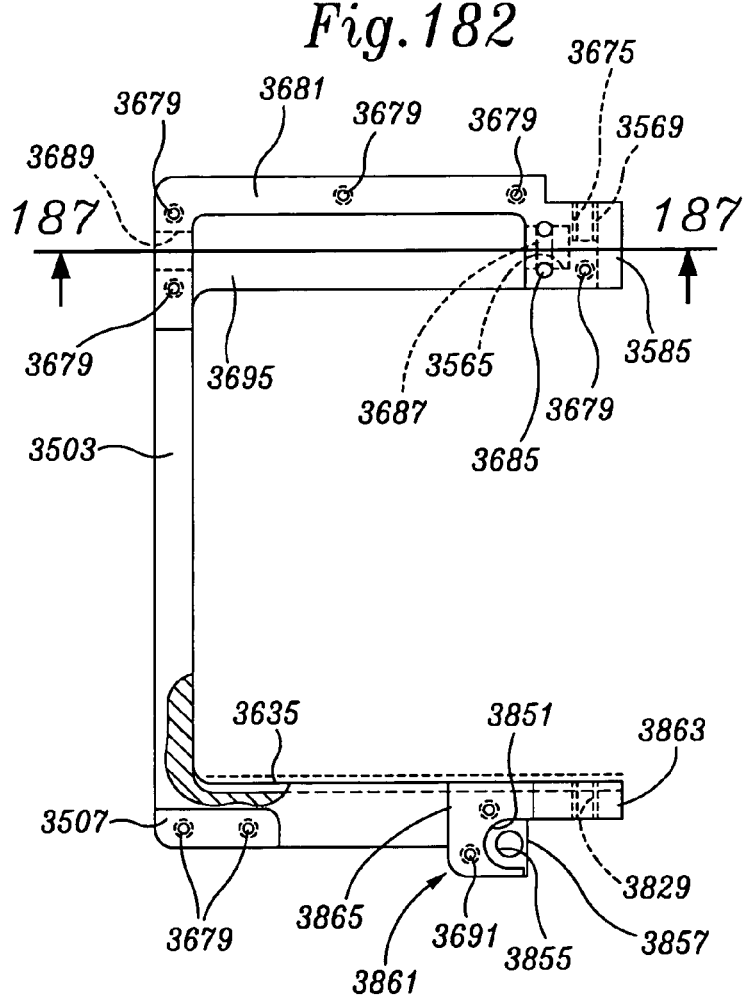
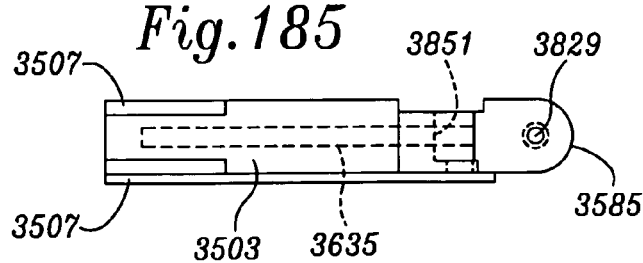

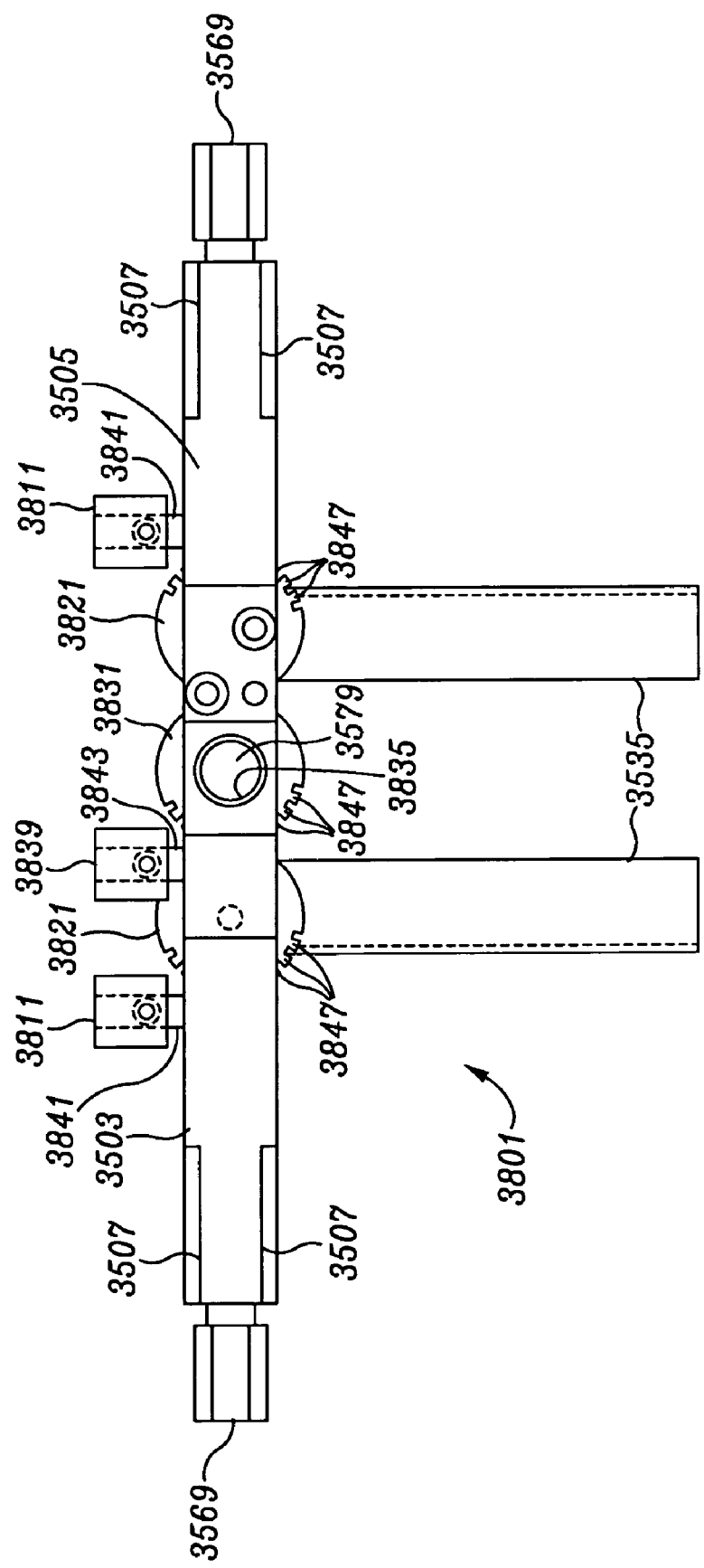
Fig.196 (RIGHT SIDE)

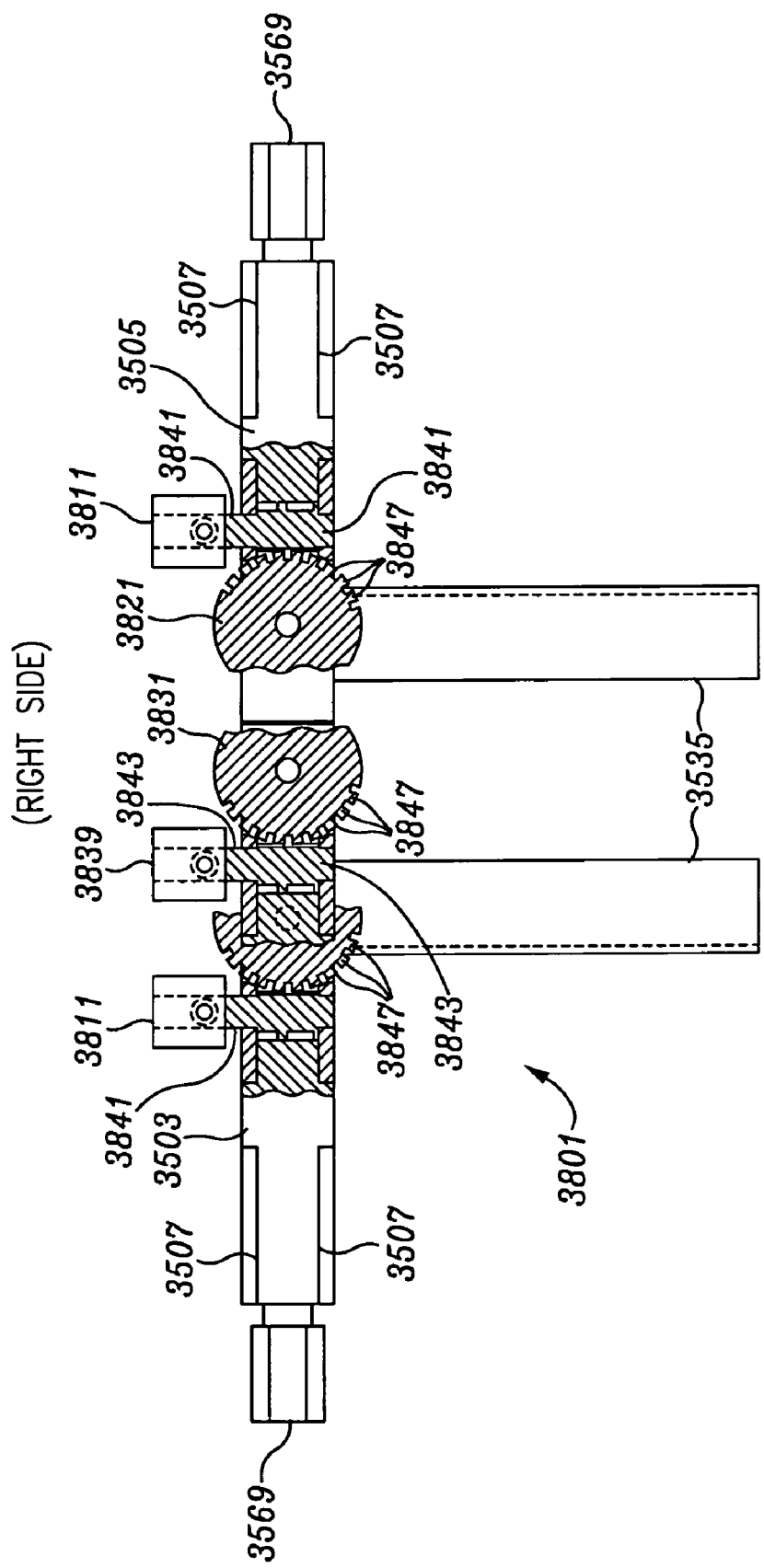
Fig.197 (RIGHT SIDE)

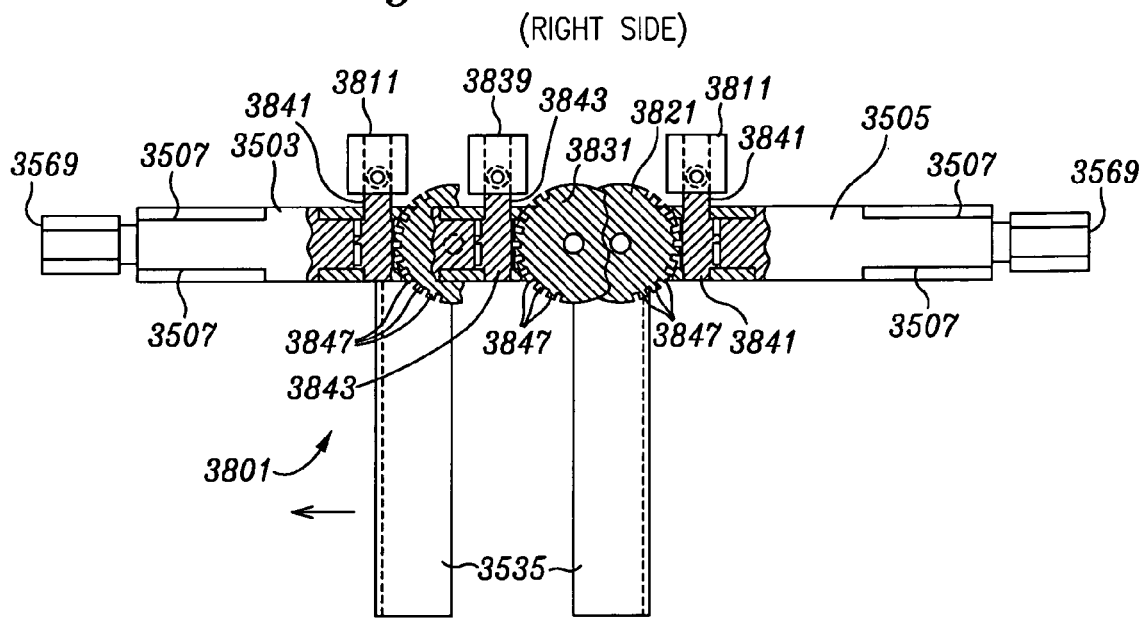
Fig. 198 (RIGHT SIDE)
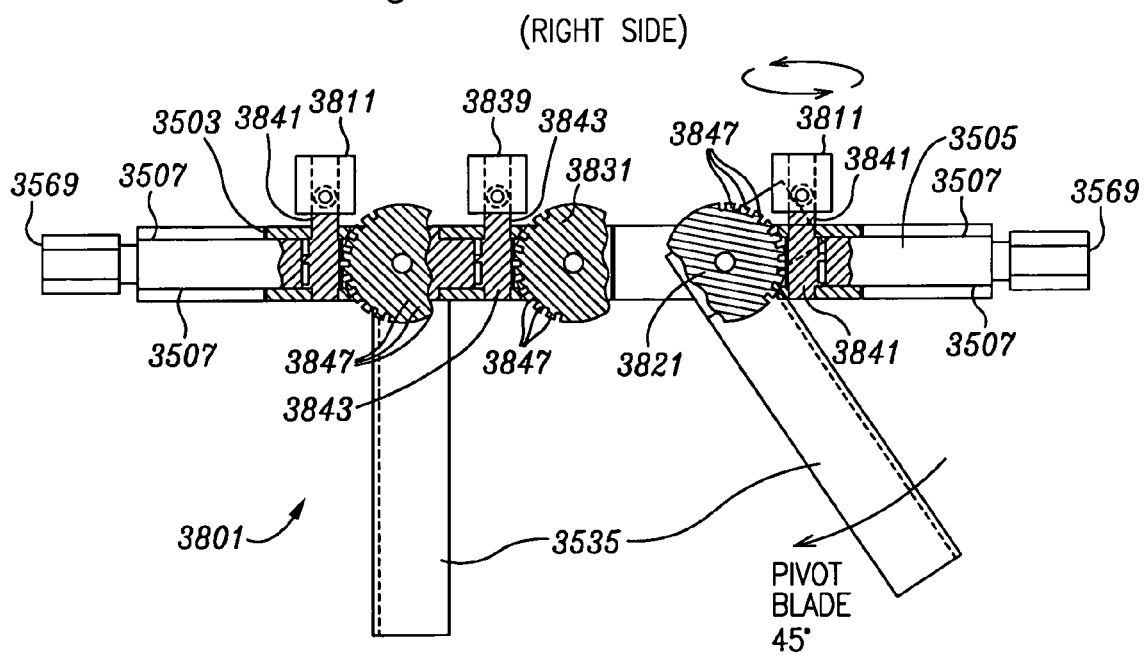
Fig. 199 (RIGHT SIDE)

(RIGHT SIDE)

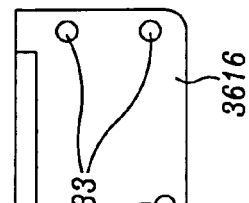
Fig.208
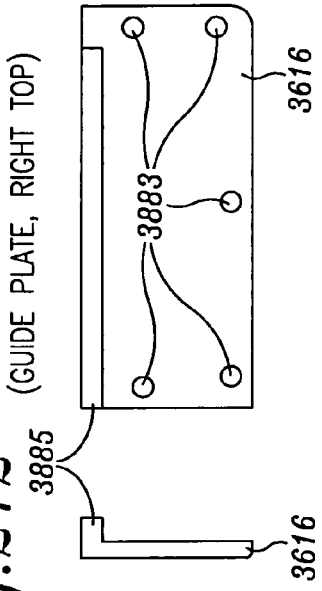
Fig.207 (GUIDE PLATE, LEFT TOP)
Fig.211 (GUIDE PLATE, RIGHT TOP)
Fig.212
Fig.209
Fig.213
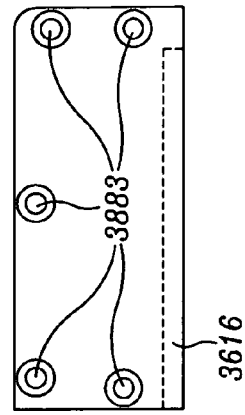
Fig.214
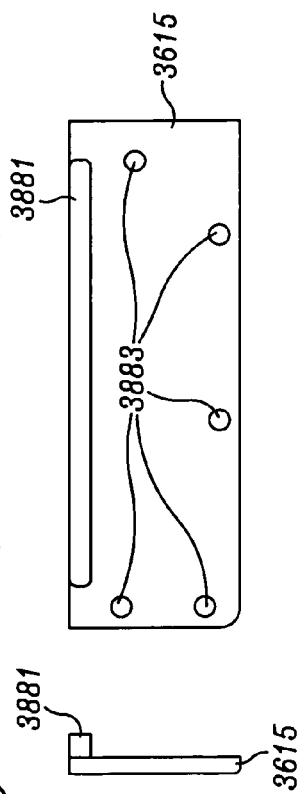
Fig.210
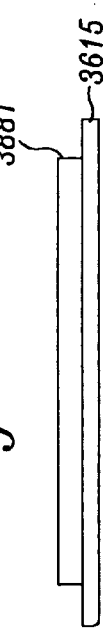
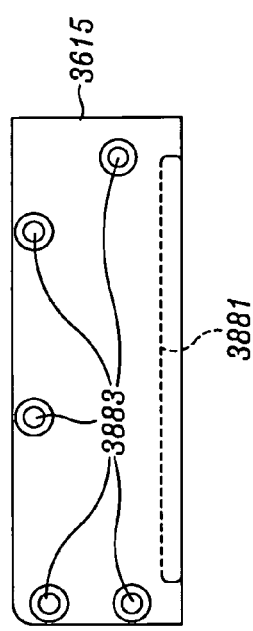

MINIMAL INCISION MAXIMAL ACCESS MIS SPINE INSTRUMENTATION AND METHOD

CROSS-REFERENCE TO RELATED APPLICATOINS

This application is a continuation-in-part application of U.S. patent application Ser. No. 11/489,858 filed Jul. 19, 2006 now U.S. Pat. No. 7,850,608, which is a continuation-in-part patent application of U.S. patent application Ser. No. 11/267,618 filed Nov. 4, 2005, which is a continuation-in-part patent application of U.S. patent application Ser. No. 11/230,420 filed Sep. 19, 2005, which is a continuation-in-part application of U.S. patent application Ser. No. 11/165,295 filed Jun. 22, 2005 now U.S. Pat. No. 7,883,522, which is a continuation-in-part application of U.S. patent application Ser. No. 11/001,628 filed Nov. 30, 2004 now U.S. Pat. No. 7,173,240, which is a divisional application of U.S. Ser. No. 10/280,624 filed Oct. 25, 2002, now U.S. Pat. No. 6,849,064, the entire contents of each of which are incorporated by reference herein.

FIELD OF THE INVENTION

The present invention relates to improvements in the field of minimal invasive surgery and more particularly to instrumentation which allows for maximal access to the surgical field through the smallest possible incision. Greater access is allowed into the working field while enjoying the reduction of trauma and disturbance to surrounding tissues, which results in a reduced time necessary to complete the operative procedure, increased safety of the procedure, and further patient recovery and rehabilitation, as well as less blood loss. Increased accuracy by providing an expanded working field is another goal to help the surgical practitioner perform well within a short time.

BACKGROUND OF THE INVENTION

Microscopic Lumbar Diskectomy techniques were developed and championed by Dr. Robert Williams in the late 1970's and by Dr. John McCullough in the late 1980's and 1990's. For the first time since the advent of Lumbar Disc Surgery by Mixter and Barr in 1934 a method was introduced allowing Lumbar Disc Surgery to be performed through a small incision safely resulting in faster patient recovery and converting a two to five hospital stay procedure virtually to an outpatient procedure.

The special retractors developed by Drs. Williams and McCullough however were often difficult to maintain in optimum position and relied on the interspinous and supraspinatus ligaments for a counter fixation point severely stretching these structures. This stretching along with the effects of partial facectomy, diskectomy, removal of the ligamentum flavum and posterior longitudinal ligament contributed to the development of Post Diskectomy Instability. Taylor retractors were also used but were cumbersome, required larger incisions and often injured the facet joints.

A second generation MIS retractor system was introduced by Dr. William Foley in 1997, and which was a tubular system mated to an endoscope which he labeled a Minimal Endoscopic Diskectomy (MED) system. It featured sequentially dilating the Lumbar Paraspinous Muscles allowing a working channel to be advanced down to the level of operation through which nerve root decompression and Diskectomy Surgery could be performed. Minor changes were made with the second generation METRx system. However, there were several disadvantages to the MED and METRx systems.

In the MED and METRx systems, the cylindrical working channel considerably restricted visualization and passage of instruments. It also compromised the "angle of approach" necessary for safe usage of the operating instruments. This problem was proportionately aggravated with the long length of the tube. This compromised visualization contributed to the following problems, including nerve injury, dural tear, missed disc fragments, inadequate decompression of the lateral recess, increased epidural bleeding, difficulty controlling epidural bleeding, inadequate visualization of the neuroforamen, and inadequate decompression of neuroforamen.

The repetitive introduction of successively larger dilators caused skin abrasion with the potential for carrying superficial skin organisms down to the deeper tissue layers hypothetically increasing the risk of infection. The learning curve for operating in a two dimension endoscopic field proved to be arduous and contributed to the above complications.

The attempted use of the METRx system for more complex procedures such as fusion was further hazardous by inherent limitations. Endius in September of 2000 then introduced a similar device which differed by having an expandable foot piece to allow greater coverage of the operative field. However, the enlarged foot piece was unwieldy and difficult to seat properly. Exposure of the angle of approach was also limited by having to operate through a proximal cylindrical tube with its limitations as described before. In comparison to the METRx system the working area was improved but access was again restricted by the smaller proximal cylinder.

Both systems offered endoscopic capability but many spine surgeons chose to use an operating microscope or loupes to maintain 3-Dimensional visualization rather than the depth impaired 2-Dimensional endoscopic presentation. Keeping debris off of the endoscopic lens has also proved to be a troubling challenge.

More recently, the third generation of MIS Retractors have been designed for spine surgery (Nuvasive (Pimenta et al)), Quadrant (Branch et al), Depuy-Pipeline (Raymond et al). There have also been modifications of older devices offering to enter the arena of MIS Spine Surgery (Koros). The plethora of proposed surgical retraction devices and methods have led to a confusion of meaning of the "MIS Spine Surgical Technique." Surgical incisions of up to five inches in length have been described for MIS Surgery. Usage of the term "MIS Surgery" as applied to spine surgery, appears to have evolved to mean a surgical incision less than the traditional one or two levels above and below the surgical field of interest. However, the combined length of two incisions (right and left) often is longer than the single midline incision. The true advantage of MIS Surgery over the traditional technique is the specificity of exposure such that only the required amount of retraction of soft tissue is used to safely accomplish the specific surgical procedure.

Ideally, there are certain prerequisites for a MIS spine retractor that should be fulfilled in order to accomplish the objective that only the required amount of retraction of soft tissue is used:
1. The retractor must provide sufficient direct visualization of the neural elements, related blood vessels, and bony landmarks to accomplish safe spine surgery.
2. The retractor should require the least amount of resection of adjacent tissue muscle, fascia, bone, and joints to accomplish the task.
3. The retractor should be self-retaining instead of hand-held (Ritland).

4. Deployment of the surgical retractor should be able to be prompt and precise in location.
5. The retractor should be easy to adjust for length, width, and angle of exposure.
6. The retractor support, such as a frame, must have the capability to lie flat to the surface contour of the body so that the attached retractor blades could be as short as possible.
7. The retractor support, such as a frame and blades must be stable once optimum surgical exposure is obtained.
8. There should be a minimum of "fiddle factor" so the surgeons attention can remain focused on the operation and not distracted by the complexity of using the retractor.
9. The retractor must be "strong enough" in design not to flex and lose exposure.
10. Particularly for surgery of the posterior lumbar spine, the retractor must be designed to counter the powerful paraspinal muscle resistance without using large incremental changes (e.g. widely spaced ratcheted gap).
11. With longer exposure length, there must be an efficient means to retract muscle that encroach between the retractor blades.
12. The need for ancillary equipment such as light source attachments, etc., are self evident.

Currently available surgical retractor systems fail to fulfill all of the above requirements. Consequently there is a severe need for structures and procedures to meet such requirement.

Due to the spine surgeon's desire to utilize the advantages of MIS Surgery to evermore complex procedures, the MIS Surgical Retractors have evolved to attempt accommodate this need. For example. the Danek MED Tube evolve to the X-Tube and then to the Quadrant system (U.S. Pat. No. 6,945,933 to Branch et. al, Dewey et al). Still other retractor inventions have come to market including the three-bladed, Nuvasive design for the lateral approach to the Lumbar Interbody Space, the Depuy "pipeline" retractor, a highly complex four-bladed retractor system with a curved ratchet arm. None of the above retractor Systems incorporate the full complement of prerequisites listed above.

The Branch, et al. System's new retractor creates a "working channel" with insertion of sequentially larger dilating tubes. This method of introduction into the body while acceptable for use with an enclosed tube encounters problems when the newer systems with retractor blades which can be opened apart are utilized. With the serial dilation techniques the strong fascia and paraspinal muscles have remained intact, and therefore a monumental battle develops between the separating blades and the intact muscle and fascia resisting the expansion. This necessarily results in tearing and shredding of the muscle as the blades are forced apart.

This is acknowledged by Branch et al '933 reference at page 10, paragraph 2. "In use, the resistance to retraction provided by the tissue may prevent distal ends from separating as far as proximal ends." In the Branch/Dewey system this is always the case when spine surgery is attempted at more than one level. Since the muscles have retained their strong attachment to the bone, forcing of the retractor blades apart necessarily requires ripping and shredding of the muscles and associated blood vessels and nerves.

The Quadrant System retractor blade separation is also based on a straight ratchet bar and therefore cannot accommodate for Lumbar lordosis which is often forty degrees at the lumbosacral junction. This requires retractor blades to be longer as the frame tends to "ride up from the surface of the skin" due to the curvature of the surface anatomy.

The retraction blades of the Quadrant system are also cantilevered a considerable distance from their attachment point on the ratchet bar creating unwanted movement, stress, and loss of muscle retraction compromising exposure. Applying a force from such a distance tends to (1) lose control of soft tissue retraction and therefore compromises the "working channel", (2) loads stress into bending and compression moments of a mechanical apparatus, and (3) having the mechanical apparatus block the surgical area while it is being employed. Therefore, the Quadrant system's retractor blades location at a considerable distance from its base attachment point on its ratchet bar creates a long lever arm moment which lends instability to the retractor blades. The Branch reference also shows a curved frame but this cannot adjust to different lordotic angles of the patient's posterior lumbar area.

The Pipeline retractor, while adequate for one level posterior lateral fusion procedure, has the deficiencies as described in the Quadrant System because of the serial dilation introduction method and suffers from negative effects of its extreme complexity. Raymond attempts to address the need to accommodate for lower lumbar lordosis by using a curved ratchet frame, but their fixed curvature cannot adjust to different lordotic angles. In addition, the Pipeline retractor has proven extremely difficult to spread the retractor blades up an inclined slope along the arc of the ratchet arms against the strong resistance of the muscle and fascia even using a separate spreader device. The Pipeline device also has proven to be so complex that it is very difficult and time consuming to set up, operate, and learn to use.

The Nuvasive Retractor (Pimenta) is suitable for the lateral approach to the L2, L3 and L4 levels for which the retractor was designed. The deficiencies of a three bladed retractor like Nuvasive's become apparent when used for other procedures such as a posterolateral lumbar fusion. If the Nuvasive retractor is deployed such that the middle blade is lateral, then visualization of the spinal canal can be difficult. If the Nuvasive middle blade is placed medial, there is significant muscle encroachment as the blades are spread apart.

Another reference, Cocchia's U.S. Pat. No. 6,224,545 has a number of shortcomings, including (1) a surgical frame having no structure to allow flexion and extension, (2) retractor blades which are rotated with an awkward force plate device, and (3) the knobs used to control movement of the device are difficult to use due to the proximity on the patient's skin and inability to apply adequate torque.

Further, Cocchia's device requires a completely open slot in the arms of the main frame, along which is run a cylindrical guide bar. The Cocchia device also requires two additional "traveling rods" on the thread assembly cross piece to keep the moving parts from binding. Coccia's design also has an exposed, open end of the screw device which can tear surgical gloves and tissues predisposing to infection.

Coccia's use of a force plate method to provoke angulation of the retractor blade, also lacks the control to return to neutral from outward deflection. The force control of Coccia's device furthermore does not contemplate force movement to an inwardly angled position. As a result, Coccia's device is impractical for advanced retraction needs.

As discussed above, it is advantageous to have a retractor frame that can adjust to the body surface where the surgery is being performed. Historically, several retractors for general purposes have had a hinge, usually on the handles of the retractor (Beckman) or on the frame (Koros, Watanabe) to lower a portion of the retractor out of the way of the surgeon's hands. The hinges did not serve the purpose of contouring the device to the surface of the body.

The axis of rotation of these hinge devices is therefor cephalo-caudal or in the longitudinal axis of the body. Turning these retractors 90° would be counter to the general intended use of these retractors. Furthermore, the retractor hinges were "free moving" and did not have control devices.

The Bookwalter retractor did have two hinges connecting two halves of a circular or elliptical frame with an angular control device. The angulation was controlled by interdigitating rings which were locked into position with thumbscrews. This allowed flexion and extension of the basic hoop frame, but required loosening of the thumbscrews, disengaging the ratchets, adjusting to a new position, reengaging the ratchets and re-tightening the screws. This arduous process is allowable for abdominal surgery but is unacceptable for MIS spin surgery.

In order to attain ideal exposure at the surgical work area, it is also important to have customized retractor tips. The value of "docking" of the distal end of the retractor has been described for closed tube MIS retractor systems by Michelson (U.S. Pat. No. 6,080,155) and Simonson (U.S. Pat. No. 7,008,431). These concepts have not been able to be employed in higher level retractor systems.

SUMMARY OF THE INVENTION

The system and method of the invention, hereinafter minimal incision maximal access (MIMA) system, includes a surgical operating system that allows for maximum desirable exposure along with maximum access to the operative field utilizing a minimum incision to be described.

The MIMA system disclosed offers advantages over other MIS spine retractor systems in several respects, as follows.

1. Instead of multiple insertions of Dilating Tubes, the Invention is a streamlined single entry device. This avoids repetitive skin surface entry for one level procedures.

2. For greater exposure, the MIMA system contemplates soft tissue release prior to deployment of the retractor by using a fascial incisor/dissector.

3. The MIMA system offers the capability to expand to optimum exposure size for the surgery utilizing hinged bi-hemispherical or oval Working Tubes applied over an introducer Obturator which is controllably dilated to slowly separate muscle tissue.

4. The MIMA system maximizes the deeper surgical area with fine adjustment capability.

5. The MIMA system provides expanded visual and working field to makes the operative procedure safer in application and shorten the surgeons's learning curve because it most closely approximates the open microdiskectomy techniques.

6. The MIMA system has a tapered ended Obturator which allows for tissue spread on entry.

7. The MIMA system controls muscle oozing into the operative field which is controlled by simply opening the tubes further. This also thereby controls the bleeding by pressure to the surrounding tissues.

8. In contrast to the closed cylindrical tube based systems such as the METRx and Simonson the MIMA system offers a larger working area in proportion to the entry opening. The enlarged footprint of the MIMA system is a major difference from any other minimal access system.

9. The expandable design of the MIMA system allows for excellent exposure for more complex procedures such as fusion and instrumentation including TLIF, PLIF, and TFIF (Transfacet Interbody Fusion), as well as allowing application for surgery on other areas of the body. For example, MIMA system can be used for anterior lumbar interbody fusion be it retroperitoneal, transperitoneal or laproscopic from anterior or lateral approaches 10. Another advantage of the MIMA system is the customized retractor tips. For example, in lumbar microdiskectomy, the medial oval cutout of the retractor blade forming the working tube allows more central docking on the spine which is problematic for other devices. A medialized docking provides access for easier and better and safer dural retraction to address midline pathology.

11. The anti-reflective inner surface of the retractor blades which eliminates unwanted glare.

12. The MIMA system includes the slanted and contoured distal end of the retractor blade which allows minimal resistance for entry and advancement to the docking site.

13. Another advantage MIMA system is the provision for different shaped retractor blades (round, oval, flat, etc.) According to the needs of the surgical procedure and location. This minimizes unnecessary muscle spread and resection.

14. The larger retractor blade of the MIMA system also features one or two "skirts" to cover the lateral aperture created by the spread of the two retractor blades when opened. This prevents soft tissue and muscle ingress into the exposure zone. The skirts are attached to the working tube either at the hinge or on one or both of the two halves of the retractor blades.

15. An advantage of the MIMA system is the provision of a modular design in which the retractor blades can be quickly removed, changed and reapplied. In this version the proximal port can also be modular and changeable to fit the needs of a specific surgical procedure.

16. The MIMA systems retractor blades can be made out of metal, ceramic or plastic, can be opaque or translucent, and can have tips of different shapes for different applications.

17. The provision of snap lock connections of the major parts of the Invention provides for easy assembly and disengagement for cleaning and sterilization purposes.

18. The obturator of the MIMA system is cannulated for carrying a central Guide Pin Passage. It has a Handle component which remains superficial to the skin. The obturator houses an internal hinge device which allows for spread of the two obturator tips.

19. Another advantage of the MEMA system is the uniquely designed facial incision and dissection which creates the least traumatic way to traverse the muscle layer by incision of the firm fascia and aponeurosis splitting the muscle in the direction of its fibers and the technique of detaching the muscle attachment to the bone rather than tearing and ripping of the muscle.

20. A further advantage involves the possibility that the improved retractor can range in complexity from a single axis single hinge, two-blade retractor which allows expansion at the deep end of the retractor blades to other versions, but which will also permit enlargement of the proximal opening as well.

21. Another advantage is the use of a simple modification of a Gelpi-type retractor enables retraction perpendicular to the direction of spread of the main retractor.

22. Another advantage is that in further embodiments, a double support, such as a frame can be connected by a controllable hinge which allows flexion and extension to accommodate the contour of the patient's body surface.

23. Another advantage is that the retractor blades are interchangeable and have independent control features.

24. Another advantage is that overall, the focus of this invention's design has been to maintain simplicity and efficiency in the use of the retractor.

25. A further advantage of our approach (both retractor and surgical) is achieved by incising the fascia and spreading the muscle in the direction of its fibers before the retractor is deployed.

Advantages of the MIMA System

In contrast to the shortcomings of presently commercially available retractors, the inventive retractor offers the following advantages:
1. Atraumatic one step entry into the body.
2. Pre-deployment soft tissue is released in a controlled least-traumatic fashion.
3. Streamlined retractor design can accomplish tissue retraction with only three controls.
4. Micro-control feature with a simple screw-activated design gives precise control and mechanical advantage.
5. In one embodiment, a "hands away from the body design" utilizes an innovative ratchet.
6. The frame/support is connected by micro-adjustable hinge to customize flexion or extension to match the body contour. The micro-controllable hinge design of the present invention allows the resting of the support structure, such as a frame, close to the patient's skin surface so that it is as "flat" or close to the body surface as possible. This allows for the shortest working depth which maximizes the visual line of sight into the working area. The shortest working depth allows for shorter instruments to be used and decrease the chance of inadvertent surgical mistakes.
7. Customized retractor blade tips to "dock" to the surgical work site.
8. Modular, easy to change design for the retractor blades and tips.
9. Method to retract muscle ingress by customized deep Gelpi-type retractor customized for use with the retractor of the invention.
10. MIS retractor design applicable for surgery to several areas of the body and specifically for the lumbar spine allowing access for up to a three level instrumented fusion which is not currently possible with any other MIS spinal retractor.
11. The "screw-in-frame" design provides a simple yet powerful way to open or close at least one retractor blade. Turning of the threads allows a slow separation of the muscle, fascia, blood vessels and nerves, instead of a forceful fixed magnitude incremental jumps in separation.
12. The control grooves on either the retractor legs or the first inner translatable frame member, in the case where a frame member enables quick change out of retractor blades, guides and controls the opening and closing of at least one retractor blade housing in a stable, positive, strong, controllable manner.
13. A screw and captured head design enables a continuously viewable positive control with visual verification of operation. The surgical practitioner can see the position of pivoting members, which gives an instant feedback of the expected ease or resistance of operation. Further, the screw and captured head design, with a threaded member operating from within internal threads of a rotational block fitting, where the threaded member has an externally viewable ball fitting structure fitting within a rotational block fitting provides a control linkage which is nearly 100% exposed for sterilization purposes. The result is a set of structures whose integrity are immediately knowable, and which give a positive, exposed manner of interactive operation.
14. A new, bidirectional ratchet uses a custom bi-directional ratchet having a hex or other shaped head. A flow through design provides complete wettable sterilization, and a quick dis-assembly construction provides complete break down and re-assembly for fine cleaning and service.
15. The designs of the retractor system enable the surgical practitioner to operate around the device without exposing the surgeons hands and gloves to surfaces which might damage the gloves and expose the patent's tissues to infection. Further, the bidirectional ratchet enables even further isolation of the surgeons hands and gloves from mechanical surfaces and structures which might otherwise compromise the sterile integrity of the operation.
16. The use of a bidirectional ratchet which can be quickly mated to actuation points, used and then moved to another point, enables the surgical practitioner to focus more on each element of adjustment and upon satisfaction of proper adjustment, remove the bidirectional ratchet from the surgical field during the operation.
17. The importance of the use of custom designed retractor blade tips which are specific for the needs of a particular surgical procedure cannot be underestimated. A bi-valved tubular blade with medial cutout, for example, is ideal for a one level lumbar microdiscectomy because of maximum lateral soft tissue retraction with good access to the spinal canal provided by the medial cutout. In another example, an inverted "U" cutout with a modified medial cutout is ideal for TLIF procedures as it allows for "docking" of the retractor tips on the prominence of the facet joints or transverse process, and still provides good access to the spinal canal and is well positioned for pedicle screw insertion.
18. Quick blade change can be combined with differential retractor blade use where one type of blade is used on one portion of the retractor and another type of blade is used on the opposite portion of the retractor, or elsewhere.
19. Quick change locking screws or latches, enable the surgical practitioner to pull and examine, and then change retractor tips without having to fuss with small parts or tiny mechanisms which could come loose. As by example, there are times when tubular shaped retractor blades are preferable while at other times a "U" shaped or a flat blade is preferable. The flange on the proximal end of the retractor blades will provide for a strong and very stable attachment structure. The use of a quick turning pair of set screws for each side of the flanges provides a positive lock and unlock with clear visual indication of lock. This further gives confidence that the positive lock will enable the secure retractor blades to be urged apart against strong resistance of the muscle and other soft tissue. Other types of locks are possible including spring urged locks, detent locks and the like. The flange on the proximal end provides for a strong and stable attachment.
20. Customized deep Gelpi-type retractors can be advantageously utilized with the retractor systems described to allow wider medial-lateral soft tissue retraction than the boundaries of the retractor frame. This opens up the central part of the operative field, retracting tissue that would otherwise encroach into the surgical field. The contour of the retractor stems also accommodates changing depth needs.
21. The simplicity of design and usage, including the combination of all parts described herein has culminated in a strong, reliable, versatile MIS retractor system that is easy to master and use. For those skilled in the surgical arts, this multi-faceted feature is highly prized and appreciated as it can allow for shorter operative time, decreased blood loss, reduced tissue trauma and less surgical error.

BRIEF DESCRIPTION OF THE DRAWINGS

The invention, its configuration, construction, and operation will be best further described in the following detailed description, taken in conjunction with the accompanying drawings in which:

FIG. 2 is a perspective assembled view illustrating the relative positions of the obturator and working tube;

FIG. 3 is a perspective assembled view illustrates the position of the obturator after it has been inserted into the working tube;

FIG. 4 is a view taken along line 4-4 of FIG. 2 and looking into the working tube of FIG. 1;

FIG. 5 is a sectional view taken along line 5-5 of FIG. 2 and looking into the hinge of working tube of FIG. 1, illustrating its hinge connections;

FIG. 6 is an side end view of the working tube of FIGS. 1-5 and illustrating predominantly one of the rigidly connected halves of the invention;

FIG. 7 is a side sectional view taken along line 7-7 of FIG. 6 and showing the internal bearing pivot;

FIG. 8 is a side sectional view taken along line 8-8 of FIG. 5 and illustrating a option for external bevel for the working tube;

FIG. 15 is a sectional view taken along line 14-14 of FIG. 12 and gives a sectional view from the same perspective seen in FIG. 14;

FIG. 16 is a view of the obturator similar to that seen in FIG. 15, but turned ninety degrees along its axis and illustrates the wedge as having a narrower dimension to lend internal stability;

FIG. 17 is a closeup view of the external hinge assembly seen in FIG. 1 and illustrates the optional use of a plug to cover the exposed side of a circular protrusion;

FIG. 18 is a view taken along line 18-18 of FIG. 11 and illustrates the use of an optional skirt having flexible members which spread from an initial curled position to a straightened position to better isolate the surgical field;

FIG. 19 is a view of the lower tube hemicylindrical or curved portions 65 and 69 in a close relationship illustrating the manner in which the skirts sections within their accommodation slots areas;

FIG. 20 is a cross sectional view of the a patient and spine and facilitates illustration of the general sequence of steps taken for many procedures utilizing the minimal incision maximal access system disclosed;

FIG. 21 illustrates a fascial incisor over fitting a guide pin and further inserted to cut through external and internal tissue;

FIG. 22 illustrates the assembled Working Tube-Obturator being inserted into the area previously occupied by the fascial incisor and advanced to the operative level lamina;

FIG. 23 illustrates the obturator 33 being actuated to a spread orientation to which automatically actuates the working tube to a spread orientation;

FIG. 24 is a view of the working tube 35 is in place and supported, held or stabilized in the field of view by a telescopy support arm and engagement, the opposite end of the stabilizing structure attached to the operating table;

FIG. 29 illustrates a further variation on the obturator seen previously in FIG. 1 and illustrates the use of a central ball nut;

FIG. 30 is a sectional view taken along line 30-30 of FIG. 29 and illustrates the use of a central support block to support the central threaded surface;

FIG. 31 is a top view of a thin, inset hinge utilizable with any of the obturators herein, but particularly obturators of FIGS. 1 and 29;

FIG. 34 illustrates a top and schematic view of the use of a remote power control to provide instant control of the working tube using an adjustable restriction on the upper angled curved portions of the working tube;

FIG. 35 is a view taken along line 35-35 of FIG. 34 and illustrating the method of attachment of the cable or band constriction;

FIG. 36 is a mechanically operated version of the nut and bolt constriction band seen in FIG. 25;

FIG. 37 is an isolated view of two curved tube sections shown joined in a tubular relationship and indicating at least a pair of pivot axes on each curved tube section;

FIG. 38 is an isolated view of two curved tube sections as seen in FIG. 38 which are angularly displaced apart about a shared first pivot axis on each of the curved tube sections;

FIG. 39 is an isolated view of two curved tube sections as seen in FIGS. 38 and 39 which are angularly displaced apart about a shared second pivot axis on each of the curved tube sections;

FIG. 40 is a plan view of a given width supplemental side shield having a width of approximately the separation of the curved tube sections as seen in FIG. 39;

FIG. 41 is a top view of the supplemental side shield of FIG. 40;

FIG. 52 is a side view of the system of FIGS. 50-52;

FIG. 53 illustrates a top view double pivot hinge fitting and illustrating the gear surfaces;

FIG. 54 illustrates the action of the pivot hinge which produces an even angular deflection;

FIG. 55 illustrates a top view of a bookwalter device mounted atop a central hinge box seen in FIG. 53;

FIG. 56 is a top view of a retractor system employing many of the components seen in FIGS. 50-52 for applying force from a distance;

FIG. 66 is a side view of the frame retractor system seen in FIGS. 61-65;

FIG. 67 is a perspective view of a wire retractor utilizable with the frame retractor system of FIGS. 61-67;

FIG. 68 is an isolated view of the ends of the wire retractor shown in an opening pattern;

FIG. 69 is an isolated view of the ends of the wire retractor shown superimposed in a crossing pattern to reduce the profile for entry into the frame retractor system of FIGS. 61-66;

FIG. 73 illustrates a plan view of a manual tool with a main handle portion and interfitting blades;

FIG. 74 illustrates a different interchangeable blade attachment for the manual tool of FIG. 73;

FIG. 75 is a further embodiment of the manual tool seen in FIGS. 73 and 74;

FIG. 76 illustrates a view looking into the slip fitting of the manual tool of FIG. 75;

FIG. 77 illustrates a top view of a further embodiment of a frame retractor system;

FIG. 78 illustrates a bottom view of the embodiment of FIG. 77;

FIG. 83 illustrates a top view of a first generally curved retractor member utilizable with a frame retractor system;

FIG. 84 illustrates a top view of a second retractor member which may be utilizable with the first retractor member of FIG. 83;

FIG. 85 illustrates a left side view of the first retractor member of seen in FIG. 83;

FIG. 86 illustrates a right side view of the second retractor member of seen in FIG. 84;

FIG. 87 illustrates a rear view of the second retractor member of FIGS. 84 and 86;

FIG. 88 illustrates a top view of a first generally rectangular profile retractor member having curved edges and utilizable with a frame retractor system;

FIG. 89 illustrates a top view of a second retractor member utilizable with the first retractor member of FIG. 88;

FIG. 90 illustrates a left side view of the first retractor member of seen in FIG. 88;

FIG. 91 illustrates a right side view of the second retractor member of seen in FIG. 89;

FIG. 92 illustrates a rear view of the second retractor member of FIGS. 89 and 91;

FIG. 93 illustrates a right side view of the a retractor member having a bulge near its lower extent;

FIG. 94 illustrates a rear view of the retractor member of FIG. 93;

FIG. 95 illustrates a right side view of the a retractor member having a grossly but gently serrated lower shape;

FIG. 96 illustrates a rear view of the retractor member of FIG. 93;

FIG. 97 illustrates a right side view of the a retractor member having a rounded cutout at its lower edge;

FIG. 98 illustrates a rear view of the retractor member of FIG. 97;

FIG. 99 is a left side view of the frame retractor system of FIGS. 77 to 82 in which the retractor members are shown parallel and separated from each other;

FIG. 114 illustrates a side view looking into and partially through a ratchet actuation tool utilizable for force adjustment in a sterile surgical environment;

FIG. 115 illustrates a view of the ratchet actuation tool including the first plate & supported components seen with the second plate removed;

FIG. 116 illustrates a plan view of the ratchet actuation tool first plate;

FIG. 117 illustrates a plan view of the ratchet actuation tool second plate;

FIG. 118 illustrates a sectional view taken along the midline of the ratchet actuation tool first plate;

FIG. 119 illustrates a sectional view taken along the midline of the ratchet actuation tool second plate;

FIG. 120 illustrates an end view looking into the first socket;

FIG. 121 is a plan view of the first socket;

FIG. 122 is a top end view of the first socket seen in FIGS. 120 and 121;

FIG. 123 is a rear end view of the second socket;

FIG. 124 illustrates a plan view of the second socket;

FIG. 125 illustrates an end view looking into the second socket seen in FIGS. 123 and 124;

FIG. 126 illustrates a plan view of the ratchet sprocket engagement head;

FIG. 127 illustrates an end view of the ratchet sprocket engagement head;

FIG. 128 illustrates a plan view of the sprocket;

FIG. 129 illustrates a plan view looking downward on the spacer clip;

FIG. 130 is an exploded sectional detail illustrating the relationship of the first and second plates, how the spacer clip is secured to the first plate, how the spacer clip secures the second plate and how the spacer clip acts to control the spacing between the first and second plates;

Figure 134:
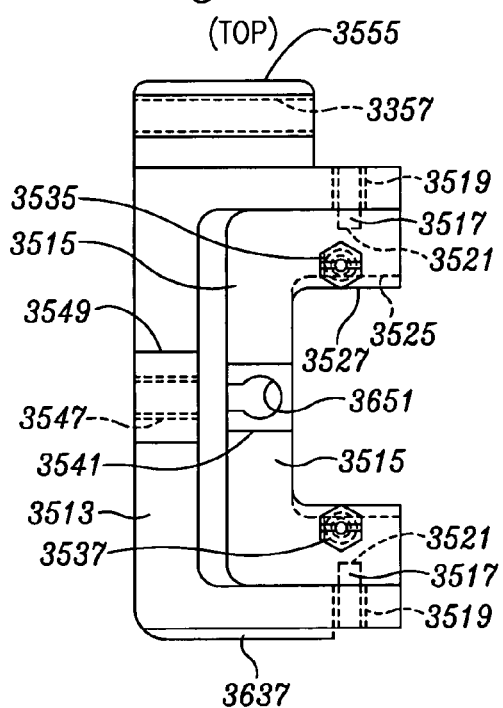
Figure 135:
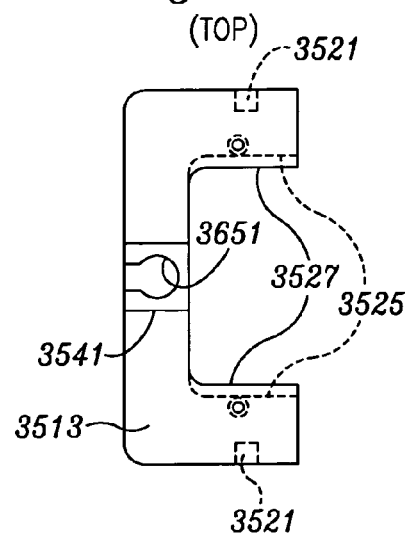
Figure 136:
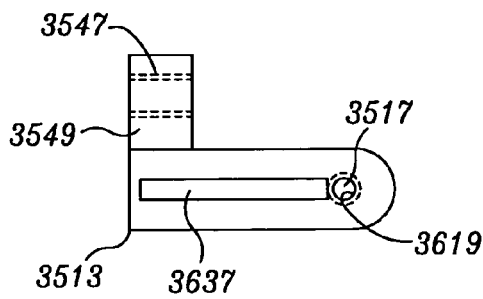
Figure 138:
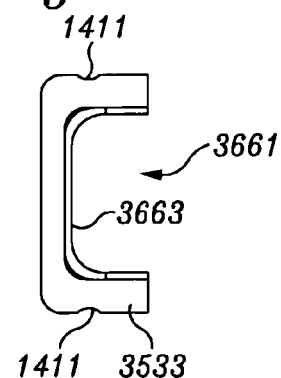
Figure 137:
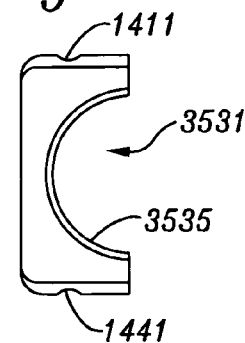
Figure 133:
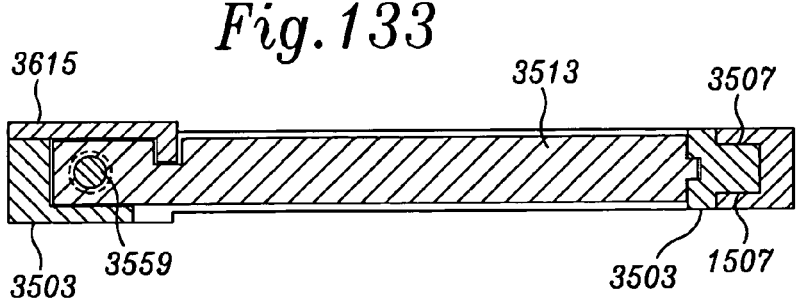
Figure 153:
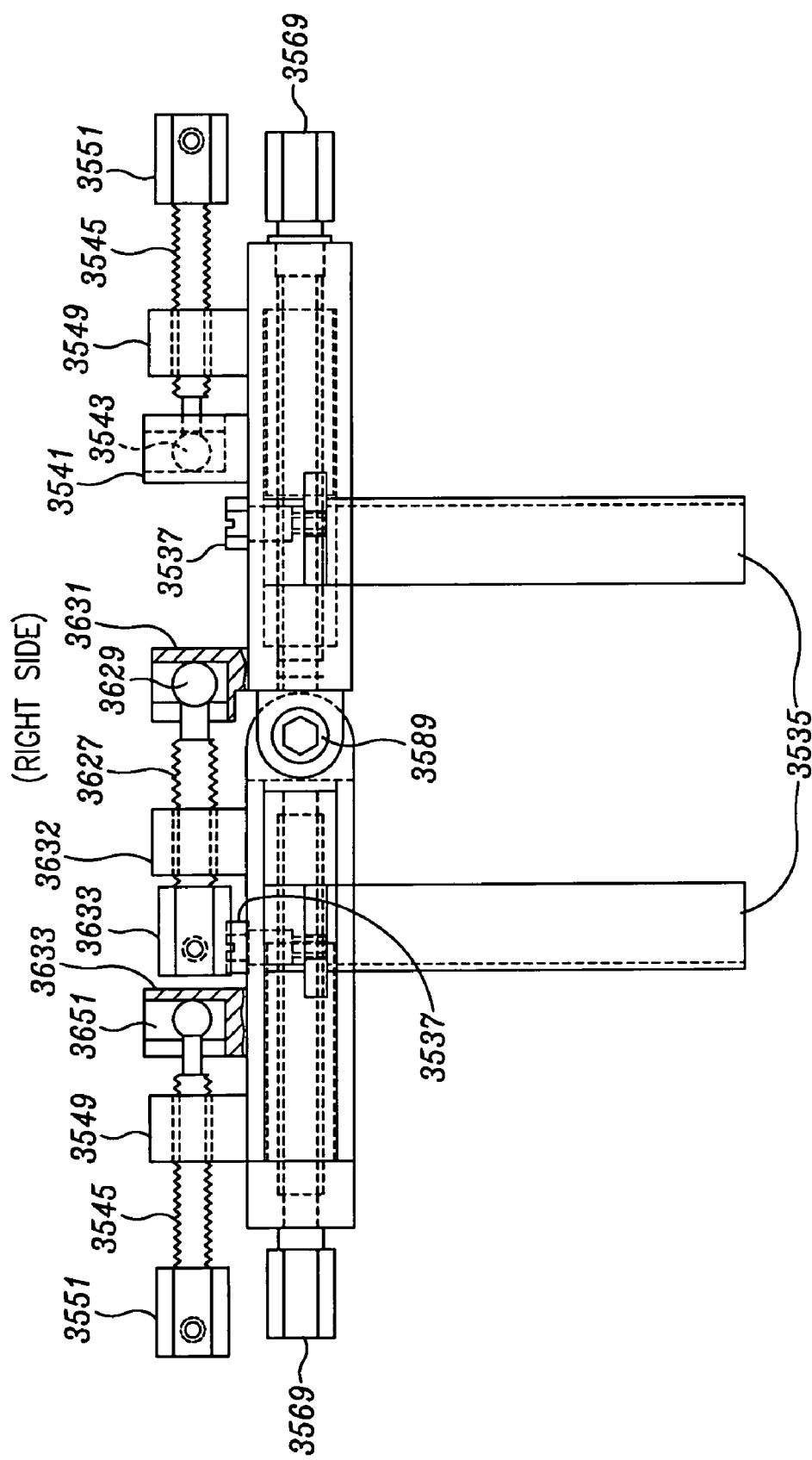
Figure 154:
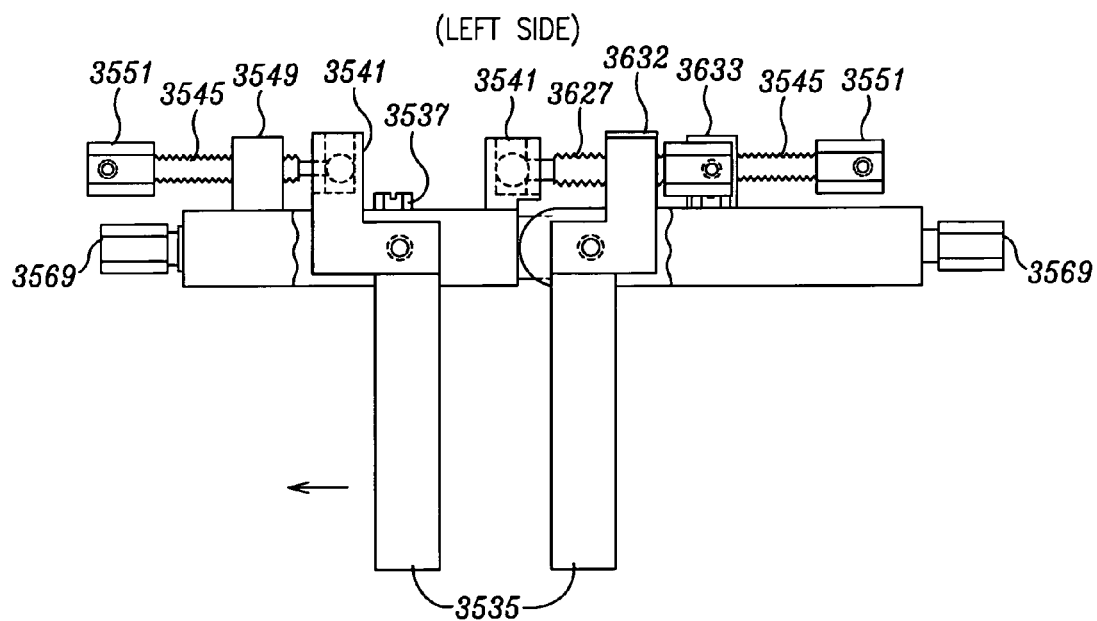
Figure 155:
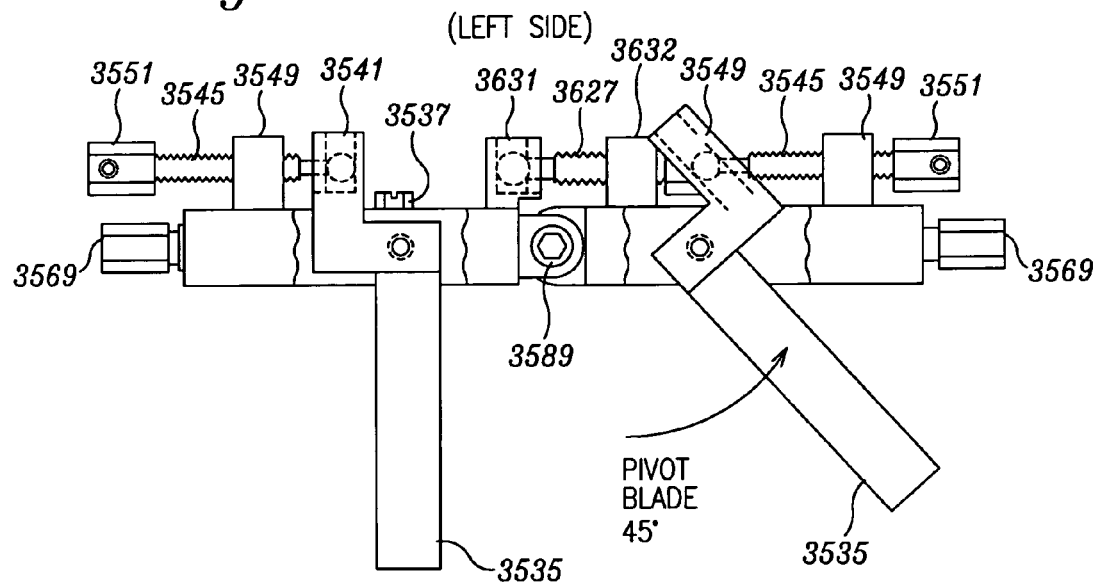
Figure 156:
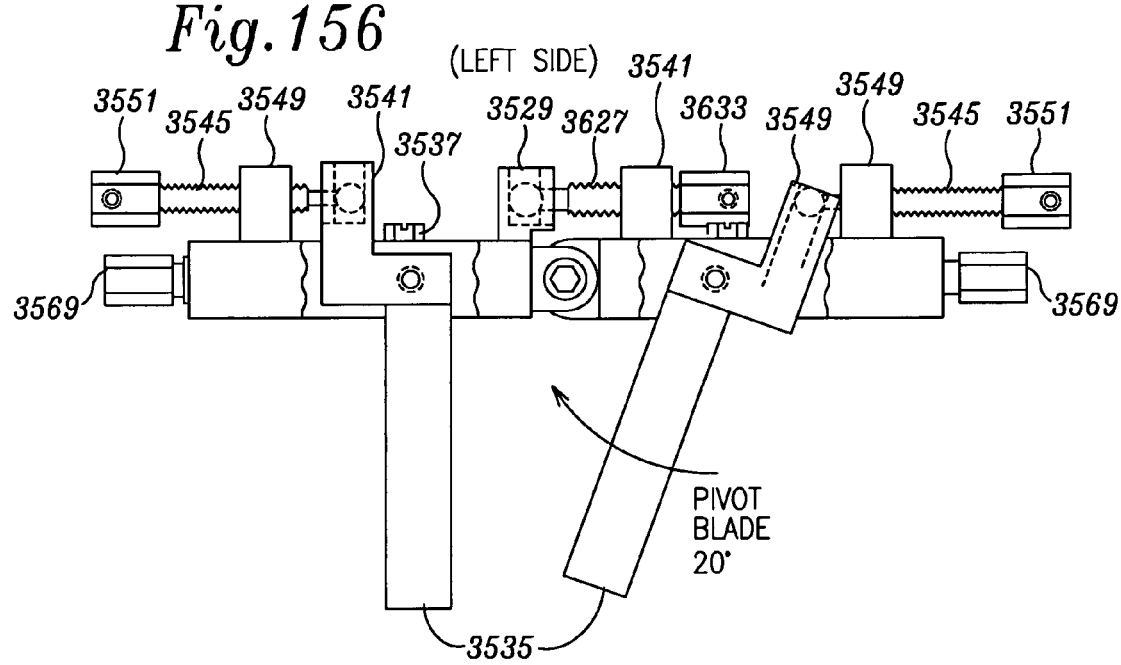
Figure 157:
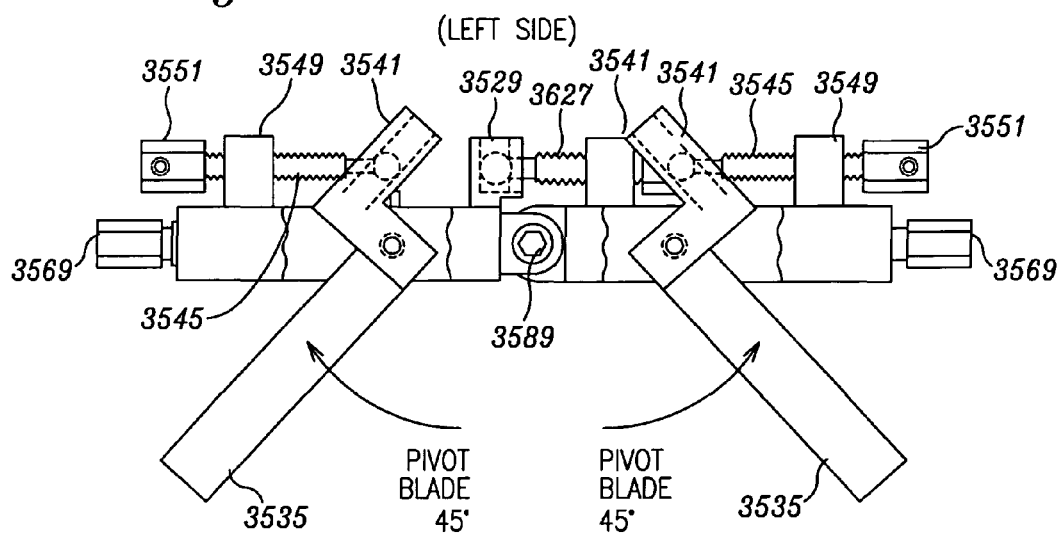
Figure 158:
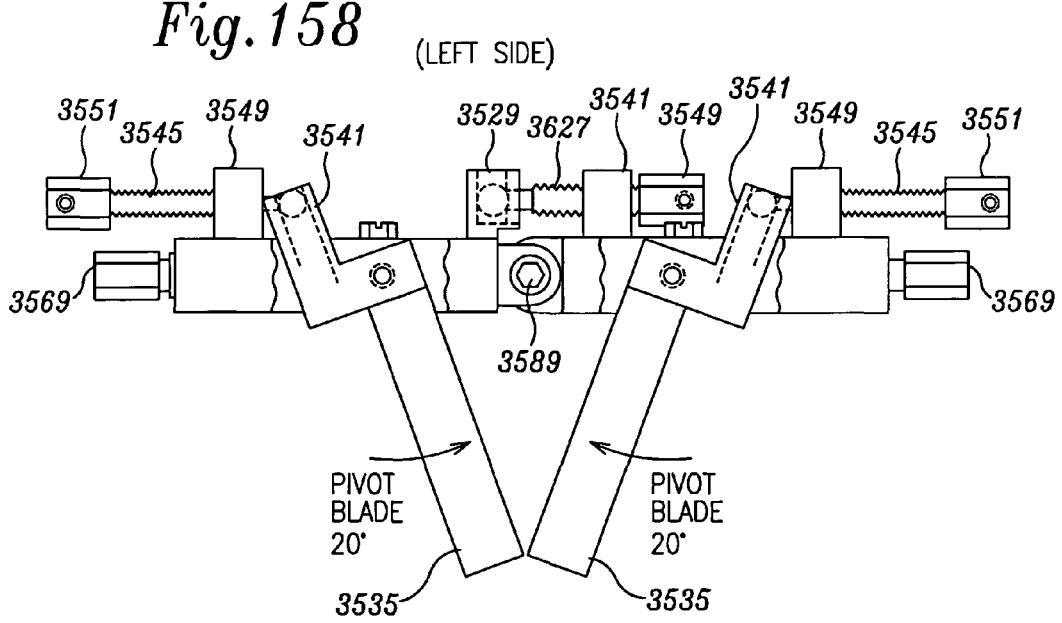
Figure 161:
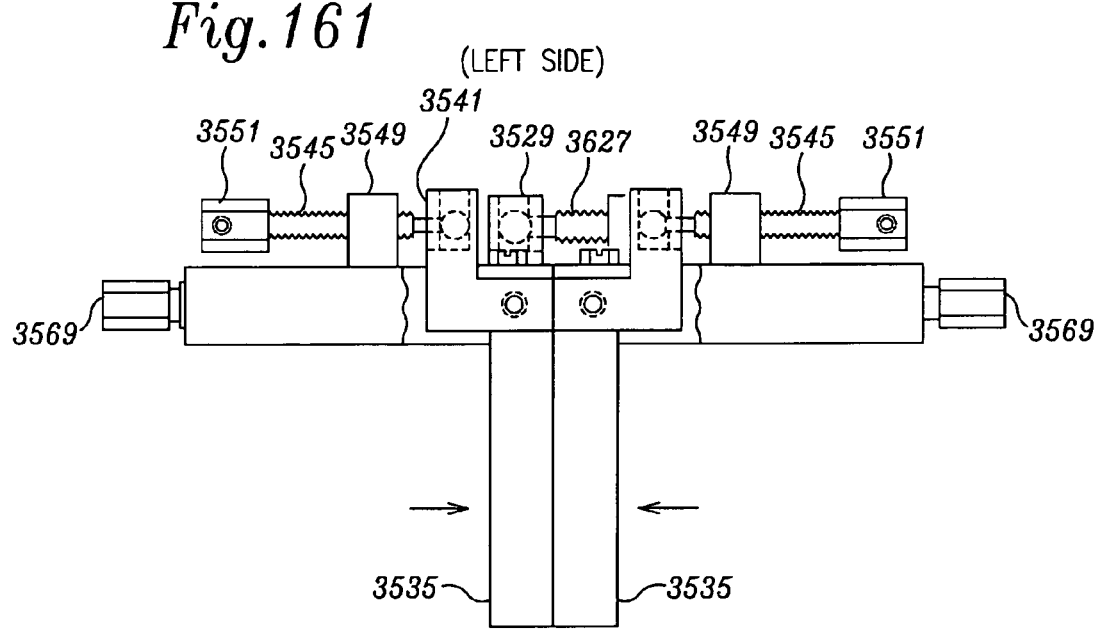
Figure 162:
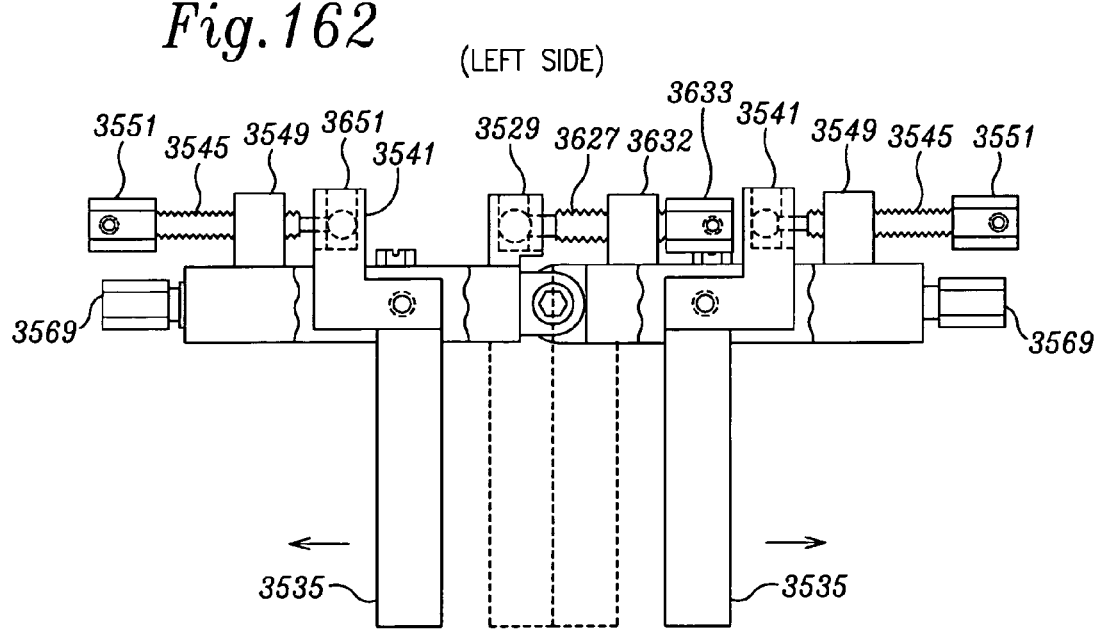
Figure 166:
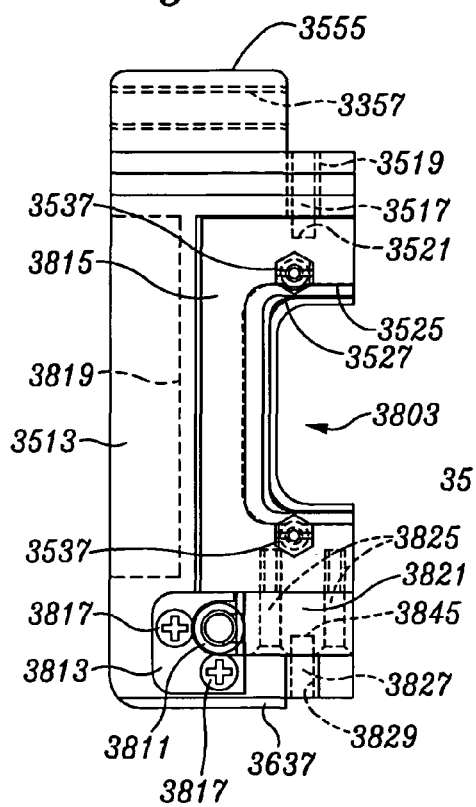
Figure 167:
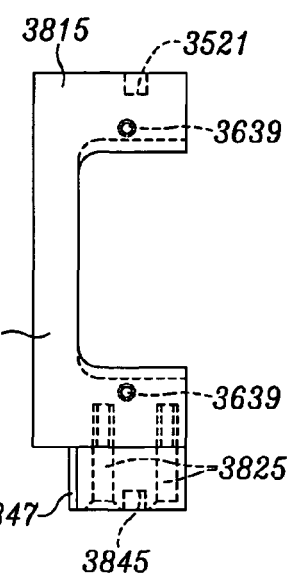
Figure 168:
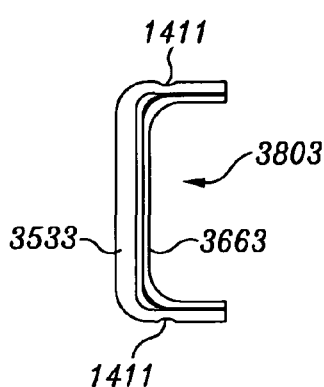
Figure 169:
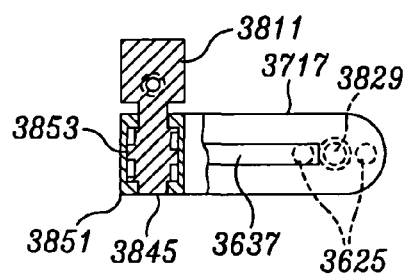
Figure 186:
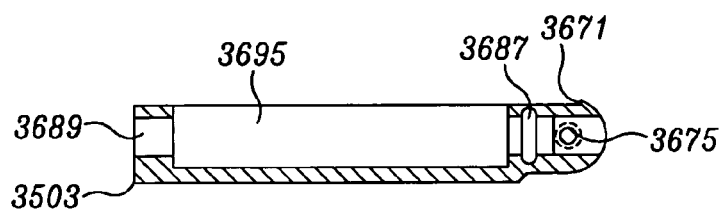
Figure 187:
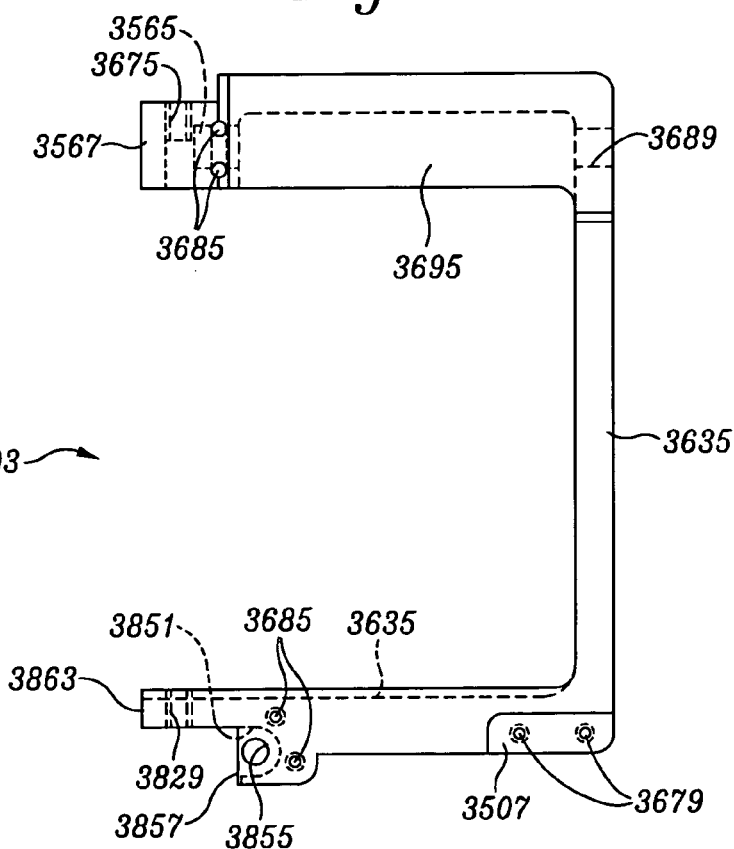
Figure 188:
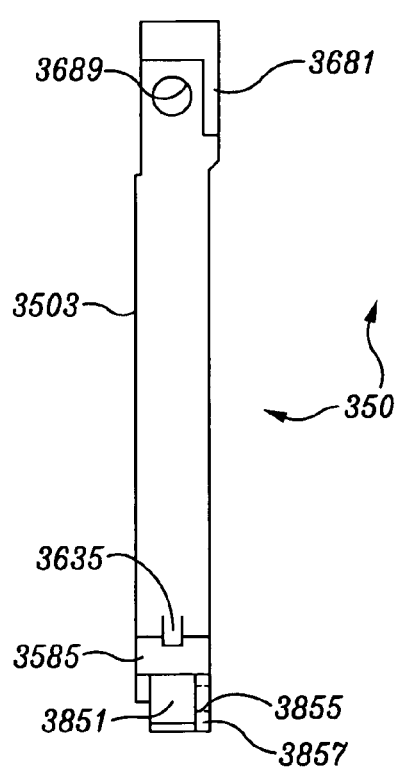
Figure 190:
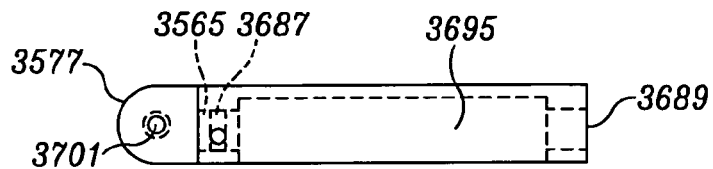
Figure 189:
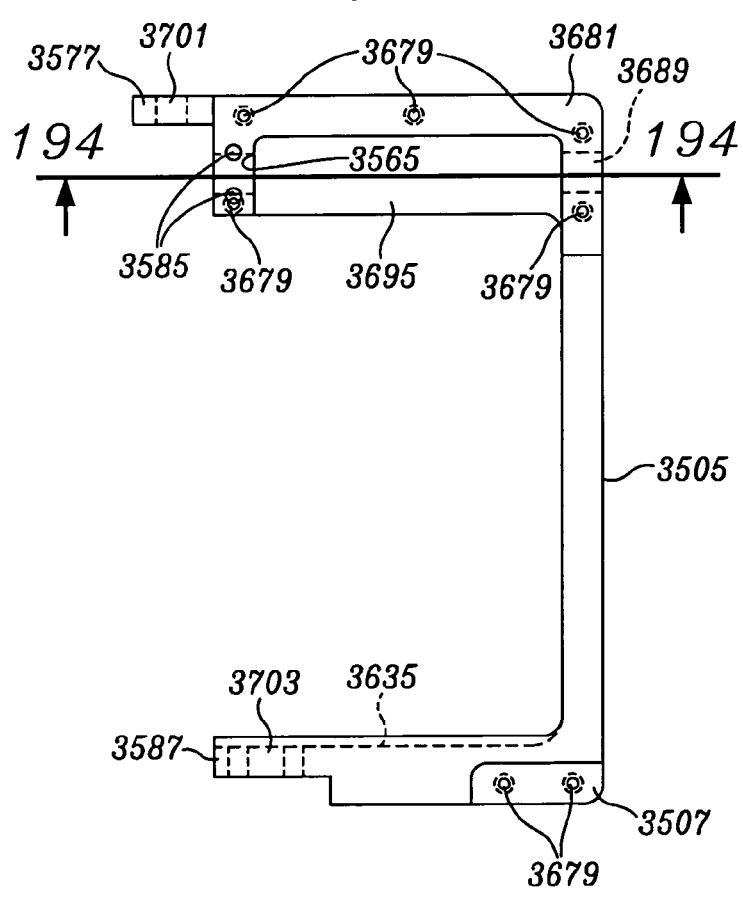
Figure 192:
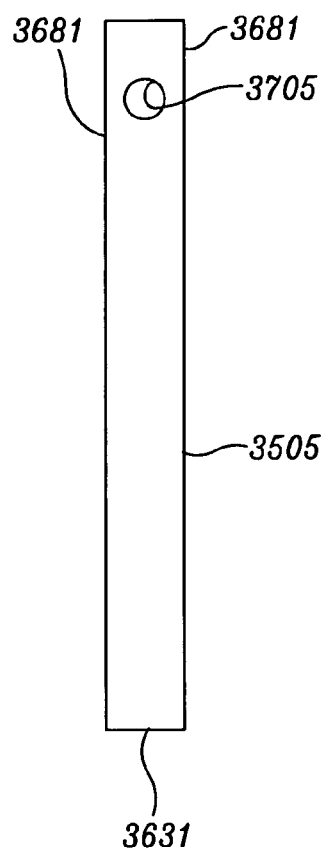
Figure 191:
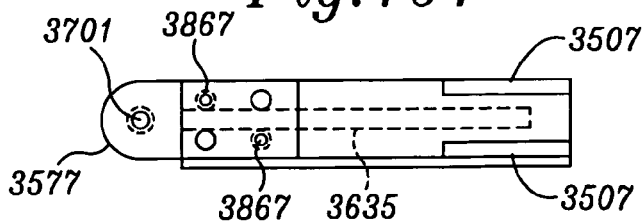
Figure 193:
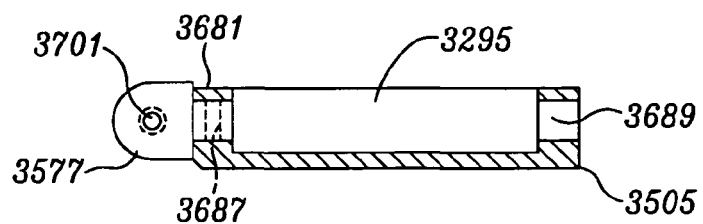
Figure 194:
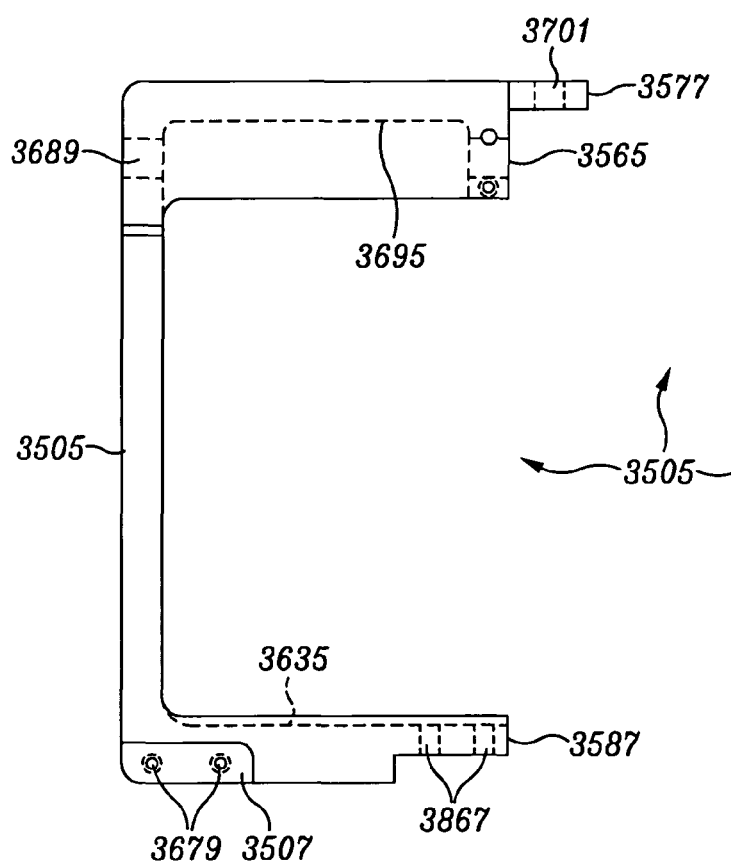
Figure 195:
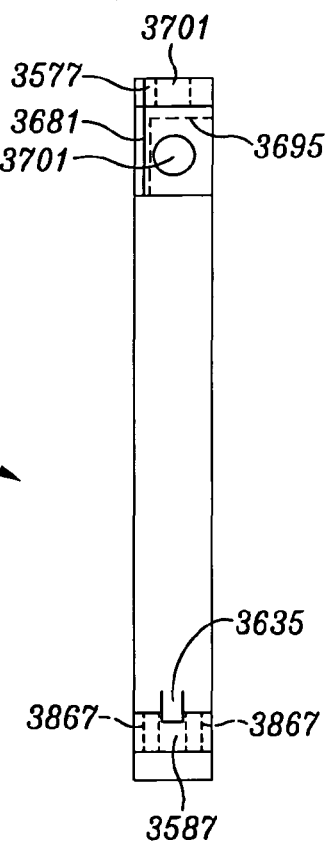
Figure 200:
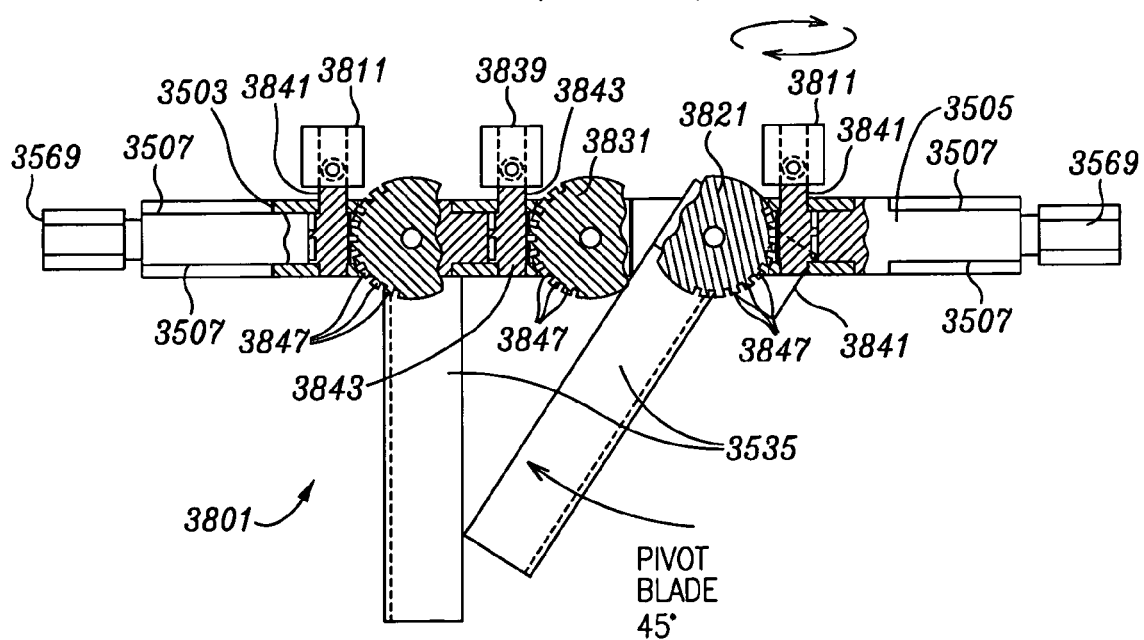
Figure 201:
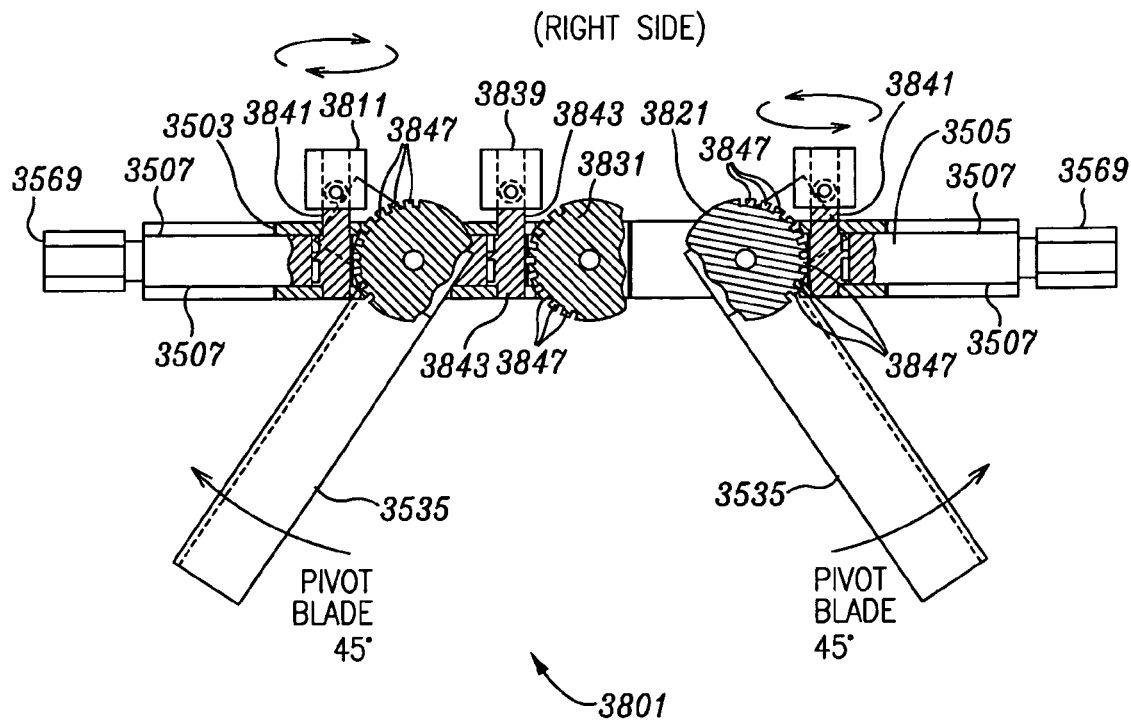
Figure 202:
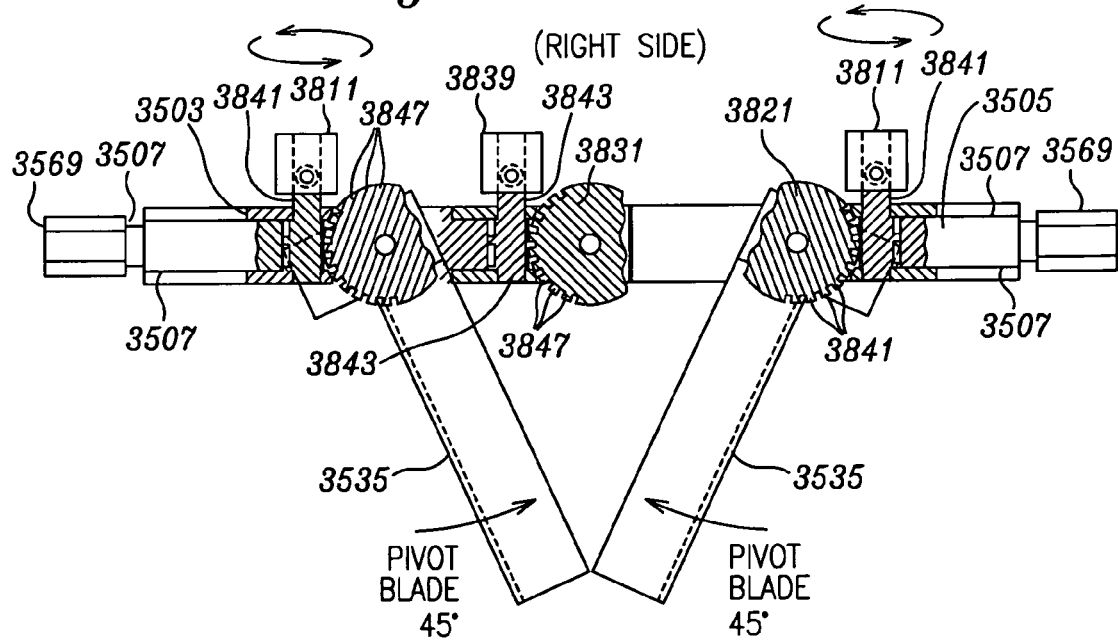
Figure 203:
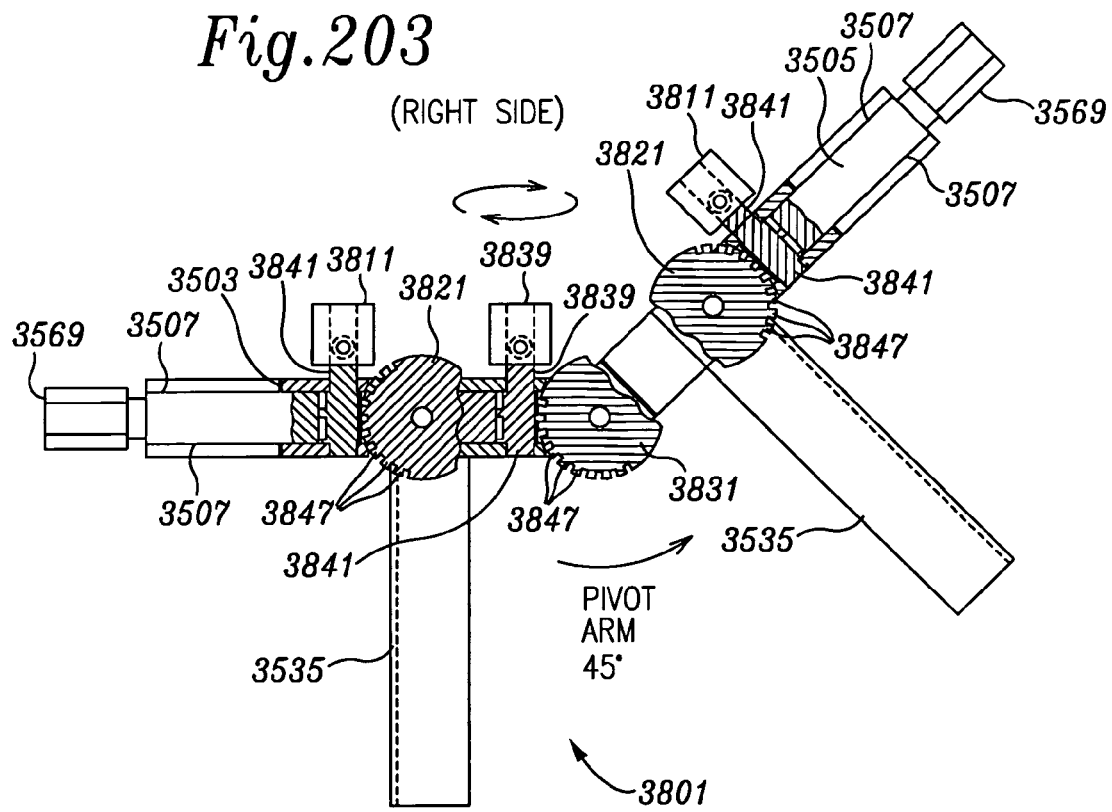
Figure 204:
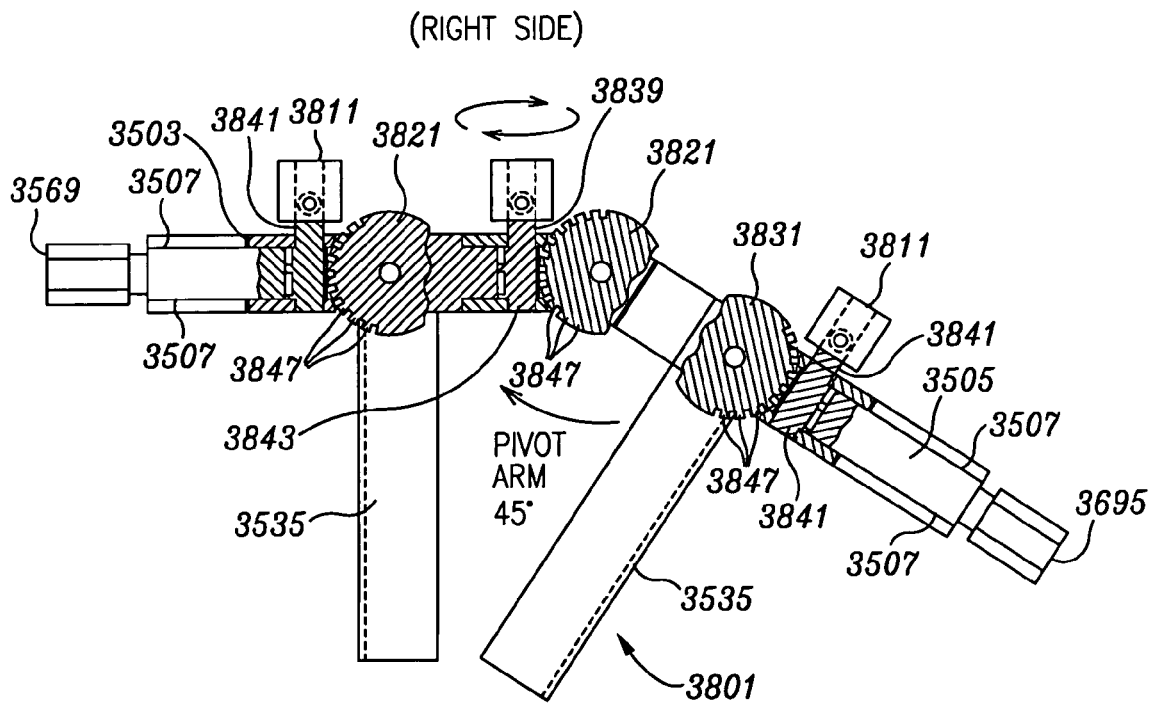
Figure 205:
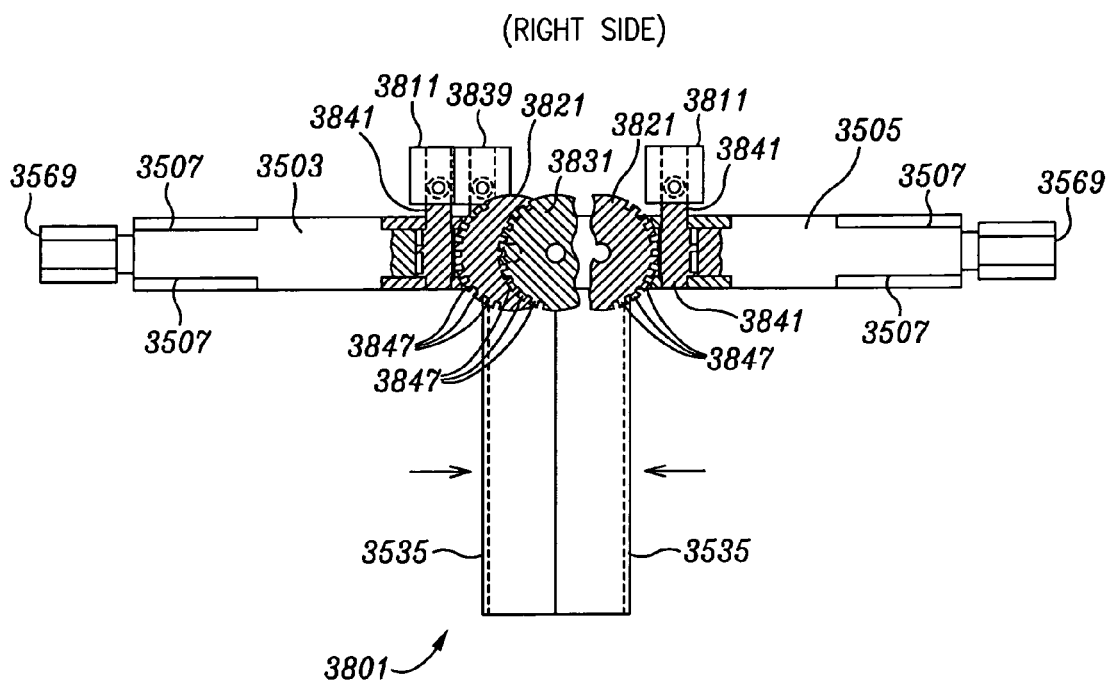
Figure 206:
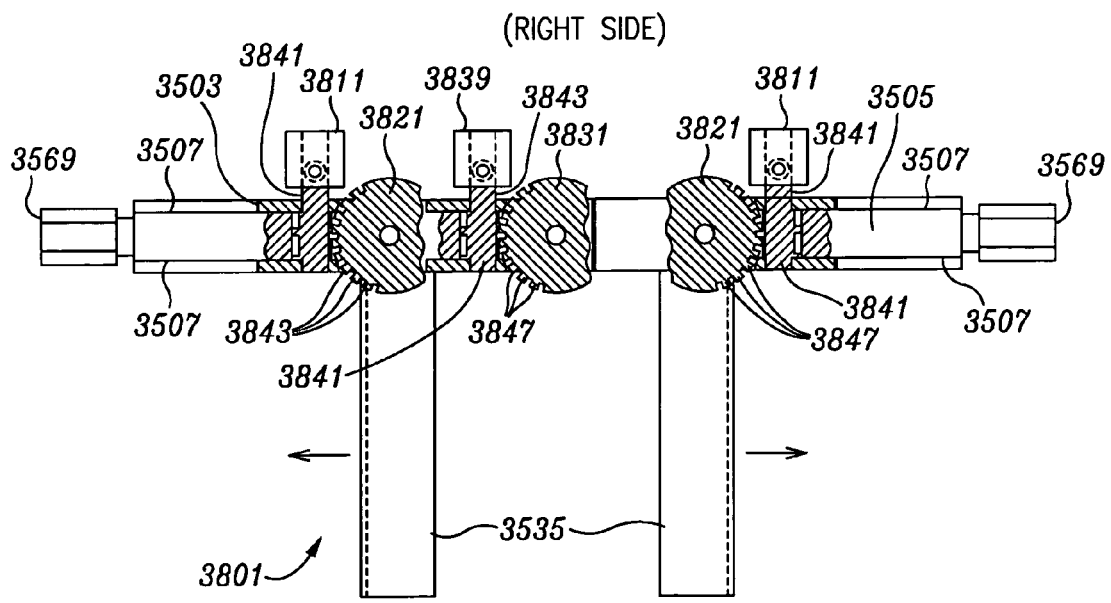

FIG. 131 illustrates a top view of a further embodiment of a frame retractor system;

FIG. 132 illustrates a bottom view of the embodiment of FIG. 131;

FIG. 133 illustrates a side sectional view taken along line 133-133 of FIG. 131 illustrates further details of the cover plate;

FIG. 134 illustrates an isolated view of the first inner translatable frame member shown with the first pivotable frame member in operative position;

FIG. 135 illustrates an isolated view of the pivotable frame member with the pins removed;

FIG. 136 illustrates a side view of the pivotable frame member with a more prominent view of the tongue structure;

FIG. 137 illustrates an isolated view of the first retractor half;

FIG. 138 illustrates an isolated view of an alternative embodiment of a first retractor half;

FIG. 139 illustrates an isolated view of first main frame member with components removed;

FIG. 140 illustrates a view looking into the top side of the first main frame member most adjacent the traveling space;

FIG. 141 illustrates a view looking into the main length of the first main frame member;

FIG. 142 illustrates a view looking into the side of the first main frame member most closely adjacent the rotational fitting block;

FIG. 143 illustrates a section taken along line 143-143 of FIG. 139;

FIG. 144 illustrates the underside of the first main frame member;

FIG. 145 illustrates a view looking into the main length of the first main frame member and looking into the terminal ends of the first main frame member;

FIG. 146 illustrates an isolated view of second main frame member section with its components removed;

FIG. 147 illustrates a view looking into the side of the second main frame member section most closely adjacent the traveling space;

FIG. 148 illustrates a view looking into the side of the second main frame member section most closely adjacent the rotational fitting block;

FIG. 149 illustrates a view looking into the main length of the second main frame member section;

FIG. 150 illustrates a section taken along line 150-150 of FIG. 146;

FIG. 151 illustrates the underside of the first main frame member;

FIG. 152 illustrates a view looking into the main length and two terminal ends of the second main frame member section;

FIG. 153 illustrates a side elevation view of the frame retractor system taken with respect to the bottom of FIG. 131;

FIG. 154 illustrates a side elevation view of the frame retractor system taken with respect to the top of FIG. 131;

FIG. 155 illustrates rotation of the tilt control knob into its bore to cause lower extension member to swing away from the other lower extension member;

FIG. 156 illustrates rotation of the knob back out of the threaded bore to causes the lower extension member to swing toward the other lower extension member;

FIG. 157 illustrates rotation of the tilt control knobs into their threaded bores to cause the lower extension members to angularly swing away from each other;

FIG. 158 illustrates the ability at least one of the lower extension members to angularly swing toward each other;

FIG. 159 illustrates that the a frame retractor system includes the ability for the first main frame member to form an angle with respect to the second main frame member section;

FIG. 160 illustrates that the a frame retractor system includes the ability for the first main frame member to form an angle in the opposite direction than shown in FIG. 159 with respect to the second main frame member section;

FIG. 161 illustrates that the a frame retractor system includes the ability for the lower extension members to come together in close parallel fashion to form a working tube;

FIG. 162 illustrates that the a frame retractor system includes the ability for the lower extension members to apart from each other in parallel fashion to widen the working space;

FIG. 163 illustrates a top plan view of a further embodiment of the frame retractor system in which the structures for controlling tilting which were provided as horizontal axis structures are replaced by vertical axis controls using worm gear sets;

FIG. 164 illustrates a view taken along line 164-164 of FIG. 163 and showing the frame retractor system taken from just inside the main extent of the first main frame member;

FIG. 165 illustrates a bottom view of the frame retractor system of FIG. 163;

FIG. 166 illustrates a top view of the inner translatable frame member with its pivotable frame member, the inner translatable frame member shown in isolation from the remainder of the frame retractor system of FIG. 163;

FIG. 167 illustrates a top view of the inner pivotable frame member, the inner translatable frame member shown in isolation from the remainder of the frame retractor system of FIG. 163;

FIG. 168 illustrates a top view in isolation of the thin top profile retractor half seen in the frame retractor system of FIG. 163;

FIG. 169 illustrates a semi-sectional view looking into the tongue structure of the inner translatable frame member;

FIG. 170 illustrates an isolated view of first inner translatable frame member of FIG. 163 with components removed;

FIG. 171 illustrates a view looking into the side of the first inner translatable frame member of FIG. 170;

FIG. 172 illustrates a view looking into the slide block end of the first inner translatable frame member of FIG. 170;

FIG. 173 illustrates a view looking into the tongue end of the first inner translatable frame member most closely adjacent the worm gear cavity;

FIG. 174 illustrates a view looking into the open side of the first inner translatable frame member of FIG. 170;

FIG. 175 illustrates a view looking into the bottom side of the first inner translatable frame member of FIG. 170;

FIG. 176 illustrates an isolated view of second inner translatable frame member of FIG. 163 with components removed;

FIG. 177 illustrates a view looking into the outside side of the first inner translatable frame member of FIG. 176;

FIG. 178 illustrates a view looking into the slide block end of the first inner translatable frame member of FIG. 176;

FIG. 179 illustrates a view looking into the tongue end of the first inner translatable frame member most closely adjacent the rotational fitting block;

FIG. 180 illustrates a view looking into the open side of the first inner translatable frame member of FIG. 176;

FIG. 181 illustrates a view looking into the bottom side of the first inner translatable frame member of FIG. 176;

FIG. 182 illustrates an isolated view of first main frame member of FIG. 163 with components removed;

FIG. 183 illustrates a view looking into the side of the first main frame member of FIG. 182 most closely adjacent the traveling space;

FIG. 184 illustrates a view looking into the main length of the first main frame member of FIG. 182;

FIG. 185 illustrates a view looking into the side of the first main frame member of FIG. 182 most closely adjacent the tongue end;

FIG. 186 illustrates a section taken along line 186-186 of FIG. 182;

FIG. 187 illustrates the underside of the first main frame member of FIG. 182;

FIG. 188 illustrates a view looking into the main length of the first main frame member of FIG. 182 but into the terminal ends;

FIG. 189 illustrates an isolated view of second main frame member section of FIG. 163 with its components removed;

FIG. 190 illustrates a view looking into the side of the second main frame member section of FIG. 189 most closely adjacent the traveling space;

FIG. 191 illustrates a view looking into the side of the second main frame member section of FIG. 189 most closely adjacent the inner groove shown in phantom;

FIG. 192 illustrates a view looking into the outside main length of the second main frame member section;

FIG. 193 illustrates a section taken along line 193-193 of FIG. 189;

FIG. 194 illustrates the underside of the first main frame member of FIG. 189;

FIG. 195 illustrates a view looking into the main length and two terminal ends of the second main frame member section of FIG. 189;

FIG. 196 illustrates a side elevation view of the frame retractor system taken with respect to the bottom of FIG. 163;

FIG. 197 illustrates a side elevation view of the frame retractor system similar to that seen in FIG. 196 but with a semi section taken through the worm gear engagement interfaces with the pivot gear plates and the outer frame gear plate controlled by the worm gears, and in which rotation of the right side knob causes the right extension member to move to the right;

FIG. 198 illustrates a side elevation view of the frame retractor system similar to that seen in FIG. 197 and in which rotation of the right side knob causes the right extension member to move to the left;

FIG. 199 illustrates rotation of the knob of the right tilt control causes the rotation gear plate to rotate to cause the lower extension member to swing away from the other lower extension member;

FIG. 200 illustrates rotation of the knob of the right tilt control in a direction opposite to the rotation in FIG. 199 causes the rotation gear plate to rotate to cause the lower extension member to swing toward the other lower extension member;

FIG. 201 illustrates rotation of the knob of the right and left tilt controls in opposite directions cause their rotation gear plates to rotate to cause the lower extension member to swing away from each other;

FIG. 202 illustrates rotation of the knob of the right and left tilt controls in opposite directions and oppositely with regard to FIG. 201 to cause their rotation gear plates to rotate to cause the lower extension member to swing toward from each other;

FIG. 203 illustrates rotation of the knob of the frame pivot control in a first direction to cause the second main frame member section to angle upward with respect to the first main frame member;

FIG. 204 illustrates rotation of the knob of the frame pivot control in a second direction to cause the second main frame member section to angle downward with respect to the first main frame member;

FIG. 205 illustrates rotation of the knobs controlling the slide blocks in a first direction to cause the slide blocks to move toward each other to bring the lower extension members, which are in a parallel relationship, to move toward each other;

FIG. 206 illustrates rotation of the knobs controlling the slide blocks in a second direction to cause the slide blocks to move away from each other to bring the lower extension members, which are in a parallel relationship, to move away from each other;

FIG. 207 is a bottom view of a guide and cover plate which fits over a portion of the left slide block of the first main frame member;

FIG. 208 is an end view of the guide and cover plate of FIG. 207;

FIG. 209 is a front view of the guide and cover plate of FIG. 207;

FIG. 210 is a top view of the guide and cover plate of FIG. 207;

FIG. 211 is a bottom view of a guide and cover plate which fits over a portion of the right slide block of the second main frame member;

FIG. 212 is an end view of the guide and cover plate of FIG. 211;

FIG. 213 is a front view of the guide and cover plate of FIG. 211; and

FIG. 214 is a top view of the guide and cover plate of FIG. 211.

DETAILED DESCRIPTION OF THE PREFERRED EMBODIMENT

The description and operation of the minimal incision maximal access system will be best described with reference to FIG. 1 and identifying a general system 31, although FIGS. 1, 2 & 3 should be referenced simultaneously. System 31 includes an obturator 33 and a working tube 35. The orientation of the obturator 33 is in a slightly displaced from a position of alignment with the working tube 35 for entry into working tube 35 and to provide the initial carefully controlled force for spreading the working tube 35, as will be shown.

Obturator includes an upper control housing 37 and a pair of spreading legs 39 and 41. The spreading legs 39 and 41 are seen as coming together to form a conical tip and thus have hemi-conical end portions. The spreading legs 39 and 41 over fit the attachment leg portions 43 and 45, respectively. At the top of the upper control housing 37 a boss 47 surrounds and supports the extension of a control shaft 49. A knurled thumb knob 50 sits atop the control shaft 49 to facilitate controlled turning of the control shaft 49 to control the degree of spreading of the spreading legs 39 and 41. Thus spreading can be controlled independently of pressure applied along the length of the obturator 33.

Below the upper control housing 37 is the bottom of the control shaft 49 which operates against a wedge 51. The wedge 51 operates within a pair of opposing slots 52 in an upper portion 53 of the overfit attachment leg portions 43 and 45. The lower ends of the overfit attachment leg portions 43 and 45 include insertion tangs 55 which fit within insertion slots 57 of the spreading legs 39 and 41. The overfit attachment leg portions 43 and 45 are pivotally attached to the upper control housing 37 internally by pivot blocks 59 which fit within access apertures 60.

The working tube 35 has a first lower extending connection tang 61 and a second lower extending connection tang 63. First lower extending connection tang 61 connects into a slot 64 of a lower tube curved portion 65. The first lower extending connection tang 61 is fixed to an upper angled curved portion 67. The second lower extending connection tang 63 connects into a slot 68 of a lower tube curved portion 69. Second lower extending connection tang 61 is fixed to and an upper angled curved portion 71. The upper angled curved portion 67 may have a reinforced wear plate 73 for applying upper pressure and force on the upper angled curved portions 67 and 71 toward each other to cause the first and second lower extending connection tangs 61 & 63 and their connected lower tube curved portions 65 and 69 to be urged away from each other.

At the side of the working tube 35 at the transition between the upper angled curved portions 67 and 71 and at a point just above the first and second lower extending connection tangs 61 & 63 is an external hinge assembly 77. Hinge assembly 77 may include an optional first guide plate 79 (seen in FIG. 2) and first circular protrusion 81 attached to upper angled curved portions 67, and a first slotted plate 83 positioned adjacent to first guide plate 79 and having a slot partially surrounding the circular protrusion 81.

Upper angled curved portion 71 has a pair of spaced apart facing surfaces facing a matching pair of facing surfaces of the upper angled curved portion 67, of which a dividing line 85 is seen. Upper angled curved portions 67 and 71 are be brought together to cause the first and second lower extending connection tangs 61 & 63 and their connected lower tube curved portions 65 and 69 to spread apart.

Figure 1:
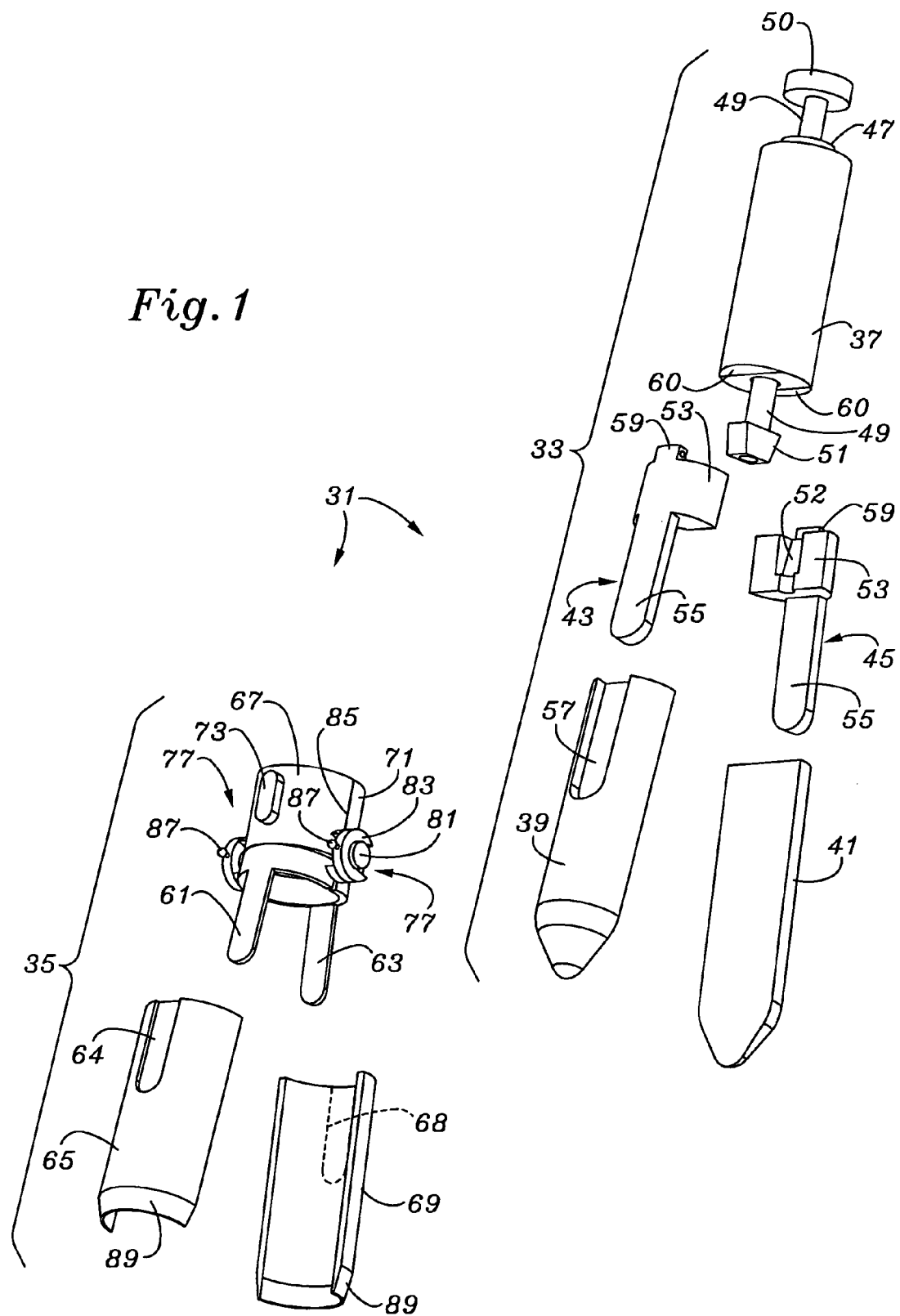
FIG. 1 is a perspective view of a working tube with an angled upper section and shown in position with respect to an obturator insertable into and workable within the working tube.

In the view of FIG. 1, the first and second lower extending connection tangs 61 & 63 are shown in a spread apart relationship. A locking pin 87 is seen which can be used to engage angularly spaced apart apertures in the circular protrusion 81 to provide a detent action to hold the working tube 35 in various degrees of spread. Also seen is a slight exterior bevel 89 on the lower tube curved portions 65 and 69.

Note the angled separation of the upper angled curved portions 67 and 71. The angle of the opposing surfaces (only opposing surface 91 is seen in FIGS. 2 & 3) equals the angle of spread of the first and second lower extending connection tangs 61 & 63.

Referring more closely to FIG. 2, a perspective assembled view illustrates the relative positions of the obturator 33 and working tube 35 in a position for the obturator 33 to be inserted into the working tube 35 and before any spreading takes place.

Referring to FIG. 3, a perspective assembled view illustrates the position of the obturator 33 after it has been inserted into the working tube 35 and again before any spreading takes place. Note that the pivot axes of the first and second lower extending connection tangs 61 & 63 are on par with the pivot axes of the insertion tangs 55. The tip of the obturator 33 extends slightly beyond the bottom most part of the working tube 35 so that the completed assembly can be smoothly urged past muscle and other tissue.

Referring to FIG. 4, a view taken along line 4-4 of FIG. 1 is a view looking down into the working tube 35. Other features seen include a wear plate 93 located on the upper angled curved portion 71. In both of the wear plates 73 and 93 a universal port 94 is provided as a bore for insertion of a tool or lever to assist in bringing the upper angled curved portions 67 and 71 into a tubular relationship. Further, an identical hinge assembly 77 on the side opposite that seen in FIG. 1 is shown with the same numbering as the components which were seen in FIG. 1.

Also seen are the pair of opposing surfaces 91 on upper angled curved portion 71 and a pair of opposing surfaces 97 on upper angled curved portion 67. Also seen is a central working aperture 99.

Referring to FIG. 5, a view taken along line 5-5 of FIG. 1 is a sectional view looking down into the working tube 35. The connectivity of the structures seen in FIG. 4 are emphasized including the connection of circular protrusion 81 to the upper angled curved portion 71, and the connection of first slotted plate 83 to upper angled curved portion 67, and which is indicated by the matching section lines. Further, an identical hinge assembly 77 on the side opposite that seen in FIG. 1 is shown with the same numbering as the components which were seen in FIG. 1.

Referring to FIG. 6, a view of one end of the working tube 35 illustrates predominantly the second angled half portion 63. Elements seen in FIGS. 1-3 are made more clear in FIGS. 6-11.

Referring to FIG. 7, a side sectional view taken along line 7-7 of FIG. 6 and shows the internal bearing pivot consisting of a slightly greater than hemispherical side bump projection 101 located on upper angled curved portion 71, and a slightly less than hemispherical side circular groove 103 located on upper angled curved portion 67. Also seen is the interconnect slots 64 and 68 as well as the first and second lower extending connection tangs 61 and 63. In the showing of FIG. 7 an external bevel 105 is utilized Referring to FIG. 8, a side semi-sectional view taken along line 8-8 of FIG. 5 illustrates the integral connectivity of circular protrusion 81 with the upper angled curved portion 71. Seen for the first time in isolation are a pair of pin apertures 107 for engaging the locking pin 87.

Figure 9:
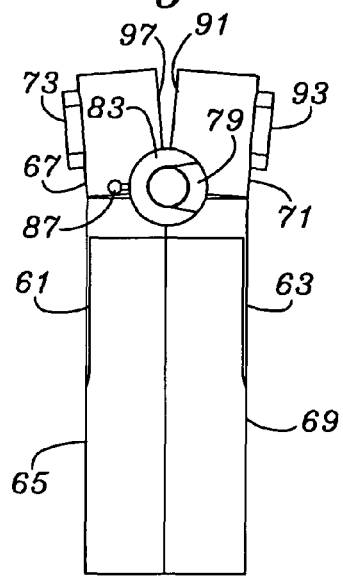
FIG. 9 is a side view of the working tube of FIGS. 1-8 shown with the lower portions in parallel alignment and the upper portions angled with respect to each other.

Referring to FIG. 9, an illustration of a side plan view and in which the lower tube curved portions 65 and 69 are in matching straight alignment and forming a lower tube shape, while the upper angled curved portions 67 and 71 are angled apart.

Figure 10:
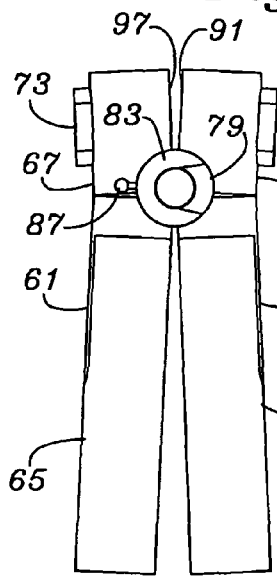
FIG. 10 is a side view of the working tube as seem in FIG. 9 and shown with the lower portions in an angled relationship and the upper portions in a closer angled relationship with respect to each other.

Referring to FIG. 10, a midpoint of movement is illustrates wherein the lower tube curved portions 65 and 69 have begun to move apart widening the lower tube shape previously formed into an angled apart opposing curved shape, while the upper angled curved portions 67 and 71 are brought closer together to have a closer though angled apart an angled apart opposing curved shape.

Figure 11:
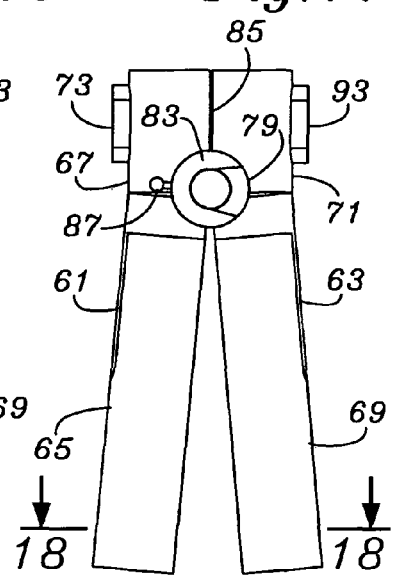
FIG. 11 is a side view of the working tube as seen in FIGS. 9 and 10 and shown with the lower portions in a maximally angled relationship and the upper portions in parallel alignment signaling maximal spread of the lower portions in bringing the upper portions into parallel alignment.

Referring to FIG. 11, a completed movement, with respect to the view of FIG. 4 illustrates a state where the lower tube curved portions 65 and 69 have moved apart to their maximum extent into a maximally angled apart opposing curved shape, while the upper angled curved portions 67 and 71 are brought completely together to form an upper tube shape. It is the position of FIG. 6 which is the ideal working position once the lower tube curved portions 65 and 69 are within the body, and provides an expanded working field at the base of the working tube 35. Surgical work is ideally performed through the upper, abbreviated axial length tube shape formed by the upper angled curved portions 67 and 71.

Figure 12:
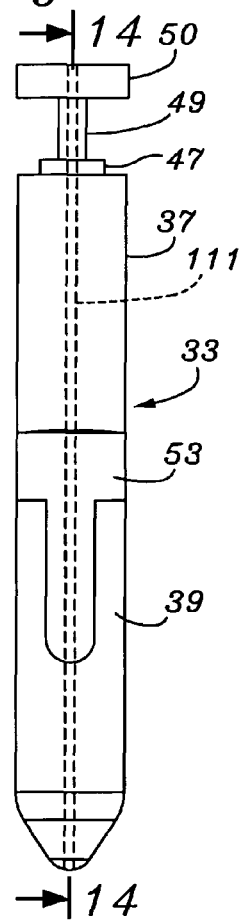
FIG. 12 is a side view of the obturator of FIG. 1 and seen in an assembled view and emphasizing a through bore seen in dashed line format.

Referring to FIG. 12, a side view of the obturator 33 of FIG. 1 is seen in an assembled view and emphasizing in dashed line format a through bore 111 which extends though the obturator 33 from the knurled knob 50 through to the tip of the pair of spreading legs 39 and 41 (leg 41 is not seen in FIG. 12.

Figure 13:
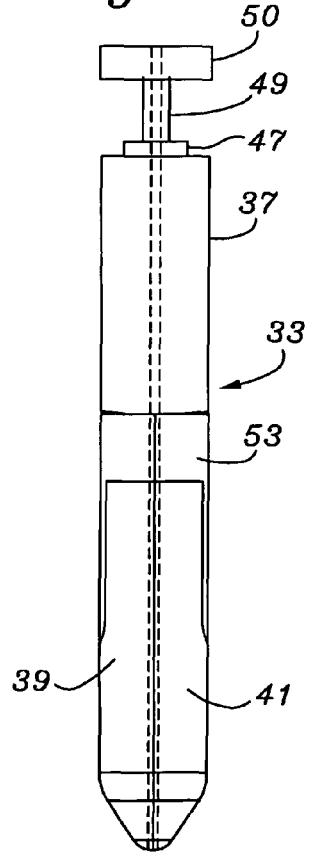
FIG. 13 is a side view of the obturator of FIG. 11 as seen in an assembled view but turned ninety degrees about its axis and emphasizing the through bore.

Referring to FIG. 13, a side view of the obturator 33 of FIG. 11 is seen in an assembled view but turned ninety degrees about its axis, and again emphasizing in dashed line format the through bore 111 which extends though the obturator 33 from the knurled knob 50 through to the tip of the pair of spreading legs 39 and 41. It is from this position that further actuation will be illustrated.

Figure 14:
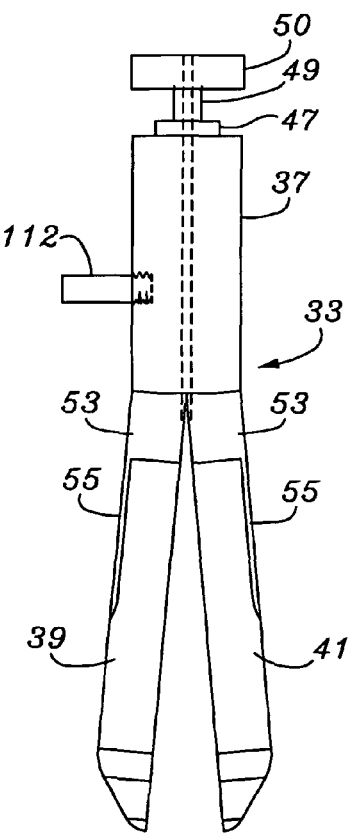
FIG. 14 shows a side view of the obturator 33 of FIG. 13 with the spreading legs in an angled apart relationship.

Referring to FIG. 14, a side view of the obturator 33 of FIG. 13 is seen but with the spreading legs 39 and 41 in an angled apart relationship. An optional support 112 is supported by the upper control housing 37 to enable independent support and location of the obturator 33 should it be needed. Once the knurled knob 50 is turned, the wedge 51 seen in FIG. 1 is driven downward causing the spreading of the spreading legs 39 and 41.

Referring to FIG. 15, a sectional view taken along line 14-14 of FIG. 12 gives a sectional view from the same perspective seen in FIG. 14. Pivot blocks 59 are seen as having pivot bores 113 which enable the upper portions 53 to pivot with respect to the upper control housing 37 and which enable the downward movement of the wedge 51 to translate into a spreading of the spreading legs 39 and 41.

As can be seen, the knob 50 and control shaft 49 and the wedge 51 have the through bore 111. In the configuration shown, the control shaft 49 includes a threaded portion 114 which engaged an internally threaded portion 115 of an internal bore 117 of the upper control housing 37. The boss 47 is shown to be part of a larger insert fitting within a larger fitted bore 119 within the upper control housing 37. This configuration pushes the wedge 51 downwardly against an internal wedge conforming space 123 to cause the insertion tangs 55 and upper portions 53 to spread apart. The wedge conforming space 123 need not be completely wedge shaped itself, but should ideally have a surface which continuously and evenly in terms of area engages the wedge 51 to give even control. Further, the wedge 51 can be configured to be rotatable with or independently rotationally stable with respect to the control shaft 49. As can be seen, the through bore 111 continues below the internal wedge conforming space 123 as a pair of curved surfaces 125 in the upper portion 53, as well as a pair of curved surfaces 127 in the pair of spreading legs 39 and 41.

Referring to FIG. 16 a view of obturator 33 similar to that of FIG. 15, but turned ninety degrees along its axis is seen. In this view, the wedge 51 is seen as having a narrower dimension to lend internal stability by narrowing the bearing area of the wedge 51 action in opening the pair of spreading legs 39 and 41.

Referring to FIG. 17, a closeup view of the external hinge assembly 77 seen in FIG. 1 illustrates the optional use of a plug 131 to cover the exposed side of the circular protrusion 81.

Referring to FIG. 18, a view taken along line 18-18 of FIG. 11 illustrates a view which facilitates the showing of an optional skirt, including a skirt section 133 welded or otherwise attached to lower tube curved portion 65, and a skirt section 135 welded or otherwise attached to lower tube curved portion 69. The skirts sections 133 and 135 are made of thin flexible metal and interfit within a pair of accommodation slots 137 and 139, respectively.

Referring to FIG. 19, a view of the lower tube curved portions 65 and 69 in a close relationship illustrates the manner in which the skirts sections 133 and 135 fit within the accommodation slots 137 and 139 when the lower tube curved portions 65 and 69 are brought together to a circular configuration.

Referring to FIG. 20, a cross sectional view of a patient 151 spine 153 is shown for illustration of the general sequence of steps taken for any procedure utilizing the minimal incision maximal access system 31. There are several procedures utilizable with the minimal incision maximal access system 31. Only a first procedure will be discussed using illustrative figures. Other procedures will be discussed after minor variations on the minimal incision maximal access system 31 are given below.

Procedure I: Diskectomy and Nerve Decompression

The patient 151 is placed prone on radiolucent operating table such as a Jackson Table. The patient 151 is then prepared and draped. The operative area is prepared and localized and an imaging device is prepared. A guide pin 155 is insert through the patient's skin 157, preferably under fluoroscopic guidance. The insertion of guide pin 155 into a patient determines a depth from a skin surface and establishes a correct level of surgery of said patient to a facet joint of said patient;

In the alternative and or in combination, the patient 151 skin can be incised with a scalpel. Other features in FIG. 20 include the dural sac 159, and ruptured intervertebral disc 161.

Referring to FIG. 21, a fascial incisor 169 over fits the guide pin 155 and is further inserted to cut through external and internal tissue. The fascial incisor 169 is then removed while the guide pin 155 is left in place. Next, using the obturator 33, the surgeon clears the multifidus attachment with wig-wag motion of the obturator 33 tip end. Next the obturator 33 is actuated to gently spread the multifidus muscle, and then closed.

Referring to FIG. 22, next the assembled Working Tube 35-Obturator 33 is inserted into the area previously occupied by the fascial incisor 169 and advanced to the operative level lamina and remove the obturator 33. As an alternative, and upon having difficulty, the obturator 33 could be initially inserted, followed by an overfit of the working tube 35. In another possibility, a smaller size of obturator 33 and working tube 35 or combination thereof could be initially utilized, followed by larger sizes of the same obturator 33 and working tube 35. The assembled Working Tube 35-Obturator 33 in place is shown in FIG. 22 with the working ends very near the spine. The working tube 35 may be held or stabilized in the field of view by a support 181 which may have an engagement sleeve 183 which fits onto the working tube.

Referring to FIG. 23, the obturator 33 is actuated to a spread orientation, which automatically actuates the working tube 35 to a spread orientation. Spread is had to the desired exposure size. The obturator 33 is thin actuated to a closed or non-spreading position. The obturator and working tube is then again advanced to dock on the spine. The working tube 35 is then fixed to assume an open position either by utilization of the locking pin 87 or other fixation device to cause the working tube 35 to remain open. Then, once the working tube 35 is locked into an open position, the obturator 33 is actuated to a closed or non-spread position and gently removed from the working tube 35.

Referring to FIG. 24, the working tube 35 is in place. The working tube 35 may be secured by structure ultimately attached to an operating table. As can be seen, the operative field adjacent the spine area is expended even though the incision area is limited. The deeper a given size of working tube 35 is inserted, the smaller its entrance area. After the working tube 35 is stabilized, the surgeon will typically clear the remaining multifidus remnant at the working level and then set up and insert an endoscope or use operating microscope or loupes. The surgeon is now ready to proceed with laminotomy.

Figure 25:
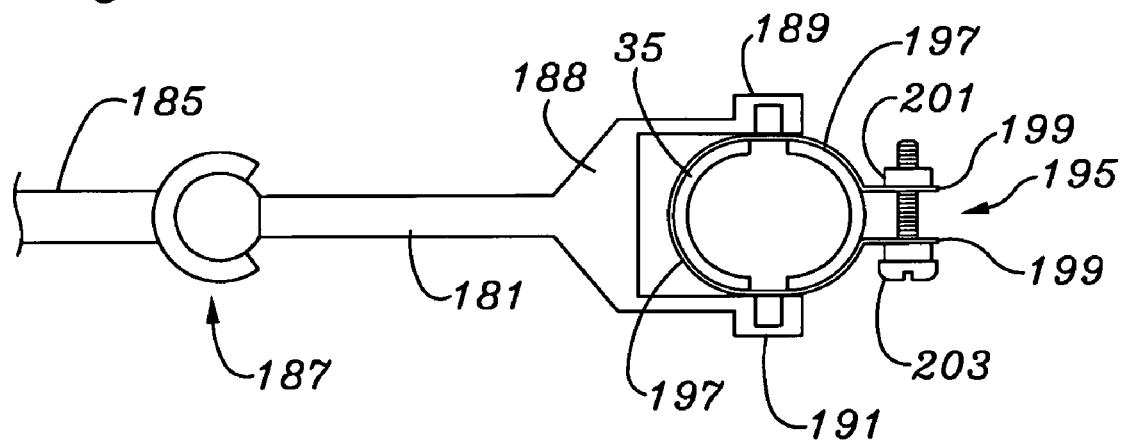
FIG. 25 illustrates further details of the support arm seen in FIG. 24, especially the use of a ball joint.

Referring to FIG. 25, further detail on the support 181 and engagement sleeve 183 is shown. A base support 185 may support a ball joint 187, which may in turn support the support 181. The support 181 is shown as supporting a variation on the engagement sleeve 183 as a pivot point support engagement end 188 having arm supports 189 and 191. The arm supports 189 and 191 engage the external pivot structure on the working tube 35 which was shown, for example, in FIG. 1 to be the external hinge assembly 77.

As a further possibility, the upper angled curved portions 67 and 71 are shown as being engaged about their outer periphery by an adjustable clamp 195. Adjustable clamp 195 includes a band 197 encircling the upper angled curved portions 67 and 71. The ends of band 197 form a pair of opposing plates 199 and are engaged by a nut 201 and bolt 203 assembly.

Figure 26:
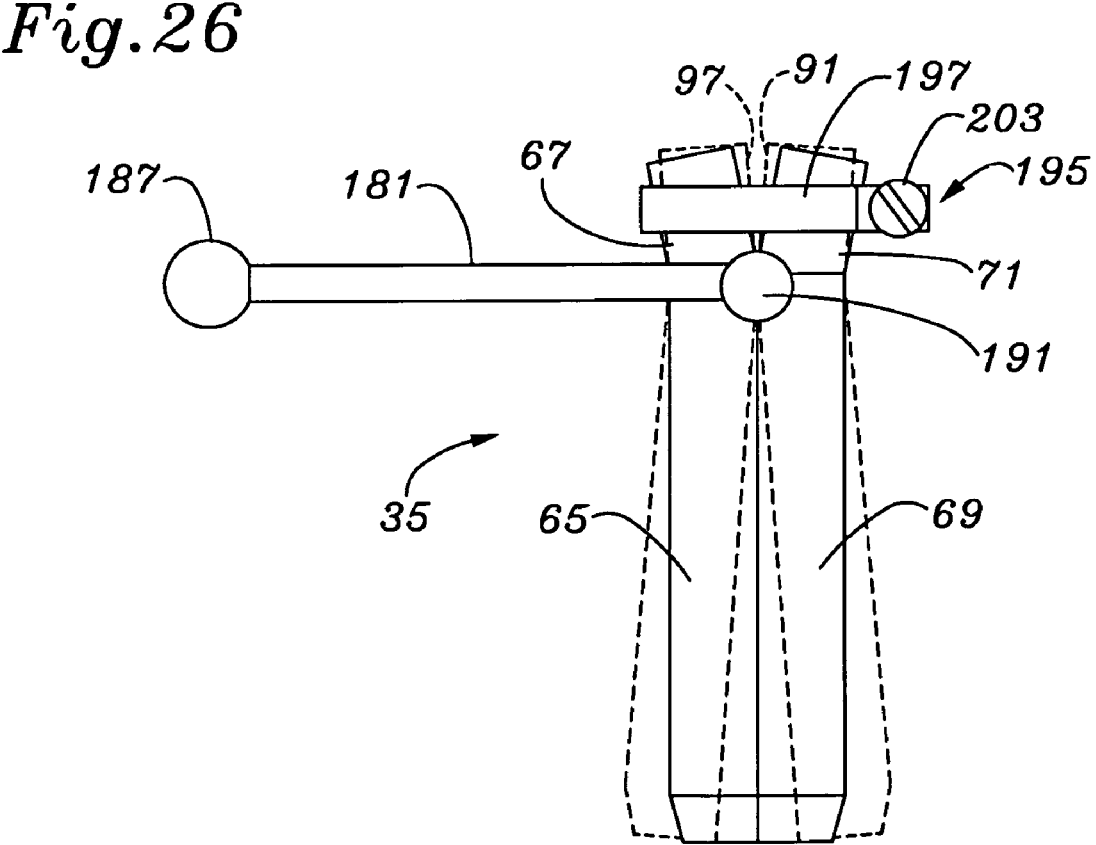
FIG. 26 illustrates a side view of the assembly seen in FIG. 25 is seen with an adjustable clamp operable to hold the working tube open at any position.
Figure 27:
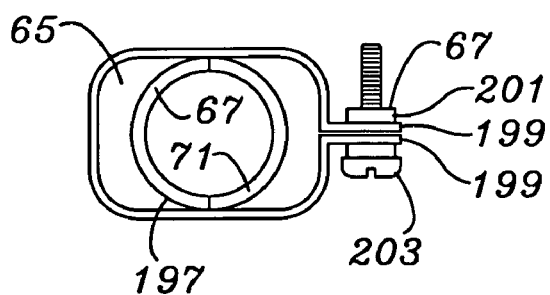
FIG. 27 is a top view looking down upon the adjustable clamp seen in FIGS. 25-26 and shows the orientation of the working tube and adjustable clamp in fully closed position.

Referring to FIG. 26, a side view of the assembly seen in FIG. 25 is seen with the adjustable clamp 195 operable to hold the working tube 35 open at any position. Referring to FIG. 27, a top view looking down upon the adjustable clamp 195 seen in FIGS. 25-27 shows the orientation of the working tube 35 and adjustable clamp 195 in fully closed position. When used in conjunction with the adjustable clamp 195, the Reinforced wear plates 73 and 93 are eliminated so as to provide a smooth interface against the exterior of the upper angled curved portions 67 and 71.

Figure 28:
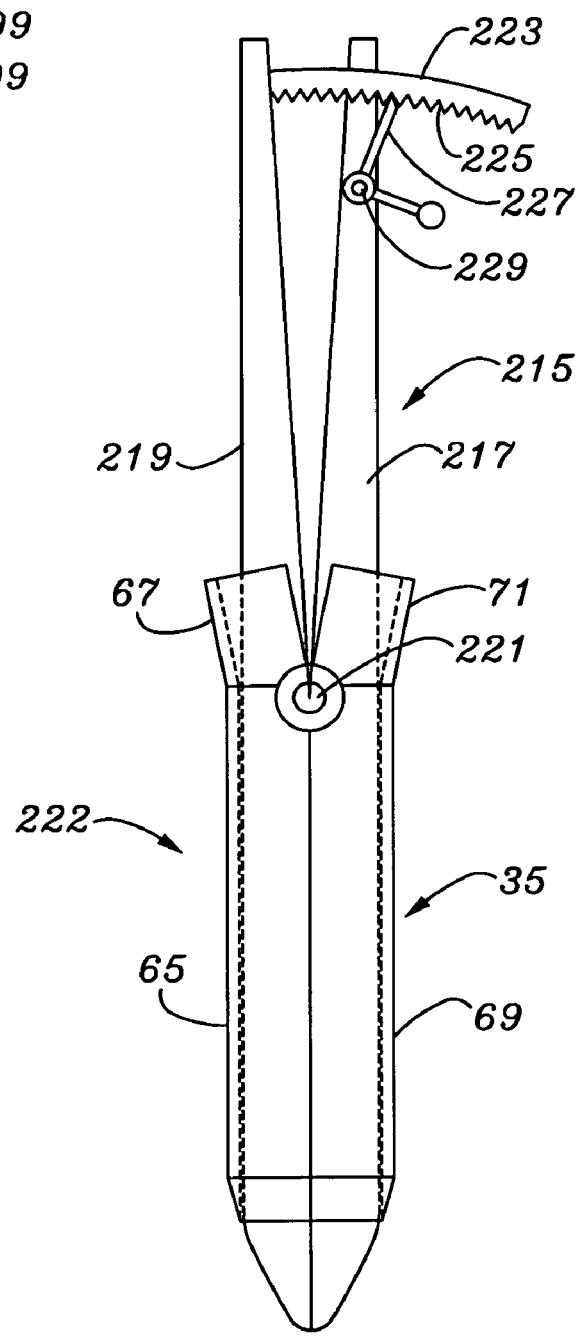
FIG. 28 shows a variation on the obturator seen previously in FIG. 1 and illustrates the use of handles which are brought together.

Referring to FIG. 28, a variation on the obturator 33 is seen. An obturator 215 has handles 217 and 219 which operate about a pivot point 221. A working tube 222 is somewhat simplified but is equivalent to the working tube 35 and is shown as including upper angled curved portions 67 and 71. Handle 219 has a ratchet member 223 extending from it and a latch 227 pivotally connected about pivot point 229 to handle 217.

Referring to FIG. 29, a variation on obturator 33 is seen as an obturator 241 having an upper housing 243, control shaft 245 having a threaded section 247 and operating through a ball nut 249. A wedge 251 is extendable down through an operation space made up of a half space 253 in a leg 255 and a half space 257 in a leg 259. Hinge structures 261 are shown attaching the legs 255 and 259 to the upper housing 243. A through bore 111 is also seen as extending from the knob 261 through to the bottom of the wedge 251. An access groove 263 is carried by the leg 259 while An access groove 263 is carried by the leg 259 while an access groove 265 is carried by the leg 255.

Referring to FIG. 30, a sectional view taken along line 30-30 of FIG. 29 illustrates the use of a central support block 271 to support the a central threaded surface 273 and the legs 255 and 259.

Referring to FIG. 31, a view of a thin, inset hinge 281 utilizable with any of the obturators, but particularly obturators 33 and 241, is shown. In the case of obturator 33, by way of example, upper portions 53 accommodate control shaft 49 with its through bore 111. Inset hinge 281 may be have an inset 283 and secured with machine screws 285. Inset hinge 281 may be made of a "living hinge" material such as a hard plastic, or it can have its operations base upon control bending of a pre-specified length of steel, since the angle of bend is slight. The connection between the upper portions 53 and the upper control housing 37 may be by any sort of interlocking mechanism, the aforementioned pivot blocks 59 or other mechanism.

Figure 32:
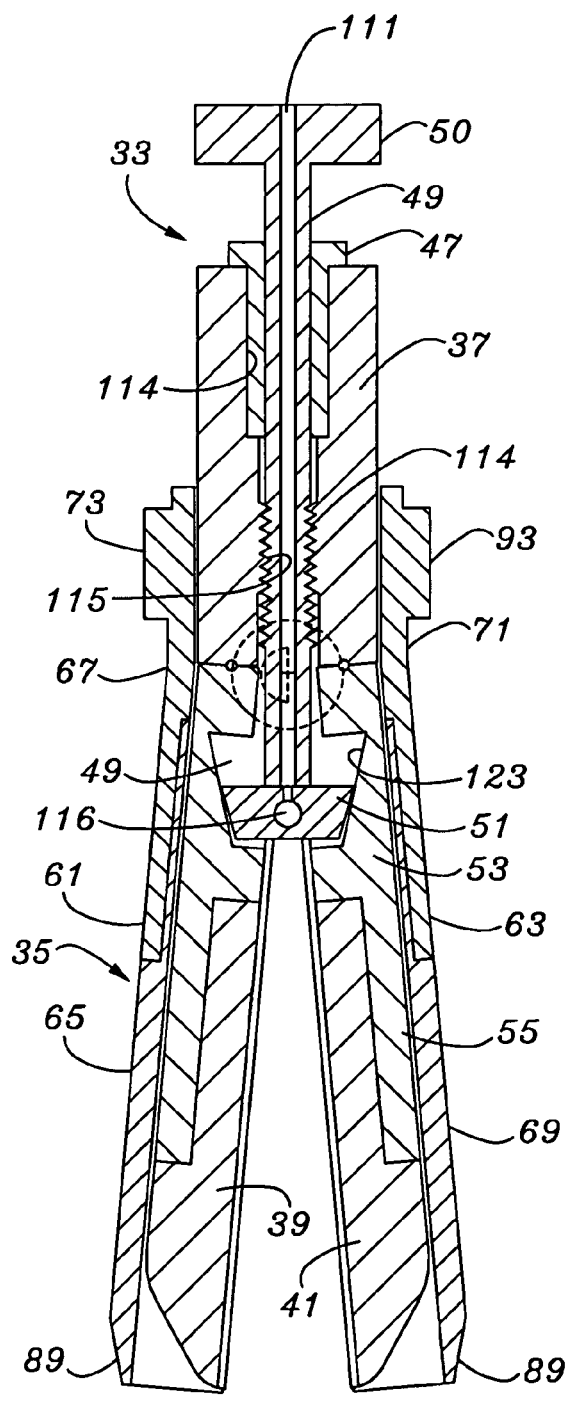
FIG. 32 is a sectional view of the obturator of FIG. 1 within the working tube of FIG. 1 with the wedge 51 seen at the bottom of an internal wedge conforming space.
Figure 33:
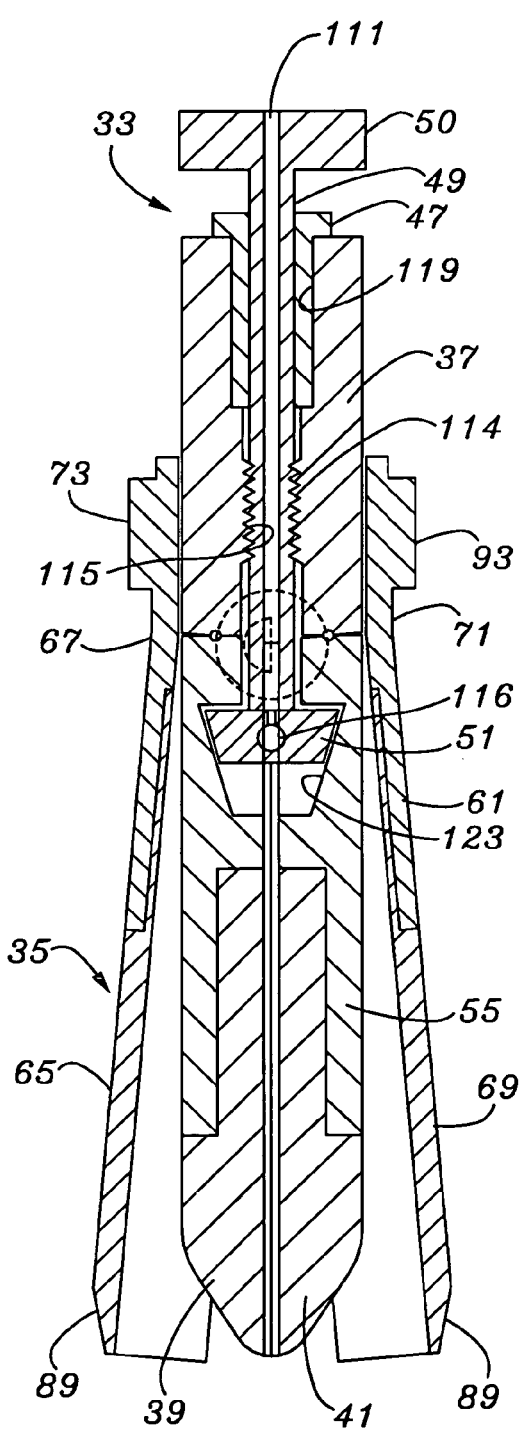
FIG. 33 illustrates the obturator seen in FIG. 32 as returned to its collapsed state.

Referring to FIG. 32, a sectional view of the obturator 33 within the working tube 35 is seen. The wedge 51 is seen at the bottom of the internal wedge conforming space 123. Once the spreading of the working tube 35 is accomplished the working tube 35 is kept open by any of the methods disclosed herein. Also seen is a pivot ball 116 to allow the control shaft 49 to turn with respect to the wedge. The pivot ball will continue to support a central aperture bore 111. Once the working tube 35 is stabilized in its open position, the obturator 33 is returned to its collapsed state as is shown in FIG. 33.

Provision of electro-mechanical power to the operation of the working tube 35 can provide a surgeon an additional degree of instant control. Referring to FIG. 34, a top and schematic view of the use of a remote power control to provide instant control of the working tube 25, similar to the view seen in FIG. 25 illustrates the use of a remote annular control cable 301 using an internal cable 303 which is closely attached using a guide 305 and which emerges from the guide 305 and circles the upper angled curved portion 67 and 71, terminating at an end fitting 307.

The annular cable 301 is controlled by a BATTERY MOTOR BOX 311 having a forward and reverse switch 313 (with off or non actuation being the middle position). This enables the surgeon to expand the surgical field as needed and to collapse the surgical field to focus on certain working areas. BATTERY MOTOR BOX 311 is configured with gears to cause the cable 303 to forcibly move axially within the annular cable 301 to transmit mechanical power to the working tube 35.

Referring to FIG. 35, a view taken along line 35-35 of FIG. 34 illustrates how the cable 303 is held in place and a closeup of the end termination 307.

Referring to FIG. 36, a mechanically operated version of the nut 201 and bolt 203 constriction band seen in FIG. 25. The mechanical power linkage can be provided remotely as by a rotating annular cable, but the basic mechanical setup shown illustrates the mechanical principles. On the bolt 203, a gear head 325 is placed, either by attachment or by the provision of a threaded member and gear head made together. A second gear head 327 is utilized to show the possibility of providing a right angle power take-off in the event that the power connection interferes with the area around the surgical field. A shaft 329 extends from a BATTERY MOTOR BOX 331. The BATTERY MOTOR BOX 331 has a forward and reverse switch 333, (with off or non actuation being the middle position). Shaft 329 could be flexible and connected directly into axial alignment with the threaded member of bolt 201 or an integrally formed threaded member.

Advantages Over Existing Surgical Techniques

In terms of general advantages, there are differences between the minimal incision maximal access system 31, and its components as described in all of the drawings herein (but which will be referred throughout herein simply as the minimal incision maximal access system 31, or simply system 31) and other devices and procedures.

1. With regard to the Traditional microdiskectomy technique, the minimal incision maximal access system 31 allows for at least the same, if not better visualization access of the operative field. System 31 offers the same 3-Dimensional work ability or, if preferred, an endoscope can be utilized. System 31 minimizes muscle injury with spread versus extensive cautery dissection. System 31 has clear advantage on the challenging obese and very large patient where the traditional microdiskectomy technique is almost impossible to be applied.
2. With regard to open pedicle screw insertion procedures, system 31 offers muscle approach minimizing muscle devascularization and denervation. The traditional approach had required at least one level proximal and one level distal additional exposure causing extensive muscle injury often leading to "fibrotic" muscle changes resulting in chronic painful and stiff lower back syndrome. System 31 offers the most direct approach to the pedicle entry point selecting the avascular plane between the longissimus and multifidus muscles.
3. With regard to the Sextant Procedure, system 31 offers clear advantage over the Sextant procedure. First, the system 31 offers a procedure which is not a blind pedicle screw technique. System 31 can be applied to larger and more obese patients in which the Sextant procedure cannot be utilized. In this procedure using system 31 oosterolateral fusion can be performed along with insertion of the pedicle screws. The sextant procedure is strictly a tension band stabilization.

In general, the components of the minimal incision maximal access system 31 are very simple the hemispherical shapes used for the working tube can be round or oval or flat. A keying system can be had to align the obturator 33 to the working tube 35. In the case of an oval system, the alignment would be automatic.

The minimal incision maximal access system 31 is a modular system with interchangeable parts for both the working tube 35 and the obturator 33. The guide Pin 155 is of simple construction, as is the fascial incisor 169. The working tube 35 has a limited number of basic parts, and can be made in the simple, two main piece version of FIG. 28, or the multi-piece version of FIG. 1, which enables retractor-sleeve substitution. A hinge and stabilization mechanism completes the simplified construction.

The obturator 33 is also of simple construction, with upper control housing 37, pair of spreading legs 39 and 41, and an internal hinge, whether the pivot blocks 59 or hinge 281 and its ability to support a control shaft 49 having a bore 111 for a guide pin 155. Guide pin 155 may preferably have a size of from about 0.3 mm to 0.40 mm diameter and 30 cm to 40 cm in length. The fascial incisor may preferably be cannulated for usage with the guide pin 155 and have a width of about 2 mm more than the associated retractor. The overall cutting head length of about 1.2 cm has a shape as indicated in the Figures and has a thickness slightly larger than that of the guide pin 155.

The working tube 35 can have several variations and added details including the simplest shapes as dictated by intended usage. Working tube 35 can have a simple fluted hemi-tube shape or a Slanted box shape. Further, the possibility of a fluted oval shape is dictated when the approach is more angular. The working tube 35 can have an attachment for an endoscope. Working tube 35 can also have a non-symmetric appearance as by having longitudinal cross sectional shape with half of its shape being rounded and one half of its shape being rectangular or box shaped. This could also give rise to a similarly shaped obturator 33. The working tube 35 should have an anti-reflective inner coating and may be of modular construction.

The preferred lower dimensions for the lower tube curved portions 65 and 69 include an overall shape which is semi tubular round or oval and having a width of from about 1.6-3.0 cm and a length of from about 4.0-18 cm. Curved portions 65 and 69 may have custom cut outs depending upon planned application.

The hinge assembly 77 may have male-female post or male-female dial lock design, as well as a hinge housing and a bias (by spring or other mechanism) to keep angular displaceable portions of the working tube 35 closed. a "universal" port provides a point of attachment of an endoscopic or stabilizer bar.

The obturator 33 may be any controlled opening device including a circular band or cable, force Plates, or a device attached to hinge assembly 77 or other hinge assembly.

All sleeve attachments including the attachable legs 39 and 41, as well as the lower tube curved portions 65 and 69 should be of the friction grip type or snap and lock type or other suitable connection method or structure.

Obturator 215 may have squeeze grip scissor style handles 219 and 217 and a controlled dilator. It may utilize an enclosed design with a handle cover having a no-slip surface. It may be attached to the hinge housing of the working tube or separate hinge housing. In fact, it may be of a design to be held in place solely by the working tube 35. Ideally a cavity will be provided through the center axis to contain the shaft for the dilator mechanism if applicable.

The central bore 111 of the obturator 33 may have a diameter of from about 5-10 mm, depending upon the size of the obturator 33 utilized. Obturator 33 should be provided in various widths and length to match working tube. The working tips of the spreading legs 39 and 41 may be changeable according to surgical procedures as described in the operative procedures herein. It may have an inner chamber, or internal wedge conforming space 123 slanted in shape wider proximal and more narrow distal to accommodate the wedge 51. The internal wedge conforming space 123 can be enclosed with expanding, contracting sleeve.

Other Procedures

Many other procedures can be facilitated with the use of the inventive minimal incision maximal access system 31 and methods practiced therewith. Procedure I, a diskectomy and nerve decompression procedure was described above with reference to the Figures. Other procedures are as follows:
Procedure II: Facet Fusion
 1. Patient prone on Jackson Table with normal lordosis preserved. This can be increased by placing additional thigh and chest support to increase lumbar lordosis.
 2. Insert percutaneous special guide pin perpendicular to the floor at a point 1 cm caudal to the Alar-Superior facet notch for determining depth from a skin surface and to establish a correct level of surgery of said patient to a facet joint of said patient.
 3. Apply a flag guide to a first guide pin 155 #1.
 4. Measure skin to bone depth from the scale on guide pin 155 #1.
 5. Slide drill guide mechanism on the flag guide to match the skin bone distance.
 6. Insert guide pin 155 #2 through the drill guide to dock on the superior facet.
 7. Make a small skin incision for the obturator 33.
 8. Working tube 35 should be small oval or round with medial cutout to maximally medialize the working tube 35.
 9. Advance the working tube 35 to the L5-S1 joint and dock.
 10. Drill the guide pin across the joint medial to lateral, rostral to caudal. If in proper position, advance across the joint to engage the ala.
 11. Drill across the joint with a cannulated drill.
 12. Check depth flouroscopically and measure.
 13. Pick appropriate screw length.
 14. Insert specially designed facet screw and protective bracket, secure tightly.
Procedure III: Posterior Lumbar Interbody Fusion (PLIF)
 1. First half of the procedure similar to microdiskectomy (Procedure I) except for the use of a larger diameter sized working tube 35. Use a 20-25 mm round or elliptical diameter working tube 35 with a medial cutout to allow docking as close to midline as possible.
 2. Following diskectomy enlarge the laminotomy to accommodate the tools use for the specific PLIF such as Brantigan cage or Tangent.
Procedure IV: Transfacet Interbody Fusion (TFIF)
 1. Follow the same procedure as the PLIF in terms of selecting and inserting the Working Tube 35.
 2. Following the diskectomy, resect the facet joint.
 3. Approach the posterolateral disc space through the medial ⅔ of the facet joint. Take care not to injure the exiting root above.
 4. Proceed with Brantigan cage instruments and interbody cages.
Procedure V: Pedicle Screw Instrumentation Technique
 1. Place the patient 151 Prone position on a Jackson Table.
 2. Guide pin 155 is docked on facet joint angled 30 degree lateral to medial in the plane between the longissimus muscle longitudinally and multifidus muscle medially.
 3. Make skin incision.
 4. Fascial incisor introduction.
 5. Introduce the obturator 33 working tube 35 assembly between the longissimus and multifidus and progressively open the obturator 33 tip ends of the legs 39 and 41, gradually reaching from the joint above and the joint below.
 6. Advance the working tube 35 and retract the obturator 33.
 7. Use the elliptical Working Tube size 2.5 cm wide and open up to 5 cm.
Procedure IV: Anterior Lateral Lumbar Diskectomy Fusion
 1. Mid lateral decubitus position left side up. Place a "waist roll" to prevent sag of the mid lumbar spine.
 2. Identify proper level of surgery fluoroscopically.
 3. Insert a guide pin 155 #1 percutaneously into the superior facet perpendicular to the spine.
 4. Measure depth skin to joint on the scaled guide pin 155 #1.
 5. Insert cannulated flag guide over guide pin 155 #1.
 6. Slide the drill guide to match the depth.
 7. Insert a guide pin 155 #2 down to the disc space.
 8. Make skin incision and insert fascial cover.
 9. Insert the working tube 35 and Obturator 33 combination.
 10. Progressively dilate the obturator 33.
 11. Advance the working tube 35.
 12. Perform anterolateral diskectomy and interbody fusion as taught above.
 13. Use a round or oval shaped retractor or lower tube curved portion 65 and 69 as inserts preferably with distal end cutouts in each.
Procedure VII: Posterior Cervical Foramenotomy and Lateral Mass Plating
 1. The patient is placed in a prone position on a Jackson table.
 2. Fluoroscopic identification of the level of surgery is had.

3. Percutaneously insert guide pin 155 with AP and lateral fluoroscopic views.

4. Make the initial skin incision.

5. Apply the working tube 35 with obturator 33 into the incision.

6. Perform slow dilation of the muscle.

7. Advance the working tube 35 and collapse and remove the obturator 33.

8. Proceed with surgery. Type of sleeve or lower tube curved portion 65 should be round or oval with slanted and to match the slanted lamina.

9. For application for Lateral mass plating use an oval working tube 35 for a greater exposure.

Procedure VIII: Anterior Cervical Diskectomy Fusion

1. Begin with standard anterior cervical diskectomy fusion approach with a incision on the left or right side of the neck.

2. Blunt finger dissection is performed between the lateral vascular structures and the medial strap muscle and visceral structures down to the prevertebral fascia.

3. Establish the correct level to be operated on fluoroscopically and the guide pin 155 inserted into the disc.

4. Apply the working tube 35 and obturator 33 combination and dock at the proper level of the anterior spring.

5. Open the working tube 35 and obturator 33.

6. Mobilize longus colli muscle.

7. Use special Bent Homen Retractor specifically design to retract the longus colli.

8. Proceed with surgery.

Procedure IX: Anterior Lumbar Interbody Fusion

1. Begin with the standard approach whether it is retroperitoneal, transperitoneal or laparoscopic.

2. Apply the special anterior lumbar interbody fusion working tube 35 and obturator 33. This is a design with a medial lateral opening. It is oval shape and preferably with skirts 133 and 135. The distal end of the retractor blade is slightly flared outward to retract the vessels safely. There is a skirt 133 or 135 applied to the cephalad side and possibly to the caudal side.

3. With the vessels and the abdominal contents safely retracted out of harms way, proceed with diskectomy and fusion.

Procedure X: Method of Midline Incision MIS Transforamenal Lumbar Interbody Fusion (TLIF) Spine Surgery 1. Insert a guide pin 155 and C/arm to localize level of intended surgery;

2. Make midline skin incision equivalent to one and a half times the length of a MIS unilateral paraspinous skin incision;

3. Circumferentially dissect the subcutaneous tissue plane for a distance of about three centimeters from the midline;

4. Make paraspinous fascial incision approximately two centimeters from the midline;

5. Dissect the plane between at least one of the longissimus muscle laterally and the multifidus muscle medially;

6. Mobilize at least one of the longissimus muscle and the multifidus muscle adequate to expose the lamina, facet joints, and transverse processes to the length of the intended surgery;

7. Apply MIS retractor and deploy to expose the operative field as required;

8. Proceed with MIS TLIF and instrumentation insertion;

9. Repeat steps 1-7 on the opposite side for insertion of internal fixation.

Procedure X has the advantage of having a shorter incision length than the additive incision length of a bilateral exposure. It also preserves the vascularity of the lumbar skin in the event that an open larger procedure is required with a midline incision.

One of the aspects emphasized up to this point for the system 31 is structure and circumstance to minimize the upper entry point of the surgery while providing an expanded working area at the distal end of the tube. Structures which achieve this geometry have been shown, and include a flared upper end so that the aperture remains open regardless of the angle of spread.

In other applications it is permissible to expand the aperture opening at the top of the working sleeve assembly. Expansion can be for the purposes of introducing further working devices into the working tube, as well as to expand and protect the visual field. For example, further working devices may include implant tools and their held implants, tools to insert plates and screws, and tools to manipulate all of these into their final positions.

Visual field protection can be introduced where the surrounding tissue may tend to flow, move or obstruct the surgical working field. Where the bottom-most portions of the spread apart curved tube are spread apart, tissue tends to enter the space between the bottom parts of the tube. Additional guarding structure needs to be introduced.

A description of the desired articulation of what is hereinafter referred to as a working tube assembly 417, and including the working tube curved portions is begun with respect to FIG. 37. The designation of working tube assembly 417 refers to all of the tube structures seen in the earlier FIGS. 1-36 and as seen in any of the following Figures.

FIG. 37 is an isolated view of two curved tube sections shown joined in a tubular relationship and indicating at least a pair of pivot axes on each curved tube section.

At the top of the structure shown in FIG. 37 a dashed line indicates an optional fluted structure 419. Fluted structure is omitted from the drawings for FIGS. 37-49 in order that the views from the top will not be obscured. The optional fluted opening 419 and is often employed both to maintain the visual field upon opening, as well as to make it easier to add instrumentation into the surgical field. This structure is recommended, as well as all reasonable accommodation to facilitate its use.

a first curved tube 421 is shown in alignment with a second curved tube 423. Rather than having the upper ends flared out to maintain a circular visual field on a full open position, a clearance notch 425 is provided in first curved tube 421, while a clearance notch 427 is provided in second curved tube 423.

The lowermost extent of the clearance notches 425 and 427 coincide with an upper pivot axis 431 of first curved tube 421 and upper pivot axis 433 of first curved tube 421. The pivot axes 431 and 433 may include supports either derived from structures going into or out of the first and second curved tubes 421 and 423. In the view of FIGS. 37-39, the structures seen facing the viewer are repeated on the opposite side. Thus, pivot axes 431 and 433 are also located on the side opposite that seen in FIGS. 37-39. The same is true for all of the numbered structures. In this position, the simultaneous pivoting about the pivot axes 431 and 433 of the first and second curved tubes 421 and 423 will not cause interference by portions of the first and second curved tubes 421 and 423 which would otherwise interfere.

Further, a lower pivot axis 435 is provided below the upper pivot axis 431 of first curved tube 421. Similarly, a lower pivot axis 437 is provided below the upper pivot axis 433 of second curved tube 423. Pivot axes 441, 433, 435 and 437 may also be expected to translate. The geometry and pivot points having been identified, double headed arrows illustrate that the pivot points should be able to move toward and away from each other. Ideally, the only limitation should be the interference from the lower ends of the first and second curved tubes 421 and 423 with each other. Where the mechanism for moving the first and second curved tubes 421 and 423 has maximum independence, secondary considerations of interference are eliminated and only the primary interference between the first and second curved tubes 421 and 423 will remain. Where the control mechanism for movement is lesser than that which allows maximum independence, savings can be had in terms of complexity of the mechanism at the expense of the freedom of movement.

FIG. 37 illustrates the first and second curved tubes 421 and 423 in a closely aligned relationship where the upper pivot axis 431 is closest to the upper pivot axis 433 and where the lower pivot axis 435 is closest to the lower pivot axis 437. This is the position expected to be used for entry into the body of the patient, especially along with a guide (to be shown) which will be located within and extending below the assembled and parallel linear tube formed by first and second curved tubes 421 and 423 to provide a reduced insertion resistance.

Ideally, the first and second curved tubes 421 and 423 will be inserted as shown in FIG. 37 and then manipulated to a position shown in FIG. 38. FIG. 38 is an isolated view of two curved tube sections as seen in FIG. 38 which are angularly displaced apart about a shared first pivot axis on each of the curved tube sections. The position in FIG. 38 is characterized by the fact that upper pivot axes 431 and 433 have the same separation as seen in FIG. 37, but in which the lower pivot axes 435 and 437 have moved apart. The position seen in FIG. 38 will be likely achieved just after insertion and in which the internal tissues have been pushed apart. Depending upon the surgical procedure, the first and second curved tubes 421 and 423 will be chosen based upon length, so that the lower end will be at the correct height for the tissues to be viewed, manipulated and treated. The action can continue until the lower ends of the first and second curved tubes 421 and 423 are sufficiently spaced apart for view and manipulation of the tissues between and adjacent the lower ends. If there is a sufficient viewing opening based upon the original distance of separation of the upper pivot axes 431 and 433, the procedure may continue through an aperture about the same size of the tube shape seen in FIG. 37.

Where more of an opening is needed, the first and second curved tubes 421 and 423 upper pivot axes 431 and 433 can move more widely apart until a position such as that seen in FIG. 39 is achieved. FIG. 39 is an isolated view of the two first and second curved tubes 421 and 423 which are angularly displaced apart about a shared second pivot axis on each of the curved tube sections. It should be emphasized that the position seen in FIG. 39 is a position where both the first and second curved tubes 421 and 423 are parallel and separated from each other, but this need not be the case. From the position seen in FIG. 38, the upper pivot axes 431 and 433 can be moved apart from each other while the lower pivot axes 435 and 437 either remain a constant distance from each other or are brought together. This range of articulation described can be used to physically manipulates the tissues in contact with the first and second curved tubes 421 and 423 for any number of reasons, including introduction of further instruments if necessary, as well as to react to changing conditions of tissue at the lower tube.

In both FIGS. 38 and 39 a pair of opposing edges 439 can be utilized to support structures introduced between the first and second curved tubes 421 and 423. Other structures can be used including depressions, apertures and internal projections, such as hooks or latches. An internal structure within the first and second curved tubes 421 and 423 would pose little risk of nick to the patient and can be designed to do nothing more than have a minimal interference effect with respect to the visual field.

As will be shown, a number of external structures can be employed to achieve the relative separation positions of the upper pivot axes 431 and 433, as well as the lower pivot axes 435 and 437 that nearly any type of angle can exist on either side of a parallel relationship between the first and second curved tubes 421 and 423, but that most will be in a range of from a parallel relationship to some form of angular relationship seen in FIG. 38, where the upper ends at the clearance notches 425 and 427 are closer together than the lower ends distal to the upper pivot axes 431 and 433 and lower pivot axes 435 and 437.

One example of a side shield 441 is seen in FIG. 40. FIG. 40 is a plan view of a given width supplemental side shield 441 having a width of approximately the separation of the curved tube sections as seen in FIG. 39, while accompanying FIG. 41 is a top view of the supplemental side shield 441 of FIG. 40 emphasizing its shape. The side shield 441 can be of any shape, but is shown in a rectangular shape to correspond with the first and second curved tubes 421 and 423 in a parallel position as seen in FIG. 39. The side shield 441 has a main portion which includes a first side 443 and a pair of lateral engagement portions 445. The side shield 441 can depend from a number of other structures, but the side shield 441 seen in FIGS. 40 and 41 utilize an offset surfaces as engagement portions 445. This geometry, will, absent any interfering structures which are attached to manipulate the first and second curved tubes 421 and 423, enable the side shield 441 to be introduced linearly from the top of first and second curved tubes 421 and 423. The introduction of side shield 441 may be guided somewhat into engagement by the clearance notches 425 and 427. Much smaller engagement portions 445 could be used to engage the outer edges 439 of the first and second curved tubes 421 and 423, so long as the orientation is so as to protect the surrounding tissues. FIG. 41 emphasizes the geometry and shows a second side 447.

In the orientation shown, the second side 447 would face toward the inside of the general tube formed in the orientation of FIG. 39. If two of the side shields 441 were used, one on either side of the opening seen in FIG. 39, the tube shape would be closed on both sides, and an oval viewing area would be formed. It should be emphasized that the side shield 441 can depend from any structure, and not just the opposing edges 439 seen in FIG. 39. Structure used to manipulate the first and second curved tubes 421 and 423 can be used to both guide and secure any side shield 443.

In terms of a structure to manipulate the first and second curved tubes 421 and 423, it is preferable that the upper pivot axes 431 and 433 may be urged toward and away from each other independently of the urging of the lower pivot axes 435 and 437 toward and away from each other independently. a mechanism which would prevent all manipulations of the first and second curved tubes 421 and 423 to a position of binding is desirable, but its complexity may obstruct the surgical field. For example, it would be good to have a mechanism which would prevent upper pivot axes 431 and 433 from moving away from each other while the lower pivot axes 425 and 437 are in their close proximity as depicted in FIG. 37. In some cases operator knowledge and skill will probably be required.

Figures 42, 43:
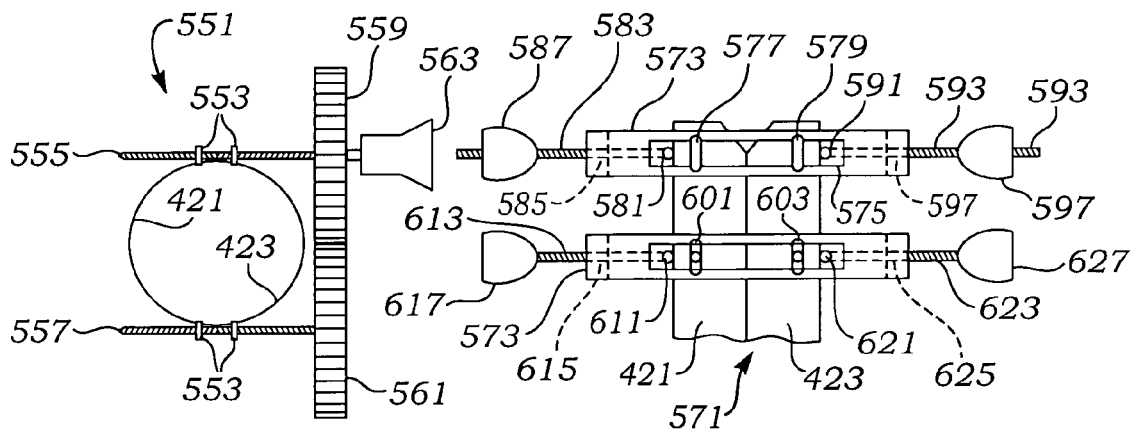
FIG. 42 is a pivoting thread support system in which a pair of opposing flank threaded members operate a pivoting support and are connected by a gear mechanism shown in exaggerated format to give single knob separation control.
FIG. 43 illustrates a surrounding support system utilized to provide and enable pivoting and translation.

In terms of supporting the upper pivot axes 431 and 433 and lower pivot axes 425 and 437, the pivoting and movement may be passive with mechanisms to push or pull directly on the first and second curved tubes 421 and 423 or structures which are mechanically attached. As an example of the use of force and movement urging at the pivot points, FIG. 42 illustrates one such system as a pivoting thread support system 551. The gearing is shown as unduly expansive to illustrate simply the action, but in reality, several gears may be used.

Further, since the a pivoting thread support system 551 is viewed from the top, and as operating the upper pivot axes 431 and 433, a similar arrangement would be used for the lower pivot axes 425 and 437. a set of four pivot fittings 553 provide a threaded interior spaced apart from the first and second curved tubes 421 and 423, or fittings supporting the first and second curved tubes 421 and 423. The fittings 553 enable the first and second curved tubes 421 and 423 to tilt while keeping the threaded apertures in alignment.

a first threaded member 555 has a pair of threaded areas in which the threads are oppose pitched. The threads engaging the fitting 553 of first curved tube 421 are set to urge first curved tube 421 away from second curved tube 423, at the same time that the same turning of the first threaded member engages fitting 553 of first curved tube 423 set to urge first curved tube 423 away from second curved tube 421. This means that the turning of first threaded member 555 in one direction urges the first and second curved tubes 421 and 423 evenly away from each other, and alternatively, the turning of first threaded member 555 in the opposite direction urges the first and second curved tubes 421 and 423 evenly toward each other.

Likewise, a second threaded member 557 has a pair of threaded areas in which the threads are oppose pitched. The threads engaging the fitting 553 of first curved tube 421 are set to urge first curved tube 421 away from second curved tube 423, at the same time that the same turning of the first threaded member engages fitting 553 of first curved tube 423 set to urge first curved tube 423 away from second curved tube 421, but in an oppose orientation than the threads of first threaded member 555. This means that the turning of second threaded member 557 in the other direction (while the first threaded member 555 is turned in a first direction) urges the first and second curved tubes 421 and 423 evenly away from each other. a pair of over sized gears, including a first gear 559 associated with the first threaded member 555, and a second gear 561 associated with the second threaded member 557 act to cause the first and second threaded members 555 and 557 to move simultaneously and oppositely. a knob 563 is used to manipulate both the first gear 559, which manipulates the second gear 561. In a realization in which more gears 559 and 561 are provided, the size of the gears can be reduced and for each intermediate gear, the sense of the threaded members 555 and 557 will change from opposite to same.

Figure 44:
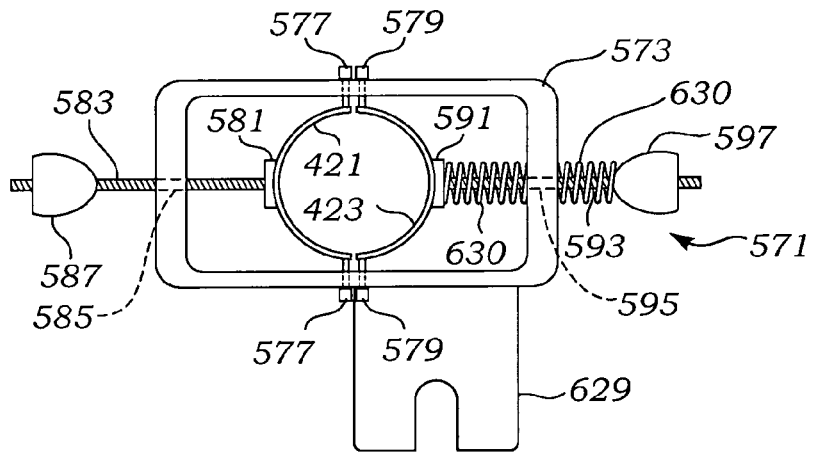
FIG. 44 illustrates a view looking down into the structure of FIG. 43 shows the overall orientation and further illustrates an optional securing tang.

Referring to FIGS. 43 and 44, a surrounding frame system 571 is seen which is utilized to provide and enable pivoting and translation. A surrounding frame 573 has an open slot 575 which accommodates a pair of pins 577 and 579 which preferably have some tracking along the slot 575 to insure that neither the first curved tube 421 nor the second curved tube 423 are able to turn within the frame 573. The opposite side of the frame 573 will have a similar slot 575. However, where the structures which engage the slot are especially over sized, or where the structural integrity is sufficient, only one slot need be used. The structural dependence on the frame 573 should be such that the two opposing first and second curved tubes 421 and 423 will always oppose each other and cannot twist away from each other and can only pivot along their long axis.

a turn fitting 581 enables a threaded member 583 to turn while being axially fixed to the first curved tube 421. The threaded member 583 may be threadably engaged to an internal thread 585 at the end of the frame 573. In this case a knob 587 is used to manually turn the threaded member 583 independently to move the first curved tube 421 to the left or to the right. A turn fitting is a structure which holds the end of the threaded member and allows the threaded member 583 to urge the fitting forward or backward while continuing to turn.

In the alternative, knob 587 may have an internal thread, and turned with respect to the threaded member 583 draw the threaded member out of the frame 573. In this case, a spring (as will be shown) could be used to help reverse this operation. Where the knob 587 is internally threaded, the end of the threaded member may be fixed directly to its first curved tube 421.

In sum, there are three ways to affect motion, preferably the internal threads 585 enable the threaded member 583 to turn to urge first curved tube 421 in both directions with respect to the frame 573. In the alternative, the threaded member 583 may act only to urge the first curved tube 421, and the tubes 421 and 423 may have another mechanism urging them apart or simply move apart based upon other forces or other structures present. Third, the threaded member 583 may have an end anchored to the first curved tube 421 with an internally threaded surface inside knob 587 to enable the knob 587 to be turned to cause the length of threaded member 583 to be withdrawn from the frame 583. A spring, or other fitting can be used to help reverse the direction of travel. All of the knobs and threaded members shown hereafter have the ability for all three modes of action.

Similarly, a turn fitting 591 enables a threaded member 593 to turn while being axially fixed to the second curved tube 423. The threaded member 593 threadably engaged to an internal thread 595 at the end of the frame 573. a knob 597 is used to manually turn the threaded member 593 independently to move the second curved tube 423 to the left or to the right.

Similarly, a second surrounding frame 573 has an open slot 575 which accommodates a pair of pins 601 and 603 having expanded heads which fit outside the slot 575 to provide tracking along the slot 575 to further insure that neither the first curved tube 421 nor the second curved tube 423 are able to turn within either of the frames 573.

a turn fitting 611 enables a threaded member 613 to turn while being axially fixed to the first curved tube 421. The threaded member 613 is threadably engaged to an internal thread 615 at the end of the frame 573. a knob 617 is used to manually turn the threaded member 613 independently to move the first curved tube 421, at its lower pivot axis 435 at the center of the pin 601. Similarly, a turn fitting 621 enables a threaded member 623 to turn while being axially fixed to the second curved tube 423. The threaded member 623 threadably engaged to an internal thread 625 at the end of the lower located frame 573. a knob 627 is used to manually turn the threaded member 623 independently to move the second curved tube 423 to the left or to the right at its lower pivot axis 437 at the center of the pin 603.

With the configuration of FIG. 43, the position within the upper located frame 573 and separation of the pivot axes 431 and 433 (represented by the pins 577 and 589) can be exactly specified. Likewise, the position within the lower located frame 573 and separation of the pivot axes 435 and 437 (represented by the pins 601 and 603) can be exactly specified. In typical use, the knobs 617 and 627 and will be activated after insertion to achieve the configuration seen in FIG. 38, and then followed by the use of the knobs 587 and 597 to achieve the configuration seen in FIG. 39, if necessary. Thereupon the optional side shield 441 may be employed. Where a lesser separation than that seen in FIG. 39 is used, a narrower side shield 441 may be employed. In a surgical kit, several such shields 441 of different size and shape may be available.

Referring to FIG. 44, a view looking down into the structure of FIG. 43 shows the overall orientation and further illustrates an optional securing tang 629 which may be used with either of the upper located or lower located frame 573, and may be located in any position, or extended in any direction, to better enable the surgeon to stabilize and manipulate any of the assemblies 417, 551 and 571 seen. Any structure can be used to help secure the frame 573 and or the first and second curved tubes 421 and 423. FIG. 44 is an equivalent view through the lower of the frames 573, including the knobs 617 and 627 as the two frames 573 have equivalent action. Note that having complete control over both the separation, angular relationship, and position of the first and second curved tubes 421 and 423 within the frame 573 will enable the surgical practitioner to position the line of sight of the working tube along the frame 573 length and to generally have complete control.

Also shown in FIG. 44 is an optional spring 630 which can be used to bias the force acting upon either of the first and second curved tubes 421 and 423, or it can be used to bias a knob 597 away from the frame 573. Although shown as an option, the use of a spring 639 may contribute significantly where force is to be had in one direction only, as well as to lock a threaded member such as 593 into a turn fitting by keeping a pulling bias in place.

Figure 45:
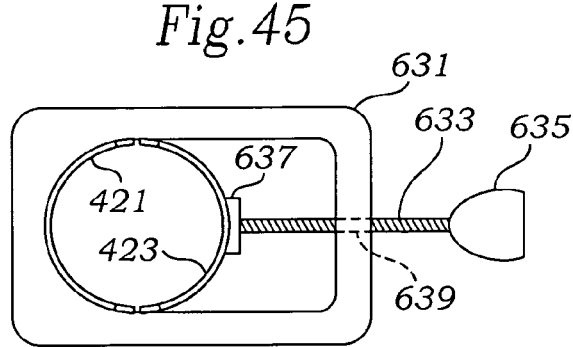
FIG. 45 illustrates a simplified control scheme in which simplicity is emphasized over controllability with less moving parts and expense.

In some cases it may be desired to reduce the number of controls to accomplish certain objectives, such as simplicity, less controllability, less moving parts, inexpense, or the critical need for space about the upper part of any of the assemblies 417, 551 and 571. One example of an arrangement is seen in FIG. 45. a frame 631 has an interior having one surface which may generally match one of the first and second curved tubes 421 and 423, and in this case first curved tube 421. The frame 631 may be attached to the first curved tube 421 by tack welding or the like, or other means. A single threaded member 633 includes a knob 635. a structure 637 can be either an engagement turning block to enable the threaded member 633 to both push and pull on the second curved tube 423, or it may simply be a wear block to allow the threaded member 633 to push against it and to protect the second curved tube 423 from wear.

Because half of the tube assembly of first and second curved tubes 421 and 423 is supported by the frame 631, the second curved tube 423 is left to move only slightly and assuming that FIG. 45 is an upper view and that the pivoting of the second curved tube 423 is accomplished at a lower level, especially at the level of lower pivot axis 437, the frame 631 is left to control second curved tube 423 by simply pushing, or by pushing and pulling. Where structure 637 is a turning block, there is a bulbous expansion at the end of threaded member 633 which snaps into structure 637 as a turning block and is free to turn and both push and pull second curved tube 423. The threaded member 633 is threadably engaged into an internal threaded bore 639 within the frame 631.

Figure 46:
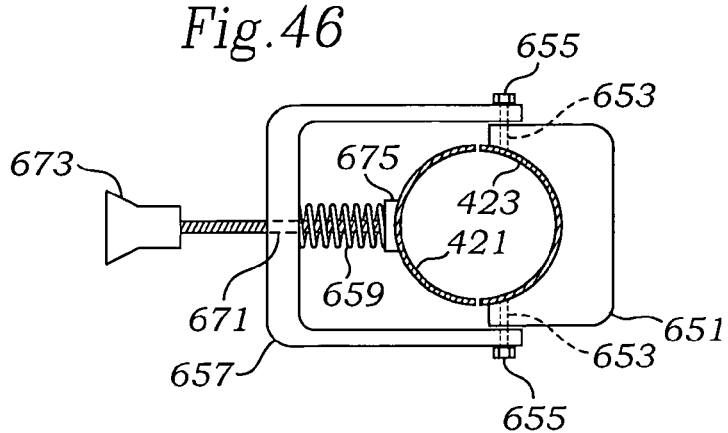
FIG. 46 illustrates a further embodiment of a manipulative structure which works well with the structure of FIG. 45.

Referring to FIG. 46, one embodiment of a manipulative structure which works well with the structure of FIG. 45 is shown. The structure shown is a partial section taken at the lower pivot axis level and includes means for pushing and pulling, or pushing alone. Preferably, when used with the structure of FIG. 45, it will include pushing and pulling, especially if the structure of FIG. 45 performs pushing alone. Either of the structures in FIG. 43 at either the upper or lower pivot axis levels can be substituted for either of the structures shown in FIGS. 45 and 46 as the structures in FIG. 43 provide both pushing, pulling, pivoting and level support.

Where the structures of FIG. 45 provides both pushing and pulling, it can be used along with a second structures at the lower pivot axis as any structure which provides both pushing and pulling will also provide some pivoting support. Further, the structure shown in FIG. 46 is hinged to provide additional pivoting support. The structure of FIG. 46 can be used at either the upper pivot axes 431 and 433 or the lower pivot axes 435 and 437. Both the structures of FIGS. 45 and 46 demonstrate clearly that lesser control structures than are shown in FIG. 43 can be used to control the first and second curved tubes 421 and 423, along with lesser control inputs, and less control specificity, but also with less moving parts and a lesser mechanical complexity.

Referring again to FIG. 46, second curved tube 423 is seen as tack welded to a reinforcement 651. The purpose of reinforcement 651 is to provide an expanded thickness of material so that pivoting can occur closer to the opposing edge 439 as is possible. It is further possible to continue the extent of the reinforcement 651 and its pivot point in the direction of first curved tube 421 if the other geometries of the other components permit. Reinforcement 651 contains a pair of threaded bores 653, each of which accommodates one of the threaded screws or bolts 655 shown. The bolts 655 each extend through one end of a "U" shaped fitting 657, so that the reinforcement 651 and attached second curved tube 423 pivots with respect to the fitting 657. a threaded member 659 engaged an internal threaded bore 671, and has a knob 673 for ease of manual operation.

The threaded member is connected to a turn fitting 675 the first curved tubes 421 to be moved toward and away from second curved tube 423. The use of the structure of FIGS. 45 and 46 may be used together to give the ability to provide control, although not as much control as is seen in FIG. 43.

Figure 47:
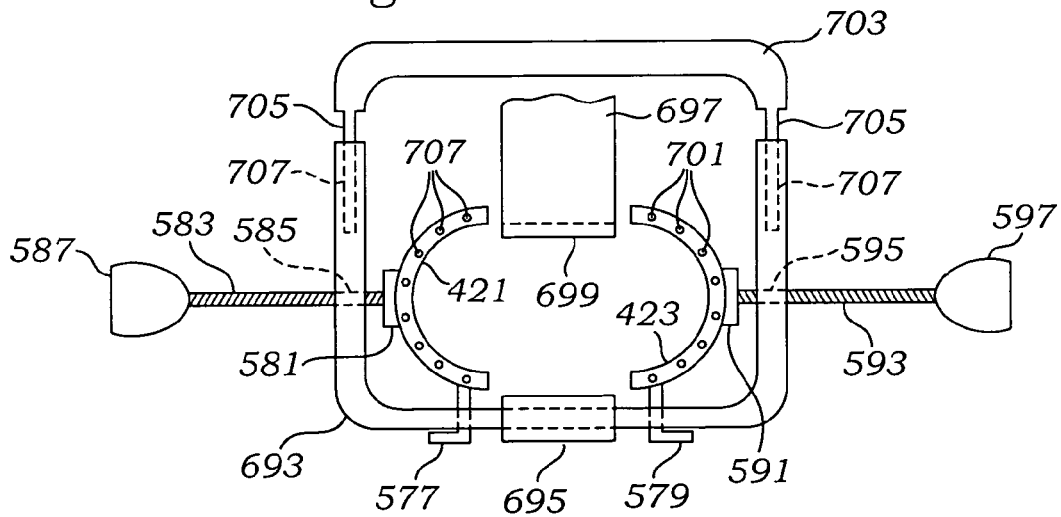
FIG. 47 illustrates another possible realization which combines the control mechanisms of selected portions of FIGS. 37-46, combined with other possible options.

Referring to FIG. 47, another possible realization is seen, combining the control mechanisms of selected portions of FIGS. 37-46, combined with other possible options. An open frame system 691 is seen as having a frame 693 which is either open on at least one side, or which has a side expanded to a distance sufficient to introduce other structures to expand in that direction. Some of the components previously seen include pins 577 and 579 extending through slot 575. Pins 577 and 579 may have extended vertical and horizontal extent to garner additional stability from the frame 693, especially where one side is open.

Other structures may be used to insure that neither the first curved tube 421 nor the second curved tube 423 are able to turn within the frame 573. Also seen are turn fitting 581, threaded member 583, knob 587, turn fitting 591, threaded member 593, and knob 597. The view of FIG. 47 is from above, and thus the structures most closely correspond to the upper structures seen in FIG. 43 and in FIG. 44.

As can be seen in FIG. 47, a four point retractor system can be formed with the components and structures of the foregoing Figures. The first and second curved tubes 421 and 423 are shown in the open position. On the longer connector arm of the frame 693, a side shield 695 is supported. The side shield 695 can derive its ability to hold tissue out of the visual field by being locked down onto the frame 693 in the same manner as a wrench fits a bolt head. In this configuration, the side shield can be inserted into the center of the surgical field and then rotated into position and moved down slightly to lock it into place. On the opposite side from side shield 695 is a retractor 697 which has a flat portion entering the surgical field and which is controlled from a point remote with respect to open frame system 691. An angled portion 699 turns from the flat portion seen entering the surgical field and extends down into the area between the open first and second curved tubes 421 and 423.

Also seen are a series of small circular structures 701 about the peripheral upper surface of first and second curved tubes 421 and 423. These structures are at least one of embedded fiber optics and ports for accepting fiber optics. The apertures formed in the metal open at a slight angle to the inside of the first and second curved tubes 421 and 423 to direct light into the surgical field without producing a back reflection or other scatter. In cases where the fiber optic is permanently affixed, a light ring section can simply be snapped to or placed on the first and second curved tubes 421 and 423. In cases where the apertures are provided, surgery can continue without fiber optics, or a fiber optics set can be added which can range from an illuminated ring (relying on low angle of incidence and Snell's law) to direct light through the openings which open to the inside of the first and second curved tubes 421 and 423 at a low angle of incidence. Intermediary solutions, such as a light ring having a series of short fiber optic members for insertion into the apertures can be used. To facilitate the use of fiber optics, the curved tubes 421 and 423 may be made from a composite material in which the fiber optic components may be present during formation of the tube structures. Other material may be used for tubes 421 and 423, including materials that either transmit light or have portions which transmit light.

As an alternative to the three sided frame 693, the open portion of the frame could be enclosed by an expandable member 703 which can have any manner of interlock with the three sided frame 693. One such interlock is illustrated as simply an annular piston dependence where the expandable member 703 includes a smaller tubular insert 705 which fits closely into a matching bore 707 seen in the terminal ends of the three sided frame 693. The expandable member 703 can be used to lend additional support to the three sided frame 693, especially forces produced by the threaded members 583 and 593. The expandable member 703 is also useful to help support the retractor 697 where such provision is made. The main purpose of expandable member 703 is the adjustability to give greater clearance and access. The same adjustability could be had on the side of three sided frame 693 which supports side shield 695, especially with a more complex mechanism to enable the frame expansion to be locked into place. A locking mechanism for expandable member 703 is not shown so that the drawings may be simplified, but lock ability can be achieved in the same manner as any metal to metal frame construction known in any field of art.

Figure 48:
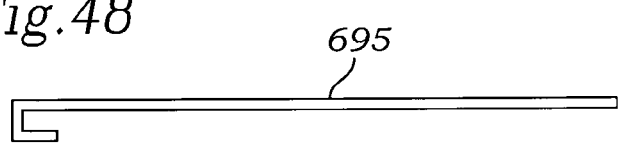
FIG. 48 illustrates a side view of the side shield seen in FIG. 47.

Referring to FIG. 48, a side view of the side shield 695 is seen. The clearance for locking onto the frame 693 is about the same as the width of the frame 693 so that non rotational fixation can be transmitted along the length of the side shield 695.

Figure 49:
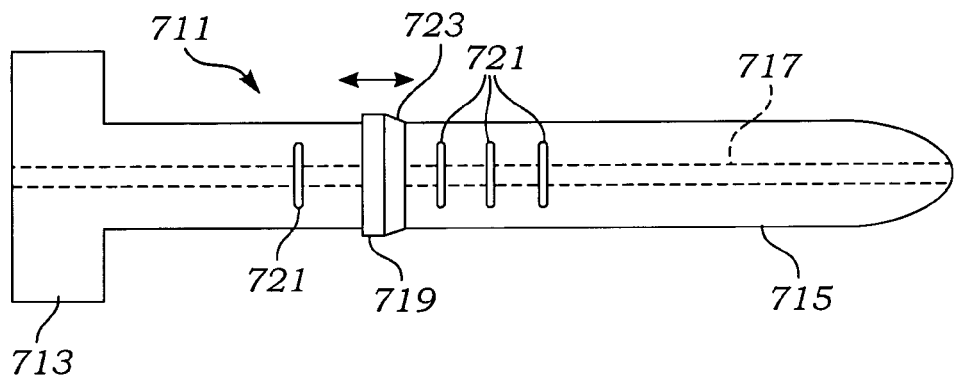
FIG. 49 illustrates one possible configuration for a variable depth guide which is utilizable with any of the devices seen in FIGS. 37-46 or any other tubular, minimally invasive system.

Referring to FIG. 49, one possible configuration is seen for a variable depth guide 711 which is utilizable with any of the devices seen in FIGS. 37-46 or any other tubular, minimally invasive system. Variable depth guide 711 has a handle 713 controlling a shaft 715. Shaft 715 has a through bore 717 which is used to insert a guide line or guide pin to help insert any minimal access system seen in the earlier Figures.

A translatable detent ring 719 interacts with a series of detent indentations 721. The position of the detent ring 719 will correspond to the lengths of the first and second curved tubes 421 and 423 with which the variable depth guide 711 is used. Once the practitioner inserts the variable depth guide 711 into any assembly containing a first and second curved tubes 421 and 423, the necessary height can be adjusted so that the tip of the variable depth guide 711 extends just beyond the lower extent of the joined first and second curved tubes 421 and 423. The height is adjusted by forcing the detent ring 719 to the proper detent indentation 721, and then inserting it into a closely associated first and second curved tubes 421 and 423 to form an overall bullet shape for insertion, preferably a guide pin 155. Once inserted, the variable depth guide 711 is removed. The detent ring 719 carries a frusto-conical surface 723 where it is used with first and second curved tubes 421 and 423 having fluted top areas as seen in FIG. 37 and in previous figures. Any mechanism can be used to achieve a detent action, including an internal pressure ring or a spring loaded bar, or protruding ball bearings. The positional stability of the detent ring can be specified by the spring action of the detent member, and should be sufficiently stable to enable deliberate manual fixation with no inadvertent movement occurring even where significant resistance is encountered.

Figure 50:
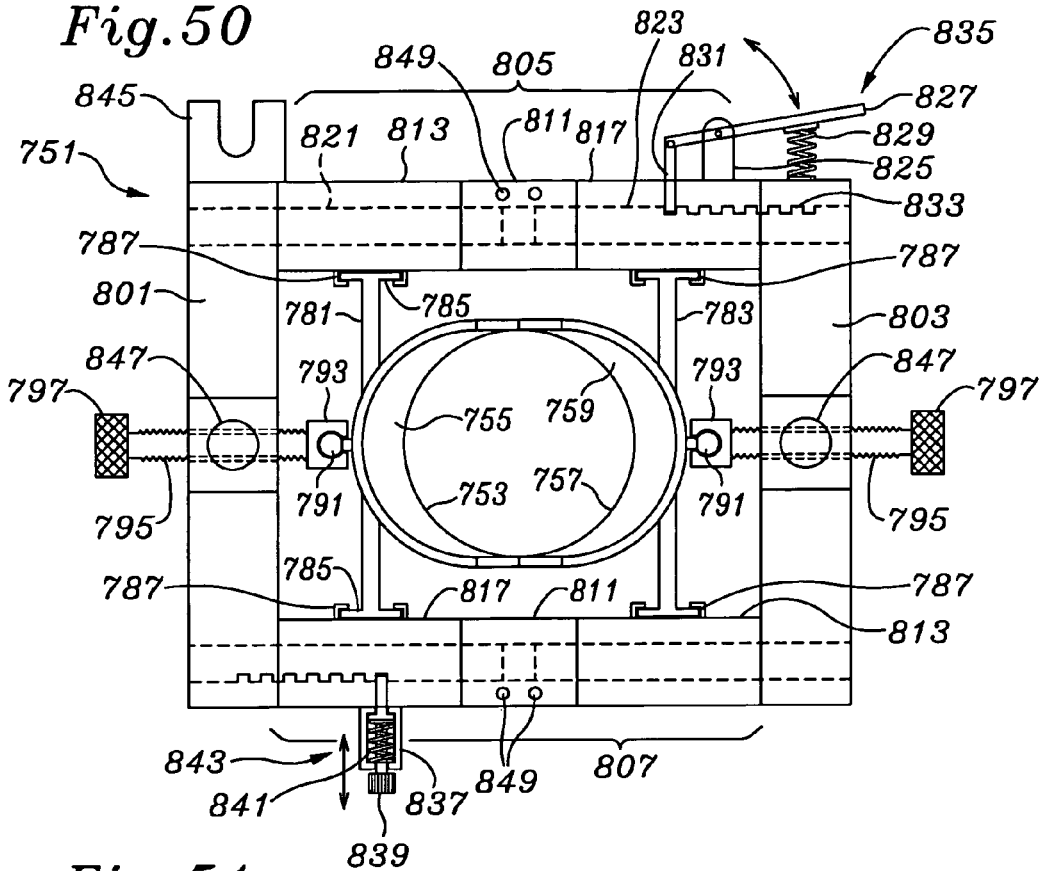
FIG. 50 is a vertical plan view of an expandable frame system which uses detents to set the frame size and which uses an angular distribution system.

Referring to FIG. 50 is a vertical plan view looking down upon an expandable frame system 751 which uses detents to set the frame size and which uses an angular distribution system. A frame is used as a support and reference point to manipulate a working tube in much the same way as FIGS. 37-47. Expandable frame system 751 enables the user to control the size of the operating theater as needed. Where the task can be accomplished with minimum opening access, such minimum opening is all that needs to be taken. Where greater access is needed, the expandable frame system 751 provides both an expanded work space, and additional surfaces for support of other instrumentation.

As before, the retractor blades are seen as a first curved tube 753 having an upper flared portion 755 and a second curved tube 757 having an upper flared portion 759. Each of the first and second curved tubes 753 and 757 have two points of variable pivoting attachment.

Curved tube 753 has a pivot bar 781 which may be attached somewhat tangentially to the first curved tube 753, or may include a pair of extensions attached to the outside of the first curved tube 753. Likewise, curved tube 757 has a pivot bar 783 which may be also attached somewhat tangentially to the first curved tube 753 in the same manner.

Pivot bar 781 has circular lands 785 which fit into support fittings 787. Likewise pivot bar 783 also has circular lands 785 which fit into support fittings 787. The support fittings 787, as seen from above, show the lands 785. In this configuration the lands 785 can be dropped in from above. This is an over-simplified illustration, as some other locking mechanism can be utilized, including ball shape instead of disc shape or other. It would be preferable that the manner of pivoting engagement will firstly enable an ease of assembly and disassembly and secondly provide good stability against dislodgement with respect to any forces experienced when the expandable frame system 751 is in an operational position.

Above the point of pivot of the pivot bars 781 and 783, each of the first and second curved tubes 753 and 757 are fitted with a pivot bearing fitting 791. The pivot bearing fittings 791 can depend from either the first and second curved tubes 753 and 757 or their upper flared portions 755 and 759. The pivot bearing fittings 791 can be hinge type of ball type, or any other type which will enable the upper part of the first and second curved tubes 753 and 757 to be force moved to pivot them with respect to the pivot fittings 781 and 783 in either direction.

Figure 51:
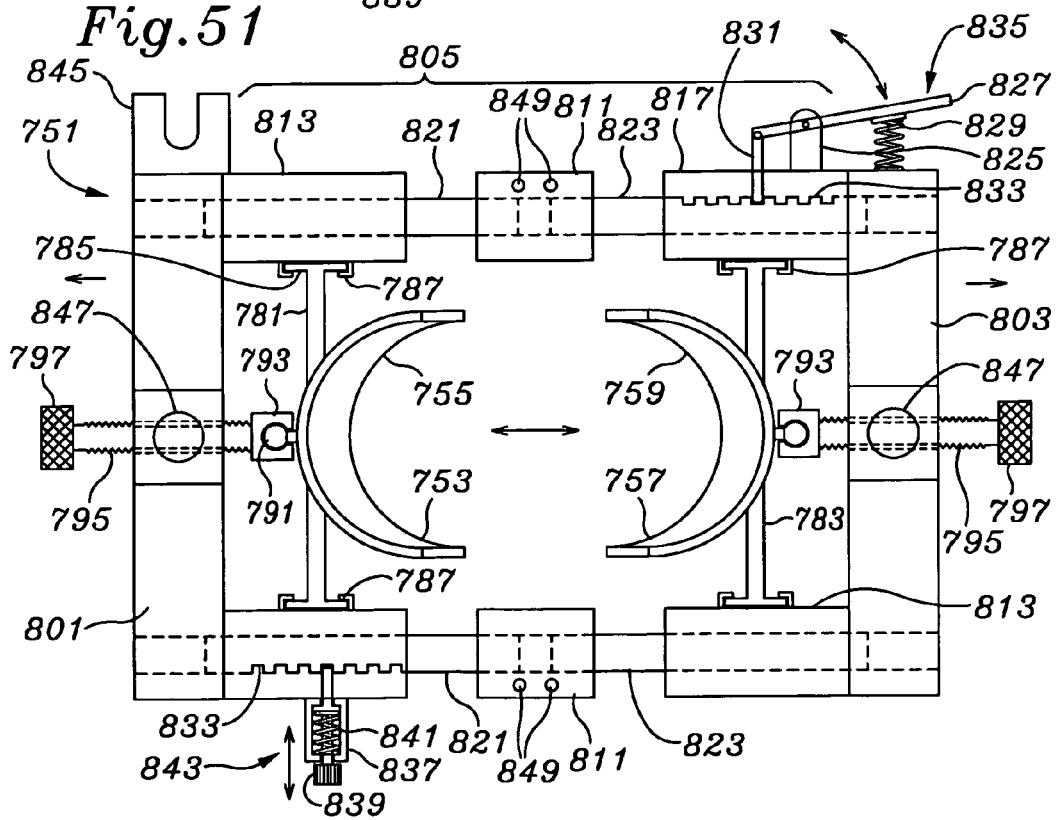
FIG. 51 is a top view of the system of FIG. 51 in an expanded position.

The pivot bearing fitting 791 is engaged by a cooperating fitting 793 which enables the pivot bearing fitting 791 to pivot with respect to the cooperating fitting 793. The cooperating fitting 793 is moved with a threaded member 795, having a thumb control wheel as a tilt screw knob 797. In the drawings of FIGS. 50 and 51, the fittings 791 are located above the pivot bars 781 and 783, but they need not be.

In the embodiments of FIGS. 50 and 51 the movement of the axes of the pivot bars 783 are affected by the expansion of a frame support including a first lateral member 801 and a second lateral frame member 803. The ends of firs and second lateral members 801 and 803 are connected to two telescoping frame members 805 and 807. Telescoping frame member 805 has a central hinge box 811 which is positioned between a first sleeve 813 and a second sleeve 817. The central frame section pivotally supports a pair of internal spreading bars, including a first spreading bar 821 which extends within first sleeve 813 and a second spreading bar 823 having a ratchet or detent structure (to be described) which extends within second sleeve 817.

Although not shown in FIGS. 50 and 51, the spreading bars 821 and 823 will preferably have an internal gear mesh so that both will preferably have an equal angular displacement with respect to the central hinge box 811. The articulation within the central hinge box 811 will enable the selection of three angular frames of reference with regard to the surface of a patient, namely the angle of first sleeve 813, the angle of central hinge box 811, and the angle of second sleeve 817. Where other objects, such as retractors, light sources etc have to be anchored, three reference angle surfaces are available.

The spreading bars 821 and 823 are thus axially fixed with respect to the central hinge box 811, with the spreading bars 821 and 823 axially slidable within the first and second sleeves 813 and 817. Many mechanisms can be utilized to fix the position of the spreading bars 821 and 823 within the first and second sleeves 813 and 817. One such mechanism is show schematically in its most rudimentary form in FIG. 38 as including a pivot support 825 which supports a lever 827. The lever 827 operates against a spring 829 and operates an engagement member 831 with respect to detent structures 833 located on the spreading bars 823. These structures form a first ratchet stop 835. Operational depression of the lever 827 disengages the detent structures 833 of the spreading bar 823 to slide within the sleeve 817 and releasing the lever 827 enables the spring 829 to act to cause engagement of the engagement member 831. With this mechanism, or a similar mechanism, the expansion of the expandable frame system 751 can be controlled, with the expansion of the second lateral frame member 803 away from the central hinge box 811. Similarly the first lateral member 801 is independently movable away from central hinge box 811 with the use of a mechanism similar to the one shown with respect to the pivot support 825, lever 827, spreading bar 823 engagement member 831, and detent structures 833.

The detent structures 833 could be made triangular shaped for sliding in one direction with some form of fixation hold against movement in the other direction. A second mechanism similar to the one shown with respect to the pivot support 825, lever 827, spreading bar 823 engagement member 831, and detent structures 833 is omitted from FIGS. 50 and 51 for simplicity. Regardless of the structure, the expandable frame system 751 can be exactly positioned. Other assisted mechanisms can be employed, including a threaded member or a pinion or other device which will give the user mechanical advantage in extending the expandable frame system 751. Further, the fittings illustrated, including pivot bars 781 & 783 with circular lands 785 and slip fitting into support fittings 787, as well as the pivot bearing fitting 791 and cooperating fitting 793 suggest that the expandable frame system 751 may be added to the operating theater after the first and second curved tubes 753 and 757 have been employed into the surgical opening. This will free the surgeon to position the first and second curved tubes 753 and 757 without having to handle the supporting frame members.

Between the other ends of the first lateral member 801 and second lateral frame member 803 the second telescoping frame member 807 also has a central hinge box 811. Again, the central hinge box 811 which is positioned between a first sleeve 813 and a second sleeve 817. The central frame section pivotally supports a pair of internal spreading bars, including the first spreading bar 821 within first sleeve 813 and the second spreading bar 823 which extends within second sleeve 817.

The interfit between the first and second sleeves 813 and 817 and the first and second spreading bars 821 and 823 in both the first and second telescoping frame members 805 and 807 is expected to be of sufficiently tight tolerance so that both of the central hinge boxes 811 remain directly across from each other to enable a common effective pivot axis. If the latch mechanism supported by the second lateral frame member 803 is released the second lateral frame member 803 should move away from the central hinge box 811. In other words, one of the central hinge boxes 811 should not displace to a position other than directly across from each other.

The second telescoping frame member 807 could have the same mechanism as the first telescoping frame members 805, but a slightly different mechanism is shown in order to emphasize the variability which can be employed with respect to the expandable frame system 751. A retention housing 837 is attached to second sleeve 817 and houses a lock pin 839 and a spring 841 which urges it into the second sleeve 817 where it lockably interfits with the detent structures 833. These structures may be collectively referred to as a second ratchet stop 843. The expansion of the expandable frame system 751, if properly toleranced will enable the right and left sides to be independently controlled in movement toward and away from the away from the central hinge box 811. The actuation of one release mechanism will enable balanced displacement of its associated first or second lateral members 801 and 803.

Movement of the associated first or second lateral members 801 and 803 by one of the latches shown gives a parallel distance separation of the first curved tube 753 with respect to the second curved tube 757, regardless of their respective angular positions (assuming no interference). However, the angularity of the first and second curved tube 753 and 757 are set by the movement of the threaded member 795. As such, the expandable frame system 751 enables independent angularity adjustment for the first and second curved tube 753 and 757 and independent parallel separation for the first and second curved tube 753 and 757 based upon expansion of the frame.

Other features seen in FIGS. 50 and 51 include a support tang 845 and a pair of manipulation sphere projections as spreader projections 847 to assist in manually manipulating the expandable frame system 751. FIG. 51 illustrates a condition in which the expandable frame system 751 is in an expanded orientation, with first lateral member 801 and second lateral frame member 803 equally expanded from central hinge box 811. Either of the first and second lateral members 801 and 803 could have been extended from the central hinge box 811. This feature gives the surgeon the flexibility to adjust the positioning of the central hinge box 811. The central hinge box 811 may also have support structures for other instrumentation, including bores 849 in the central hinge box 811 such as a bookwalter support (to be shown). Bores 849 can be used for locational registry or for threaded attachment. A bookwalter device is especially useful for supporting an additional retractor, in addition to the first and second curved tubes 753 and 755.

Referring to FIG. 52, a side view of the system of FIGS. 50-51 illustrates further details. The angle of the incline of the upper flared portions 755 and 759 are illustrated. A scale 851 helps the surgeon to ascertain the depth to which the first and second curved tubes 753 and 755 are inserted into the patient (with the additional consideration of any further extension which may be added to the first and second curved tubes 753 and 755).

One possible configuration for the first and second curved tubes 753 and 755, include the use of an upper tube portions along with a lower extension. The scale 851 could also be utilized, in conjunction with the extension to indicate depth. A notch 853 in each of the first and second curved tubes 753 and 755 can be used as a reference surface to engage an extension. Another surface can include a raised portion or depressed portion matched to an extension (as will be shown) in each of the first and second curved tubes 753 and 755.

FIG. 53 illustrates a double pivot hinge fitting within the central hinge box 811. A pair of threaded members 861 extend into machined spaces within central hinge box 811 and hold the spreading bars 821 and 823 into a close proximate location such that the complementary gear teeth 863 located on the abutting ends of the spreading bars 821 and 823 intermesh with each other. This arrangement insures that the angular displacement of the spreading bars 821 and 823 with respect to the central hinge box 811 will be equi-angular. This is shown in FIG. 54 where the angle γ on both sides indicates equi angular displacement.

Referring to FIG. 55, a top view of the central hinge box 811 illustrates a bookwalter retractor device 871 mounted on the upper surface of the central hinge box 811. The bookwalter device has a central through bore 873 through which a retractor rail or extension may pass. Typically the retractor extension (not shown) will have a series of detents similar to the detents 833 seen in FIG. 53. As the detents emerge from the through bore 873, they are engaged by a pivoting latch 875 which operates under urging force from a spring 877. A turnbuckle or other force control structure would enable operation of a gear mechanism to move any type of "east west" retractor blades towards or away from the center.

Referring to FIG. 56, a plan view is shown of a remote force retraction system employing many of the structures seen in FIGS. 50-55, but with a remote force system such as disclosed and shown in U.S. Pat. No. 4,747,394, to Robert S. Watanabe, and incorporated by reference herein. The technique of application of remote force to leave the surgical field open as applied to the expandable frame system 751 is seen as an open minimally invasive expansion system 901. At the surgical field, many of the components previously seen have the same numbering.

A pinion box 903 carries a (removable) key insertable gear 905 seen inside an aperture 907 having teeth 911 which engage a linear gear 913 on a first rack 915, and which also engage linear gear 917 on a second rack 919. To enable the pinion box 903 to move independently and proportionately with regard to structures through which the rack 915 passes, rack 915 is fixedly attached to a first main support 921 while rack 919 is fixedly attached to a second main support 923. As the gear 905 is turned clockwise, the rack 915 freely feeds through an aperture 931 (seen in dashed line format) in second main support 923, through the pinion box 903 and pushes first support 921 farther away from the pinion box 903. At the same time, the gear 905 pushes the rack 919 freely feeds through an aperture 933 (seen in dashed line format) in first main support 921, through the pinion box 903 and pushes second support 923 farther away from the pinion box 903.

The result is that two strong support members, namely first support 921 and second support 923 are being forced away from each other remotely, by the turning of the key insertable gear 905. Note that the areas on either side of the first and second curved tubes 753 and 755 are clear to enable other structures to be employed, either unsupported, or independently supported, or possibly supported from structures which support first support 921 and second support 923.

A ratchet latch lever 935 is mounted is mounted to pivot with respect to first support 921 by the action of a spring 937. The ratchet latch lever 935 is fork shaped to fit around the tip fixed end of rack 914 and to actuate an internal latch 939 which operates within the first support 921 between the first rack 915 and second rack 919.

Also seen is a hinge 941 on first support 921, and a hinge 943 on second support 923. The hinges 941 and 943 should preferably have the same angular range and would ideally be from about zero degrees (flat) to about fifteen degrees down with the hinges 941 and 943 rising to form the apex. The hinges 941 and 943 permit the lateral force components to be angularly sloped down, or draped to provide an angled working presentation, and to take up less lateral space in the same plane as the working area. Beyond the hinges 941, the first support 921 is connected to a first extended support 945 while the second support 923 is connected to second extended support 947.

Both the first and second extended supports 945 and 947 include angular extensions 949 which support the support fittings 787 and other structures previously shown. The first and second extended supports 945 and 947 also support tilt screw knob 797 and manipulation sphere projections as spreader projections 847. The support details for the first and second curved tubes 753 and 755 is essentially the same as was shown for FIGS. 50 & 51.

In addition, an optional pair of tilt fittings enable the first and second extended supports 945 and 947 to tilt where it may be more advantageous to locate open minimally invasive expansion system 901 over portion of a patient's body which is angled. A first tilt adjustment fitting 951 can be used to provide tilt to the main extent of first extended support 945, while a second tilt adjustment fitting 953 can be used to provide tilt to the main extent of second extended support 947. Typically the first and second tilt adjustment fittings 951 and 953 will be used to set the tilt before an operation begins. As to both of the first and second tilt adjustment fittings 951 and 953, a support plate 955 is rigidly supported by the portion of the respective first and second extended supports 945 and 947 nearest the hinges 941. The support plate 955 supports a retention housing 837. The retention housing includes a lock pin 839 and a spring 841 which urges it through apertures of the support plate 955 and across to a selector plate 957. As to both of the first and second tilt adjustment fittings 951 and 953, the selector plate 957 is rigidly supported by the portion of the respective first and second extended supports 945 and 947 on the other side of the respective first and second tilt adjustment fittings 951 and 953.

Although shown in somewhat schematic view, a tilt pin 961 joins portions of first extended support 945 rigidly while enabling the tilting of the portion of the first extended supports 945 on one side of the first tilt adjustment fitting 951 to pivot with respect to the portion of the first extended supports 945 on the other side of the first tilt adjustment fitting 951. Likewise, a tilt pin 963 joins portions of second extended support 947 rigidly while enabling the tilting of the portion of the second extended supports 947 on one side of the second tilt adjustment fitting 953 to pivot with respect to the portion of the second extended supports 947 on the other side of the second tilt adjustment fitting 953. In reality, in order to transmit the force rigidity, more complex internal fittings may be utilized. The support plate 955 and selector plate 957 are simple mechanical mechanisms which are located far enough off the axis of pivot to enable selection of a number of angular positions.

Other structures can be supported from the both the first and second extended supports 945 and 947. A pair of slot openings 965 at the far ends of the first and second extended supports 945 and 947 can support additional instrumentation. In addition, the first and second extended supports 945 and 947 include structures 965 which may be apertures or projections or other structures which will enable support to be derived for other retractors. A cross support 971 supports a mechanical housing 973 through which a linear gear 975 can extend. A retractor 976 (which can be of any type) is attached to one end of the linear gear 975. A hand wheel 977 operates a gear 979 which moves the linear gear 975 through the housing 973. This assembly is a first cross supported retractor set 981. A second cross supported retractor set 983 is also shown. This gives the surgical practitioner good control and leverage to operate the "north-south" retractors.

Figure 57:
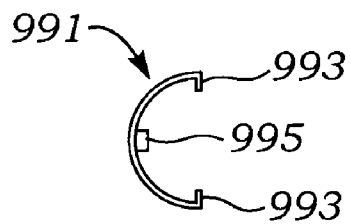
FIG. 57 is a top view of a curved retractor tube extension.

An illustration of an extension previously mentioned is illustrated in FIG. 57 which illustrates a top view of a curved extension 991 standing alone. Curved extension 991 may have several pair of inwardly directed members 993 (or a single large inwardly directed member 993) for engagement against the notches 853 seen in FIG. 52. An inwardly directed angled "snap" protrusion 995 springs into a matching opening on either of the first and second curved tubes 753 and 755. The curved extension 991 will fit on the outside of the matching first or second curved tubes 753 and 755 and the force on the curved extension 961 is expected to be inward at its lower extent during spreading.

Figure 58:
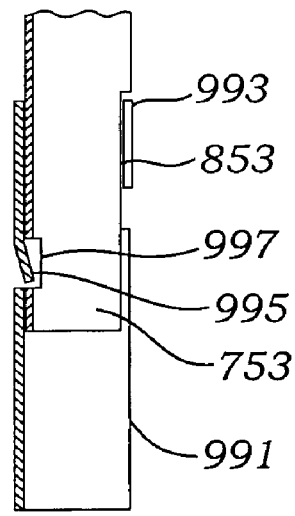
FIG. 58 is a side sectional view of the curved retractor tube extension of FIG. 57 attached to the curved tube seen in FIG. 52.

Referring to FIG. 58, a side semi-sectional view is shown. A lower portion of first curved tube 753 having groove 853, and a slot 997 is seen in a sectional view. Adjacent the semi section curved tube 753 is the curved extension 991 in an attached position. The upper end of the notch 853 fixes against up motion, and the slot 997 fixes against down motion when it engaged with inwardly directed angled "snap" protrusion 995. A stable support relationship is shown.

Figure 59:
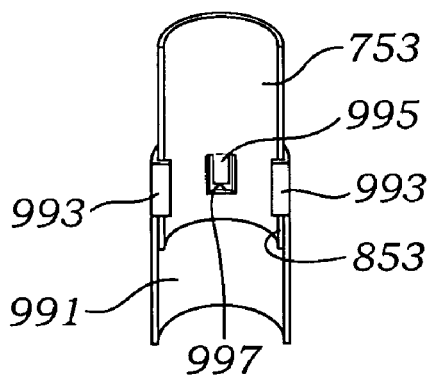
FIG. 59 is a view looking down into the inside of the curved retractor tube extension of FIGS. 57 and 58.

Referring to FIG. 59, a view looking down into the inside of the combination of the first curved tube 753 and curved retractor tube extension 99 of FIGS. 57 and 58. It can be seen how the large inwardly directed members 993 wrap around the groove 853 and can be slid upwardly until the inwardly directed angled "snap" protrusion 995 engages.

Figure 60:
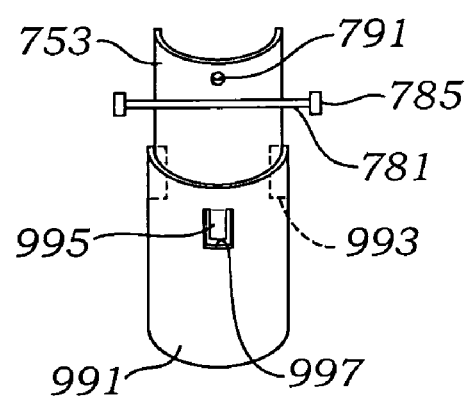
FIG. 60 is a view looking down onto the outside of the curved retractor tube extension of FIGS. 57-59.

Referring to FIG. 60, a view looking down onto the outside of the combination of the first curved tube 753 and curved retractor tube extension 99 of FIGS. 57-59 is seen. In addition, the pivot bar 781 with circular lands 785 are also seen below the pivot bearing fitting 791, for reference. The large inwardly directed member 993 is partially shown in dashed line format. The bottom of the curved extension 991 may be of any shape.

Figure 61:
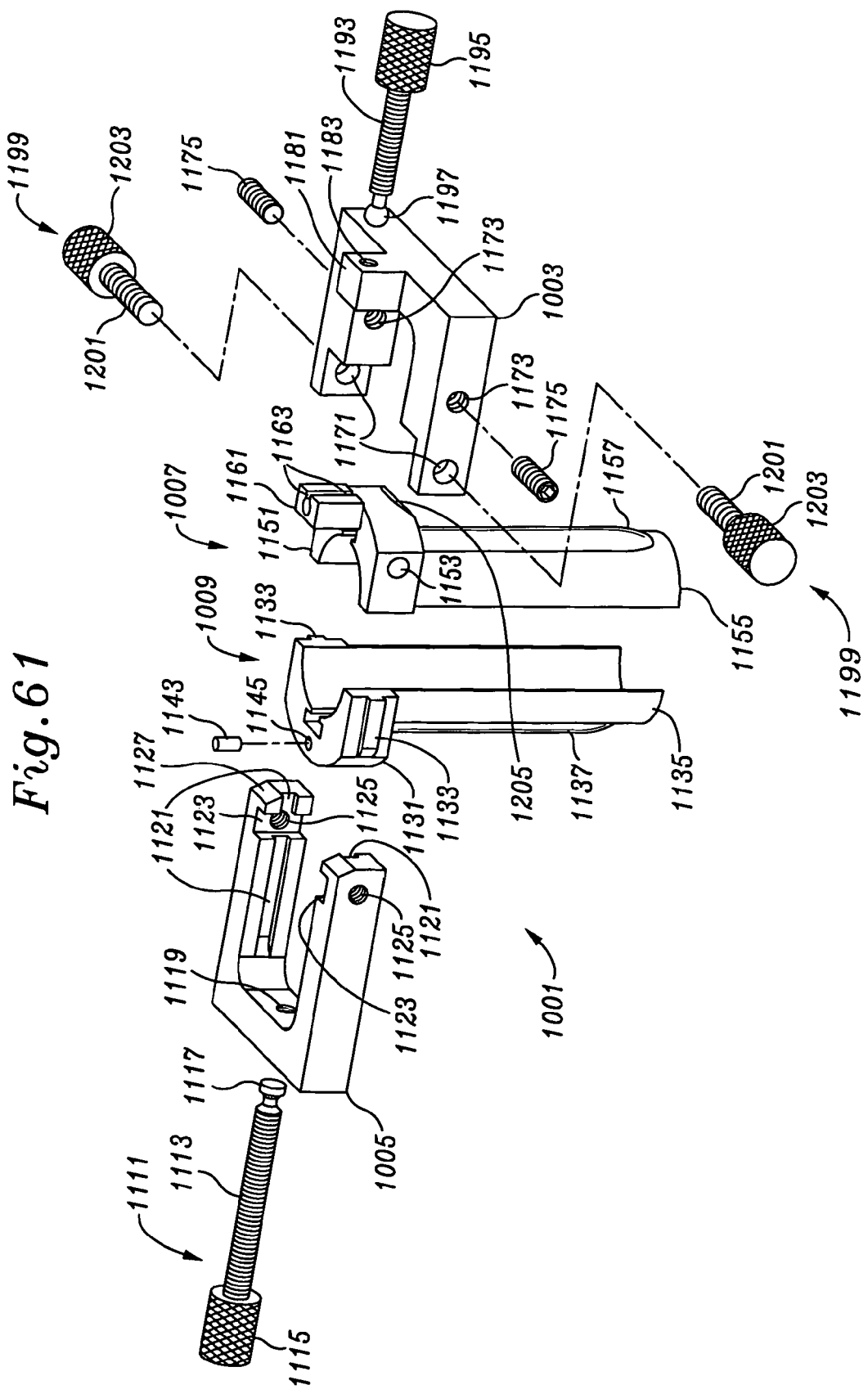
FIG. 61 is an exploded view of a further embodiment of a frame retractor system utilizing a base frame and raised tube manipulator.

Referring to FIG. 61, an exploded view of a frame retractor system 1001 is seen. The articulation of the frame retractor system 1001 is achieved by using a main outer first frame section 1003 which laterally overlaps a smaller laterally inner second frame section 1005. The frame sections 1003 and 1005 are joined and circumferentially envelop a first retractor member 1007 and a second retractor member 1009. As seen in the earlier embodiments, each degree of motion achieved in retraction, namely separation and independent angular articulation each require a series of actuators and it may be desirable to reduce the number of actuators both for simplicity and quick controllability. In the configuration seen in FIG. 61, the angular articulation of the second retractor member 1009 is surrendered with respect to the second frame section 1005, but the second frame section 1005 is made limitingly pivotable with respect to the first frame section 1003.

Beginning further discussion at the left of FIG. 61, a threaded actuator 1111 includes a threaded shaft 1113, an expanded diameter actuator knob 1115, and a rotation capture fitting 1117 which will enable the threaded actuator 1111 to be captured axially and yet turn. The threaded actuator 1111 threaded shaft 1113 engages an internally threaded bore 1119 within the second frame section 1005 to enable it to be axially moved through the second retractor member 1009.

Second frame section 1005 includes a pair of internally disposed slots 1121, each of which is interrupted by a vertical accommodation slot 1123. Immediately adjacent the internally disposed slots 1121 are internally threaded bores 1125. The uppermost ends of the overall "U" shape of the second frame section 1005 includes an angled portion 1127 which is used in combination with other structures to limit the amount of pivot of the second frame section 1005 with respect to the first frame section 1003.

Second retractor member 1009 has thickened structurally reinforced upper head portion 1131 having a pair of outwardly disposed tongues 1133 which slidably fit within the slots 1121. Second retractor member 1009 has a lower extension member 1135 which may include an insertion accommodation slot 1137. The insertion accommodation slot 1137 has a lower extent which curves into the lower extension member 1135 to guide the terminal end of any member inserted into the insertion accommodation slot 1137 inwardly. Insertion accommodation slot 1137 has an upper end which opens from an upper surface of the reinforced upper head portion 1131.

A set screw 143 is seen over and insertable into a threaded bore 1145 which leads into a position to partially obstruct a bore (not seen in FIG. 61) and capture the rotation capture fitting 1117 within the thickened structurally reinforced upper head portion 1131.

The first retractor member 1007 also has a thickened structurally reinforced upper head portion 1151, but has a pair of pivot bores 1153, one of which is visible in FIG. 61. First retractor member 1007 also has a lower extension member 1155 which may also include an insertion accommodation slot 1157. The insertion accommodation slot 1157 has a lower extent which also curves into the lower extension member 1155 to guide the terminal end of any member inserted into the insertion accommodation slot 1157 inwardly. Insertion accommodation slot 1157 has an upper end which opens from an upper surface of the reinforced upper head portion 1151.

From an upper surface of the reinforced upper head portion 1151, an upper actuation block 1161 is seen as having a key slot 1163 extending vertically throughout its length. The vertical length of the key slot 1163 enables a member to both pull and push the upper actuation block 1161 as it angularly tilts since the key slot 1163 will operate to enable pushing and pulling throughout a range of angles assumed by the first retractor member 1007.

First frame section 1003 includes a more distal pair of frame pivot bores 1171, which are aligned with each other and also alignable with the internally threaded bores 1125 of second frame section 1005. First frame section 1003 also includes a less distal pair of internally threaded bores 1173, which are aligned with each other and also alignable with the pair of pivot bores 1153 of the reinforced upper head portion 1151 of the first retractor member 1007. A pair of internally threaded bores 1173 are engaged by a pair of externally threaded set screws 1175 to gather support to further engage pivot bores 1153 carried by the thickened structurally reinforced upper head portion 1151 of the first retractor member 1007. Threaded set screws 1175 enable first retractor member 1007 to pivot with respect to first frame section 1003.

Generally, the first frame section 1003 has a first level which includes the more distal pair of frame pivot bores 1171 and the less distal pair of internally threaded bores 1173. This level may be on a corresponding first level of second frame section 1005 and a same first level on second frame section 1005 is seen to include the internally threaded bores 1125, and the internally threaded bore 1119. As a result, the threaded actuator 1111 acts to move the second retractor member 1009 at a level directly across from the pivoting connection of the pivoting connection of the first retractor member 1007 to the first frame section 1003 and directly across from a pivoting connection of first frame section 1003 to second frame section 1005 (as will be shown).

A second level of first frame section 1003 is seen as a raised fitting 1181. The raised fitting 1181 is a block which supports an internally threaded bore 1183 at a second level, above the first level occupied by the more distal pair of frame pivot bores 1171 and the less distal pair of internally threaded bores 1173.

To the right of internally threaded bore 1183, a threaded actuator 1191 includes a threaded shaft 1193, an expanded diameter actuator knob 1195, and a rotation capture fitting 1197 which will enable the threaded actuator 1191 to be captured horizontally within the upper actuation block 1161 key slot 1163. Capture of the rotation capture fitting 1197 will allow it to urge the upper actuation block 1161 forward and rearward to cause the first retractor member 1007 to pivot. The key slot 1163 will continued engagement of the rotation capture fitting 1197 regardless of the angle of the first retractor member 1007.

A pair of main threaded members 1199 each have an externally threaded portion 1201 and a knob 1203. The threaded portions pass through the more distal pair of frame pivot bores 1171 and threadably engage the internally threaded bores 1125 of the second frame section 1005. The knobs 1203 of the pair of main threaded members 1199 can be tightened to fix the angle of the first frame section 1003 with respect to second frame section 1005. Also seen is a small bevel cut 1205 on the thickened structurally reinforced upper head portion 1151 to better enable the thickened structurally reinforced upper head portion 1151 to tilt forward.

Figure 62:
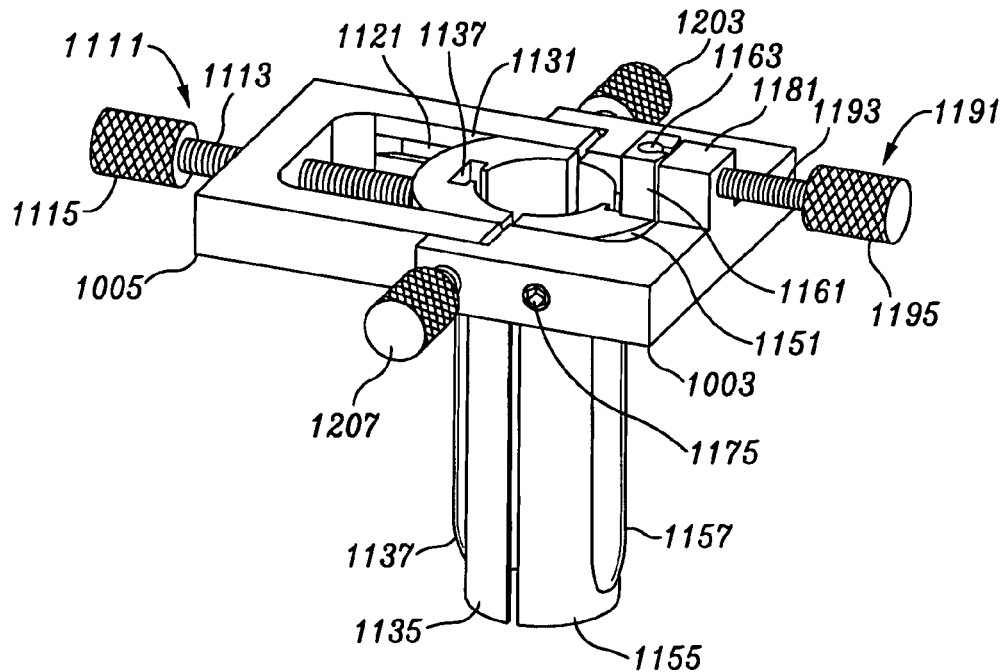
FIG. 62 is a perspective view of the frame retractor system seen in FIG. 61.

Referring to FIG. 62, a view of the assembled frame retractor system 1001 is seen. The co-planarity of the first and second frame sections 1003 and 1005 is seen. In the assembled position, it is more readily seen that the threaded actuator 1191 can actuate the upper actuation block 1161 away from the raised fitting 1181. It can also be seen that the co-planarity of the first and second frame sections 1003 and 1005 can be maintained even as the thickened structurally reinforced upper head portion 1131 and lower extension member 1135 move parallel to the left.

Figure 63:
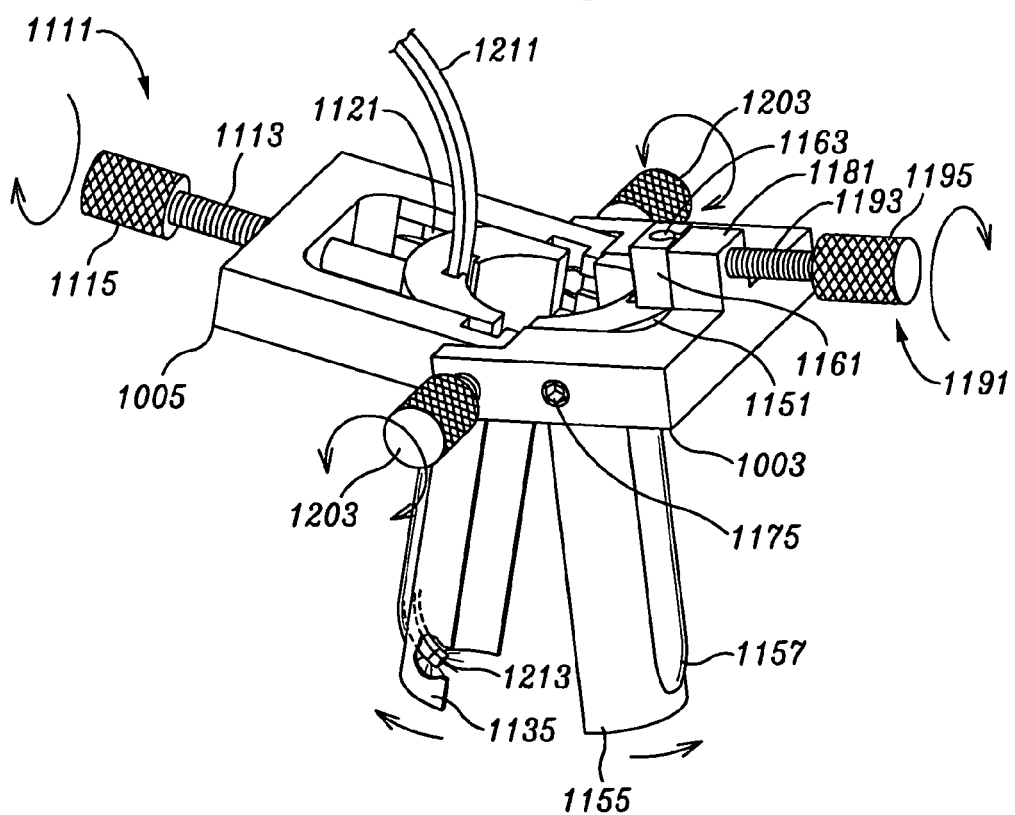
FIG. 63 is a perspective view of the frame retractor system from the same perspective as seen in FIG. 61 and illustrated as being fitted with a fiber optic illuminator.

Referring to FIG. 63, a perspective view of the frame retractor system from the same perspective as seen in FIG. 61 is illustrated as being fitted with a fiber optic illuminator seen as a length of fiber optic cable 1211 which is guided into the insertion accommodation slot 1137. As could be noted from FIGS. 61 and 62, the slot is a key-type slot having an opening into the inside of the lower extension member 1135. The fiber optic cable 1211 can thus be set to emit at a terminal end 1213, any point near the terminal end, or along the length of the lower extension member 1135 through the portion of the slot along the length of the lower extension member 1135.

Also noted in FIG. 63 is the upward angular displacement of the second frame section 1005 with respect to the first frame section 1003. Note that the pivot axis is about a line between the knobs 1203, and through the more distal pair of frame pivot bores 1171 and pair of pivot bores 1153 which were better seen in FIG. 61. Turn arrows are shown around the knobs 1203 as they can be slightly loosened or tightened to control the tension and capability to hold or change the angle of the second frame section 1005 with respect to the first frame section 1003.

Also note that regardless of the angular position of the second frame section 1005 with respect to the first frame section 1003 seen in FIGS. 61 and 62 that the threaded actuator 1111 can be independently manipulated to increase or decrease the distance the lower extension member 1135 occupies with respect to the lower extension member 1155. Independently of this, threaded actuator 1191 can be used to determine the angle which lower extension member 1155 takes with respect to first frame section 1003. The angular separation of the lower extension member 1135 occupies with respect to the lower extension member 1155 seen in FIG. 63 is due to the angular position of the second frame section 1005 with respect to the first frame section 1003. Further separation of the lower extension member 1135 occupies with respect to the lower extension member 1155 can be achieved by actuation of the expanded diameter actuator knob 1195.

Figure 64:
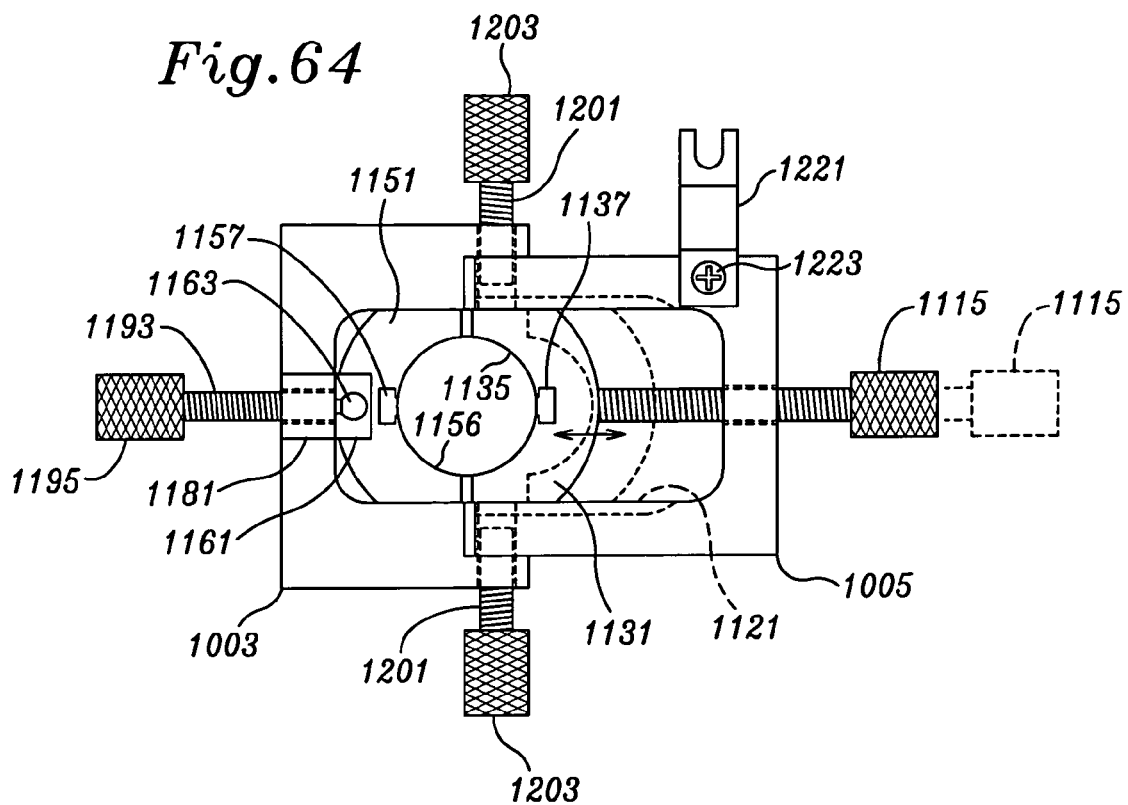
FIG. 64 is a top view of the frame retractor system seen in FIGS. 61-63.

FIG. 64 is a top view of the frame retractor system 1001 seen in FIGS. 61-63. Also seen an anchoring structure 1221 held in by a threaded member 1223. The dashed line portions of the drawing of FIG. 64 illustrate the action in moving the thickened structurally reinforced upper head portion 1131 and lower extension member 1135 along the second frame section 1005 by using the pair of outwardly disposed tongues 1133 within the pair of internally disposed slots 1121.

Figure 65:
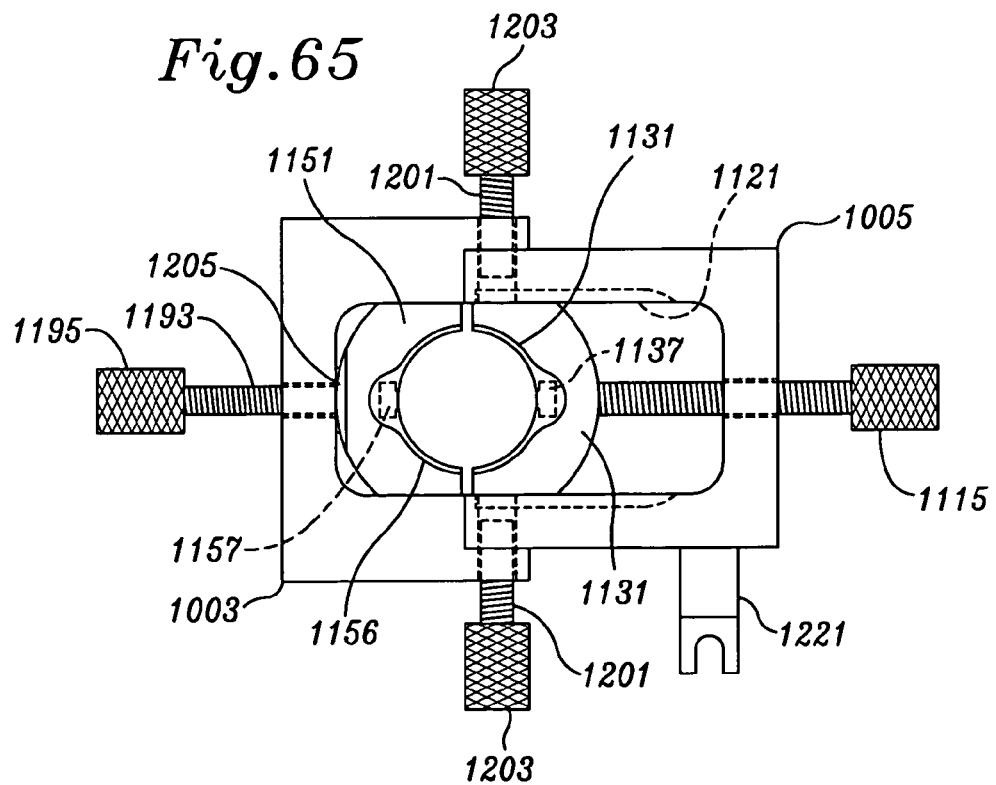
FIG. 65 is a bottom view of the frame retractor system seen in FIGS. 61-64.

Referring to FIG. 65, a bottom view of the frame retractor system 1001 seen in FIGS. 61-64 illustrates the nature of the insertion accommodation slots 1137 & 1157.

Referring to FIG. 66 a plan view of the frame retractor system 1001 is seen. An additional structural connector 1227 is seen connected to the anchoring structure 1221.

Referring to FIG. 67, a wire retractor 1251 is seen. Wire retractor 1251 has a scissors rear portion 1253 which is shown in a horizontal position and a generally vertical front portion 1255. As shown, the scissors rear portion may have a ratchet mechanism 1257 for helping to hold the scissors portion 1253 in a closed position which will hold generally vertical front portion 1255 in an open position.

Generally vertical front portion 1255 includes a pair of relatively thin members 1261 and 1263, which are connected to scissor arms 1265 and 1267, respectively. Thin member 1261, after an angular change 1271 from scissor arm 1265, includes a somewhat square inward detour as an accommodation portion 1273. Likewise, thin member 1263, after an angular change 1275 from scissor arm 1265, includes a somewhat square inward detour as an accommodation portion 1277.

Below and beyond the accommodation portions 1273 and 1277 each of the thin members 1261 and 1263 have a pair of wing extensions 1279. The wing extensions 1279 limit the ability of the relatively thin members 1261 and 1263 to move past one another, and limit the amount that the accommodation portions 1273 and 1277 actually do move past each other as will be seen.

Below the wing extensions 1279 the relatively thin members 1261 and 1263 each turn outward and taper to a point 1281. The point 1281 is used to penetrate muscle and to further stabilize the operational field. Referring to FIG. 68, the relatively thin members 1261 and 1263 are shown in a position separated from each other, with the accommodation portions 1273 and 1277 being separated. The outwardly directed parts of the accommodation portions 1273 and 1277 are shown in a position to fit within the rounded upper opening of the frame retractor system 1001. This enables the practitioner to perform lateral retraction while "locking" the wire retractor 1251 into a stable position with respect to the frame retractor system 1001.

Referring to FIG. 69, an isolated view of the generally vertical front portion 1255 illustrates the wire retractor shown superimposed in a crossing pattern to reduce the width profile for entry into the frame retractor system 1001 of FIGS. 61-66 even when the retractor system 1001 is in a position where the lower extension member 1135 is closest to lower extension member 1155.

Figure 70:
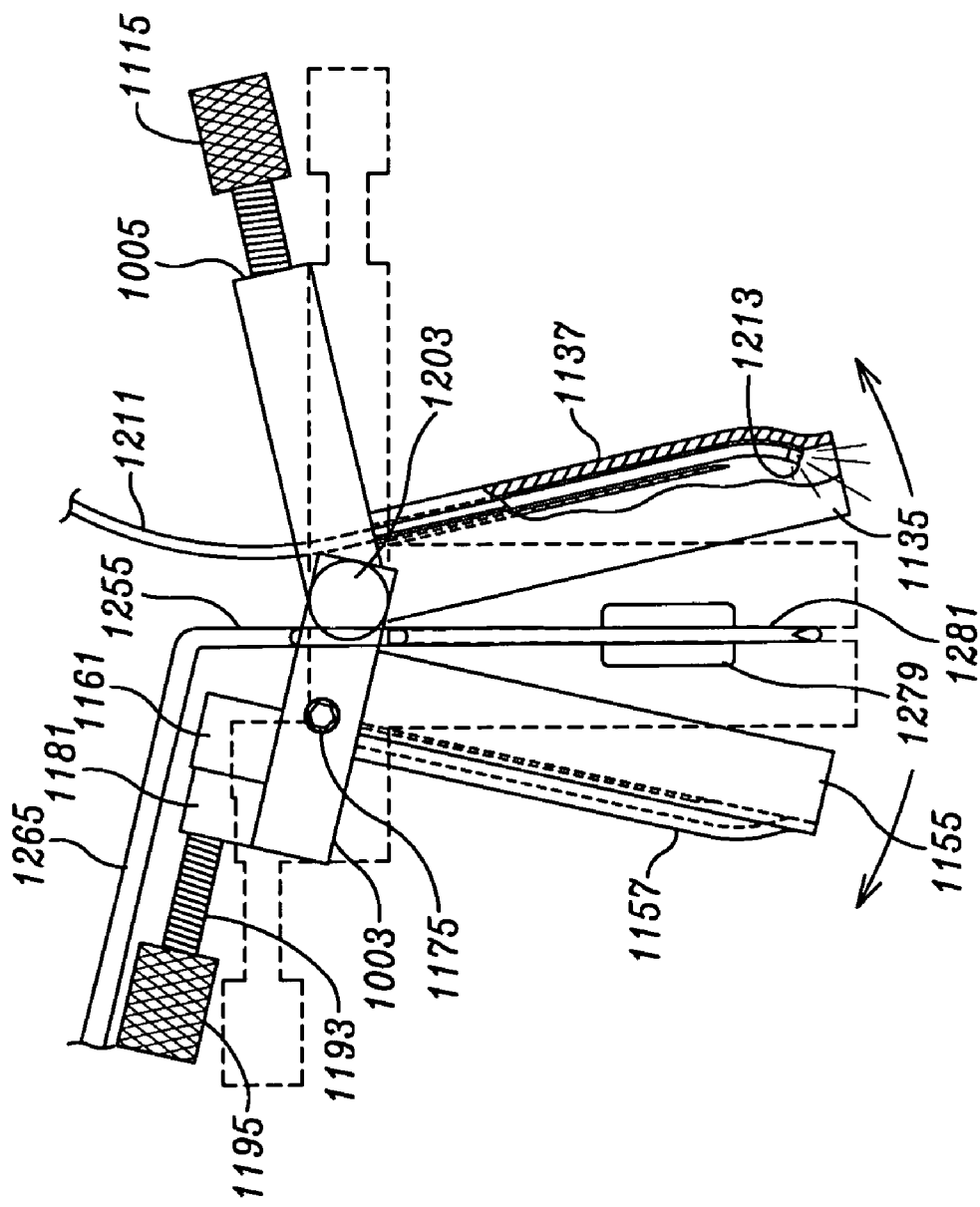
FIG. 70 is a side view of the frame retractor system seen in FIGS. 61-63, and illustrating portions of an optional wire guide retractor.

Referring to FIG. 70, a side view of the frame retractor system 1001 illustrates the position in which the wire retractor 1251 takes within the frame retractor system 1001. The lower extension member 1135 need only be slightly separated from the lower extension member 1155 to accommodate the wire retractor 1251. The wire retractor 1251 is simply used to hold back tissue which is already stressed below the bottom of the lower extension members 1135 and 1155 and need only transmit some retention forces to be effective.

Figure 71:
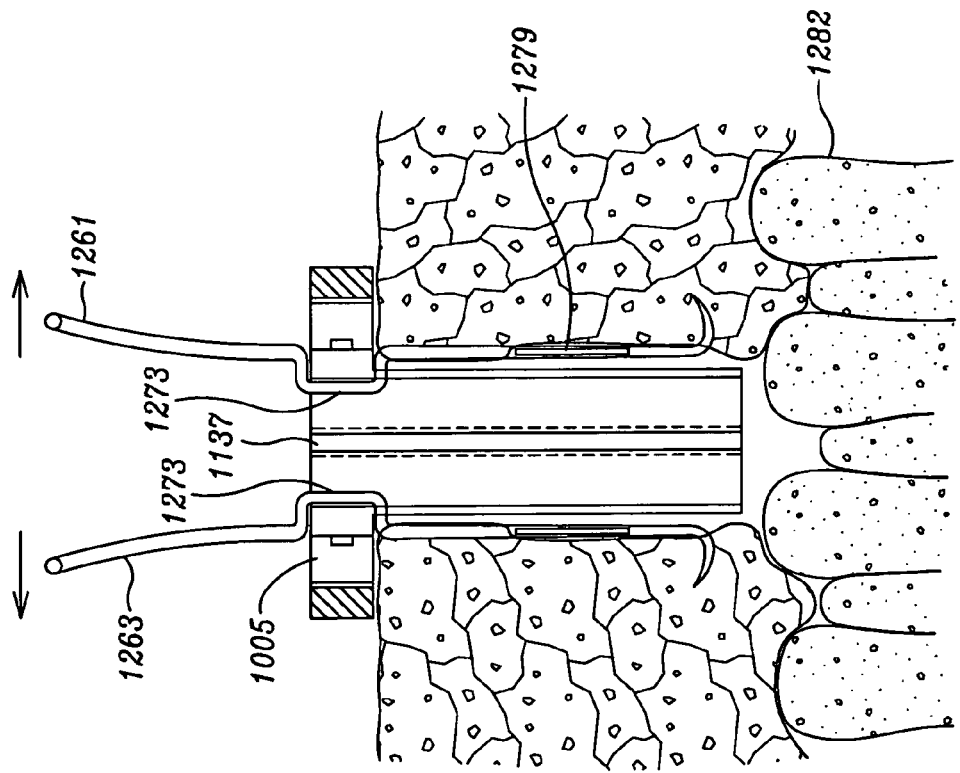
FIG. 71 illustrates the frame retractor system and wire retractor shown with respect to tissue.

Referring to FIG. 71 illustrates the frame retractor system 1001 and wire retractor 1251 shown with respect to tissue 1285 and which is positioned over deeper tissues 1282. Note that the pair of wing extensions 1279 are positioned close together. This is the position which the generally vertical front portion 1255 assumes upon insertion into the lower extension members 1135 & 1155 when lower extension members 1135 & 1155 are in close proximity to each other.

Figure 72:
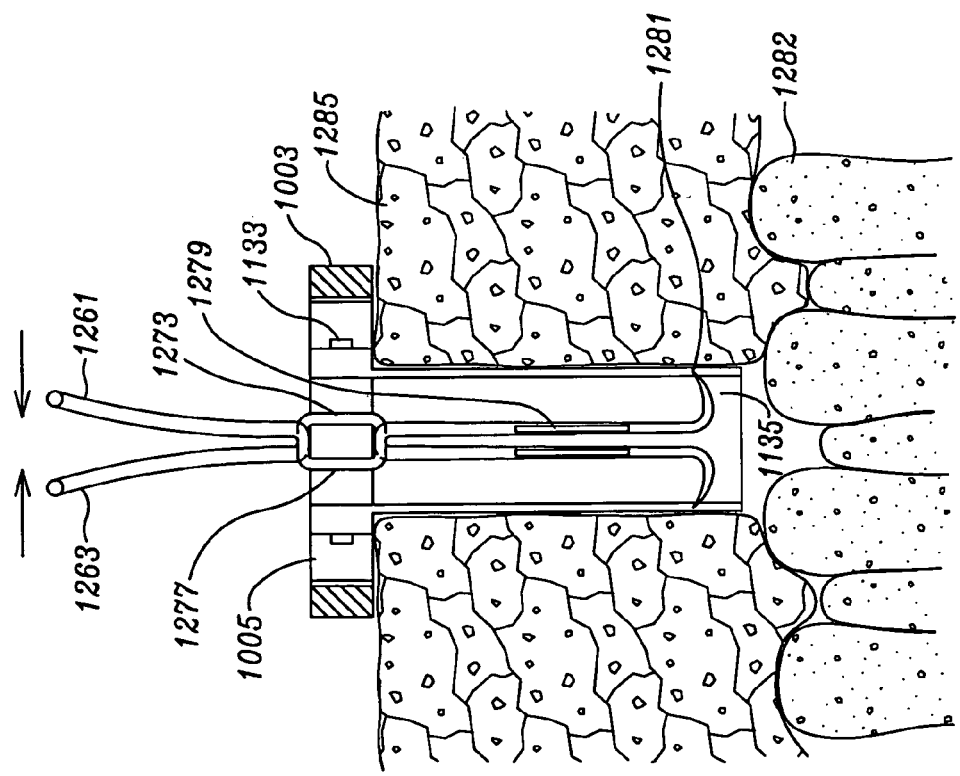
FIG. 72 illustrates the wire retractor being opened to an open position within the frame retractor system and within the tissue.

Referring to FIG. 72, a view illustrating the wire retractor 1251 being opened to a stable open position within the frame retractor system 1001 is seen. The tissue 1285 to the sides are held back even where lower extension members 1135 & 1155 are separated from each other.

Referring to FIG. 73, a manual tool 1283 includes a main handle portion 1284 supporting a forward fitting 1285. The fitting 1285 shown includes an internal bore and a key slot 1286. An interchangeable blade attachment 1287 has a rear end which includes a stop collar 1288 and a key projection 1289 which fits with respect to the key slot 1286. A working tip end of the interchangeable blade attachment 1287 includes a pair of oppositely disposed triangular blades 1288.

Referring to FIG. 74, a different interchangeable blade attachment 1289 is shown as having a flat rounded end 1289. Referring to FIG. 75, a manual tool 1290 is shown as having a slip fitting 1291 with manual register. A slip ring 1292 is movable toward the handle portion 1284 to unlock and away from the handle portion 1284 to lock. FIG. 76 illustrates a view looking into the slip fitting 1292 and illustrates the concentric location of the slip ring 1292 surrounding a split ring portion 1293. A registry block 1294 is seen which insures that the interchangeable blade attachment 1449 cannot rotate on its axis when supported by the main handle portion 1443.

Referring to FIG. 77, a top view of a further embodiment of a frame retractor system 1301 is shown. Referring to FIG. 78, a bottom view of the embodiment of FIG. 77 is shown. Referring to both FIGS. 77 and 78, a frame retractor system 1301 includes a first main frame member 1303 shown to the left and which has an overall outer dimension generally matching that of a second member section 1305. The tops and undersides of the first and second main frame members 1303 and 1305 have formed depressions 1307 which are fitted with threaded bores (not shown) which fit with a series of threaded members 1309 and can be used to securely lock down any matching structure, with an inner contour of the depressions 1307 to match the outer contour of an object to be secured to first and second main frame members 1303 and 1305. One such object is shown as an anchoring structure 1311 having a curved portion matching an curved portion of the depression 1307.

The first main frame member 1303 surrounds a first inner pivotable frame member 1313. A pair of pivot pin members 1315 are shown as extending through bores 1317 at the opposite sides of the first main frame member 1303 and into blind pivot bores 1319 in the second frame section 1305. The pivot pin members 1315 may preferably have a threaded exterior engaging matching threads in bores 1319 to securely lock the pivot pin members 1315 in place.

The first main frame member 1303 is pivotally connected to the second main frame member 1305 by a similar pivoting arrangement. Pivot pins 1323 extend through bores 1325 in the first main frame member 1303, and into through bores 1327 in the second main frame member 1305. The pivot pins 1323 extend short of interference with an internal groove 1329.

The first inner pivotable frame member 1313 supports a first retractor half 1331 which includes a thickened structurally reinforced upper head portion 1333 and a lower extension member 1335. The upper head portion 1333 is sized to fit closely within the first inner pivotable frame member 1313 to facilitate quick change out. A pair of rotational locks 1337 secure the structurally reinforced upper head portion 1333 with respect to the first retractor half 1331. With this method and configuration, different sized retractors can be quickly selected and locked into the frame retractor system 1301 to enable retraction structures of different shape, depth, diameter and different accessory capability, to be used with the frame retractor system 1301. Rotational locks 1337 can be threaded members which lock the first retractor half 1331 by securing the top edge of the reinforced upper head portion 1333 down onto the inner pivotable frame member 1313. Rotational locks 1337 can also be cam members which rotate protrusions into slots carried by the reinforced upper head portion 1333.

The second frame member 1305 supports a first inner translatable frame member 1341 which is linearly translatable within the internal groove 1329 in the second frame member 1305. The first inner translatable frame member 1341 has a tongue 1343 which fits within the internal groove 1329 and has a length and other dimensions sufficient to stably support the first inner translatable frame member 1341 with respect to the second frame member 1305.

The first inner translatable frame member 1341 supports a second retractor half 1345 which includes a thickened structurally reinforced upper head portion 1347 and a lower extension member 1349. The upper head portion 1347 is also sized to fit closely within the first inner translatable frame member 1341, and is held in place by a pair of rotational locks 1337 in the same manner as upper head portion 1347. Both first and second retractor halves 1331 and 1345 can be quickly and easily changed. Also seen in the underside view of FIG. 78 are bores 1351 in which the pair of rotational locks 1337 may operate.

There are three main mechanical controls seen in FIGS. 77 & 78. At the left side, a knob 1355 is attached to a threaded member 1357 which is threadably engaged into a raised block 1359 mounted atop first main frame member 1303. The threaded member 1357 continues beyond the threaded portion and terminates in a ball shaped fitting 1361. Ball shaped fitting 1361 is engaged in the axial direction by a rotational fitting block 1363. The rotational fitting block 1359 enables the threaded member 1357 to be urged axially forward and rearward by turning threaded engagement with the internally threaded raised block 1359 while urging the rotational fitting block 1363 toward and away from the raised block 1359 to cause the first inner pivotable frame member 1313 to pivot with respect to the first main frame member 1303.

At the right side a knob 1365 is attached to a threaded member 1367 which is threadably engaged into a bore 1369 within second main frame member 1305. Threaded member 1367 continues beyond the threaded portion and terminates within first inner translatable frame member 1341. The threaded member 1367 has a groove 1371 for interfitting with a ring lock fitting 1373. The combination of the groove 1371 and ring lock fitting 1373 enables the threaded member 1367 to freely rotate within the first inner translatable frame member 1341 to cause the first inner translatable frame member 1341 to be moved along internal groove 1329.

As a result of the first two controls, the separation and angularity of the lower extension members 1335 and 1349 can be independently controlled. A third control controls the angularity of the first main frame member 1303 with respect to the second frame member 1305, and can somewhat equalize the angular position of the lower extension members 1335 and 1349 with respect to the average angle of the first and second main frame members 1303 and 1305.

Best seen in the lower portion of FIG. 77, an adjustment knob 1375 is attached to a threaded member 1377. At the opposite end of threaded member 1377 a ball fitting structure 1379 is seen. The ball fitting structure 1379 rotatably fits within a rotational block fitting 1381 which may have a top opening to allow the threaded member 1377 to be rotated upward to disengage the rotational block fitting 1381.

The threaded portion of the threaded member 1377 fits inside a threaded support block 1383 having at least a portion of an internal space threaded (as shown in FIG. 77). A detent mechanism may be supplied within the threaded support block 1383, including a threaded member 1385 capturing a spring 1387 which urges a detent ball 1389 into contact with the threads of threaded member 1377. Opposite the detent ball 1389 are at least a partial set of internal threads 1391 are seen. Where the internal threads 1391 are only lateral threads, the threaded member 1385 may be lifted up, out of contact with such internal threads 1391. This type of action is desirable where an obturator 33, 215 or 241 are or may be used to set the angular displacement of the lower extension members 1335 and 1339.

In this case, and depending upon the detent setting, the surgeon can select between disengagement and remaining engagement of the mechanism, hereafter referred to as frame angle mechanism 1393 including adjustment knob 1375, threaded member 1377, ball fitting structure 1379, rotational block fitting 1381, threaded support block 1383, threaded member 1385, spring 1387 and a detent ball 1389, and internal threads 1391. The frame angle mechanism 1393, being located to the side of the working space, can be re-engaged at any time by turning the knob 1375 and threaded member 1377 to a position corresponding to the angular relationship of the first main frame member 1303 with respect to the second frame member 1305.

Figure 79:
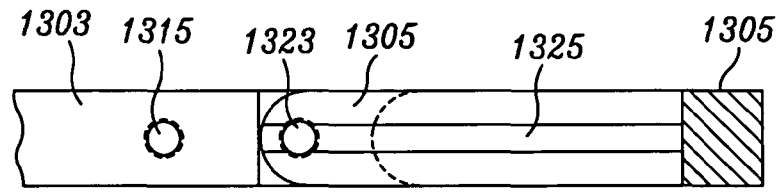
FIG. 79 illustrates a sectional view taken along line 79-79 of FIG. 77.

Also seen is an optional fiber optic system 1395 which can be utilized with the frame retractor system 1301 or any frame retractor system disclosed. The fiber optic system 1395 may be a laser source powered remotely, or it may simply be a support for a guided fiber optic. It is shown as being secured by the threaded members 1309 and has a terminus 1397 extends into the Referring to FIG. 79, a sectional view taken along line 79-79 of FIG. 77 illustrates further details of the pair of pivot pin members 1315 and pivot pins 1323. Also seen more clearly is the internal groove 1329.

Figure 80:
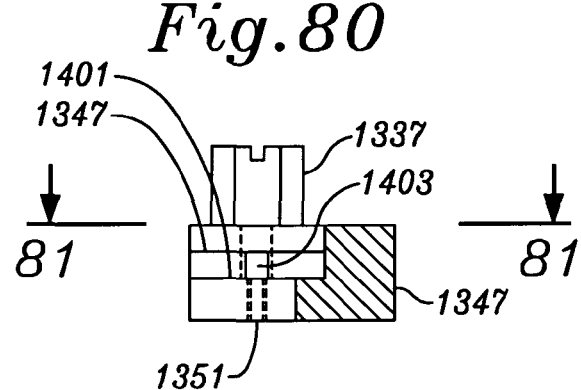
FIG. 80 illustrates a sectional view taken along line 80-80 of FIG. 77.

Referring to FIG. 80, a sectional view taken along line 80-80 of FIG. 77 illustrates further details of the inside of first inner translatable frame member 1341. The upper extent of the second retractor half 1345 is seen. A lower support surface 1401 is seen to provide an even resting place for thickened structurally reinforced upper head portion 1347. A rotatable member 1403 is seen as being rotatable between a locking position and an unlocked position.

Figure 81:
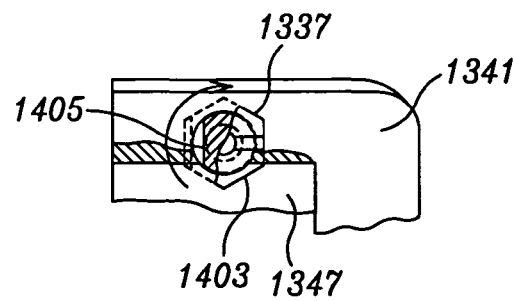
FIG. 81 a top semi sectional detail view of the inside corner of the first inner translatable frame member seen in FIGS. 77 & 78 and shown in locked position.

Referring to FIG. 81, a top semi sectional view sectional view focusing on the inside corner of the first inner translatable frame member 1341 illustrates further details of the locking mechanism. The upper extent of the second retractor half 1345 is seen. A rotatable member 1403 is seen as being rotatable between a locking position and an unlocked position. Rotatable member 1403 carries a flat side 1405 which can be rotated to face an indentation (to be shown) in either of the reinforced upper head portions 1333 or 1347 to allow such reinforced upper head portions 1333 or 1347 to slide out of held contact within the first inner pivotable frame member 1313 and the first inner translatable frame member 1341, respectively. Again, the configuration shown is but one of many physical realizations which will allow quick changeout and placement of the first and second retractor halves 1331 and 1345.

Figure 82:
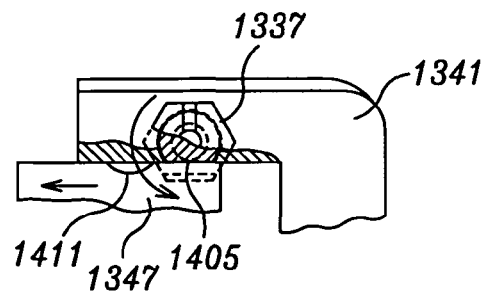
FIG. 82 is a view in accord with FIG. 81 but illustrating the unlocked position.

Referring to FIG. 82 one of the indentations 1411 on the structurally reinforced upper head portion 1347 is seen. In the position shown, the rotational lock 1337 has been turned to present the flat side 1405 toward the structurally reinforced upper head portion 1347 and thus rotate the rounded side of the rotatable member 1403 out of occupation of the space of the indentation 1411 which allows upper head portion 1347 to be removed from the first inner translatable frame member 1341.

Further details of the first and second retractor halves 1331 and 1345 are shown in FIGS. 83-87. A broken line is seen in FIGS. 85-87 to illustrate variable length. FIG. 83 is a bottom view of first retractor half 1331 looking up into the lower extension member 1335 and illustrating a cutout 1415 which can be considered a partial removal of material for enhanced ease of insertion and or registry with respect to an obturator, if desired.

FIG. 84 is a bottom view of a second retractor half 1345 and also illustrating a complementary cutout 1415. FIG. 85 is a side view the first retractor half 1331 shown in FIG. 83 and illustrating a front profile of the cutout 1415. FIG. 86 illustrates a matching side view the second retractor half 1345. FIG. 87 is a view looking into the curved back side of second retractor half 1345 and illustrating a profile of the cutout 1415 illustrating it to be a an ark removing about half of the bottom periphery of the second retractor half 1345.

Further details of a second set of non-circularly curved first and second retractor halves are seen in FIGS. 88-92. Again a broken line is seen in FIGS. 88-92 to illustrate variable length. The shape of FIGS. 88-92 provide a rectangularization of the viewing profile into the shape provided by the retractor halves to open the view space, yet retain the gentle curvature at the edges. FIG. 88 is a bottom view of first retractor half first retractor half 1421 which includes a thickened structurally reinforced upper head portion 1423 and a lower extension member 1425. As before, the upper head portion 1423 is sized to fit closely within the first inner pivotable frame member 1313 to facilitate quick change out. As before indentations 1411 are present so that the structures shown in FIGS. 83-98 can be utilized with the frame retractor system 1301.

FIG. 89 is a bottom view of a second retractor half 1427 and also illustrating complementary indentations 1411, upper head portion 1429 and lower extension member 1431. FIG. 90 is a side view the first retractor half 1421 shown in FIG. 88 and illustrating a side profile. FIG. 91 illustrates a matching side view the second retractor half 1427. FIG. 92 is a view looking into the rear back side and curving edges. FIGS. 93 and 94 illustrate a right side and rear view of a retractor half 1432 similar to that seen in FIGS. 88-92, but having a bulge 1433 at a middle but lower portion of the lower extension member 1425. FIGS. 95 and 96 illustrate a right side and rear view of a retractor half 1434 similar to that seen in FIGS. 88-92, but having a serrated shape 1435 formed along the bottom of the lower extension member 1425. FIGS. 97 and 98 illustrate a right side and rear view of a retractor half 1436 similar to that seen in FIGS. 88-92, but having a rounded cutout 1437 formed along the bottom of the lower extension member 1425.

FIG. 99 illustrates a side elevation view taken somewhat with respect to the orientation seen in FIG. 77 and looking into the side closest to the adjustment knob 1375. Details which are noticeable include the support of the threaded support block 1383 from the second frame member 1305. As can be seen, the translation control of the first inner translatable frame member 1341 with the knob 1365 is had a lower or first level, generally at the levels of the first and second main frame members 1303 and 1305. The pivoting control of first inner pivotable frame member 1313 by the controlling engagement of the knob 1355 occurs a second level, above the levels of the first and second main frame members 1303 and 1305. It is also noted that the pivoting control of the first main frame member 1303 with respect to the second frame member 1305, via the control knob 1375, occurs at a level above the levels of the first and second main frame members 1303 and 1305.

In reality, translating control of the first inner translatable frame member 1341 with the knob 1365 can be accomplished with a fitting raised above the levels of the first and second main frame members 1303 and 1305. In addition, the pivoting control of first inner pivotable frame member 1313 with the knob 1355 can occur at the level of the first and second main frame members 1303 and 1305 by placing the support structures surrounding the pair of pivot pin members 1315 above or below the first and second main frame members 1303 and 1305. Similarly, the pivoting control of the first and second main frame members 1303 and 1305 with respect to each other can be had by placing the adjustment knob 1375, threaded member 1377 and ball fitting structure 1379 either at the level of the first and second main frame members 1303 and 1305 with placement of pivot moment structures elsewhere, or by placing the adjustment knob 1375, threaded member 1377 and ball fitting structure 1379 below the frame structure. Other mechanical structures for providing pivoting control of the first and second main frame members 1303 and 1305, each of the first inner pivotable frame member 1313 and first inner translatable frame member 1341 may be provided. Such other mechanical structures may provide for separate or integrated controls. Integrated controls may be provided electromechanically or mechanically and with or without the use of a microprocessor and pressure sensitive feedback sensing.

Continuing to refer to FIG. 99, it can be seen that the surgical practitioner can adjust the positions of the lower extension members 1335 and 1339 in terms of their separation from each other regardless of angle, their angularity regardless of separation, and independently set the relationship of the first main frame member 1303 with respect to the second frame member 1305. Subsequent FIGS. 94-99 will illustrate only some of the movement possibilities.

Figure 100:
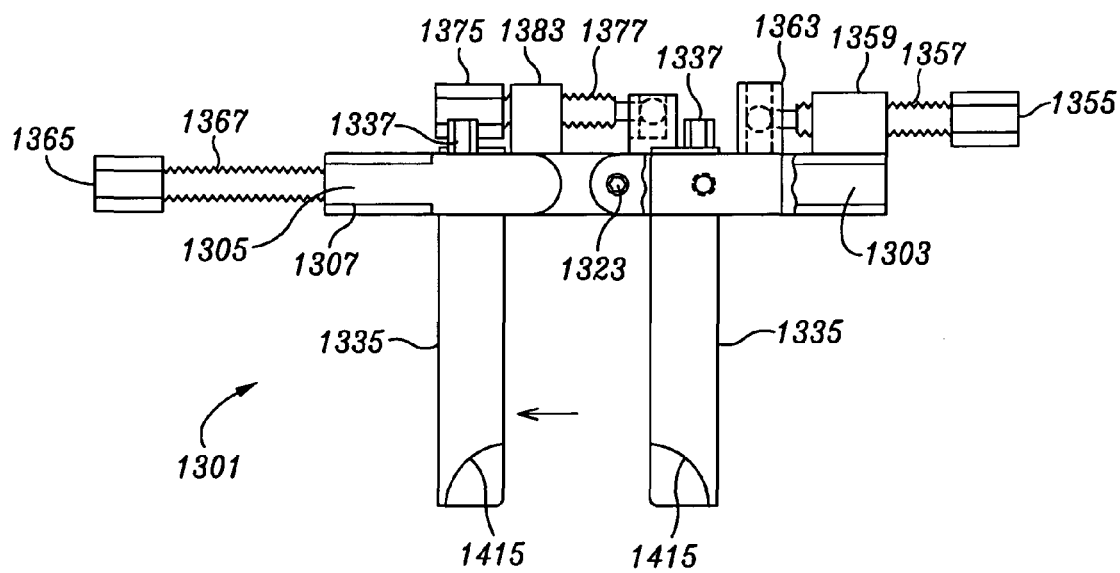
FIG. 100 is a right side view of the frame retractor system similar to that seen in FIG. 99 and in which the retractor lower extension members are shown parallel and separated from each other.

Referring to FIG. 100, a plan elevational view is shown similar to that seen in FIG. 99, but with the frame retractor system 1301 show from the opposite side from that seen in FIG. 99. The knob 1365 has caused the threaded member 1367 to extend outside the second frame member 1305 to draw the first inner translatable frame member 1341 back into the second frame member 1305 to cause the lower extension member 1349 to move away from the lower extension member 1335.

Figure 101:
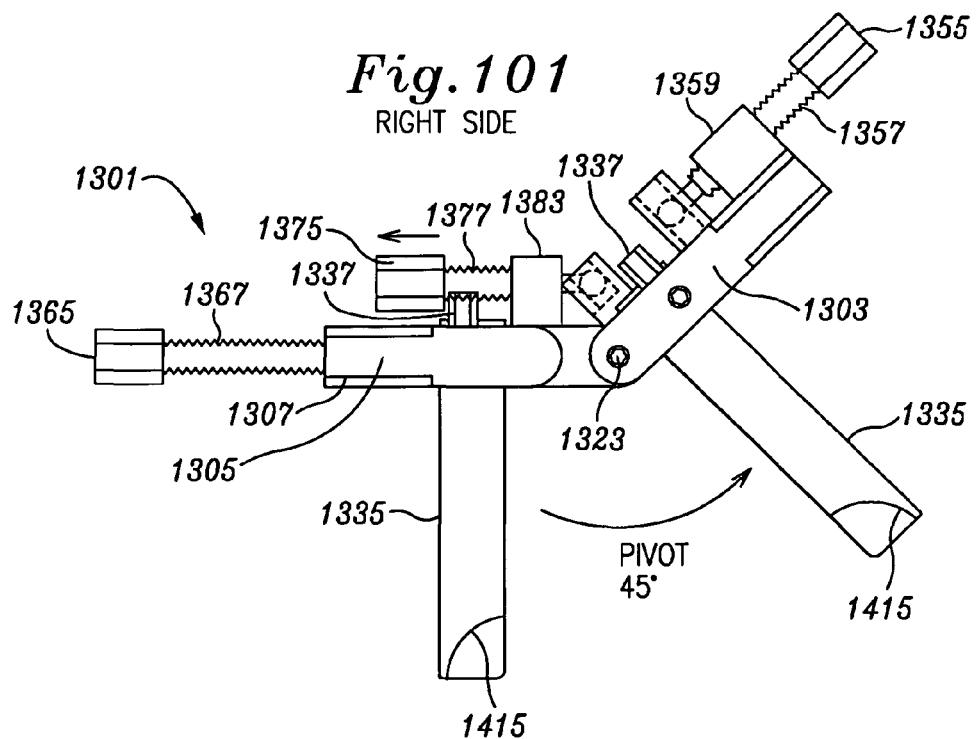
FIG. 101 is a right side view of the frame retractor system similar to that seen in FIGS. 99 to 100 and showing angular displacement of the first main frame member with respect to the second main frame member.

Referring to FIG. 101, a view from a common perspective as seen for FIG. 100 illustrates the activation of knob 1375 has caused the threaded member 1377 to withdraw through the threaded support block 1383 to cause the first main frame member 1303 to move upwardly to form an angle with second frame member 1305. The ability to precisely control the angle of first main frame member 1303 with respect to the second frame member 1305 enables the user to adjust the mean or average position of the frame members 1303 and 1305 with respect to the general orientation of the extension members 1335 and 1349. This enables the user to avoid having the frame members 1303 and 1305 assume a mean angle with respect to each other which is not somewhat centered by the angle of the frame members 1303 with respect to frame member 1305.

Figure 102:
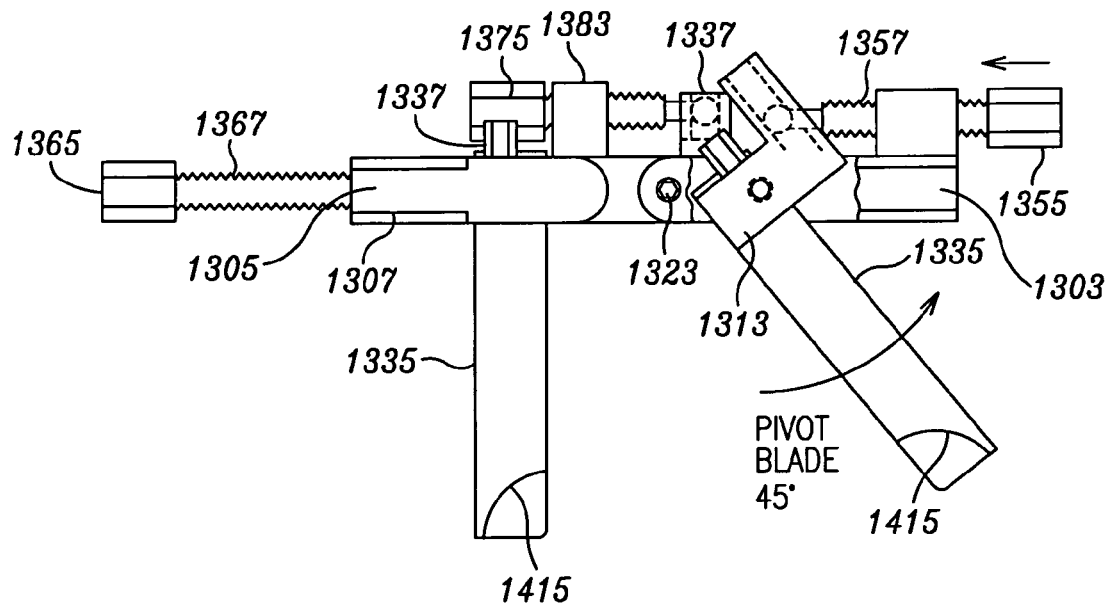
FIG. 102 is a right side view of the frame retractor system similar to that seen in FIGS. 99 to 101 and showing angular displacement of the first inner pivotable frame member causing the lower extension members to angle away from each other.
Figure 103:
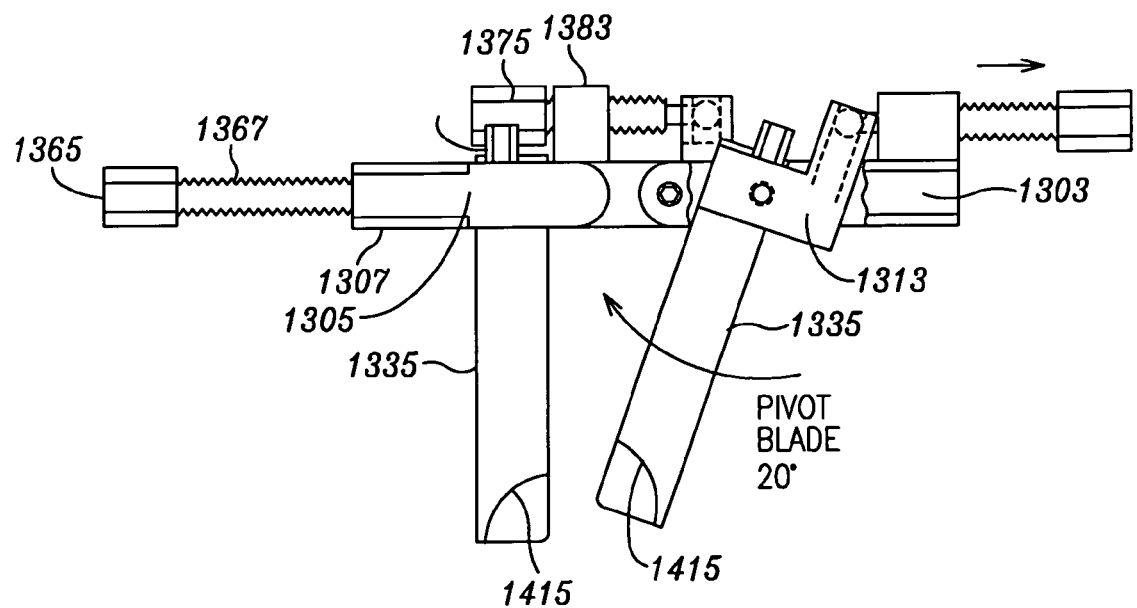
FIG. 103 is a right side view of the frame retractor system similar to that seen in FIGS. 99 to 102 and showing angular displacement of the first inner pivotable frame member causing the lower extension members to angle toward each other.

Referring to FIGS. 102 and 103, a view from a common perspective as seen for FIGS. 96 and 97 illustrates the activation of knob 1355 has to cause the threaded member 1377 to either withdraw through the threaded support block 1359 to cause the first inner pivotable frame member 1313 to tilt the lower extension member 1335 toward the lower extension member 1349; or conversely to cause the threaded member 1377 to move forward through the threaded support block 1359 to cause the first inner pivotable frame member 1313 to tilt the lower extension member 1335 away from the lower extension member 1349.

With regard to the description for FIG. 101, it can readily be seen that an angular displacement of the lower extension member 1335 with respect to the lower extension member 1349 as seen in FIG. 102 might be achieved by some angular displacement of the frame members 1303 with respect to frame member 1305, with the remainder of angular displacement being provided by actuation of the lower extension member 1335. Angular displacement of the frame members 1303 with respect to frame member 1305 can occur in either direction if a sufficient length of threaded member 1377 is provided.

Figure 104:
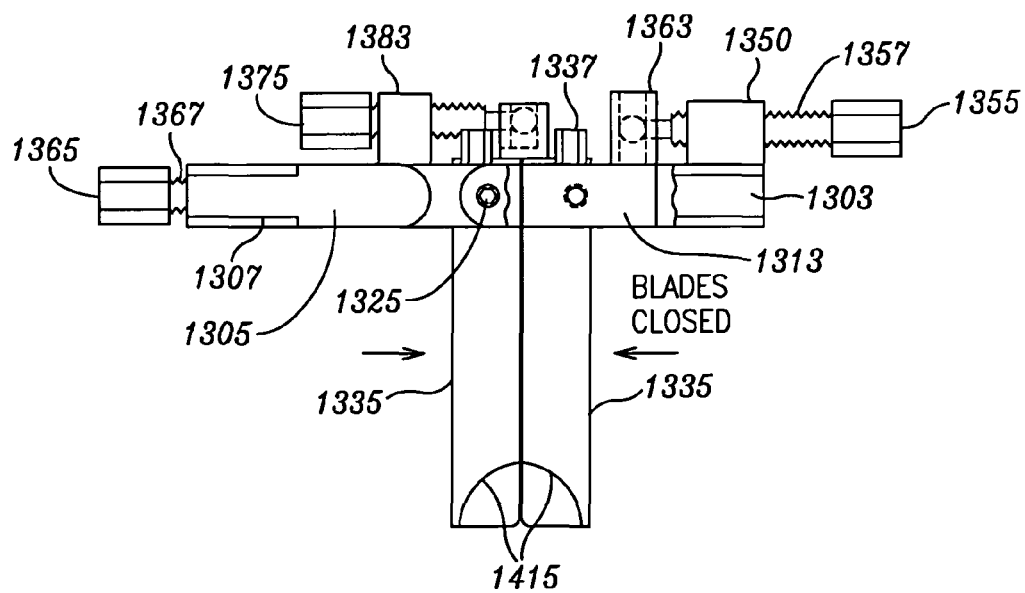
FIG. 104 is a right side view of the frame retractor system similar to that seen in FIGS. 99 to 103 and showing retractor lower extension members parallel and adjacent each other.
Figure 105:
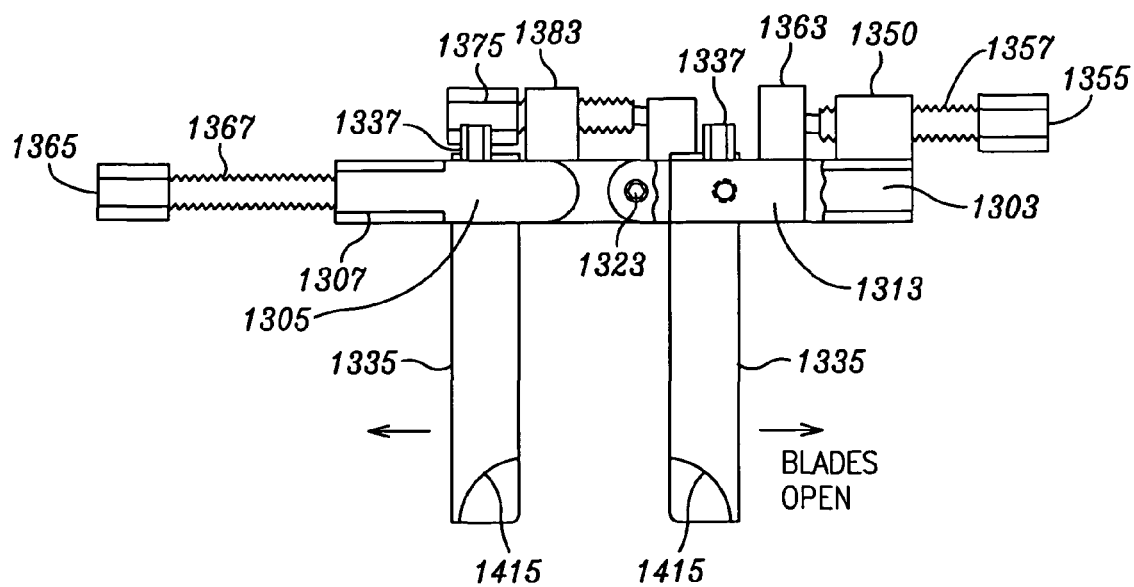
FIG. 105 is a right side view of the frame retractor system similar to that seen in FIGS. 99 to 104 and showing retractor lower extension members parallel and displaced from each other.

Referring to FIGS. 104 and 105, a view from a common perspective as seen for FIGS. 100-103 illustrates the activation of knob 1365 has to cause the threaded member 1367 to either rotatably extend into the internally threaded second frame member 1305 to cause the first inner translatable frame member 1341 to move toward the first main frame member 1303 to move the lower extension member 1349 toward the lower extension member 1335 (as seen in FIG. 104); or to rotatably withdraw from the internally threaded second frame member 1305 to cause the first inner translatable frame member 1341 to move away from the first main frame member 1303 to move the lower extension member 1349 away from lower extension member 1335 (as seen in FIG. 99).

Figure 106:
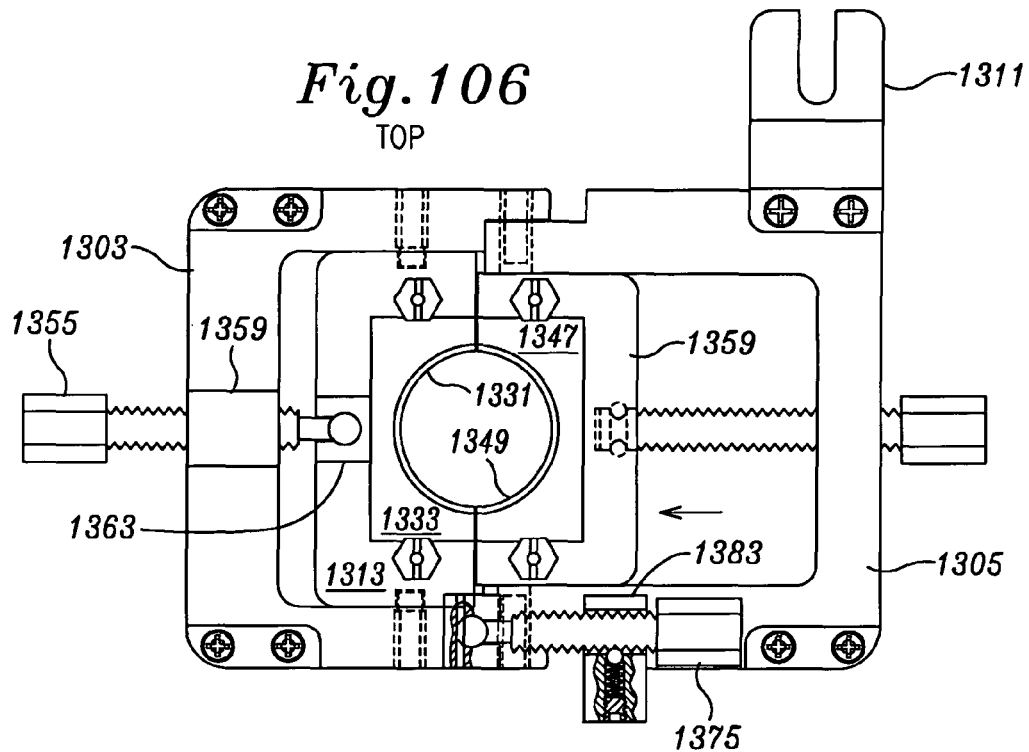
FIG. 106 illustrates a top view of frame retractor system similar to that seen in FIGS. 99 to 105 and showing retractor lower extension members parallel and in adjacent relationship as seen in FIG. 104.

Referring to FIG. 106, a top view having a position equivalent to the position seen in FIG. 104 is shown. The first inner translatable frame member 1341 is in a position having been moved all the way toward the first inner pivotable frame member 1313 to have the lower extension members 1335 and 1349 into a circular profile forming a tube. FIG. 106 illustrates that the structures which provide angular control of the first main frame member 1303 with respect to the second frame member 1305 are well clear of the tube formed by the lower extension members 1335 and 1349, and even clear of adjacent structures, including thickened structurally reinforced upper head portions 1333 and 1347, as well as the first inner pivotable frame member 1313 and first inner translatable frame member 1341. Essentially, the angular control of the first main frame member 1303 with respect to the second frame member 1305 is restricted to a dimension which is about the width of the first and second main frame member 1303 and 1305.

Figure 107:
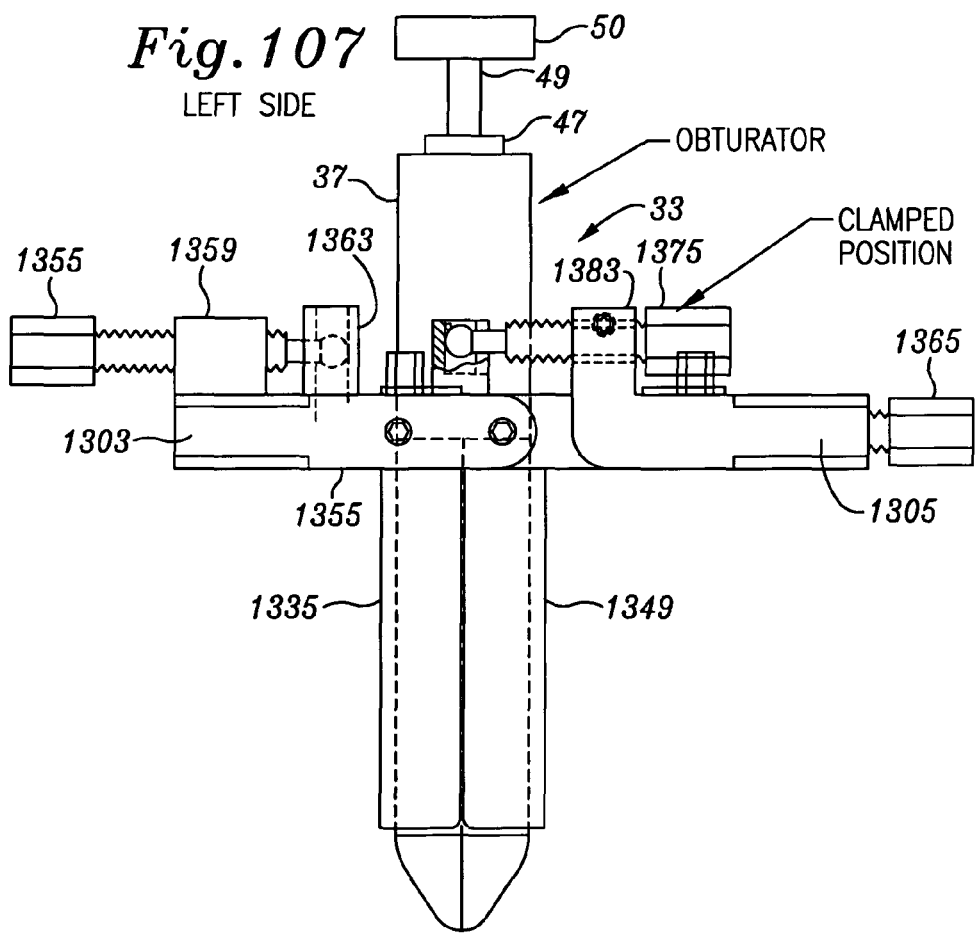
FIG. 107 illustrates a right side view of frame retractor system similar to that seen in FIGS. 99 to 106 and showing an obturator used in conjunction with the frame retractor.

Referring to FIG. 107, the frame retractor system 1301 is shown with respect to the obturator 33 seen in FIG. 1. The presence of the obturator 33 provides an additional conical spreading structure with the advance of the ends of the pair of spreading legs 39 and 41 just beyond the distal most portion of the lower extension members 1335 and 1349. As has been seen in FIG. 14, the obturator 33 can provide force at a distance and can assist in separating the first and second main frame member 1303 and 1305.

Figure 108:
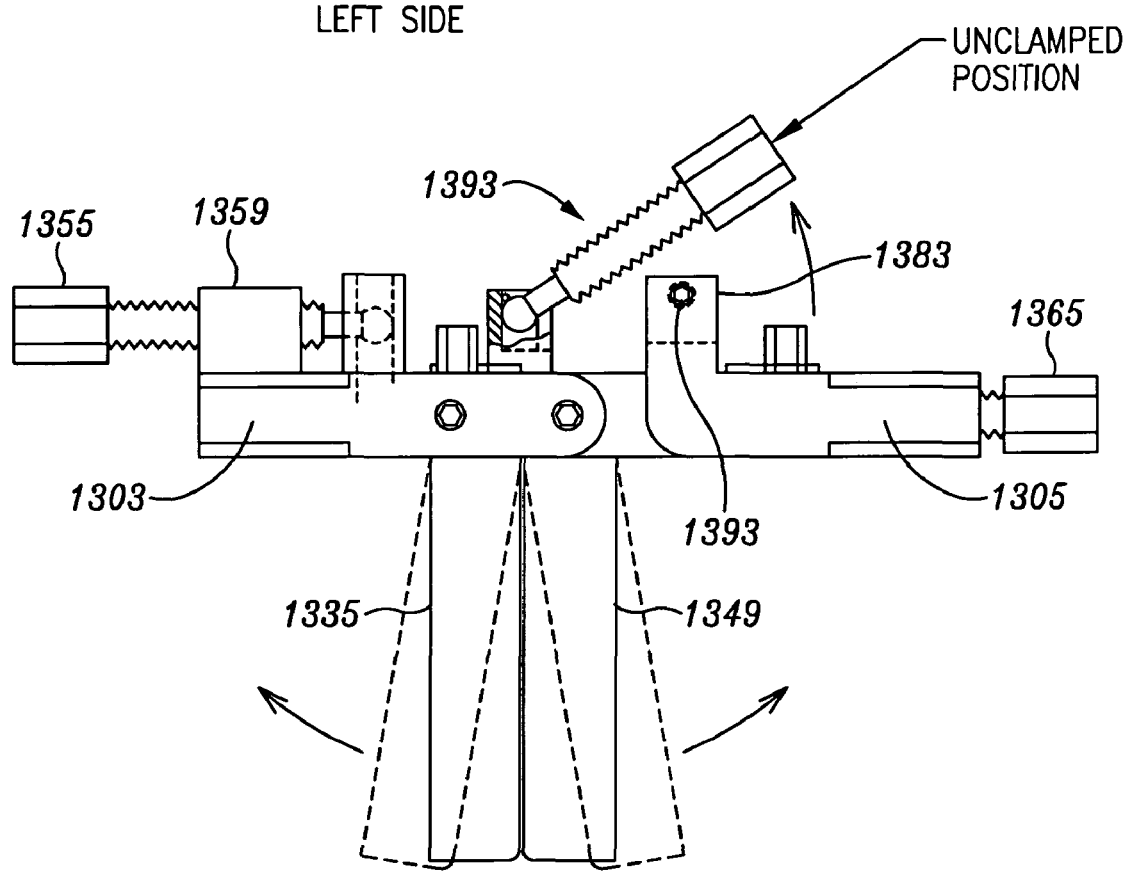
FIG. 108 illustrates a left side of the frame retractor system similar to that seen in FIGS. 99 to 107 and showing disengagement of the angular displacement mechanism to permit free angular movement.

Referring to FIG. 108 an option for disengagement and re-engagement of the frame angle mechanism 1393 is seen. Where the threaded support block 1383 has an open upper portion such that the threaded member 1377 can be snapped out of the support block 1383 and pivoted upward, the detent ball 1389 can be removed from its rotational fitting block 1363 and removed. The obturator 33 can then be employed to manipulate the lower extension members 1335 and 1349. The threaded member 1377 can be replaced once the lower extension members 1335 and 1349 have been moved to the desired position. Once the threaded member 1377 is replaced, the obturator 33 can be removed. Again, where the spring 1387 and detent ball 1389 arrangement is permissibly loose, the obturator 33 can be operated against the frame angle mechanism 1393 as a force detent. In this mode, the obturator would force the extension members 1335 and 1349 as the frame angle mechanism 1393 clicks open to a desired position. In this arrangement, the obturator 33 does not operate on either of the first inner translatable frame member 1341 or first inner pivotable frame member 1313, both of which are expected to be non movable by the obturator 33, but operates on the frame angle mechanism 1393.

Figure 109:
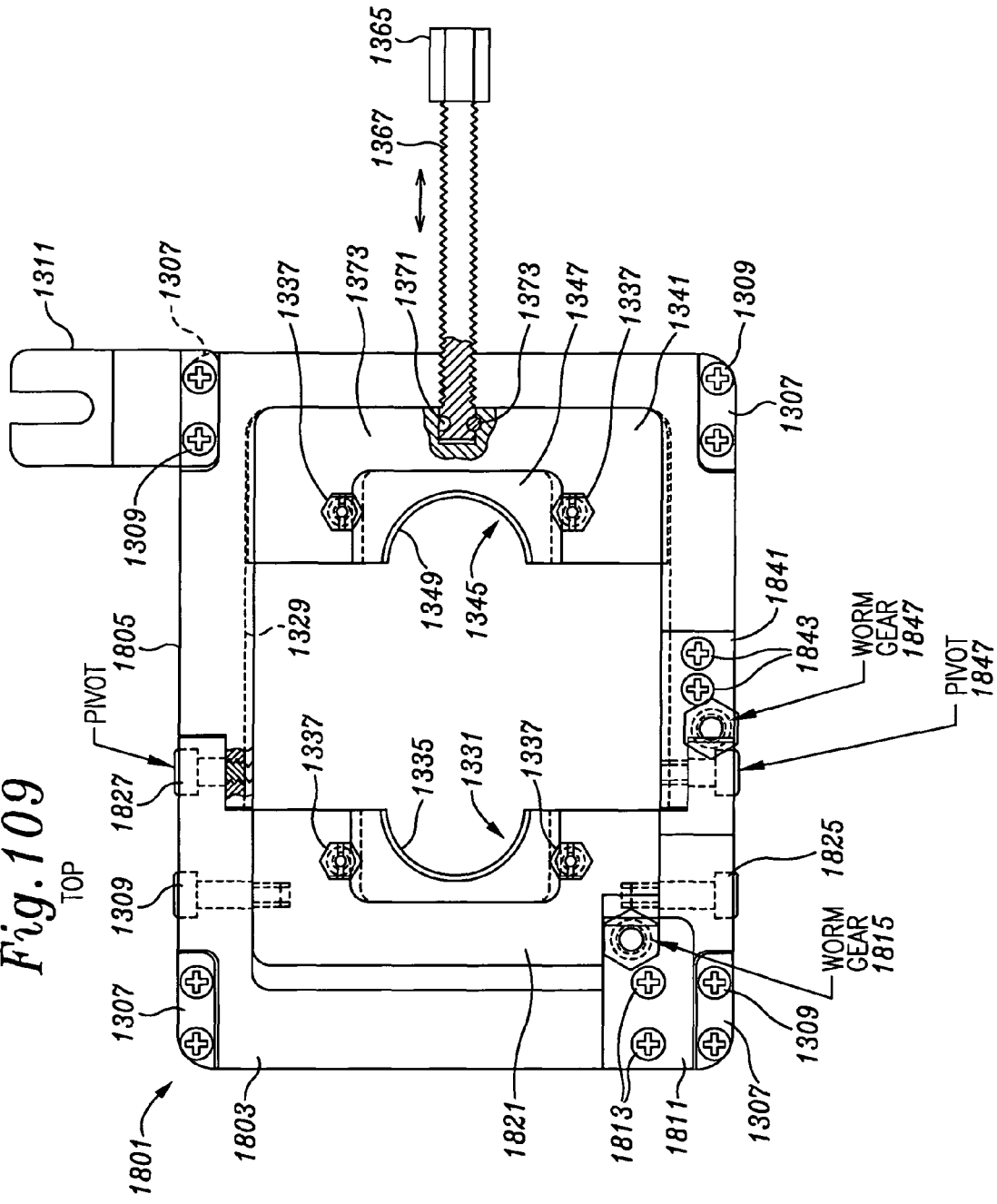
FIG. 109 illustrates a top view of a variation on the frame retractor system in FIGS. 99 to 108 as having two external controls moved inside the outer surface of the frames and including a worm gear system for angular adjustment of the retractor members and first and second main frame members.

Referring to FIG. 109, a variation on the frame retractor system 1301 in FIGS. 77-102 is seen as a frame retractor system 1801. The portion of frame retractor system 1801 generally appearing in the right third of FIG. 109 is the same as was shown in FIG. 77, and these structures will retain their original numbering. Note that first and second main frame members 1803 and 1805 are slightly more compact and more closely fitting with respect to each other.

The frame retractor system 1301 relied upon force structure located in a spaced relationship from the pivot axis, externally located with respect to the frame retractor system 1301 to operate. The relied upon force structure for tilt typically involved a threaded member 1357 or 1377 which could be seen externally. In both of these cases the axis of the threaded member 1357 or 1377 were external to the main vertical extent of the main structural members of the frame retractor system 1301. The axis of the threaded members 1357 or 1377 can be displaced from the pivot axes they control and provide enhanced mechanical advantage.

The frame retractor system 1801 provides control generally within the vertical limits of a first and second main frame members 1803 and 1805. Mechanical advantage can be achieved by selection of the pitch of the gears which follow. The method of control is to provide a relatively low profile knob having a vertical shaft which contains a worm gear. The worm gear acts upon an gear having an effective horizontal axis to either tilt a structure equivalent to the prior first inner pivotable frame member 1313 or to tilt the a first main frame member 1803 with respect to the second main frame member 1805.

Referring to the lower left side of FIG. 109, a first gear works cover 1811 is secured by a pair of threaded members 1813. A low profile knob 1815 extends upward from the level of the first gear works cover 1811 to provide for manual user control. A first inner pivotable frame member 1821 is similar to the first inner pivotable frame member 1313, but is shown as having some material removed to accommodate the mechanism being described.

A pair of oppositely disposed pin members include a first pivot member 1825 and a second pivot member 1827. The first pivot member 1825 is set to have a terminal portion within first inner pivotable frame member 1821 which turns with the first inner pivotable frame member 1821. The second pivot member 1827 need only support the first inner pivotable frame member 1821 and allow it to pivot with respect to the second main frame members 1805.

The low profile knob 1815 is attached to a worm gear (not seen in FIG. 109). Adjacent worm gear (not shown in FIG. 109) an elongate cylindrical gear structure may be located which will rotate with first inner pivotable frame member 1821. Such a gear surface may be located on a special gear within the first inner pivotable frame member 1821, or in the alternative, such a gear surface may be formed on the external surface of the first inner pivotable frame member 1821. Since the first inner pivotable frame member 1821 need only tilt slightly, the arrangement for the pitch of the worm gear assembly can yield significant mechanical advantage. Further, because the angular displacement is small, the size of the gear elements (deeper wider grooves) should not be adversely impacted by a relatively high mechanical advantage.

A similar arrangement is had with respect to the angular adjustment of first main frame member 1803 with respect to second main frame member 1805. Referring to the bottom center of FIG. 104, a second gear works cover 1841 is secured by a pair of threaded members 1843. A low profile knob 1845 extends upward from the level of the first gear works cover 1841 to provide for manual user control. The low profile knob 1845 and second gear works cover 1841 engages a portion of the second main frame member 1805 and moves the angular relationship of the first main frame member 1803 with respect to second frame member 1805.

A pair of oppositely disposed pin members include a first pivot member 1847 and a second pivot member 1849. The first pivot member 1847 is set to have a terminal portion within first main frame member 1803 enables first main frame member 1803 to become angularly displaced from second main frame member 1805 while securing the pivot point between first main frame member 1803 and second main frame member 1805.

Again, the low profile knob 1845 is attached to a worm gear (not seen in FIG. 109). Adjacent worm gear (not shown in FIG. 109) may be an elongate cylindrical gear structure will be located which will rotate with first inner pivotable frame member 1821. Such a gear surface may be located on a special gear within the first main frame member 1803, or in the alternative, such a gear surface may be formed on the external surface of the first main frame member 1803, such as the rounded area adjacent second main frame member 1805 near the pivot point.

As before, since the first and second main frame members 1803 and 1805 can change their relative angular position only slightly, the arrangement for the pitch of the worm gear assembly can yield significant mechanical advantage without sacrificing the size and depth of the gear elements.

Figure 110:
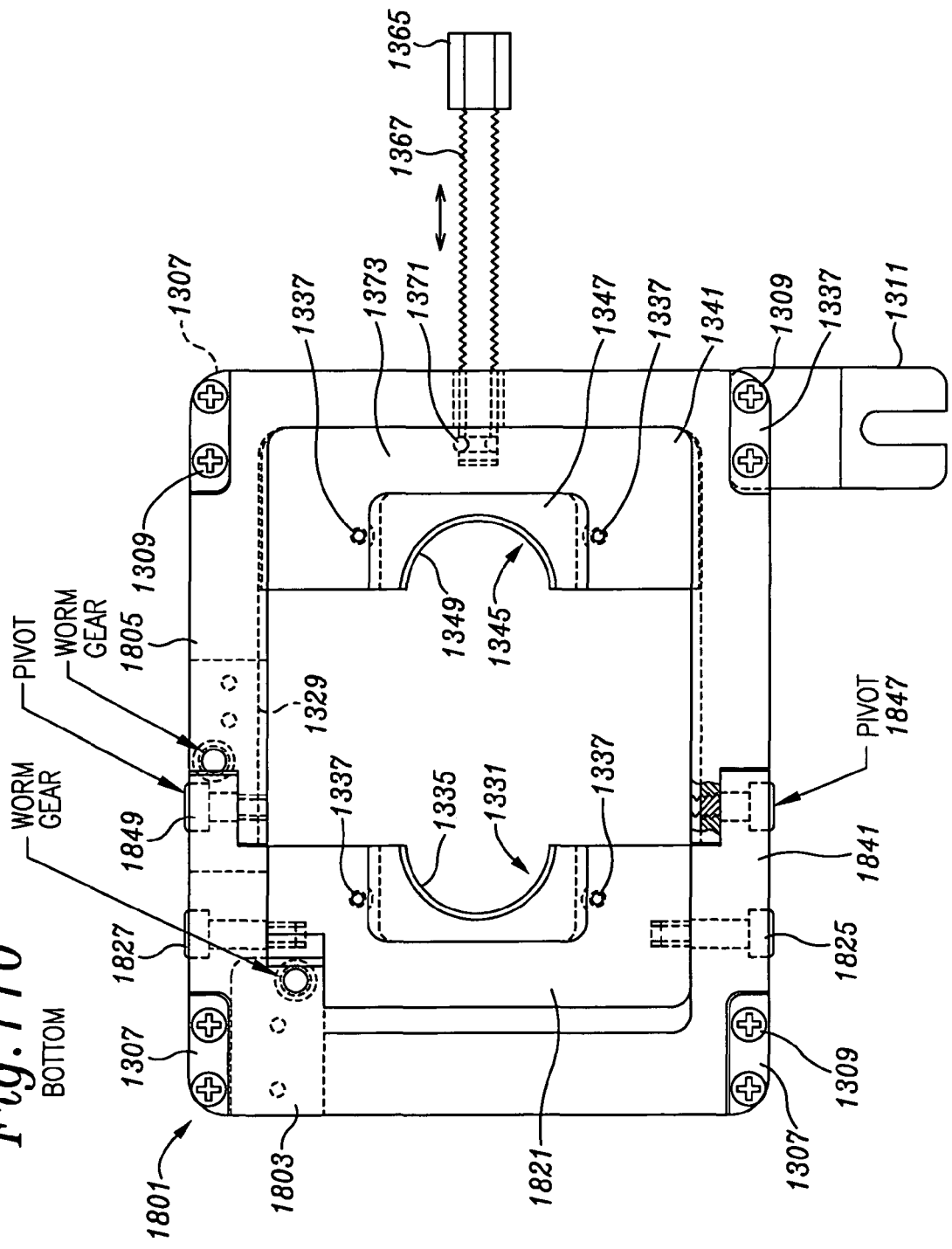
FIG. 110 is a bottom view of the retractor system seen in FIG. 109.
Figure 111:
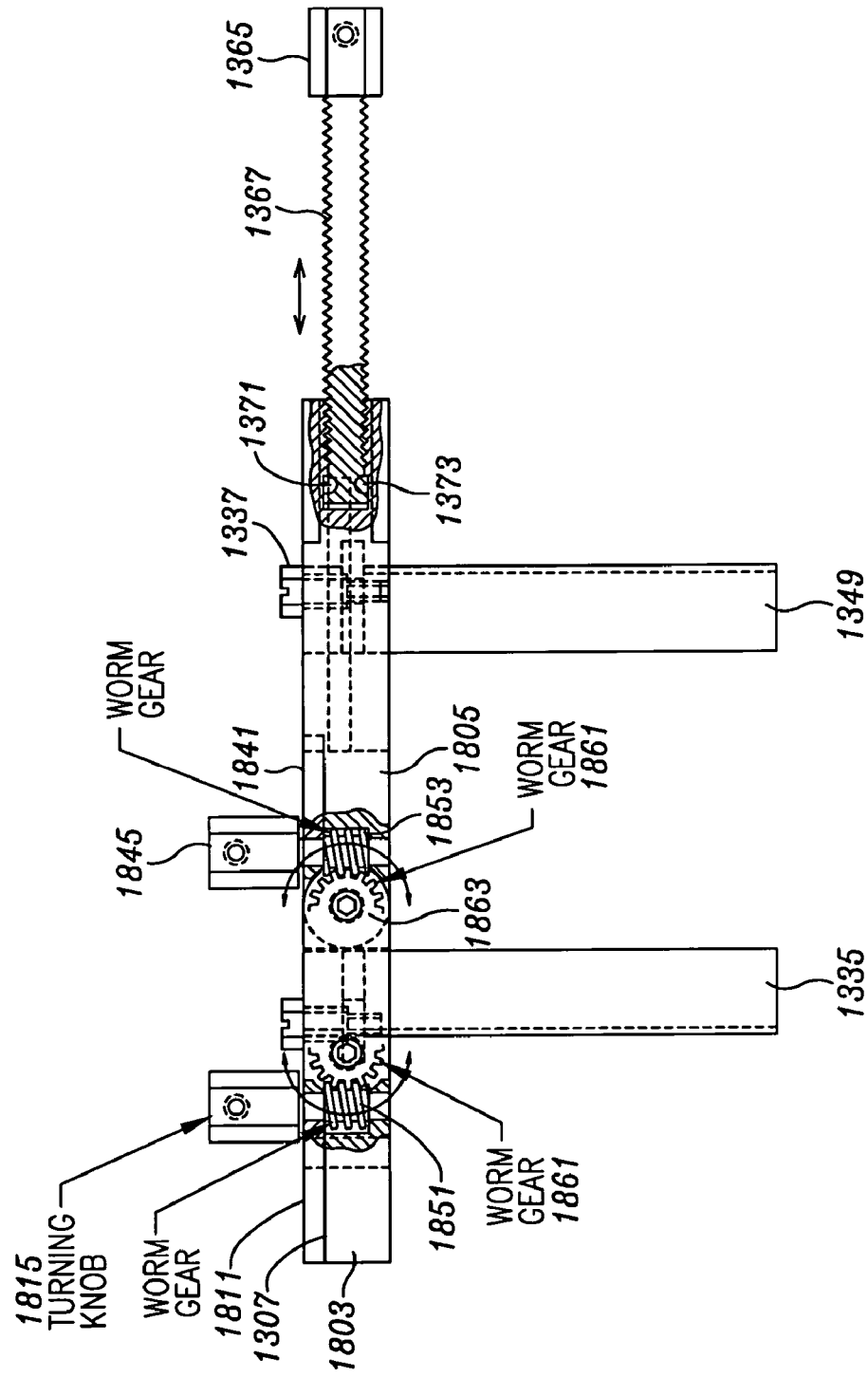
FIG. 111 is a bottom view of the retractor system seen in FIGS. 109 and 110.

Referring to FIG. 110, a bottom view of the frame retractor system 1801 is shown and illustrating the underside elements. Referring to FIG. 111, a side view illustrates further details of the frame retractor system 1801 seen in FIGS. 109 and 110. This pan semi sectional view illustrates a first worm gear 1851 associated with low profile knob 1815 and a second worm gear 1853 associated with low profile knob 1845. A first pivot gear 1861 is seen engaging the first worm gear 1851, while a second pivot gear 1863 is seen engaging the second worm gear 1853. The first and second pivot gears 1861 and 1863 may be completely circular or may be semi-circular. The showing of FIG. 110 can be a partial showing or it can be a showing greater than what is provided as the angle of tilt will not be great.

One of the advantages seen in both the frame retractor systems 1301 and 1801 is the ability to remove the first and second retractor halves 1331 and 1345 vertically. This enables, without moving the overall frame retractor systems 1301 and 1801, the first and second retractor halves 1331 and 1345 to be removed or replaced. Removal and replacement can be achieved simply by actuation of the pair of rotational locks 1337. Such interchange ability can permit the surgical practitioner to quickly change out first and second retractor halves 1331 and 1345 for other types and depths of retractors, or to remove the retractors in favor of other structures.

Figure 112:
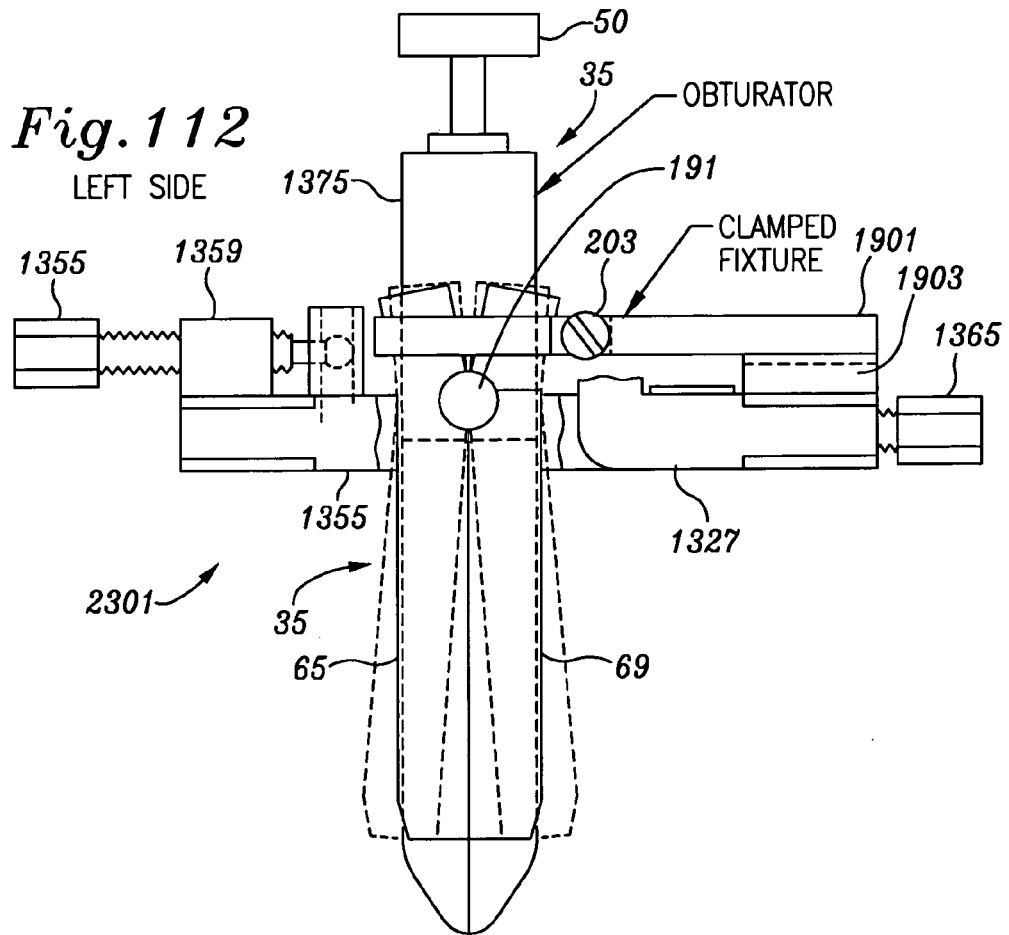
FIG. 112 is a left side view of the retractor system seen in any of the FIGS. 99 to 111 and in which the obturator and working blade of FIG. 1 is supported by the first and second main frame members where the interfitting retractor members have been removed.
Figure 113:
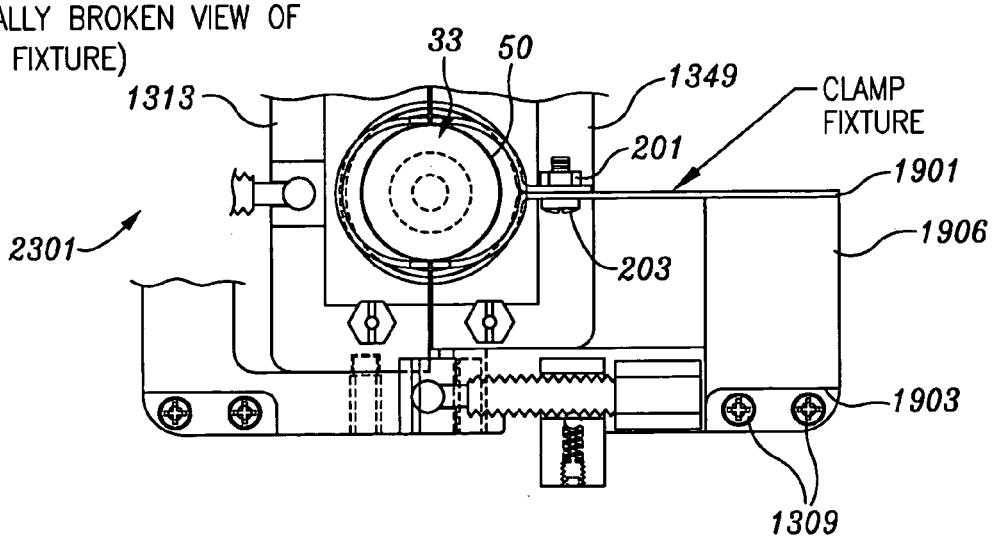
FIG. 113 is a top view of the arrangement seen in FIG. 112.

Referring to FIG. 112 the frame retractor system 1301 is shown with the first and second retractor halves 1331 and 1345 removed, and with the working sleeve 35, previously seen in FIG. 1, suspended with a clamp fixture 1901. As can be seen, clamped fixture 1901 has a base portion 1903 which is attached onto one of the formed depressions 1307 and secured by the series of threaded members 1309 which remain readily available for quick attachment of any utility structure. Referring to FIG. 113, the base 1903 can be seen as extending across to a horizontal web portion 1906, and then upward to a strap portion 1907. The end of the strap portion is attached to the a nut 201 and bolt 203 assembly previously seen in FIG. 25. Other strap supports can be employed on both the frame retractor systems 1301 and 1801 to enable wide flexibility in use.

In all of the devices shown, including the retractors devices such as working sleeves 35, 222, retractors 555, 571, 691, 573, 631, 657, 691, 751, 901, 1001, 1301, 1801 and obturators 33, 241, a manual control was shown including knobs 50, 587, 597, 597, 617, 627, 635, 673, 797, 1115, 1195, 1355, 1365, 1375, 1815, 1845 and more, as well as threaded member 203, and knob 261. Some are shown as knurled members and others as hexagonal members, but in fact the hexagonal shapes and knurled shapes can be used interchangeably.

Depending upon the size of the tool, its working depth and other factors, tremendous working forces can be generated. A review of the literature illustrates resort to massive mechanical members which project far from the medical instrument are often employed to generate the forces needed. The approach to all of the medical instrumentation herein has been one of low profile, and to occupy no more of the surgical field than is absolutely necessary. Where the actuation members lie parallel and close to the patient's body they may be more difficult to actuate in the presence of significant tissue resistance to retraction. Therefore, a sterilizable ratchet has been developed in order to enable quick, temporary, enhanced mechanical actuation of the retractor members. Mechanical advantage may thus be had based upon mechanical advantage embodied in the particular retractor operation structure (including obturators) and in addition by a sterilizable ratchet tool which gives even more precise control for the medical practitioner. Any ratchet engagement is possible. A hexagonal bore could be provided within the knurled knobs to facilitate both direct manual and ratchet driven operation.

Referring to FIG. 114 a ratchet actuation tool 3001 is shown. One of the problems with tools used in surgery is the ability to dis-assemble and sterilize and dis-assemble, if necessary the instrumentation. A ratchet or other common mechanical tool which would otherwise be a great help in the surgical theater is a problem from a sterilization standpoint. Most commonly known mechanisms include closed spaces, snap fit, and are not intended for disassembly. The ratchet actuation tool 3001 utilizes one-way permitted turning with a pair of socket heads and utilizes a simplistic internal mechanism with flow-through liquid wetting.

FIG. 114 is a side view looking through the ratchet actuation tool 3001. The ratchet actuation tool 3001 includes a first socket 3003 having a socket opening 3005 shown in dashed format. A first plate 3009 includes an aperture (not shown in FIG. 114) which provides rotational support. A second plate 3011 is spaced apart from the first plate 3009. An "open air" or through opening to the other side is labeled as 3013. To the left of through opening 3013 is seen a spring 3021, and spring bias post 3025 which is seen extending into the first plate 3009. A threaded member 3027 is seen attaching the end of the spring to a ratchet sprocket engagement head 3029. The ratchet sprocket engagement head 3029 engages a sprocket 3031.

All of the components located just above the lower plate 3009, have a liquid gap between those components and either the first plate 3009 and second plate 3011, meaning that the components are not tightly jammed together to have a danger of creating significant sealed spaces. A second socket 3035 has a socket opening 3037. Second socket 3035 extends above second plate 3011. The first socket 3003 includes a through member having a threaded post which a matching threaded bore within the second socket 3035 which engages the threaded post. In the case of a right hand thread, the turning of the plates 3009 and 3011 and post will cause the second socket to be even more securely turned and locked onto the post. The use of a double socket design enables reliance upon turning in only one direction.

At the opposite end of the ratchet actuation tool 3001, a spacer clip 3045 has a spacer portion 3051 and a threaded bore 3053. A hook portion 3055 includes a rising vertical portion and a hook to help hold the second plate toward the first plate. A threaded member 3059 holds the spacer clip 3045 down into an accommodation space 3061.

The spacer portion 3051 has a height in excess of the depth of the accommodation space 3061 which will positively and securely set the height of the first plate 3009 with respect to the second plate 3011. The threaded member passes through a bore 3065 before it engages the threaded bore 3053. A groove 3067 is seen to extend partially around a cutaway 3069 with the groove to accommodate the forward portion of the hook portion 3055 and the cutaway 3069 to accommodate the bulk of the hook 3055. As can be seen, the removal of the threaded member 3059 causes spacer clip 3053 to fall away and frees the first plate 3009 from the second plate 3011 at the end opposite the first and second sockets 3003 and 3035.

Also shown is a round pivot bar 3071 which is preferably jam fit within a bore 3075 in the first plate 3009 and extends through the ratchet sprocket engagement head 3029 and then loosely through a bore 3077 in the second plate 3011.

Referring to FIG. 115, a view is shown with the second plate 3011 removed, but with the spacer clip 3045 having been re-attached to show its position. Additional elements seen include the round pivot bar 3071 and the forward end 3081 of the ratchet sprocket engagement head 3029. The spring 3021 can be seen as acting on the ratchet sprocket engagement head 3029 to urge the forward end 3081 of the ratchet sprocket engagement head 3029 into locking contact with the sprocket 3031.

The sprocket 3031 is seen as having a square opening 3091. A threaded post 3093 has threads on the round portion shown and has a lower square member for interfitting with the square opening 3091 of the sprocket 3031. Referring to FIG. 118, a view with many of the elements seen in FIG. 115 is shown. The jam fit round pivot bar 3071 remains after the assembly consisting of the spring 3021, threaded member 3027, and ratchet sprocket engagement head 3029 is removed. Removal of the first socket 3003 reveals a first large aperture 3095 through which the threaded post 3093 extended in the assembled state.

Referring to FIG. 117, a view of the top plate 3009 illustrates a second large aperture 3097. Also seen are the previously mentioned bore 3077, groove 3067 and cutaway 3069. Referring to FIG. 118, a side sectional view of the first plate 3009 also illustrates a jam aperture 3099 previously occupied by the spring bias post 3025. Referring to FIG. 119, a side sectional view of the second plate 3011 illustrates another view of the second large aperture 3097.

Figure 121:
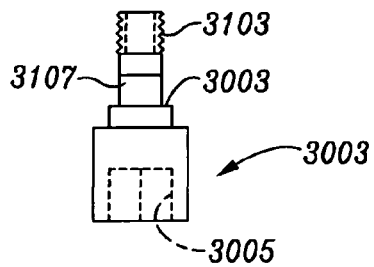
Figure 120:
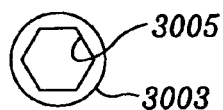

Other figures illustrate further details. Referring to FIG. 120 an end view looking into the first socket 3003 is shown. Referring to FIG. 121, a plan view of the first socket 3003 illustrate the details thereof. A stepped surface 3103 is larger than the first large aperture 3095 and prevents the first socket 3003 from passing through the first large aperture 3095. A rectangular section 3107 engages square opening 3091 of the sprocket 3031. This enables engagement of the ratchet sprocket engagement head 3029 onto the sprocket 3031 to translate into rotational fixation of the first socket 3003. Above the rectangular section 3107 is a threaded section 3109 which will engage a matching threaded bore in the second socket 3035.

Figure 125:
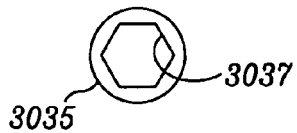
Figure 124:
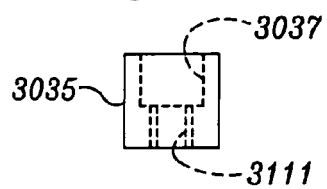
Figure 123:
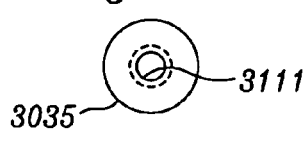

Referring to FIG. 123 a rear view of the second socket 3035 reveals a threaded bore 3111. Note that the ratchet sprocket engagement head 3029 is set to turn the threaded section 3109 clockwise into the threaded bore 3111. If the first and second plates 3009 and 3011 move in an opposite direction the sprocket 3031 moves in the other direction and simply causes the ratchet sprocket engagement head 3029 to click past the sprocket teeth. FIGS. 124 and 125 illustrate further details of the second socket 3035.

Figure 126:
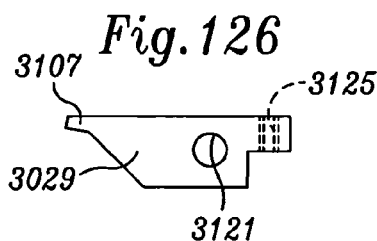
Figure 127:
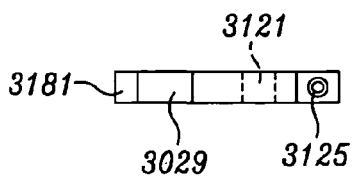
Figure 122:
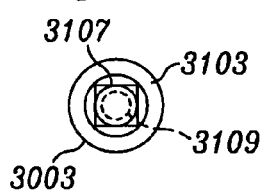

Referring to FIGS. 126 and 127 a plan and end view of the ratchet sprocket engagement head 3029 is seen in an unengaged position and without threaded member 3027. Newly seen is a main ratchet sprocket engagement head aperture 3121. Also seen is the threaded bore 3125 which is normally engaged by threaded member 3027 to hold spring 3021 in place.

Figure 128:
Figure 129:
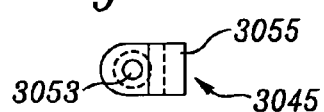

Referring to FIG. 128, a plan view of the sprocket 3031 is seen. Referring to FIG. 129, a plan view looking downward on the spacer clip 3045 illustrates further details of the spacer clip 3045, and especially the relationship of the threaded bore 3053 to the forward hook portion 3055.

Figure 130:
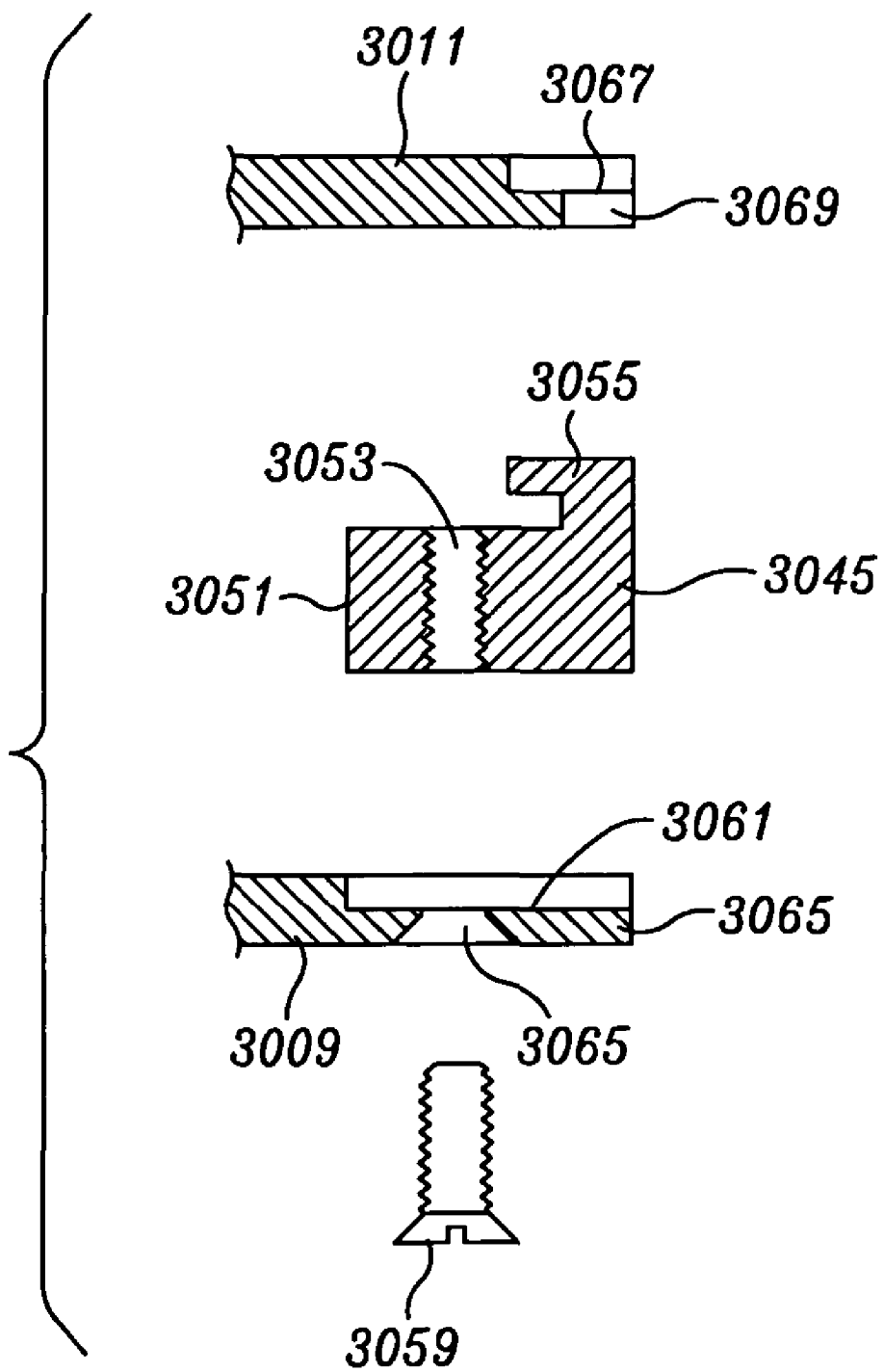

FIG. 130 is an exploded sectional detail illustrating the relationship of the first plate 3009 and second plate 3011, how the spacer clip 3045 is secured to the first plate 3009, how the spacer clip 3045 secures the second plate 3011 and how the spacer clip 3045 acts to control the spacing between the first and second plates 3009 and 3011.

The retractor systems thus described permit the following surgical procedure, some steps of which may be omitted and the order of which is not necessarily in accord with the order of steps as presented:

1. Locate a proper incision location (such as by fluoroscopy).
2. Insertion of a Guide Pin to determine a depth from skin to facet joint, to identify correct surgical level and the best angle of approach.
3. Apply the proper length surgical retractor blades to the frame.
4. Make an appropriate length incision, which may include:
    (a) one and a half times the largest diameter effective tube for microdiscectomy procedure
    (b) two times the effective tube width for two level fusion
    (c) three times the width for three level fusion
5. Insert not more than one fascial incisor/tissue dissector over the Guide Pin and incise the fascia.
6. Dissect the muscle attachments of the multifidus muscles off the spinous process, lamina, and transverse process in a longitudinal direction.
7. Insert retractor with fitted obturator into the wound and verify correct placement with fluoroscopy.
8. Partially expand the obturator and retractor blades then remove the obturator.
9. Adjust the frame to the contour of the body with proper flexion or extension of the frame.
10. Connect the frame to the operating table or other support if desired.
11. Expand the retractor blades sufficient to visualize the planned surgical procedure.
12. Dock the tip of the retractor blades to the correct anatomical site.
13. Apply the custom Gelpi-type hand held retractor to retract muscle ingress if necessary.
14. Proceed with planned surgery.
15. Make changes of the position as necessary during the surgery and relax the retractor blades every twenty minutes to allow recirculation for of the muscles and nerves.

The advantages of performing a surgical procedure with the retractor systems described in the specification, include, but are not limited to the following:

1. A single entry process can be practiced instead of sequential two dilation process.
2. Creation of a surgical field is done only to the necessary dimension with micro adjustable frame and retractor blades.
3. The use of an expanding obturator allows controlled separation of the muscle fibers so as to eliminate shredding and tearing of muscle.
4. Customized retractor tips to allow docking on specific bony sites to further stabilize exposure.
5. Surgical blade rotation is finely controllable with a threaded screw device giving both control and mechanical advantage.
6. The retractor support is adjustable to body contour.
7. Muscle compression release can be more easily carried out more often, such as every twenty minutes, for example resulting in less soft tissue damage.
8. Once deployed, the retraction system is stable such that attachment to the operating table may or may not be required.

Referring to FIG. 131 a top view of a further embodiment of a frame retractor system is illustrated and referred to as a frame retractor system 3501. Referring to FIG. 132, a bottom view of the frame retractor system 3501 is seen. The frame retractor system 3501 combines the isolated duties which were assigned to each side of earlier retractors such as frame retractor system 1301. By making such a combination, the complexity increases slightly, but adjustability and controllability is maximized. Although scalable to any size, any of the frame retractor systems seen above or below, can be selected based upon simplicity, as well as controllability. The translation & pivot motifs have been combined into an identifiable zone of the overall frame retractor system 3501.

Referring to both FIGS. 131 and 132, a frame retractor system 3501 has not only combined the translation & pivot motifs, but has integrated the controls and control forces to lie as closely to the patient's body as possible so that minimum space is occupied immediately over and around the operative field. A first main frame member 3503 shown to the left and which has an overall outer dimension generally matching that of a second main frame member 3505. The tops and undersides of the first and second main frame members 3503 and 3505 may have formed depressions 3507 which are fitted with threaded bores (not shown) which fit with a series of threaded members 3509 and can be used to securely lock down any matching structure, with an inner contour of the depressions 3507 to match the outer contour of an object to be secured to first and second main frame members 3503 and 3505. One such object is shown as an anchoring structure 3511 having a curved portion matching an curved portion of the depression 3507.

The first main frame member 3503 surrounds a first inner translatable frame member 3513. Within the first inner translatable frame member 3513, a first shown pivotable frame member 3515 is pivotally supported. The pivotable frame member 3515 is pivotally supported within the first inner translatable frame member 3513 in a manner similar to which the pivotable frame member 1313 was supported by the first main frame member 1303 as seen in FIGS. 77 & 78.

A pair of pivot pin members 3517 are shown as extending through bores 3519 at the opposite sides of the first inner translatable frame member 3513 and into blind pivot bores 3521 in the pivotable frame member 3515. The pivot pin members 3517 may preferably have a threaded exterior engaging matching threads in bores 3519 to securely lock the pivot pin members 3517 in place. The pivotable frame member 3515 may also have a pair of laterally offsetting groove members 3525 and 3527 to integrally assist in holding another object based upon close dimensioning.

The pivotable frame member 3515 supports a first retractor half 3531 which is seen as having more curved rear corners and includes a thickened structurally reinforced upper head portion 3533 and a lower extension member 3535, similar to the retractor half 1331 seen in FIGS. 77 & 78. The upper head portion 3533 is sized to fit closely within the pivotable frame member 3515 to facilitate quick change out. A pair of rotational locks 3537 may work in concert with the laterally offsetting groove members 3525 and 3527 to secure the structurally reinforced upper head portion 3533 with respect to the pivotable frame member 3515. The rotational locks 3537 can be simple threaded members which lock the structurally reinforced upper head portion 3533 down onto one of the laterally offsetting groove members 3525 and 3527, or it may act as a cam member and use laterally offsetting groove members 3525 and 3527 as a stacked pair or split to form a slot. However, the ability to move the retractor half 3531 vertically upward with respect to the frame retractor system 3501 is desirable.

Pivotable frame member 3515 supports, possibly a level higher than the level of the pair of pivot pin members 3517, a rotational fitting block 3541 which has an open slot for capturing a ball shaped fitting 3543 which rotates at the end of a threaded member 3545. The threaded member 3545 engages an internal threaded bore 3547 of a raised block 3549 supported by the first inner translatable frame member 3513. As the threaded member 3545 turns, it may be thrust forward toward the rotational fitting block 3541 to cause the upper portion of the pivotable frame member 3515 to tilt toward the second main frame member 3505 and to cause the lower extension member 3535 of the first retractor half 3531 to tilt away from the second main frame member 3505. Threaded member 3545 has a knob 3551 to facilitate turning either manually or by using ratchet actuation tool 3001.

The pivotable frame member 3515, first retractor half 3531, fitting block 3541, raised block 3747, threaded member 3545, knob 3551 and first inner translatable frame member 3513 all move translatably within the first main frame member 3503. The movement is effected by a side block 3555 having an internally threaded bore 3557 which engages a rotating threaded member 3559.

Rotating threaded member 3559 has an end having a groove 3561 which is axially captured by a lock ring or a pair of locking rods 3563 within a shallow bore 3565 within the first main frame member 3503. An access bore 3567 is provided beyond the shallow bore 3565 for sterilization access and to help axially disengage the rotating threaded member 3559 during disassembly. Threaded member 3559 has a knob 3569 to facilitate turning either manually or by using ratchet actuation tool 3001.

The frame retractor system 3501 first main frame member 3503 is pivotally connected to the second main frame member 3505 formed depressions 3507 by a pinned hinge structure. On the first main frame member 3503 a main inner lug 3575 which fits to one side of a thinner main outer lug 3577 of the second main frame member 3505. The lug 3577 has a through bore and lug 3575 has a blind bore in alignment with a pin 3579 joining and providing a common axis for the two lugs.

At the other side of the frame retractor system 3501 first main frame member 3503 is pivotally connected to the second main frame member 3505 by a pinned hinge structure in axial alignment with the first side. On the first main frame member 3503 a main inner lug 3585 fits to one side of a thinner main outer lug 3587 of the second main frame member 3505. The lug 3587 has a through bore and lug 3585 has a blind bore in alignment with a pin 3589 joining and providing a common axis for the two lugs. Pins 3579 and 3589 may preferably threadably engage either the inner lugs 3575 and 3585 respectively, or the outer lugs 3577 and 3587, respectively. The lateral thickness of the lug 3575 enables less linear space to be occupied on either side of the pin 3579, and moves it somewhat out of the way.

The features of the second main frame member 3505 in operating its retractor half are identical to the components of the first main frame member section 3503. Of the components already recited, only the first inner translatable frame member 3513 cannot be identically utilized as a common component, however, however the first inner translatable frame member 3513 must be provided as a mirror image component. Other components will keep the common numbering, except for the retractor half.

Second main frame member 3505 has features including formed depressions 3507, series of threaded members 3509, and a possibility of having at least one anchoring structure 3511.

The second main frame member 3505 surrounds a second inner translatable frame member 3601. Second inner translatable frame member 3601 has a side block 3603, but extending to the other side of the second inner translatable frame member 3601, making it a mirror image of the first inner translatable frame member 3513 rather than an exact copy. The other structures relating to the second inner translatable frame member 3601 are the same as for the first main frame member 3503, and carry the same numbering, including a second one of the pivotable frame member 3515, pair of pivot pin members 3517, through bores 3519, blind pivot bores 3521, and laterally offset groove members 3525 and 3527. A second retractor half 3611 is seen and has the same component parts as first retractor half 3531. Second retractor half 3611 is held in by pair of rotational locks 3537.

Note that the threaded member 3559 of second main frame member 3505 ends in its shallow bore 3565 open to and facing the main inner lug 3575. One optional but utilized structure is seen on both of the first and second main frame members 3503 and 3505 as a cover plate 3615 and a cover plate 3616, respectively, which may or may not be used with other structures such as hooks and which may use other threaded members 3617 other than those shown in FIG. 131.

The features of the second main frame member 3505 in operating its retractor half are identical to the components of the first main frame member 3503. Of the components already recited, only the first inner translatable frame member 3513 cannot be identically utilized as a common component, however, however the first inner translatable frame member 3513 must be provided as a mirror image component. Other components will keep the common numbering, except for the retractor half.

The last feature seen with respect to the a frame retractor system 3501 is a mechanism which enables movement and fixation of the angle between first main frame member 3503 and second main frame member 3505. Similar to the arrangement seen in FIGS. 77 and 78, a threaded member 3627 has a detent ball 3629 which fits within a rotational block fitting 3631 mounted upon second main frame member 3505. The threaded member 3627 is threadably supported by a threaded support block 3632 having a threaded internal bore 3631. Threaded member 3627 has a knob 3635 to facilitate turning either manually or by using ratchet actuation tool 3001. The threaded support block 3632 can be an open topped support block as previously shown, in order to quickly release the angle adjusting mechanism.

Also seen along the side of the a frame retractor system 3501 opposite the rotating threaded members 3559 is a groove 3635 which extends along the whole length of the inside of the first main frame member 3503 and second main frame member 3505. Also seen slightly is a tongue structure 3637 located on both the first and second inner translatable frame member 3513 and 3601 which extends into the groove 3635. The first main frame member 3503 and second main frame member 3505. Also seen slightly is a tongue structure 3637 located on both the first and second inner translatable frame member 3513 and 3601 which extends into the groove 3635. The tongue structure 3637 does not extend the complete traveling length of the side of the first and second inner translatable frame member 3513 and 3601 so that the sides of the first and second inner translatable frame member 3513 and 3601 adjacent their opposing faces would be able to extend beyond the portions of the groove 3635 near the pivot axis of the first and second main frame members 3503 and 3505. Extension beyond the groove 3635 will enable the first and second inner translatable frame member 3513 and 3601 to meet and still be pivotable about an axis near their meeting points. This enables wider flexibility for the hinge axis and eliminates the necessity to provide structure to accommodate the first and second inner translatable frame member 3513 and 3601 near the pivot axis of the first and second main frame members 3503 and 3505. Also seen are the threaded bores 3639 occupied by the rotational locks 3537

Referring to FIG. 133, a side sectional view taken along line 133-133 of FIG. 131 illustrates further details of the cover plate 3615 and how it both covers the majority of side block 3555 and helps to isolate the portion of rotating threaded member 3559 which would otherwise be exposed. Cover plate 3615 is also possibly used to access and also possibly secure the lock ring or lock rods 3563.

Referring to FIG. 134 an isolated view of the first inner translatable frame member 3513 shown with the first pivotable frame member 3515 in operative position, but with the threaded member 3545 and first retractor half 3531 removed. Features which can be seen are the keyhole shaped internal surface 3651 of the rotational fitting block 3541. The tongue structure 3637 can be more clearly seen as extending only up to the opening in which pin 3517 is located. Although portions of the first and second main frame members 3503 and 3505 could abuttingly hold the pin 3517 in place on one side of the first and second inner translatable frame members 3513 and 3601, it is preferable that the pin 3517 threadably engage one of the first and second inner translatable frame members 3513 and 3601 or pivotable frame member 3515.

Referring to FIG. 135, an isolated view of the pivotable frame member 3515 is seen with the pins 3517 removed. Also illustrated are threaded bores threaded bores 3655 used to support and engage the rotational locks 3537.

Referring to FIG. 136, a side view of the pivotable frame member 3515 illustrates a more prominent view of the tongue structure 3637 is seen as well as its adjacent relationship to the through bores 3519.

Referring to FIG. 137 an isolated view of the first retractor half 3531 is seen. Indentation 1411 is seen. The indentation 1411 either provides clearance for the shaft portion of the rotational locks 3537 and/or a cam portion of the shaft of the rotational locks 3537.

Referring to FIG. 138, an isolated view of an alternative embodiment is seen as a first retractor half 3661 is seen. First retractor half 3661 has a lower extension member 3663 having a curving rectangular shape.

Referring to FIG. 139, an isolated view of first main frame member 3503 with its components removed, is shown. Beginning at the upper right of the Figure, a raised level 3671 is a small lip where the farthest edge of the cover plate 3615 will form an even fit and cover. The pin 3579 seen in FIGS. 131 and 132 can be seen as occupying a bore 3675, which may be a threaded bore. Also seen are a series of cover plate threaded apertures 3679 used with threaded members 3617 for securing cover plate 3615. The cover plate threaded apertures 3679 open onto a lowered upper surface 3681 which has a sufficient depth such that cover plate 3615 will fit flush with respect to the remainder of the upper surface of the first main frame member 3503. Also seen is a pair of small apertures 3585 for accommodating the locking ring or locking rods 3563. Where a locking rod 3563 is used, a pair of rods inserted into the small apertures 3585 when the rotating threaded member 3559 is present, will partially occupy groove 3561 and prevent the rotating threaded member 3559 from being withdrawn. A ring or "U" shaped device can also be used. In the case of a ring, a groove 3687 may be present to help secure the groove 3561. The same action can be had with a "U" shaped member having a pair of rods and curved connector. The cover plate 3615 will secure any structure which captures the rotating threaded member 3559.

A smooth aperture 3589 is seen for admitting the rotating threaded member 3559. The threaded apertures 3679 are also seen within the area of the formed depressions 3507 and will ideally be engageable with the same threaded members 3617. A partial section at the lower left side of the first main frame member 3503 illustrates the taper of the groove 3635. Also seen is a through bore 3591 in the rotational fitting block 3541 as well as a through bore 3593 in the main inner lug 3585. Also seen fully in an unoccupied condition is the slide block traveling space 3695. The width of this space, subtracted from the width of the slide block 3555 gives the range of travel.

Referring to FIG. 140, a view looking into the side of the first main frame member 3503 most closely adjacent the traveling space 3695 illustrates further details thereof.

Referring to FIG. 141, a view looking into the main length of the first main frame member 3503 illustrates further details thereof, including a clearer view looking into the smooth aperture 3689 and the through bore 3691.

Referring to FIG. 142, a view looking into the side of the first main frame member 3503 most closely adjacent the threaded support block 3632 illustrates further details thereof.

Referring to FIG. 143, a section taken along line 143-143 of FIG. 139 illustrates further details in a section taken along the center of the path of travel of the rotating threaded member 3559 which is removed for clarity.

Referring to FIG. 144, the underside of the first main frame member 3503 is illustrated. Referring to FIG. 145, a view looking into the terminal ends of the first main frame member 3503 as seen in FIG. 139 is illustrated.

Referring to FIG. 146, an isolated view of second main frame member 3505 with its components removed, is shown. Beginning at the upper left of the Figure, thinner main outer lug 3577 is seen adjacent an abbreviated bore 3701 for accommodating the pin 3579. Also seen are the series of cover plate threaded apertures 3679 used with threaded members 3617 for securing cover plate 3615. The cover plate threaded apertures 3679 open onto another lowered upper surface 3681 which has a sufficient depth such that cover plate 3616 will fit flush with respect to the remainder of the upper surface of the first main frame member 3503. Also seen is a second set of small apertures 3585 for accommodating the locking ring or locking rods 3563. As before, where a locking rod 3563 is used, a pair of rods inserted into the small apertures 3585 when the rotating threaded member 3559 is present, will partially occupy groove 3561 and prevent the rotating threaded member 3559 from being withdrawn. A ring or "U" shaped device can also be used. As before the same action can be had with a "U" shaped member having a pair of rods and curved connector. The cover plate 3616 will secure any structure which captures the rotating threaded member 3559.

Another smooth aperture 3705 is seen for admitting the rotating threaded member 3559. The shallow bore 3565 can be seen as opening fully to the outside and adjacent but spaced apart from the thinner main outer lug 3577. As before, threaded apertures 3679 are also seen within the area of the formed depressions 3507 and will ideally be engageable with the same threaded members 3617. A partial section at the lower right side of the first main frame member 3503 also illustrates the taper of the groove 3635. Also seen is an abbreviated bore 3703 in the thinner main outer lug 3587. The rotational fitting block 3631 is also seen as having a keyhole shaped internal surface 3651.

Second main frame member 3505 also has a slide block traveling space 3695. As before width of this space, subtracted from the width of the slide block 3555 gives the range of travel which may be the same as or different from the range of travel of the slide block traveling space 3695 of first main frame member 3503.

Referring to FIG. 147, a view looking into the side of the second main frame member 3505 most closely adjacent the traveling space 3695 illustrates further details thereof.

Referring to FIG. 148, a view looking into the side of the second main frame member 3505 most closely adjacent the rotational fitting block 3541 illustrates further details thereof.

Referring to FIG. 149, a view looking into the main length of the second main frame member 3505 illustrates further details thereof, including a clearer view looking into the smooth aperture 3705.

Referring to FIG. 150, a section taken along line 150-150 of FIG. 146 illustrates further details in a section taken along the center of the path of travel of the rotating threaded member 3559 which is removed for clarity.

Referring to FIG. 151, the underside of the first main frame member 3503 is illustrated. Referring to FIG. 152, a view looking into the terminal ends of the second main frame member 3505 is illustrated.

Referring to FIG. 152, a view looking into the main length and two terminal ends of the second main frame member 3505 illustrates further details thereof, including a clearer view looking into the shallow bore 3565.

Referring to FIG. 153 a side elevation view of the frame retractor system 3501 is taken with respect to the bottom of FIG. 131, with the anchoring structure 3511 removed for clarity.

Referring to FIG. 154 a side elevation view of the frame retractor system 3501 is taken with respect to the top of FIG. 131, with the anchoring structure 3511 removed for clarity.

Referring to FIGS. 155-163, a series of views taken with respect to the orientation of FIG. 154 will illustrate the positions achievable with a frame retractor system 3501.

Referring specifically to FIG. 155, rotation of the knob 3551 into the threaded bore 3549 of raised block 3747 of the first main frame member 3503 causes the lower extension member 3535 associated with the first retractor half 3531 to swing away from the lower extension member 3535 of the second retractor half 3611. The remainder of the a frame retractor system 3501 is unchanged.

Referring to FIG. 156, rotation of the knob 3551 back out of the threaded bore 3549 of raised block 3747 of the first main frame member 3503 causes the lower extension member 3535 associated with the first retractor half 3531 to swing toward the lower extension member 3535 of the second retractor half 3611. The remainder of the a frame retractor system 3501 is unchanged.

Referring to FIG. 157, rotation of the knobs 3551 into the threaded bores 3549 of raised blocks 3747 of both the first and second main frame member 3503 causes the lower extension members 3535 to angularly swing away from each other. The angular deviation from the perpendicular is preferably at least about 45° which means that if both the lower extension members 3535 were swung wide, they would meet or exceed a 90° angular separation between them.

Referring to FIG. 158, an important aspect of frame retractor system 3501 and all of the frame retractor systems in this case is the ability at least one of the lower extension members 3535 to angularly swing toward each other, and in the case of the frame retractor system 3501 for both of the lower extension members 3535 to angularly swing towards each other. Rotation of both of the knobs 3551 out of the threaded bores 3549 of raised blocks 3747 of both the first and second main frame member 3503 causes the lower extension members 3535 to angularly swing away towards each other. Of course this can happen once both the pivotable frame members 3515 and 3601 are displaced from each other such that the bottoms of the extension members 3535 do not interfere. Based upon the angles shown, and assuming that both the pivotable frame members 3515 and 3601 are displaced from each other, each of the extension members 3535 can angle toward the other at an angle of about 20° from perpendicular. Together, the extension members 3535 form a collective angle with respect to each other of about 40°.

Referring to FIG. 159, the a frame retractor system 3501 includes the ability for the first main frame member 3503 to form an angle with respect to the second main frame member 3505. Where the components of the angle mechanism include the threaded member 3627 with knob 3633 threadably supported by a support block 3632 supported by the first main frame member 3503, the threaded member 3627 with detent ball 3629 fitting in a rotational block fitting 3631 supported by the second main frame member 3505, the knob 3633 can be turned to withdraw from the support block 3632 to create the angle seen in FIG. 159. With no angulation of the extension members 3535 with respect to their first and second main frame members 3503 and 3505, the angling of the first main frame member 3503 to form an angle with respect to the second main frame member 3505 can produce an angle of about 45° between the extension members 3535 with the distal ends of the extension members 3535 spreading apart from each other as they extend away from the first and second main frame members 3503 and 3505.

Conversely, the knob 3633 can be turned to cause the threaded member 3627 to move into the support block 3632 to create the angle seen in FIG. 160. With no angulation of the extension members 3535 with respect to their first and second main frame members 3503 and 3505, the angling of the first main frame member 3503 to form an angle with respect to the second main frame member 3505 can produce an angle of about 45° between the extension members 3535 with the distal ends of the extension members 3535 angling toward each other as they extend away from the first and second main frame members 3503 and 3505.

Referring to FIG. 162, the frame retractor system 3501 first and second main frame members 3503 and 3505 are shown in a position where they are not angled with respect to each other and are linear, generally as seen in FIGS. 131 and 132. In this configuration, when the knobs 3351 of the threaded members 3545 are turned to cause the rotating threaded member 3559 to turn to urge the side blocks 3555 and 3603 toward each other, the extension members 3535 move toward each other. For maximum closeness, the extension members 3535 should be parallel toward each other. If they are not parallel with respect to each other, some parts of the pivotable frame members 3515 and possibly the first and second retractor halves 3531 and 3611 might interfere if brought toward each other while in close, non-parallel proximity. Likewise, the distal ends of the lower extension member 3535 might interfere if brought toward each other while in close, non-parallel, proximity.

Referring to FIG. 163, the frame retractor system 3501 first and second main frame members 3503 and 3505 are shown in a position where they are not angled with respect to each other and are linear, and shown spaced apart from each other. In this configuration, when the knobs 3351 of the threaded members 3545 are turned to cause the rotating threaded member 3559 to turn to urge the side blocks 3555 and 3603 away from each other, the extension members 3535 move away from each other.

Referring to FIG. 164 a frame retractor system 3801 is illustrates as a further embodiment in which the structures for controlling tilting which were provided as horizontal axis structures are replaced by vertical axis controls. This allows several objectives to be achieved. By converting all of the external tilting mechanisms to an internal structure, the exposed threads of the threaded members 3627 and 3545 are eliminated or hidden. Further the effective height of the frame retractor system 3801 is about half of that seen in frame retractor system 3501. Only three abbreviated height knobs extend upwardly and these are easy to engage and operate with the ratchet actuation tool 3001.

FIG. 163 is a top view looking down on the frame retractor system 3801. Generally speaking, the components which are new, with respect to the FIGS. 131-162 are to one side of the frame retractor system 3801 opposite the threaded members 3559. The members which pivot the pivotable frame members 3515 are removed from near the midline and are moved in a direction opposite the side on which the threaded members 3559 lie. With the angular control for control of the angular displacement of the first main frame member 3503 and second main frame member 3505 generally in the same vicinity, the movement of the members which pivot the pivotable frame members 3515 nearby gives the surgeon an even more powerful, close-in control capability.

The components which are the same as before will have the same numbers and will generally not be discussed in high detail. New components will be introduced with new numbering. Frame retractor system 3801 is shown with the retractor half 3661 of FIG. 138. In addition, a matching retractor half 3803 is seen.

The new structures which have bilateral symmetry will be discussed first. New structures include a knob 3811 which operates just above an access plate 3813 held in place by the threaded members 3617. The access plate 3813 will be shown to form an upper turning fitting for an internal worm gear (not shown) The internal gears (not shown in FIG. 164) are connected to operably tilt a pivotable frame member 3815. The pivotable frame member 3815 is seen as having a closer relationship to a inner translatable frame member 3817. The inner translatable frame member 3817 is somewhat freed from having to carry the raised block 3747 and can thus be made lighter. The elimination of the need for a raised level force moment is another benefit. Further, the inner translatable frame member 3817 on the left is a mirror image of the inner translatable frame member 3817 on the right and thus it is given the same identification numeral.

The inner translatable frame member 3817 is shown as having a cavity 3819 to provide a lighter weight and because provision of a reinforcing support is not needed. Adjacent the knob 3811 a rotation gear plate 3821 is seen. Each rotation gear plate is securely attached to the end of the pivotable frame member 3815 by a pair of bolts 3825 shown in dashed line format. The rotation gear plate 3821 has a center having a pivot pin bore (to be shown more completely below) and shortened pivot pin 3827 supported in a through bore 3829. The shortened pivot pin 3827 can be held in by its adjacent first and second main frame members 3503 and 3505 or can be held in place by some other method. Since the structure which supports the shortened pivot pin 3827 is physically part of the inner translatable frame member 3817, and because the rotation gear plate 3821 is securely attached to the pivotable frame member 3815, the inner translatable frame member 3817 is essentially pivotally supporting a rigid series combination of pivotable frame member 3815 and rotation gear plate 3821. In this configuration, the inner translatable frame members 3817 might have to be removed from the first and second main frame members 3503 and 3505 before the shortened pivot pin 3827 can be removed to free the series combination of pivotable frame member 3815 and rotation gear plate 3821, or to even access the pair of bolts 3825 which connect the series combination.

Although not directly shown in FIG. 164, the knobs 3811 operate a worm gear which operates to cause the a rotation gear plate 3821 to turn to cause the pivotable frame member 3815 to tilt. The connectivity of the components as mentioned above lends significant strength to the frame retractor system 3801 while segregating the abbreviated height controls to defined areas of the system.

At the bottom center of the frame retractor system 3801 a similar arrangement is made. The second main frame member 3505 has undergone a modification where its thinner main outer lug 3587 and its abbreviated bore 3703 is simply removed, along with some outer material on the outside of second main frame member 3505 and inward from the terminal end.

In this general area, an outer frame gear plate 3831 is attached by two bolts 3833 secured into the second main frame member 3505. The outer frame gear plate 3831 has stepped pin bore 3835 for inserted fixation of pin 3579. As before, the threads which secure pin 3579 can exist in either the main inner lug 3585's through bore 3593 or in any portion of the stepped pin bore 3835, although the threads are shown on the through bore 3593. The physical features of the first main frame member 3503 must also be modified to work with a second main frame member 3505 with a worm gear.

Details of the features of the first main frame member 3503 will be shown in subsequent figures, but a frame pivot control cover plate 3837 is seen as being secured by threaded members 3617. The cover plates 3813 and frame pivot control cover plate 3837 are preferably of the same construction, size and shape, in order to save manufacturing expense. An abbreviated height control knob 3839 is shown next to the frame pivot control cover plate 3837.

Referring to FIG. 164, a sectional view taken along line 164-164 of FIG. 163 illustrates further details, including cavity 3819.

Referring to FIG. 165, a bottom view of the frame retractor system 3801 illustrates a more details, including the bottom surfaces of worm gears, including the worm gears 3841 associated with the knobs 3811, and worm gear 3843 associated with knob 3839.

Referring to FIG. 166 a top view of the inner translatable frame member 3817 with its pivotable frame member 3815, and the inner translatable frame member 3817 are shown in isolation from the remainder of the frame retractor system of FIG. 163.

Referring to FIG. 167 a top view of the inner pivotable frame member 3815 is shown. The inner translatable frame member 3815 is shown in isolation from the remainder of the frame retractor system of FIG. 163. The bores 3639 are also more clearly shown. The pivot gear plate 3821 is seen as having a shallow blind bore 3845 for engaging the shortened pivot pin 3827. The shallow blind bore 3845 is shown in FIG. 166 as being continuous with the bore supporting the pivot pin 3827. The shallow blind bore 3845 is positioned between the bores containing the pair of bolts 3825. A set of teeth 3847 are partially visible on the left side of the pivot gear plate 3821 as seen looking into FIG. 167.

FIG. 168 illustrates a top view in isolation of the thin top profile retractor half 3803 seen in the frame retractor system 3801 of FIG. 163. The reinforced upper head portion 3533 has much less web area. The indentations 1411 can also be seen.

FIG. 169 illustrates a semi-sectional view looking into the tongue structure 3637 of the inner translatable frame member 3817. A semi-section illustrates the existence of a worm gear cavity 3851 within which the worm gear 3841 turns. The worm gear cavity generally protects the worm gear 3841 and limits the exposure of the spiral tooth 3853 (sometimes referred to as the worm). Limiting the exposure will limit contamination and insure that the only objects to be engaged are teeth 3847 on the object to be moved, in this case the pivot gear plate 3821.

FIG. 170 illustrates an isolated view of first inner translatable frame member of FIG. 163 with components removed. The worm gear cavity 3851 can be seen as having a semi-circular wall. The wall forms a radius about a worm gear aperture 3855 which is located on a bottom wall 3857 which remains from the fact that the worm gear cavity 3851 does not extend all the way through. Bottom wall 3857 forms a bottom rotational support for the worm gear 3841. The bottom wall 3857, along with the cover plate 3837 allows the worm gear 3841 to turn freely, but keeps the spiral tooth 3853 in its rotational position.

Referring to FIG. 171, a view looking into the side of the first inner translatable frame member of FIG. 170 illustrates the cavity 3819 and the prominent tongue structure 3637.

Referring to FIG. 172, a view looking into the slide block end of the first inner translatable frame member 3817 which is symmetrically identical to the inner translatable frame member 3817 supported by the second main frame member 3505, the internally threaded bore 3557 is shown in Dashed line format.

Referring to FIG. 173, view looking into the other side of the first inner translatable frame member most closely adjacent the worm gear cavity 3851, the tongue structure 3637 is most prominently seen;

Referring to FIG. 174, a view looking into the open side of the first inner translatable frame member of FIG. 170 gives the best view of the worm gear cavity 3851 and especially the curved wall making up the bulk of the cavity partial enclosure.

Referring to FIG. 175, a view looking into the bottom side of the first inner translatable frame member of FIG. 170 illustrates the extent to which the bottom wall 3857 of the worm gear cavity 3851 is integrally wormed with respect to the inner translatable frame member 3817;

Referring to FIG. 176, an isolated view of second inner translatable frame member of FIG. 163 with components removed reveals details of the worm gear cavity 3851 and in comparison with FIG. 170 shows the mirror image symmetry of the two translatable frame members 3817 of FIG. 163;

Referring to FIG. 177, a view looking into the outside side of the first inner translatable frame member 3817 of FIG. 176 and compares as a mirror image of FIG. 170.

Referring to FIG. 178, a view looking into the slide block end of the first inner translatable frame member 3817 of FIG. 176 compares as a mirror image of FIG. 172.

Referring to FIG. 179, a view looking into the tongue end of the first inner translatable frame member 3817 most closely adjacent the worm gear cavity 3851 and compares as a mirror image of FIG. 173.

Referring to FIG. 180, a view looking into the open side of the first inner translatable frame member 3817 of FIG. 176 compares as a mirror image of FIG. 174.

Referring to FIG. 181, a view looking into the bottom side of the first inner translatable frame member 3817 of FIG. 176 compares as a mirror image of FIG. 175.

Referring to FIG. 182, an isolated view of first main frame member 3503 of FIG. 163 with components removed indicates a worm gear housing assembly which has many of the components of the worm gear housing assembly of the first and second inner translatable frame members 3817 but with the structures being inverted to protrude to the outside of the first main frame member 3503, and which may be referred to as worm gear tilt housing assembly 3861. The worm gear cavity 3851 of worm gear tilt housing assembly 3861 opens in the direction of second main frame member 3505 (not shown in FIG. 182). The other structures, including the worm gear aperture 3855 and bottom wall 3857 are also present.

To the inside of the frame a hinge member 3863 is seen having through bore 3829. The hinge member 3863 will meet a similar structure on second main frame member 3505, with outside material having been removed to accommodate the outer frame gear plate 3831 which actually carries the pivot aperture or bore which will align with the through bore 3829. The upper portion of the first main frame member 3503 adjacent the slide block traveling space 3695 of the frame retractor system 3801 is the same as was shown for the frame retractor system 3501.

Referring to FIG. 183, a view looking into the side of the first main frame member of FIG. 182 most closely adjacent the traveling space is seen.

Referring to FIG. 184 a view looking into the main length of the first main frame member of FIG. 182 from the outside, emphasizes the small amount by which the worm gear tilt housing assembly 3861 protrudes outwardly from the main extent of the frame.

Referring to FIG. 185, a view looking into the side of the first main frame member of FIG. 182 most closely adjacent the tongue end emphasizes a worm gear tilt housing assembly 3861 upper surface 3865 which is inset to accommodate the access plate 3813. The groove 3635 is shown in phantom.

Referring to FIG. 186, a section taken along line 186-186 of FIG. 182 illustrates the internal features of the structures adjacent the traveling space 3695, including pair of small apertures 3685 or groove 3687 within the shallow bore 3565, as well as the bore 3675 shown in phantom as lying beyond the section.

Referring to FIG. 187, the underside of the first main frame member of FIG. 182 is shown.

Referring to FIG. 188, a view looking into the main length of the first main frame member of FIG. 182 but into the terminal ends gives a full view of the worm gear cavity 3851, worm gear aperture 3855 shown in phantom and bottom wall 3857 of the worm gear tilt housing assembly 3861.

Referring to FIG. 189, an isolated view of second main frame member section of FIG. 163 with its components removed is illustrated. Of note is the front side including a pair of threaded bolt apertures 3867. An accommodation offset 3869 causes the remaining portion of the second main frame member 3505 to have about the same width as the hinge member 3863 of the first main frame member 3503, although it does not form part of a hinge. The accommodation offset 3869 accommodates the outer frame gear plate 3831 while the threaded bolt apertures 3867 secure it to the second main frame member 3505.

Referring to FIG. 190, a view looking into the side of the second main frame member section of FIG. 189 most closely adjacent the traveling space 3695 is seen.

Referring to FIG. 191, a view looking into the side of the second main frame member section of FIG. 189 and most closely adjacent the groove 3635. Because the groove 3635 is located on the other side of the portion of the second main frame member 3505, a greater depth is possible by vertically offsetting the threaded bolt apertures 3867, one upwardly and one downwardly.

Referring to FIG. 192, a view looking into the outside main length of the second main frame member 3505 is seen.

Referring to FIG. 193, a sectional view taken along line 193-193 of FIG. 189 illustrates further details thereof.

Referring to FIG. 194, the underside of the second main frame member 3505 of FIG. 189 is seen.

Referring to FIG. 195, a view looking into the main length and two terminal ends of the second main frame member 3505 of FIG. 189 is seen.

Referring to FIG. 196, a side elevation view of the frame retractor system 3801 is taken with respect to the bottom of FIG. 163. The curved tops and bottoms of the pivot gear plates 3821 and the outer frame gear plate 3831 are seen. These structures are rounded and gear teeth 3857 can be seen over the a partial extent of the curvature. This illustrates that the teeth 3847 can be distributed in accord with the desired limits of angular displacement. The pivot gear plates 3821 and the outer frame gear plate 3831 need not be provided in a completely round shape, and need not have gear teeth 3857 over the whole of the round shape. Further, a shield or cover (not shown) may be provided to isolate the round portions of the pivot gear plates 3821 and the outer frame gear plate 3831 to further isolate the them from contact with the surgeon. As will be shown, the remainder of the views showing the capability for the frame retractor system 3801 are taken with respect to the plan view of FIG. 196.

Referring to FIG. 197, a side elevation view of the frame retractor system 3801 similar to that seen in FIG. 196 but with a semi section taken through the worm gear worm gears 3841 and 3843 engagement interfaces with the pivot gear plates 3821 and the outer frame gear plate 3831 and in which rotation of the right side knob 3811 causes the right extension member 3535 to move to the right.

Referring to FIG. 198, a side elevation view of the frame retractor system similar 3801 to that seen in FIG. 197 and in which rotation of the right side knob 3811 causes the right extension member 3535 to move to the left.

Referring to FIG. 199, rotation of the knob 3811 of the right tilt control causes the rotation gear plate 3821 to rotate to cause the lower extension member 3535 to swing away from the other lower extension member 3535.

Referring to FIG. 200, rotation of the knob 3811 of the right tilt control in a direction opposite to the rotation in FIG. 199 causes the rotation gear plate 3821 to rotate to cause the lower extension member 3535 to swing toward the other lower extension member 3535.

Referring to FIG. 201, rotation of the knobs 3811 of the right and left tilt controls in opposite directions cause their rotation gear plates 3821 to rotate to cause the lower extension members 3535 to swing away from each other.

Referring to FIG. 202, rotation of the knob 3811 of the right and left tilt controls in opposite directions and oppositely with regard to FIG. 201 to cause their rotation gear plates 3821 to rotate to cause the lower extension members 3535 to swing toward from each other.

Referring to FIG. 203, rotation of the knob 3839 of the frame pivot control in a first direction to cause the second main frame member 3505 to angle upward with respect to the first main frame member 3503.

Referring to FIG. 204, rotation of the knob 3839 of the frame pivot control in a second direction to cause the second main frame member 3505 to angle downward with respect to the first main frame member 3503.

Referring to FIG. 205, rotation of the knobs 3569 controlling the slide blocks 3555 in a first direction to cause the slide blocks 3555 to move toward each other to bring the lower extension members 3535, which are in a parallel relationship, to move toward each other.

Referring to FIG. 206, rotation of the knobs 3569 controlling the slide blocks 3555 in a second direction to cause the slide blocks 3555 to move away from each other to bring the lower extension members 3535, which are in a parallel relationship, to move away from each other.

Referring to FIG. 207, a bottom view of the guide and cover plate 3615 illustrates a guide structure 3881 which may be provided to fit within a matching slot or other structure on the first main frame member 3503. Also seen are apertures 3883 through which the threaded members 3617 extend to hold the guide and cover plate 3615 into place.

Referring to FIG. 208, an end view of the guide and cover plate 3615 of FIG. 207 is shown.

Referring to FIG. 209, a front view of the guide and cover plate 3615 of FIG. 207 is shown.

Referring to FIG. 210, a top view of the guide and cover plate 3615 of FIG. 207 is shown.

Referring to FIG. 211, a bottom view of a guide and cover plate 3616 which fits over a portion of the right slide block of the second main frame member 3505 is shown. A guide structure 3885 may be provided to fit within a matching slot or other structure on the second main frame member 3503. Apertures 3883 are also seen through which the threaded members 3617 extend to hold the guide and cover plate 3616 into place.

Referring to FIG. 212, an end view of the guide and cover plate 3616 of FIG. 211 is shown.

Referring to FIG. 213, a front view of the guide and cover plate 3616 of FIG. 211 is shown.

Referring to FIG. 214, a top view of the guide and cover plate 3616 of FIG. 211 is shown.

While the present system has been described in terms of a system of instruments and procedures for facilitating the performance of a microscopic lumbar diskectomy procedure, one skilled in the art will realize that the structure and techniques of the present system can be applied to many appliances including any appliance which utilizes the embodiments of the instrumentation of the system or any process which utilizes the steps of the inventive system.

Although the system of the invention has been derived with reference to particular illustrative embodiments thereof, many changes and modifications of the systems shown may become apparent to those skilled in the art without departing from the spirit and scope of the inventive system. Therefore, included within the patent warranted hereon are all such changes and modifications as may reasonably and properly be included within the scope of this contribution to the art.

What is claimed:

1. A minimal incision maximal access minimal invasive surgical spine instrument comprising:
    a first retractor blade member;
    a first tilt support attached to said first retractor blade member for supporting said first retractor blade member over a range of angular motion;
    a first translation support for pivotally supporting said first tilt support;
    a second retractor blade member;
    a second tilt support attached to said second retractor blade member for supporting said second retractor blade member over a range of angular motion;
    a second translation support for pivotally supporting said second tilt support;
    a main support, for supporting said first and said second translation supports and for enabling controlled movement of said first and said second translation supports over a range of different positions with respect to said main support, wherein said main support includes a first frame member associated with said first translation support and a second frame member associated with said second translation support, and wherein said first frame member is angularly displaceable with respect to said second frame member, said first translation support defining a first plane; and
    a first translation mechanical linkage further comprising:
        a first captured threaded member having a first axis, said first captured threaded member rotatable with respect to said first frame member without axial movement with respect to said first frame member, said first axis being coplanar with said first plane;
        a first internally threaded bore located through a portion of said first translation support; and
        a first through bore located through a portion of said first frame member, said first captured threaded member being located within said first internally threaded bore and said first through bore, such that rotation of said captured threaded member causes axial translation of said first translation support within said main support.

2. The minimal incision maximal access minimal invasive surgical spine instrument as recited in claim 1 wherein said first frame member and said second frame member are attached by a frame mechanical linkage further comprising:
    a frame gear supported by at least one of said first and said second frame members;
    a worm gear assembly supported by the other of said first and said second frame members and positioned to engage and move said frame gear with respect to said worm gear assembly.

3. The minimal incision maximal access minimal invasive surgical spine instrument as recited in claim 1 wherein said first tilt support attachment to said first translation support includes a tilt mechanical linkage further comprising:
    a pivot gear supported by at least one of said first tilt support and said first translation support; and
    a first worm gear assembly supported by the other of said one of said first tilt support and said first translation support and positioned to engage and move said pivot gear with respect to said first worm gear assembly to cause said first tilt support to be angularly displaced with respect to said first translation support.

4. The minimal incision maximal access minimal invasive surgical spine instrument as recited in claim 1 wherein said first retractor blade member and second retractor blade member are angularly displaceable with respect to each of the first and second frame members.

5. A minimal incision maximal access minimal invasive surgical spine instrument comprising:
    a first retractor blade member;
    a second retractor blade member;
    a first translation support for supporting said first retractor blade member;
    a support having a first member for supporting said first translation support and a second member for supporting said second retractor blade member, said first member of said support controllably angularly pivotable with respect to said second member of said support, and wherein at least one of said first retractor blade member and said second retractor blade member is movable independent of its associated one of said first member and said second member, each of said first member and said second member have a shape in the form of a U, at least one of said first member and said second member having a pair of protrusions sized and located to complementarily fit within a pair of recesses in the other of said first member and said second member, said first member and said second member coupled along a common axis that is located through the complementary protrusions and recesses, said first member defining a first plane;
a mechanical linkage configured to rotate said first member and said second member in both a first direction and a second direction with respect to each other about said common axis, said mechanical linkage configured to maintain an angular relationship of said first member with respect to said second member; and
a first translation mechanical linkage further comprising:
　a first captured threaded member having a first axis, said first captured threaded member rotatable with respect to said first member without axial movement with respect to said first member, said first axis being coplanar with said first plane;
　a first internally threaded bore located through a portion of said first translation support; and
　a first through bore located through a portion of said first member, said first captured threaded member being located within said first internally threaded bore and said first through bore, such that rotation of said captured threaded member causes axial translation of said first translation support within said support.

6. The minimal incision maximal access minimal invasive surgical spine instrument as recited in claim 5 wherein said first frame member and said second frame member are attached by a frame mechanical linkage further comprising:
　a frame gear supported by at least one of said first and said second frame members;
　a worm gear assembly supported by the other of said first and said second frame members and positioned to engage and move said frame gear with respect to said worm gear assembly.

\* \* \* \* \*

UNITED STATES PATENT AND TRADEMARK OFFICE
CERTIFICATE OF CORRECTION

| | | |
|---|---|---|
| PATENT NO. | : 7,946,982 B2 | Page 1 of 1 |
| APPLICATION NO. | : 11/510804 | |
| DATED | : May 24, 2011 | |
| INVENTOR(S) | : James S. Hamada | |

It is certified that error appears in the above-identified patent and that said Letters Patent is hereby corrected as shown below:

Column 63, line 46, "162" should be --161--; and

Column 63, line 63, "163" should be --162--.

Signed and Sealed this
Twelfth Day of July, 2011

David J. Kappos
*Director of the United States Patent and Trademark Office*